(12) United States Patent
Wohlgemuth et al.

(10) Patent No.: US 7,604,936 B2
(45) Date of Patent: Oct. 20, 2009

(54) METHODS AND COMPOSITIONS FOR DIAGNOSIS AND MONITORING AUTO IMMUNE AND CHRONIC INFLAMMATORY DISEASES

(75) Inventors: Jay Wohlgemuth, Menlo Park, CA (US); Kirk E. Fry, Palo Alto, CA (US); Robert Woodward, Pleasanton, CA (US); Ngoc Ly, Albany, CA (US)

(73) Assignee: XDX, Inc., Brisbane, CA (US)

( * ) Notice: Subject to any disclaimer, the term of this patent is extended or adjusted under 35 U.S.C. 154(b) by 374 days.

(21) Appl. No.: 10/512,028

(22) PCT Filed: Apr. 24, 2003

(86) PCT No.: PCT/US03/13015

§ 371 (c)(1),
(2), (4) Date: Jul. 21, 2005

(87) PCT Pub. No.: WO03/090694

PCT Pub. Date: Nov. 6, 2003

(65) Prior Publication Data

US 2008/0199853 A1    Aug. 21, 2008

(51) Int. Cl.
*C12Q 1/68* (2006.01)
(52) U.S. Cl. .......................................... 435/6
(58) Field of Classification Search ........... None
See application file for complete search history.

(56) References Cited

U.S. PATENT DOCUMENTS

| | | | |
|---|---|---|---|
| 4,190,535 A | 2/1980 | Luderer et al. |
| 4,215,051 A | 7/1980 | Schroeder et al. |
| 4,350,593 A | 9/1982 | Kessler |
| 4,358,535 A | 11/1982 | Falkow et al. |
| 4,376,110 A | 3/1983 | David et al. |
| 4,582,789 A | 4/1986 | Sheldon, III et al. |
| 4,683,195 A | 7/1987 | Mullis et al. |
| 4,683,202 A | 7/1987 | Mullis |
| 4,751,001 A | 6/1988 | Saunders |
| 4,762,780 A | 8/1988 | Spector et al. |
| 4,789,630 A | 12/1988 | Bloch et al. |
| 4,800,159 A | 1/1989 | Mullis et al. |
| 4,818,418 A | 4/1989 | Saunders |
| 4,843,155 A | 6/1989 | Chomczynski |
| 4,889,818 A | 12/1989 | Gelfand et al. |
| 4,908,318 A | 3/1990 | Lerner |
| 4,946,778 A | 8/1990 | Ladner et al. |
| 4,946,952 A | 8/1990 | Kiefer |
| 4,965,188 A | 10/1990 | Mullis et al. |
| 5,053,134 A | 10/1991 | Luderer et al. |
| 5,063,162 A | 11/1991 | Kiefer |
| 5,066,584 A | 11/1991 | Gyllensten et al. |
| 5,075,216 A | 12/1991 | Innis et al. |
| 5,079,352 A | 1/1992 | Gelfand et al. |
| 5,091,310 A | 2/1992 | Innis |
| 5,120,525 A | 6/1992 | Goldenberg |
| 5,142,033 A | 8/1992 | Innis |
| 5,143,854 A | 9/1992 | Pirrung et al. |
| 5,210,015 A | 5/1993 | Gelfand et al. |
| 5,212,071 A | 5/1993 | Fearon et al. |
| 5,215,882 A | 6/1993 | Bahl et al. |
| 5,219,727 A | 6/1993 | Wang et al. |
| 5,264,351 A | 11/1993 | Harley |
| 5,278,043 A | 1/1994 | Bannwarth et al. |
| 5,310,652 A | 5/1994 | Gelfand et al. |
| 5,314,809 A | 5/1994 | Erlich et al. |
| 5,322,770 A | 6/1994 | Gelfand |
| 5,340,720 A | 8/1994 | Stetler |
| 5,346,994 A | 9/1994 | Chomczynski |
| 5,352,600 A | 10/1994 | Gelfand et al. |
| 5,374,553 A | 12/1994 | Gelfand et al. |
| 5,385,824 A | 1/1995 | Hoet et al. |
| 5,389,512 A | 2/1995 | Sninsky et al. |
| 5,393,672 A | 2/1995 | Ness et al. |
| 5,405,774 A | 4/1995 | Abramson et al. |
| 5,407,800 A | 4/1995 | Gelfand et al. |
| 5,411,876 A | 5/1995 | Bloch et al. |
| 5,418,149 A | 5/1995 | Gelfand et al. |
| 5,420,029 A | 5/1995 | Gelfand et al. |

(Continued)

FOREIGN PATENT DOCUMENTS

| | | |
|---|---|---|
| EP | 0 217 102 A2 | 4/1987 |
| EP | 0 217 992 A2 | 4/1987 |
| EP | 1 077 254 A2 | 2/2001 |
| EP | 1 162 276 A2 | 12/2001 |
| SG | 200302150-8 | 7/2002 |

(Continued)

OTHER PUBLICATIONS

EMBL-EBI Accession No. AA053887, last updated Aug. 31, 2006, located at <http://www.ebi.ac.uk/cgi-bin/dbfetch?db=embl&id=AA053887&style=raw> visited on Oct. 31, 2007. (2 pages).
EMBL-EBI Accession No. AAC77576, located at <http://www.ebi.ac.uk/cgi-bin/dbfetch?db=emblcds&id=AAC77576&style=raw> visited on Oct. 31, 2007. (1 page).
EMBL-EBI Accession No. AAK80490, located at <http://www.ebi.ac.uk/cgi-bin/dbfetch?db=emblcds&id=AAK80490&style=raw> visited on Oct. 31, 2007. (1 page).

(Continued)

*Primary Examiner*—James Martinell
(74) *Attorney, Agent, or Firm*—Morrison & Foerster LLP

(57) ABSTRACT

Methods of diagnosing or monitoring auto immune and chronic inflammatory diseases, particularly systemic lupus erythematosis and rheumatoid arthritis, in a patient by detecting the expression level of one or more genes in a patient, are described. Diagnostic oligonucleotides for diagnosing or monitoring auto immune and chronic inflammatory diseases, particularly systemic lupus erythematosis and rheumatoid arthritis and kits or systems containing the same are also described.

12 Claims, 13 Drawing Sheets

U.S. PATENT DOCUMENTS

| | | | |
|---|---|---|---|
| 5,426,039 A | 6/1995 | Wallace et al. |
| 5,445,940 A | 8/1995 | Brenner et al. |
| 5,455,170 A | 10/1995 | Abramson et al. |
| 5,459,037 A | 10/1995 | Sutcliffe et al. |
| 5,466,591 A | 11/1995 | Abramson et al. |
| 5,468,613 A | 11/1995 | Erlich et al. |
| 5,476,774 A | 12/1995 | Wang et al. |
| 5,487,970 A | 1/1996 | Rowley et al. |
| 5,487,972 A | 1/1996 | Gelfand et al. |
| 5,491,063 A | 2/1996 | Fisher et al. |
| 5,491,086 A | 2/1996 | Gelfand et al. |
| 5,501,963 A | 3/1996 | Burckhardt |
| 5,506,145 A | 4/1996 | Bull et al. |
| 5,512,462 A | 4/1996 | Cheng |
| 5,514,556 A | 5/1996 | Shearer et al. |
| 5,538,848 A | 7/1996 | Livak et al. |
| 5,561,058 A | 10/1996 | Gelfand et al. |
| 5,565,339 A | 10/1996 | Bloch et al. |
| 5,569,583 A | 10/1996 | Greenberg et al. |
| 5,571,673 A | 11/1996 | Picone |
| 5,573,906 A | 11/1996 | Bannworth et al. |
| 5,604,099 A | 2/1997 | Erlich et al. |
| 5,618,703 A | 4/1997 | Gelfand et al. |
| 5,618,711 A | 4/1997 | Gelfand et al. |
| 5,624,833 A | 4/1997 | Gelfand et al. |
| 5,635,365 A | 6/1997 | Ansari et al. |
| 5,641,864 A | 6/1997 | Gelfand |
| 5,658,744 A | 8/1997 | Ochoa et al. |
| 5,665,551 A | 9/1997 | Gelfand et al. |
| 5,674,738 A | 10/1997 | Abramson et al. |
| 5,677,152 A | 10/1997 | Birch et al. |
| 5,693,517 A | 12/1997 | Gelfand et al. |
| 5,707,807 A | 1/1998 | Kato |
| 5,716,787 A | 2/1998 | Dunn et al. |
| 5,721,351 A | 2/1998 | Levinson |
| 5,728,822 A | 3/1998 | Macfarlane |
| 5,766,585 A | 6/1998 | Evans et al. |
| 5,773,258 A | 6/1998 | Birch et al. |
| 5,789,224 A | 8/1998 | Gelfand et al. |
| 5,795,762 A | 8/1998 | Abramson et al. |
| 5,804,375 A | 9/1998 | Gelfand et al. |
| 5,807,522 A | 9/1998 | Brown et al. |
| 5,811,284 A | 9/1998 | Chang et al. |
| 5,837,832 A | 11/1998 | Chee et al. |
| 5,939,270 A | 8/1999 | Haunsø et al. |
| 5,939,292 A | 8/1999 | Gelfand et al. |
| 5,958,342 A | 9/1999 | Gamble et al. |
| 5,958,688 A | 9/1999 | Eberwine et al. |
| 5,965,366 A | 10/1999 | Ochoa et al. |
| 5,968,799 A | 10/1999 | Gelfand et al. |
| 5,973,137 A | 10/1999 | Heath |
| 5,981,481 A | 11/1999 | Fearon et al. |
| 5,994,056 A | 11/1999 | Higuchi |
| 5,994,076 A | 11/1999 | Chenchik et al. |
| 6,001,611 A | 12/1999 | Will |
| 6,004,755 A | 12/1999 | Wang |
| 6,010,853 A | 1/2000 | Kanteti et al. |
| 6,020,186 A | 2/2000 | Henco et al. |
| 6,033,860 A | 3/2000 | Lockhart et al. |
| 6,040,138 A | 3/2000 | Lockhart et al. |
| 6,040,166 A | 3/2000 | Erlich et al. |
| 6,045,996 A | 4/2000 | Cronin et al. |
| 6,048,695 A | 4/2000 | Bradley et al. |
| 6,048,709 A | 4/2000 | Falb |
| 6,060,240 A | 5/2000 | Kamb et al. |
| 6,066,322 A | 5/2000 | Levinson |
| 6,066,498 A | 5/2000 | Levinson |
| 6,084,083 A | 7/2000 | Levinson |
| 6,087,112 A | 7/2000 | Dale |
| 6,087,477 A | 7/2000 | Falb et al. |
| 6,090,556 A | 7/2000 | Kato |
| 6,099,823 A | 8/2000 | Falb |
| 6,124,433 A | 9/2000 | Falb et al. |
| 6,127,155 A | 10/2000 | Gelfand et al. |
| 6,132,997 A | 10/2000 | Shannon |
| 6,146,828 A | 11/2000 | Lapidus et al. |
| 6,150,121 A | 11/2000 | Hamawy et al. |
| 6,156,887 A | 12/2000 | Levinson |
| 6,162,604 A | 12/2000 | Jacob |
| 6,168,933 B1 | 1/2001 | Kaser et al. |
| 6,171,785 B1 | 1/2001 | Higuchi |
| 6,177,254 B1 | 1/2001 | Rattner et al. |
| 6,187,534 B1 | 2/2001 | Strom et al. |
| 6,190,857 B1 | 2/2001 | Ralph et al. |
| 6,190,872 B1 | 2/2001 | Slotman |
| 6,194,158 B1 | 2/2001 | Kroes et al. |
| 6,197,563 B1 | 3/2001 | Erlich et al. |
| 6,203,987 B1 | 3/2001 | Friend et al. |
| 6,204,371 B1 | 3/2001 | Levinson |
| 6,214,979 B1 | 4/2001 | Gelfand et al. |
| 6,218,122 B1 | 4/2001 | Friend et al. |
| 6,222,093 B1 | 4/2001 | Marton et al. |
| 6,225,084 B1 | 5/2001 | Falb et al. |
| 6,225,093 B1 | 5/2001 | Grant et al. |
| 6,228,628 B1 | 5/2001 | Gelfand et al. |
| 6,242,185 B1 | 6/2001 | Kaser et al. |
| 6,245,334 B1 | 6/2001 | Seilhammer et al. |
| 6,245,526 B1 | 6/2001 | Yue et al. |
| 6,245,527 B1 | 6/2001 | Busfield et al. |
| 6,248,527 B1 | 6/2001 | Chen et al. |
| 6,248,528 B1 | 6/2001 | Chen et al. |
| 6,251,597 B1 | 6/2001 | Shyjan |
| 6,262,244 B1 | 7/2001 | Houchins et al. |
| 6,274,312 B1 | 8/2001 | Gish et al. |
| 6,280,941 B1 | 8/2001 | Tsao et al. |
| 6,303,321 B1 | 10/2001 | Tracey et al. |
| 6,306,602 B1 | 10/2001 | Sillekens et al. |
| 6,365,352 B1 | 4/2002 | Yerramilli et al. |
| 6,403,304 B1 | 6/2002 | Stashenko et al. |
| 6,410,319 B1 | 6/2002 | Raubitschek et al. |
| 6,811,973 B1 | 11/2004 | Reich |
| 6,905,827 B2 | 6/2005 | Wohlgemuth et al. |
| 6,964,850 B2 | 11/2005 | Bevilacqua et al. |
| 7,026,121 B1 | 4/2006 | Wohlgemuth et al. |
| 7,235,358 B2 | 6/2007 | Wohlgemuth et al. |
| 2001/0021700 A1 | 9/2001 | Moore et al. |
| 2002/0042386 A1 | 4/2002 | Rosen et al. |
| 2002/0128436 A1 | 9/2002 | Strom et al. |
| 2002/0132235 A1 | 9/2002 | Avihingsanon et al. |
| 2003/0139466 A1 | 7/2003 | Peritt et al. |
| 2004/0033498 A1 | 2/2004 | Behrens et al. |
| 2004/0072181 A1 | 4/2004 | Whitehead et al. |
| 2006/0051803 A1 | 3/2006 | Wohlgemuth et al. |
| 2006/0088836 A1 | 4/2006 | Wohlgemuth et al. |
| 2006/0216707 A1 | 9/2006 | Stuhlmuller et al. |
| 2006/0263813 A1 | 11/2006 | Rosenberg et al. |
| 2007/0037144 A1 | 2/2007 | Wohlgemuth et al. |
| 2007/0037166 A1 | 2/2007 | Wohlgemuth et al. |
| 2007/0037167 A1 | 2/2007 | Wohlgemuth et al. |
| 2007/0248978 A1 | 10/2007 | Lal et al. |
| 2008/0038746 A1 | 2/2008 | Rosenberg et al. |

FOREIGN PATENT DOCUMENTS

| | | |
|---|---|---|
| WO | WO 91/18626 | 12/1991 |
| WO | WO-94/23023 A1 | 10/1994 |
| WO | WO 95/17506 | 6/1995 |
| WO | WO 96/39536 | 12/1996 |
| WO | WO-97/16568 A1 | 5/1997 |
| WO | WO 97/30065 | 8/1997 |
| WO | WO 98/24935 | 6/1998 |
| WO | WO-99/04251 A1 | 1/1999 |
| WO | WO 99/10536 | 3/1999 |
| WO | WO 99/11782 | 3/1999 |

| | | |
|---|---|---|
| WO | WO-99/11822 A1 | 3/1999 |
| WO | WO 99/15700 | 4/1999 |
| WO | WO 99/52541 | 10/1999 |
| WO | WO 99/57130 | 11/1999 |
| WO | WO 00/04191 | 1/2000 |
| WO | WO-00/04191 | 1/2000 |
| WO | WO-00/12753 | 3/2000 |
| WO | WO 00/12753 | 3/2000 |
| WO | WO 00/23573 | 4/2000 |
| WO | WO-00/23573 A3 | 4/2000 |
| WO | WO-00/46372 | 8/2000 |
| WO | WO 00/46372 | 8/2000 |
| WO | WO 00/52209 | 9/2000 |
| WO | WO-00/52209 | 9/2000 |
| WO | WO 00/55375 | 9/2000 |
| WO | WO-00/55375 | 9/2000 |
| WO | WO-00/58473 A2 | 10/2000 |
| WO | WO-00/63372 | 10/2000 |
| WO | WO 00/63372 | 10/2000 |
| WO | WO 00/73498 | 12/2000 |
| WO | WO-00/73498 A1 | 12/2000 |
| WO | WO 00/78808 | 12/2000 |
| WO | WO-00/78808 A1 | 12/2000 |
| WO | WO 01/20004 | 3/2001 |
| WO | WO-01/20004 | 3/2001 |
| WO | WO-01/23426 | 4/2001 |
| WO | WO 01/23426 | 4/2001 |
| WO | WO 01/23564 | 4/2001 |
| WO | WO-01/23564 | 4/2001 |
| WO | WO 01/25473 | 4/2001 |
| WO | WO 01/29269 | 4/2001 |
| WO | WO 01/32927 | 5/2001 |
| WO | WO 01/40302 A2 | 6/2001 |
| WO | WO 01/47944 A2 | 7/2001 |
| WO | WO 01/54733 A1 | 8/2001 |
| WO | WO 01/55164 A1 | 8/2001 |
| WO | WO 01/55201 A1 | 8/2001 |
| WO | WO 01/55203 A1 | 8/2001 |
| WO | WO 01/55205 A1 | 8/2001 |
| WO | WO 01/55328 A2 | 8/2001 |
| WO | WO 01/55368 A1 | 8/2001 |
| WO | WO-01/57182 A2 | 8/2001 |
| WO | WO 01/60860 A3 | 8/2001 |
| WO | WO 01/71005 A2 | 9/2001 |
| WO | WO 01/81916 A2 | 11/2001 |
| WO | WO 01/86003 A2 | 11/2001 |
| WO | WO 02/00677 A1 | 1/2002 |
| WO | WO 02/00928 A2 | 1/2002 |
| WO | WO 02/28999 A2 | 4/2002 |
| WO | WO-02/057414 A2 | 7/2002 |
| WO | WO-03/090694 A2 | 11/2003 |
| WO | WO-2004/042346 A2 | 5/2004 |
| WO | WO-2004/108899 A2 | 12/2004 |

OTHER PUBLICATIONS

EMBL-EBI Accession No. AI775145, last updated Jun. 21, 2002, located at <http://www.ebi.ac.uk/cgi-bin/dbfetch?db=embl&id=AI755145&style=raw> visited on Oct. 31, 2007. (2 pages).
EMBL-EBI Accession No. AK000354, last updated Sep. 12, 2006, located at <http://www.ebi.ac.uk/cgi-bin/dbfetch?db=embl&id=AK000354&style=raw> visited on Oct. 31, 2007. (3 pages).
EMBL-EBI Accession No. AV742425, last updated Oct. 10, 2000, located at <http://www.ebi.ac.uk/cgi-bin/dbfetch?db=embl&id=AV742425&style=raw> visited on Oct. 31, 2007. (2 pages).
EMBL-EBI Accession No. AW969353, last updated Jun. 8, 2000, located at <http://www.ebi.ac.uk/cgi-bin/dbfetch?db=embl&id=AW969353&style=raw> visited on Oct. 31, 2007. (1 page).
EMBL-EBI Accession No. G06338, last updated Mar. 4, 2000, located at <http://www.ebi.ac.uk/cgi-bin/dbfetch?db=embl&id=G06338&style=raw> visited on Oct. 31, 2007. (2 pages).
EMBL-EBI Accession No. L26474, last updated Jan. 9, 2007, located at <http://www.ebi.ac.uk/cgi-bin/dbfetch?db=embl&id=L26474&style=raw> visited on Oct. 31, 2007. (6 pages).
EMBL-EBI Accession No. M23068, last updated Nov. 14, 2006, located at <http://www.ebi.ac.uk/cgi-bin/dbfetch?db=embl&id=M23068&style=raw> visited on Oct. 31, 2007. (2 pages).
EMBL-EBI Accession No. V00497, last updated Nov. 20, 2004, located at <http://www.ebi.ac.uk/cgi-bin/dbfetch?db=embl&id=V00497&style=raw> visited on Oct. 31, 2007. (5 pages).
Fullerton, S. M. et al. (Mar. 1994). "Molecular and Population Genetic Analysis of Allelic Sequence Diversity at the Human Beta-Globin Locus," *Proceedings of the National Academy of Sciences* 91:1805-1809.
Griffiths, G. M. et al. (1991). "Granzyme A and Perforin as Markers for Rejection in Cardiac Transplantation," *European Journal of Immunology* 21:687-692.
Jardi, M. et al. (1994). "Urokinase Receptor (UPAR) Expression During Hematopoietic Maturation," *Journal of Drug Targeting* 8(Suppl 1):51.
Joulin, V. et al. (Oct. 25, 1988). "Isolation and Characterization of the Human 2,3-Bisphosphoglycerate Mutase Gene," *The Journal of Biological Chemistry* 263(30):15785-15790.
Supplementary European Search Report mailed Oct. 18, 2007, for EP Application No. 03799755.8 filed Apr. 24, 2003, 17 pages.
Tamayo, P. et al. (Mar. 1999). "Interpreting Patterns of Gene Expression with Self-Organizing Maps: Methods and Application to Hematopoietic Differentiation," *Proceedings of the National Academy of Sciences* 96:2907-2912.
Willems, R. et al. (May 29, 1998). "Decrease in Nucleoside Diphosphate Kinase (NDPK/nm23) Expression During Hematopoietic Maturation," *The Journal of Biological Chemistry* 273(22):13663-13668.
Dietz, A. B. et al. (2000). "Maturation of Human Monocyte-Derived Dendritic Cells Studied by Microarray Hybridization," *Biochemical and Biophysical Research Communications* 275:731-738.
Finger, L. R. et al. (1997). "The Human PD-1 Gene: Complete cDNA, Genomic Organization, and Developmentally Regulated Expression in B cell Progenitors," *Gene* 197:177-187.
Gorcynski, R. M. (1996). "Correlation of Peripheral Blood Lymphocyte and Intragraft Cytokine mRNA Expression with Rejection in Orthotopic Liver Transplantation," *Surgery* 120(3):496-502.
Krause, S. W. (1998). "Carboxypeptidase M as a Marker of Macrophage Maturation," *Immunological Reviews* 161:119-127.
Le Naour, F. et al. (May 25, 2001). "Profiling Changes in Gene Expression during Differentiation and Maturation of Monocyte-Derived Dendritic Cells Using Both Oligonucleotide Microarrays and Proteomics," *The Journal of Biological Chemistry* 276(21):17920-17931.
Australian Search Report mailed Oct. 7, 2005, for Singapore patent application No. SG 200406287-3, filed Apr. 24, 2003, 2 pages.
Bakke, Antony C. et al., (2001) "Neutrophil CD64 expression Distinguishing acute inflammatory autoimmune disease from systemic infections," Clinical and Applied Immunology Reviews, 1: 267-275.
Deuel, Thomas F. et al., (Jun. 1977) "Amino acid sequence of human platelet factor 4," Proc. Natl. Acad. Sci. USA, 74(6): 2256-2258.
Deuel, Thomas F. et al., (Jul. 1981) "Platelet factor 4 is chemotactic for neutrophils and monocytes," Proc. Natl. Acad. Sci. USA, 78(7): 4584-4587.
Dudek, Arkadiusz Z. et al., (Jun. 15, 2003) "Platelet factor 4 promotes adhesion of hematopoietic progenitor cells and binds IL-8: novel mechanisms for modulation of hematopoiesis," Blood, 101(12): 4687-4694.
Golden-Mason, Lucy et al., (Jun. 2000) "Differential Expression of Lymphoid and Myeloid Markers on Differentiating Hematopoietic Stem Cells in Normal and Tumor-Bearing Adult Human Liver," Hepatology, 31(6): 1251-1256.
Morris, Dale L. et al., (Feb. 1997) "Immunophenotyping Analysis of Peripheral Blood, Splenic, and Thymic Lymphocytes in Male and Female Rats," Journal of Pharmacological and Toxicological Methods, 37: 37-47.
Shin, Young Kee et al., (Apr. 2001) "Expression of Leukemia-Associated antigen, JL1, in Bone Marrow and Thymus," American Journal of Pathology, 158(4): 1473-1480.

Stellrecht, Christine M. et al., (1991) "Expression pattern of a hematopoietic proteoglycan core protein gene during human hematopoiesis," Differentiation, 48: 127-135.

Weast, Ed. (1968). Handbook of Chemistry and Physics, 49th Ed., The Chemical Rubber Co.: Cleveland Ohio, p. A-245.

International Search Report mailed on Sep. 30, 2004, for PCT patent application No. PCT/US03/13015, 4 pages.

Abdallah, A. N. et al. (1997) "Evaluation of plasma levels of tumour necrosis factor alpha and interleukin-6 as rejection markers in a cohort of 142 heart-grafted patients followed by endomyocardial biopsy" European Heart Journal 18: 1024-1029.

Ajjan, R. A. et al. (1996) "Intrathyroidal cytokine gene expression in Hashimoto's thyroiditis" Clin. Exp. Immunol. 105: 523-528.

Akalin, Enver et al. (2001) "Gene Expression Analysis in Human Renal Allograft Biopsy Samples Using High-Density Oligoarray Technology" Transplantation 72 (5): 948-953.

Alizadeh, A. A. et al. (2000) "Distinct types of diffuse large B-cell lymphoma identified by gene expression profiling" Nature 403: 503-11.

Alizadeh, A. et al. (1998) "Probing Lymphocyte Biology by Genomic-Scale Gene Expression Analysis" J. Clin. Immun. 18: 373-379.

Alizadeh, A. et al. (1999)"The Lymphochip: A Specialized cDNA Microarray for the Genomic-scale Analysis of Gene Expression in Normal and Malignant Lymphocytes" Cold Spring Harbor Symposia on Quantitative Biology 54, (New York: Cold Spring Harbor Laboratory Press): 71-78.

Alpert, Susan et al. (1995) "The Relationship of Granzyme A and Perforin Expression to Cardiac Allograft Rejection and Dysfunction" Transplantation 60 (12): 1478-1485.

Arnett, F. C. et al. (1988)"The American Rheumatism Association 1987 revised criteria for the classification of rheumatoid arthritis" Arthritis Rheum 31: 315-24.

Autieri MV, Kelemen S, Thomas BA, Feller ED, Goldman BI, Eisen HJ. (2002) "Allograft inflammatory factor-1 expression correlates with cardiac rejection and development of cardiac allograft vasculopathy" Circulation 106(17):2218-23.

Baechler, Emily C. et al. (2003) "Interferon-inducible gene expression signature in peripheral blood cells of patients with severe lupus" Proc. Natl. Acad. Sci. USA 100 (5): 2610-2615.

Bave, U. (2000) "The combination of apoptotic U937 cells and lupus IgG is a potent IFN-alpha inducer" J. Immunol. 165: 3519-3526.

Bave, U. (2001) "Activation of natural interferon-alpha producing cells by apoptotic U937 cells combined with lupus IgG and its regulation by cytokines" J. Autoimmun. 17: 71-80.

Bittner, M. et al. (2000) "Molecular classification of cutaneous malignant melanoma by gene expression profiling" Nature 406: 536-540.

Bombardier, C. et al. and the Committee on Prognosis Studies in SLE (1992) "Derivation of the SLEDAI, A Disease Activity Index for Lupus Patients" Arthritis Rheum. 35: 630-640.

Chang, D. M. et al. (1996) "Cytokines and Cell Surface Markers in Prediction of Cardiac Allograft Rejection" Immunological Investigations 25 (1&2): 13-21.

Chebath et al. (1987) "Four Different Forms of Interferon-induced 2', 5'-Oligo(A) Synthetase Identified by Immunoblotting in Human Cells," J. Biol. Chem. 262: 3852-2857.

Creemers P, Brink J, Wainwright H, Moore K, Shephard E, Kahn D. (2002) "Evaluation of peripheral blood CD4 and CD8 lymphocyte subsets, CD69 expression and histologic rejection grade as diagnostic markers for the presence of cardiac allograft rejection" Transpl Immunol.10(4):285-92.

Damas, J. K. et al. (2001)"Enhanced gene expression of chemokines and their corresponding receptors in mononuclear blood cells in chronic heart failure—modulatory effect of intravenous immunoglobin" J. Am. Coll. Cardiol. 38: 187-93.

Database Gen Embl, US National Library of Medicine (Bathesda, MD, USA), No. AL 591031, 'Human DNA sequence from clone RP11-151d14 on chromosome 9q13-21.2, complete sequence', Sycamore, N., Oct. 10, 2001.

Davas, E.M. et al. (1999) "Serum IL-6, TNFalpha, p55 srTNFalpha, p75srTNFalpha, srIL-2alpha levels and disease activity in systemic lupus erythematosus" Clin Rheumatol 18 (1):17-22.

Deng, Mario C. et al. (1995) "The Relation of Interleukin-6, Tumor Necrosis factor-α, IL-2, and IL-2 Receptor Levels to Cellular Rejection, Allograft Dysfunction, and Clinical Events Early After Cardiac Transplantation" Transplantation 60 (10): 1118-1124.

Doi, S. et al. (1994) "Polymerase chain reaction quantification of cytokine messenger RNA expression in peripheral blood monocular cells of patients with acute exacerbations of asthma: effect of glucocorticoid therapy" Clinical and Experimental Allergy 24: 854-867.

Dugré, Francine J. (2000) "Cytokine and Cytotoxic Molecule Gene Expression Determined in Peripheral Blood Mononuclear Cells in the Diagnosis of Acute Renal Rejection" Transplantation 70 (7): 1074-1080.

Edman, C. F. et al. (1997)"Electric field directed nucleic acid hybridization on microchips" Nucleic Acids Res. 25: 4907-14.

Eisen, Michael B. et al. (1998) "Cluster analysis and display of genome-wide expression patterns" Proc. Natl. Acad. Sci. USA 95: 14863-14868.

Felson, D. T. et al. (1995) "American College of Rheumatology. Preliminary definition of improvement in rheumatoid arthritis" Arthritis Rheum. 38: 727-35.

Fu, Guoliang et al. (2002) "Representational difference analysis in a lupus-prone mouse strain results in the identification of an unstable region of the genome on chromosome 11" Nucleic Acids Research 30 (6): 1394-1400.

Gabay C. et al. (1997) "Circulating levels of tumor necrosis factor soluble receptors in systemic lupus erythematosus are significantly higher than in other rheumatic diseases and correlate with disease activity" J Rheumatol 24(2): 303-8.

Ghosh et al. (2001) "A Specific Isozyme of 2'-5' Oligoadenylate Synthetase Is a Dual Function Proapoptotic Protein of the Bcl-2 Family," J. Biol. Chem. 276(27): 25477-25455.

Golub, T. R. et al. (1999) "Molecular Classification of Cancer: Class Discovery and Class Prediction by Gene Expression Monitoring" Science 286: 531-7.

Grant, Simon C. D. et al. (1996) "Serum Cytokines in Human Heart Transplant Recipients" Transplantation 62 (4): 480-491.

Gullestad, L. et al. (1999) "Effect of High- Versus Low-Dose Angiotensin Converting Enzyme Inhibition on Cytokine Levels in Chronic Heart Failure" J. Am. Coll. Cardiol. 34: 2061-7.

Hastie, T. et al. (2000) "'Gene shaving' as a method for identifying distinct sets of genes with similar expression patterns" Genome Biol. 1: RESEARCH0003.

Hastie, Trevor et al. (2001) "Supervised harvesting of expression trees" Genome Biology 2 (1): http://genomebiology.com/2001/2/1/research/0003 (Apr. 25, 2002): 12 pages.

Heller, R. A. et al. (1997) "Discovery and analysis of inflammatory disease-related genes using cDNA microarrays" Proc. Natl. Acad. Sci. U.S.A. 94: 2150-2155.

Hendricks, DA et al. (1995) "Quantitation of HBV DNA in human serum using a branched DNA (bDNA) signal amplification assay" Am J Clin Pathol 104 (5): 537-46.

Higuchi et al. (1998), Chemical Abstracts 129: 342625.

Hooks, J.J. (1979) "Immune interferon in the circulation of patients with autoimmune disease" N. Engl. J. Med. 301: 5-8.

Hooks, J.J. et al. (1982) "Multiple interferons in the circulation of patients with systemic lupus erythematosus and vasculitis" Arthritis Rheum. 25: 396-400.

Hsieh, Hsian-Guey et al. (2001) "IL-17 expression as a possible predictive parameter for subclinical renal allograft rejection" Tranpl Int 14: 287-298.

Iida, K. et al. (1982) "Complement receptor (CR1) deficiency in erythrocytes from patients with systemic lupus erythematosus" J. Exp. Med. 155: 1427-1438.

Jagota, Arun (2000) Data Analysis and Classification for Bioinformatics. Bioinformatics By The Bay Press: 92-93.

Kasprzycka, Monika et al. (2002) "Expression of FasL gene in T cells of renal allograft recipients" Immunol. Lett. 80 (1): 9-13.

Katz, Mitchell H (1999) Multivariable Analysis: A Practical Guide for Clinicians. Cambridge University Press: 36-42.

Khan, J. et al. (2001) "Classification and diagnostic prediction of cancers using gene expression profiling and artificial neural networks" Nat. Med. 7: 673-9.

Kimball, P. et al. (1995) "Cytokine Panel Predicts Early Rejection of Therapeutic Response After Cardiac Transplantation" *Transplantation Proceedings* 27 (1): 1286-1287.

Kobashigawa, J. et al. (1998) "A Randomized Active-Controlled Trial of Mycophenolate Mofetil in Heart Transplant Recipients" *Transplantation* 66 (4): 507-515.

Kumar et al. (2000) "Expansion and Molecular Evolution of the Interferon-Induced 2'-5' Oligoadenylate Synthetase Gene Family," Mol. Biol. Evol. 17: 738-750.

Kumar et al. (1994) "Cell Cycle-dependent Modulation of α-Interferon-inducible Gene Expression and Activation of Signaling Components in Daudi Cells," J. Biol. Chem. 269, No. 41: 25437-25441.

Legros-Maida, Sabine et al. (1994) "Granzyme B and perforin can be used as predictive markers of acute rejection in heart transplantation" *Eur. J. Immunol.* 24: 229-233.

Li, B. et al. (2001) "Noninvasive diagnosis of renal-allograft rejection by measurement of messenger RNA for perforin and granzyme B in urine" N. Engl. J. Med. 344: 947-954.

Liossis, S.N. (2001) "B-cell kinase lyn deficiency in patients with systemic lupus erythematosus" *J Investig Med*. 49 (2): 157-65.

Loftus. B.J. et al. Genome Duplications and Other Features in 12 Mb of DNA sequence from Human Chromosome 16p and 16q Genomics. vol. 60, pp. 295-308 Jul. 1999.

Magnusson, M. et al. (2001) "Importance of CpG dinucleotides in activation of natural IFN-alpha-producing cells by a lupus-related oligodeoxynucleotide" *Scand. J. Immunol.* 54: 543-550.

Marcelin, Anne-Genevieve et al. (2001) "Effects of Cyclosporine and Hydrocortisone on Kaposi's Sarcoma-Associated Herpesvirus Genome Replication and Cell Apoptosis Induction" *Transplantation* 72 (10): 1700-1708.

Melter, Michael et al. (2001) "Expression of the Chemokine Receptor CXCR3 and Its Ligand IP-10 During Human Cardiac Allograft Rejection" *Circulation* 104: 2558-2564.

Mohler, E. R. 3rd et al. "Role of Cytokines in the Mechanism of Action of Amlodipine: The PRAISE Heart Failure Trial" *J. Am. Coll. Cardiol.* 30 (1997): 35-41.

Morita, Ken et al. (2001) "Early Chemokine Cascades in Murine Cardiac Grafts Regulate T Cell Recruitment and Progression of Acute Allograft Rejection" *J. Immunol.* 167: 2979-2984.

Neto, E. D. et al. (2000). "Shotgun Sequencing of the Human Transcriptome with ORF Expressed Sequences Tags." Proceedings of the National Academy of Sciences, 97(7): 3491-3496.

Nickel, Peter et al. (2001) "Cytotoxic Effector Molecule Gene Expression in Acute Renal Allograft Rejection" *Transplantation* 72 (6): 1158-1161.

Oh, Se-Il et al. (2001) "Correlation of Fas and Fas Ligand Expression with Rejection Status of Transplanted Heart in Human" *Transplantation* 71(7): 906-909.

Perou, C. M. et al. (2000) "Molecular portraits of human breast tumours" *Nature* 406: 747-52.

Preble, O.T. (1982) "Systemic lupus erythematosus: presence in human serum of an unusual acid-labile leukocyte interferon" *Science* 216: 429-431.

Pruitt, K. D. et al. (2000) "Introducing RefSeq and LocusLink: curated human genome resources at the NCBI" *Trends Genet.* 16: 44-47.

Raychaudhuri, S. et al. (2001) "Basic microarray analysis: grouping and feature reduction" *Trends Biotechnol.* 19: 189-193.

Rebouillat et al. (1999) "The 100-kDa 2',5'-Oligoadenylate Synthase Catalyzing Preferentially the Synthesis of Dimeric pppA2'p5'A Molecules Is Composed of Three Homologous Domains" J. Biol. Chem. 274 (3): 1557-1565.

Rus, V et al. (2002) "Expression of cytokine- and chemokine-related genes in peripheral blood mononuclear cells from lupus patients by cDNA array" *Clin Immunol* 102 (3): 283-90.

Saiura, Akio et al. (2001) "A Comparison of Gene Expression in Murine Cardiac Allografts and Isografts by Means DNA Microarray Analysis" *Transplantation* 72 (2): 320-329.

Salmon, J. E. et al. (1996) "Fc-gamma-RIIA alleles are heritable risk factors for lupus nephritis in African Americans" *J. Clin. Invest.* 97: 1348-1354.

Schena, Mark et al. (1995) "Quantitative Monitoring of Gene Expression Patterns with a Complementary DNA Microarray" *Science* 270: 467-470.

Schena, Mark et al. (1996) "Parallel human genome analysis: Microarray-based expression monitoring of 1000 genes" *Proc. Natl. Acad. Sci. USA* 93: 10614-10619.

Schowengerdt et al (2000) "Increased expression of the lymphocyte early activation marker CD69 in peripheral blood correlates with histologic evidence of cardiac allograft rejection." *Transplantation* 69(10):2102-7.

Sharma, Vijay K. et al. (1996) "Molecular Executors of Cell Death-Differential Intrarenal Expression of Fas Ligand, Fas, Granzyme B, and Perforin During Acute and/or Chronic Rejection of Human Renal Allografts" *Transplantation* 62 (12): 1860-1866.

Shi, S.N. (1987) "Serum interferon in systemic lupus erythematosus" *Br. J. Dermatol.* 117:155-159.

Shirali, G. S. et al. (2001) "Association of viral genome with graft loss in children after cardiac transplantation" *N. Engl. J. Med.* 344: 1498-503.

Shoker, Ahmed et al. (2000) "Heightened CD40 Ligand Gene Expression in Peripheral CD4+ Cells from Patients with Kidney Allograft Rejection" *Transplantation* 70 (3): 497-505.

Shulzhenko, Natalia et al. (2001) "Intragraft Activation of Genes Encoding Cytotoxic T Lymphocyte Effector Molecules Precedes the Histological Evidence of Rejection in Human Cardiac Transplantation" *Transplantation* 72 (10): 1705-1708.

Shulzhenko, Natalia et al. (2001) "Monitoring of Intragraft and Peripheral Blood TIRC7 Expression as a Diagnostic Tool for Acute Cardiac Rejection in Humans" *Human Immunology* 62: 342-347.

Staudt, L. M. and P. O. Brown. (2000) "Genomic Views of the Immune System" *Annu. Rev. Immunol.* 18: 829-859.

Strehlau, Jurgen et al. (1997) "Quantitative detection of immune activation transcripts as a diagnostic tool in kidney transplantation" *Proc. Natl. Acad. Sci. USA* 94: 695-700.

Tan, E. M. et al. (1982) "The 1982 revised criteria for the classification of systemic lupus erythematosus" *Arthritis Rheum.* 25: 1271-7.

Tan, LamChin et al. (2001) "Sequential Monitoring of Peripheral T-Lymphocyte Cytokine Gene Expression in the Early Post Renal Allograft Period" *Transplantation* 71: 751-759.

Toogood, Giles J. et al. (1996) "The Immune Response Following Small Bowel Transplantation" *Transplantation* 62 (6): 851-855.

Törönen, Petri et al. (1999) "Analysis of gene expression data using self-organizing maps" *FEBS Letters* 451: 142-146.

Torre-Amione, G. et al. (1996) "Proinflammatory cytokine levels in patients with depressed left ventricular ejection fraction: a report from the Studies of Left Ventricular Dysfunction (SOLVD)" *J. Am. Coll. Cardiol.* 27: 1201-6.

Tsutamoto, T. et al. (2000) "Angiotensin II type 1 receptor antagonist decreases plasma levels of tumor necrosis factor alpha, interleukin-6 and soluble adhesion molecules in patients with chronic heart failure" *J. Am. Coll. Cardio.* 35: 714-21.

Tusher, Virginia Goss et al. (2001) "Significance analysis of microarrays applied to the ionizing radiation response" *PNAS* 98 (9) 5116-5121.

Umek, R. M. et al. (2001) "Electronic detection of nucleic acids: a versatile platform for molecular diagnostics" *J. Mol. Diagn.* 3: 74-84.

Vallin, H. (1999) "Anti-double-stranded DNA antibodies and immunostimulatory plasmid DNA in combination mimic the endogenous IFN-alpha inducer in systemic lupus erythematosus" *J. Immunol.* 163: 6306-6313.

Vandevyver, Caroline et al. (1998) "Cytokine mRNA Profile of Myelin Basic Protein Reactive T-Cell Clones in Patients with Multiple Sclerosis" *Autoimmunity* 28: 77-89.

Vasconcellos, Lauro M. et al. (1998) "Cytotoxic Lymphocyte Gene Expression in Peripheral Blood Leukocytes Correlates with Rejecting Renal Allografts" *Transplantation* 66 (5): 562-566.

Vignali D. (2000) "Multiplexed particle-based flow cytometric assays" *J. Immun. Meth.* 243: 243-55.

Vincenti, F. et al. (2001) "Multicenter Trial Exploring Calcineurin Inhibitors Avoidance in Renal Transplantation" *Transplantation* 71 (9): 1282-1287.

Watanabe-Fukunaga, R. et al. (1992) "Lymphoproliferation disorder in mice explained by defects in Fas antigen that mediates apoptosis" *Nature* 356: 314-317.

Welsh, J. B. et al. (2001) "Analysis of gene expression profiles in normal and neoplastic ovarian tissue samples identifies candidate molecular markers of epithelial ovarian cancer" *Proc. Natl. Acad. Sci. U.S.A.* 98: 1176-81.

Westin L. et al. (2000) "Anchored multiplex amplification on a microelectronic chip array" *Nat. Biotechnol.* 18: 199-204.

Whitehead, John. 2002. An Introduction to Logistic Regression. (web page: http://personal.ecu.edu/whiteheadj/data/logit/). Apr. 25, 2002: 63 pages.

Wu, J. et al. (1996) "Fas ligand mutation in a patient with systemic lupus erythematosus and lymphoproliferative disease" *J. Clin. Invest.* 98: 1107-1113.

Xia, Dongyuan et al. (2001) "Real-Time Polymerase Chain Reaction Analysis Reveals an Evolution of Cytokine mRNA Production in Allograft Acceptor Mice" *Transplantation* 72 (5): 907-914.

Yu et al. (2000) "Protein Synthesis-Dependent and Independent Induction of p69 2'-5'-Oligoadenylate Synthetase by Interferon-α," *Cytokine*, 11(10): 744-750.

Zhang, L. et al. (1997) "A New Interferon Regulatory Factor Associated with Epstein=Barr Virus Latency." Molecular and Cellular Biology, 17(10): 5748-5757.

Zucker, S. et al. (1999) "Increased serum stromelysin-1 levels in systemic lupus erythematosus: lack of correlation with disease activity." *J Rheumatol.* 26 (1): 78-80.

Alizadeh, A. A. et al. (2000). "Genomic-Scale Gene Expression Profiling of Normal and Malignant Immune Cells," *Current Opinion in Immunology* 12:219-225.

Glynne, R. et al. (2000). "B-Lymphocyte Quiescence, Tolerance and Activation as Viewed by Global Gene Expression Profiling on Microarrays," *Immunological Reviews* 176:216-246.

Glynne, R. J. et al. (2000). "Genomic-Scale Gene Expression Analysis of Lymphocyte Growth, Tolerance and Malignancy," *Current Opinion in Immunology* 12:210-214.

Marrack, P. et al. (2000). "Genomic-Scale Analysis of Gene Expression in Resting and Activated T Cells," *Current Opinion in Immunology* 12:206-209.

Supplemental Partial European Search Report mailed Jul. 9, 2007, for EP Application No. 01997055.7 filed Oct. 22, 2001, 6 pages.

Ahern, H. (Jul. 24, 1995). "Biochemical, Reagent Kits Offer Scientists Good Return on Investment," *The Scientist* 9(15):20-24.

Amaro, A. et al. (1995). "Plasma Leukocyte Elastase Concentration in Angiographically Diagnosed Coronary Artery Disease," *European Heart Journal* 16:615-622.

Aukrust, P. et al. (1999). "Enhanced Levels of Soluble and Membrane-Bound CD40 Ligand in Patients with Unstable Angina. Possible Reflection of T Lymphocyte and Platelet Involvement in the Pathogenesis of Acute Coronary Syndromes," *Circulation* 100:614-620.

Bass, C. A. (Oct. 1993). "Clinical Evaluation of a New Polymerase Chain Reaction Assay for Detection of *Chlamydia trachomatis* in Endocervical Specimens," *Journal of Clinical Microbiology* 31(10):2648-2653.

Belch, J. J. F. et al. (Apr. 1997). "The White Blood Cell Adhesion Molecule E-Selectin Predicts Restenosis in Patients With Intermittent Claudication Undergoing Percutaneous Transluminal Angioplasty," *Circulation* 95(8):2027-2031.

Boelaert, M. et al. (May 1999). "Latent Class Analysis Permits Unbiased Estimates of the Validity of DAT for the Diagnosis of Visceral Leishmaniasis," *Tropical Medicine & International Health* 4(5):395-401.

Bustin, S. A. (2000). "Absolute Quantification of mRNA Using Real-Time Reverse Transcription Polymerase Chain Reaction Assays," *Journal of Molecular Endocrinology* 25:169-193.

Chen, J. et al. (Aug. 1996). "Identification of Differentially Expressed Genes in Rat Aortic Allograft Vasculopathy," *American Journal of Pathology* 149(2):597-611.

Cheung, V. et al. (Mar. 2003). "Natural Variation in Human Gene Expression Assessed in Lymphoblastoid Cells," *Nature Genetics* 33:422-425.

Fandrey, J. et al. (Feb. 1, 1993). "In Vivo and In Vitro Regulation of Erythropoietin mRNA: Measurement by Competitive Polymerase Chain Reaction," *Blood* 81(3):617-623.

GenBank Accession No. Y10376, last updated May 14, 1997, located at <http://www.ncbi.nlm.nih.gov/entrez/viewer.fcgi?db=nuccore&id=2052057> visited on Apr. 8, 2008, 3 pages.

Harlow, E. et al. (1988). *Antibodies: A Laboratory Manual.* Cold Spring Harbor Laboratory: New York, NY, 9 pages (Table of Contents).

Hayward, A. L. et al. (1998). "Modeling and Analysis of Competitive RT-PCR," *Nucleic Acids Research* 26(11):2511-2518.

Hayward-Lester, A. et al. (1995). "Accurate and Absolute Quantitative Measurement of Gene Expression by Single Tube RT-PCR and HPLC," *Genome Research* 5:494-499.

International Search Report and Written Opinion mailed Mar. 27, 2008, for PCT Application No. PCT/US05/31806 filed Sep. 8, 2005, 14 pages.

International Search Report mailed Jul. 18, 2002, for PCT Application No. PCT/US01/47856 filed Oct. 22, 2001, 3 pages.

International Search Report mailed Mar. 1, 2001, for PCT Application No. PCT/US00/17846 filed Jun. 28, 2000, 2 pages.

Jude, B. et al. (Oct. 1994). "Evidence for Time-Dependent Activation of Monocytes in the Systemic Circulation in Unstable Angina but Not in Acute Myocardial Infarction or in Stable Angina," *Circulation* 90(4):1662-1668.

Kang, J. J. et al. (2000). "Transcript Quantitation in Total Yeast Cellular RNA Using Kinetic PCR," *Nucleic Acids Research* 28(2):e2, 8 pages.

Kassirer, M. et al. (Sep. 1999). "Increased Expression of the CD11b/CD18 Antigen on the Surface of Peripheral White Blood Cells in Patients with Ischemic Heart Disease: Further Evidence for Smoldering Inflammation in Patients with Atherosclerosis," *American Heart Journal* 138(3):555-559.

Kendler, K. S. et al. (Jun. 1998). "The Structure of Psychosis Latent Class Analysis of Probands from the Roscommon Family Study," *Archives of General Psychiatry* 55:492-499.

Lee, M.-T. et al. (Aug. 29, 2000). "Importance of Replication in Microarray Gene Expression Studies: Statistical Methods and Evidence from Repetitive cDNA Hybridizations," *Proceedings of the National Academy of Sciences* 97(18):9834-9839.

Newton, M. A. et al. (2001) "On Differential Variability of Expression Ratios: Improving Statistical Inference about Gene Expression Changes from Microarray Data," *Journal of Computational Biology* 8(1):37-52.

Pickles, A. et al. (1995). "Latent-Class Analysis of Recurrence Risks for Complex Phenotypes with Selection and Measurement Error: A Twin and Family History Study of Autism," *American Journal of Human Genetics* 57:717-726.

Quattrone, A. et al. (1995). "Quantitation of bcl-2 Oncogene in Cultured Lymphoma/Leukemia Cell Lines and in Primary Leukemia B-Cells by a Highly Sensitive RT-PCR Method," *Haematologica* 80:495-504.

Ross, S. D. et al. (1999). "Reduced Neutrophil Infiltration Protects Against Lung Reperfusion Injury After Transplantation," *The Annals of Thoracic Surgery* 67: 1428-1434.

Smith-Norowitz, T. A. et al. (Nov. 1999). "Lymphocyte Activation in Angina Pectoris," *Clinical Immunology* 93(2):168-175.

Stites, D. P. et al. eds. (1991). *Basic and Clinical Immunology.* 7th Edition, Appleton & Lange: East Norwalk, CT, 6 pages (Table of Contents).

Thomas, E. et al. (Jul. 2000). "Subtyping of Juvenile Idiopathic Arthritis Using Latent Class Analysis," *Arthritis & Rheumatism* 43(7):1496-1503.

Tibshirani, R. et al. (May 2002). "Diagnosis of Multiple Cancer Types by Shrunken Centroids of Gene Expression," *Proceedings of the National Academy of Sciences* 99(1):6567-6572.

U.S. Office Action mailed Apr. 1, 2008, for U.S. Appl. No. 10/511,937, filed Jul. 22, 2005, 6 pages.

U.S. Office Action mailed Jun. 15, 2007, for U.S. Appl. No. 11/223,492, filed Sep. 8, 2005, 20 pages.

U.S. Office Action mailed Mar. 5, 2008, for U.S. Appl. No. 11/223,492, filed Sep. 8, 2005, 13 pages.

U.S. Office Action mailed Oct. 3, 2007, for U.S. Appl. No. 10/990,275, filed Nov. 15, 2004, 6 pages.

U.S. Office Action mailed Oct. 5, 2007, for U.S. Appl. No. 10/990,298, filed Nov. 15, 2004, 5 pages.

U.S. Appl. No. 11/938,227, filed Nov. 9, 2007 for Lal et al. (17.00).

Vu, H. K. (2000). "A Method for Quantification of Absolute Amounts of Nucleic Acids by (RT)-PCR and a New Mathematical Model for Data Analysis," *Nucleic Acids Research* 28(7):e18, 9 pages.

Wu, T. (2001). "Analyzing Gene Expression Data from DNA Microarrays to Identify Candidate Genes," *Journal of Pathology* 195:53-65.

International Search Report mailed Sep. 23, 2005, for PCT application No. PCT/US03/12946, filed Apr. 24, 2003, 3 pages.

Bertone, P. et al. (Dec. 24, 2004). "Global Identification of Human Transcribed Sequences with Genome Tiling Arrays," *Science* 306:2242-2246.

Flechner, S. M. et al. (2004). "Kidney Transplant Rejection and Tissue Injury by Gene Profiling of Biopsies and Peripherals Blood Lymphocytes," *American Journal of Transplantation* 4:1475-1489.

Galon, J. et al. (Jan. 2002). "Gene Profiling Reveals Unknown Enhancing and Supppressive Actions of Glucocorticoids on Immune Cells," *The FASEB Journal* 16:61-71.

International Search Report and Written Opinion mailed Aug. 25, 2008, for PCT Application No. PCT/US07/08909 filed Apr. 9, 2007, 10 pages.

International Search Report and Written Opinion mailed Jun. 25, 2008, for PCT Application No. PCT/US06/18381 filed May 11, 2006, 8 pages.

International Search Report and Written Opinion mailed Sep. 10, 2008, for PCT Application No. PCT/US07/18135 filed Aug. 14, 2007, 12 pages.

Keembiyehetty, C. et al. (Mar. 2006). "Mouse Glucose Transporter 9 Splice Variants Are Expressed in Adult Liver and Kidney and Are Up-regulated in Diabetes," *Molecular Endocrinology* 20(3):686-697.

Kelsen, S. et al. (2004). "The Chemokine Receptor CXCR3 and its Splice Variant are Expressed in Human Airway Epithelial Cells," *American Journal of Physiology-Lung Cellular and Molecular Physiology* 287:L584-L591.

Mansfield, E. S. et al. (2004). "Arraying the Orchestration of Allograft Pathology," *American Journal of Transplantation* 4:853-862.

Seiter, S. et al. (1998). "CD44 Variant Isoform Expression in a Variety of Skin-Associated Autoimmune Diseases," *Clinical Immunology and Immunopathology* 89(1):79-93.

U.S. Office Action mailed Jul. 18, 2008, for U.S. Appl. No. 10/990,275, filed Nov. 15, 2004, 4 pages.

U.S. Office Action mailed Oct. 8, 2008, for U.S. Appl. No. 10/511,937, filed Jul. 22, 2005, 4 pages.

U.S. Appl. No. 12/235,969, filed Sep. 23, 2008 for Wohlgemuth et al.

Zhu, H. et al. (Nov. 2005). "The Role of Hyaluronan Receptor CD44 in MSC Migration in The Extracellular Matrix," *Stem Cells Express* 1-32.

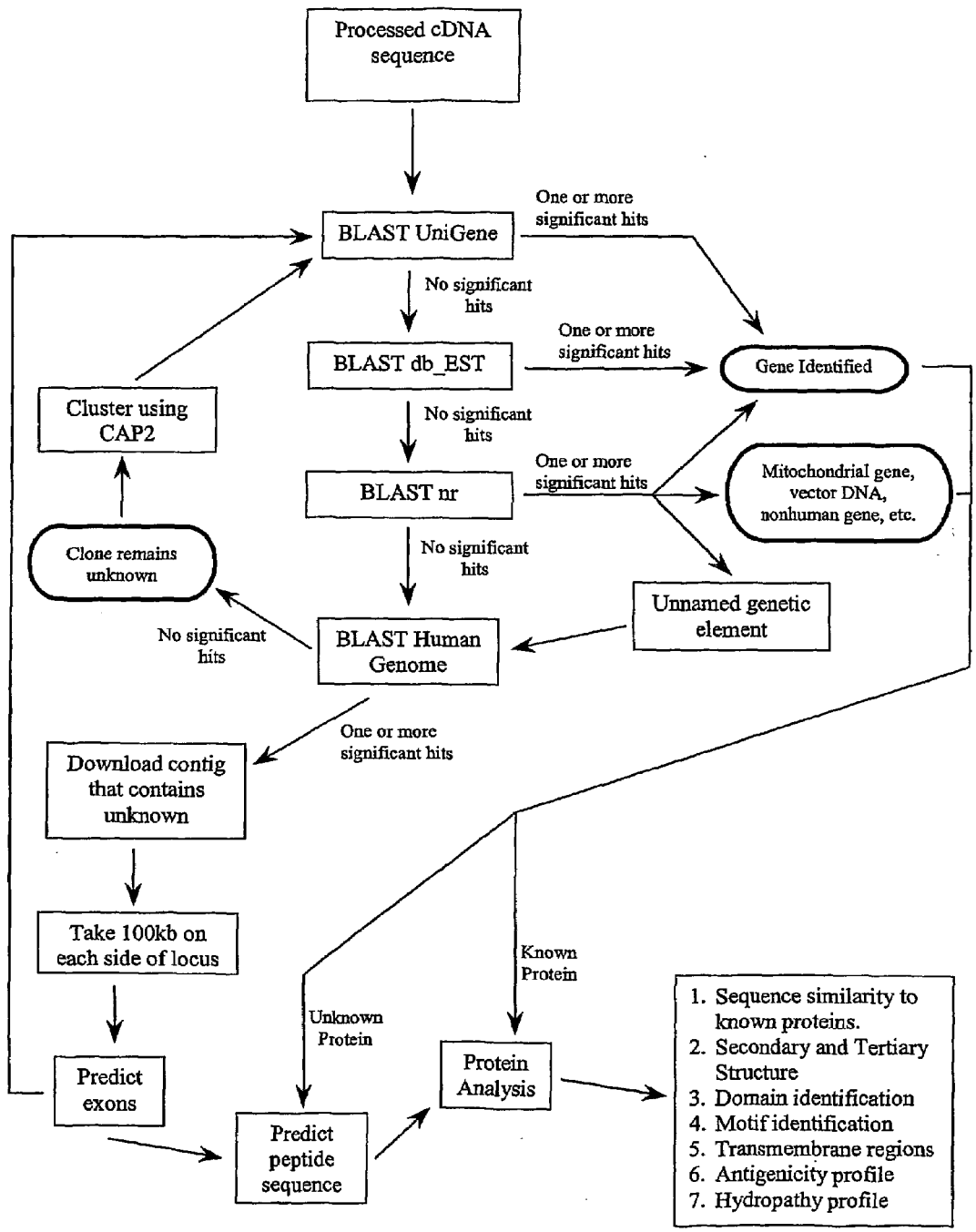
Figure 1: Novel Gene Sequence Analysis

Figure 2: Primer efficiency testing. A standard curve of Ct versus log of the starting RNA amount is shown for 2 genes.
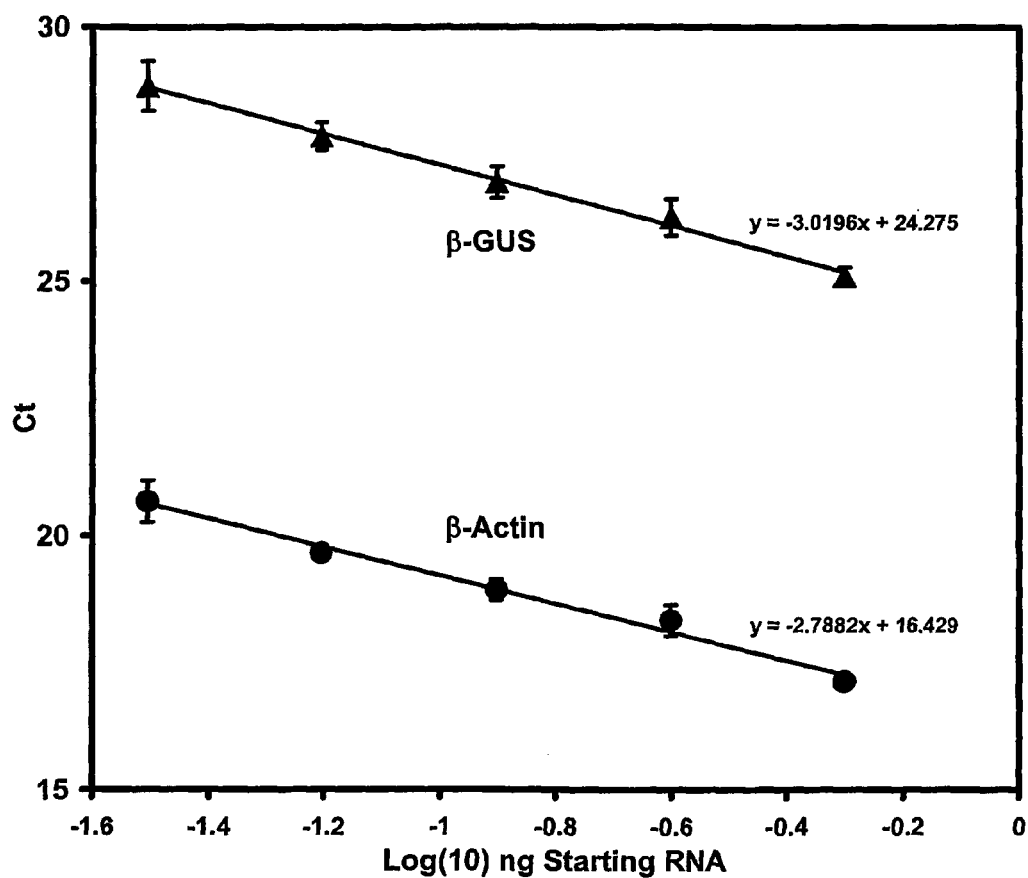

(Fig.3 pg 1 of 3)

Figure 3: Kits for discovery of, or application of diagnostic gene sets

A. Contents of kit for discovery of diagnostic gene sets using microarrays

1. Sterile, endotoxin and RNAse free blood collection tubes
2. Alcohol swabs, tourniquet, blood collection set
3. -PBS (phosphate buffer saline; needed when method of example 8 is used to derived mononuclear RNA)
4. Cell lysis buffer
5. RNA isolation kit
6. Substrates for labeling of RNA (may vary for various expression profiling techniques)
   For fluorescence microarray expression profiling:
   Reverse transcriptase and 10x RT buffer
   T7(dT)24 primer (primer with T7 promoter at 5' end)
   DTT
   Deoxynucleotides 100mM each
   RNAse inhibitor
   $2^{nd}$ strand cDNA buffer
   DNA polymerase
   Rnase H
   T7 RNA polymerase
   Ribonucleotides
   In Vitro transcription buffer
   Cy3 and Cy5 labeled ribonucleotides
7. Microarrays containing candidate gene libraries
8. Cover slips for slides
9. Hybridization chambers
10. Software package for identification of diagnostic gene set from data
    Contains statistical methods.
    Allows alteration in desired sensitivity and specificity of gene set.
    Software facilitates access to and data analysis by centrally located database server.
11. Password and account number to access central database server.
12. Kit User Manual

B. Contents of kit for application of diagnostic gene sets using microarrays

1. Sterile, endotoxin and RNAse free blood collection tubes
2. Alcohol swabs, tourniquet, blood collection set
3. -PBS (phosphate buffer saline; needed when method of example 7 is used to derived mononuclear RNA)

(Fig.3 pg 2 of 3)

4. Cell lysis buffer
5. RNA isolation kit
6. Substrates for labeling of RNA (may vary for various expression profiling techniques)
    For fluorescence microarray expression profiling:
    Reverse transcriptase and 10x RT buffer
    T7(dT)24 primer (primer with T7 promoter at 5' end)
    DTT
    Deoxynucleotides 100mM each
    RNAse inhibitor
    $2^{nd}$ strand cDNA buffer
    DNA polymerase
    Rnase H
    T7 RNA polymerase
    Ribonucleotides
    In Vitro transcription buffer
    Cy3 and Cy5 labeled ribonucleotides
7. Microarrays containing candidate gene libraries
8. Cover slips for slides
9. Hybridization chambers
10. Software package for identification of diagnostic gene set from data
    Contains statistical methods.
    Allows alteration in desired sensitivity and specificity of gene set.
    Software facilitates access to and data analysis by centrally located database server.
11. Password and account number to access central database server.
12. Kit User Manual

C. Contents of kit for application of diagnostic gene sets using Real-time RT-PCR 1. Sterile, endotoxin and RNAse free blood collection tubes
2. Alcohol swabs, tourniquet, blood collection set
3. -PBS (phosphate buffer saline; needed when method of example 7 is used to derived mononuclear RNA)
4. Cell lysis buffer
5. RNA isolation kit
6. Substrates for real time RT-PCR (may vary for various real-time PCR techniques:
    poly dT primers, random hexamer primers
    Reverse Transcriptase and RT buffer
    DTT
    Deoxynucleotides 100 mM
    RNase H
    primer pairs for diagnostic and control gene set
    10x PCR reaction buffer (Fig.3 pg 3 of 3)

Taq DNA polymerase
      Fluorescent probes for diagnostic and control gene set
      (alternatively, fluorescent dye that binds to only double stranded DNA)
      reaction tubes with or without barcode for sample tracking
      96-well plates with barcode for sample identification, one barcode for entire set, or individual barcode per reaction tube in plate 7. Software package for identification of diagnostic gene set from data
      Contains statistical methods.
      Allows alteration in desired sensitivity and specificity of gene set.
      Software facilitates access to and data analysis by centrally located database server 8. Password and account number to access central database server.
9. Kit User Manual Figure 5: SLE diagnostic genes and algorithms
A.
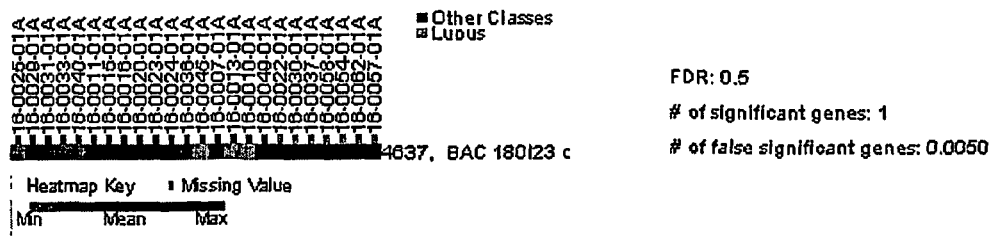
FDR: 0.5
# of significant genes: 1
# of false significant genes: 0.0050
B.
| Lupus | | Control | |
|---|---|---|---|
| Sample | Ratio | Sample | Ratio |
| 16-0022-01 | 1.05 | 16-0025-01 | 0.60 |
| 16-0030-01 | 0.96 | 16-0029-01 | 0.75 |
| 16-0037-01 | 0.87 | 16-0031-01 | 0.63 |
| 16-0058-01 | 1.05 | 16-0033-01 | 0.62 |
| 16-0054-01 | 0.99 | 16-0040-01 | 0.61 |
| 16-0062-01 | 0.98 | 16-0015-01 | 0.72 |
| 16-0057-01 | 1.14 | 16-0016-01 | 0.78 |
| | | 16-0020-01 | 0.79 |
| | | 16-0023-01 | 0.71 |
| | | 16-0024-01 | 0.69 |
| | | 16-0036-01 | 0.65 |
| | | 16-0045-01 | 0.59 |
| | | 16-0007-01 | 0.77 |
| | | 16-0013-01 | 0.60 |
| | | 16-0010-01 | 0.57 |
| | | 16-0049-01 | 0.75 |
|  | Lupus | Controls |
|---|---|---|
| Average Ratio | 1.00 | 0.68 |
| Std Dev of Ratio | 0.08 | 0.08 |
| Fold Change | 1.48 | |

| Model # genes | Relative Cost | SEQ ID 60mer | Locus | Nominal Description | CART Splitter | CART Value for Dx SLE |
|---|---|---|---|---|---|---|
| Model I 2 | 0.118 | 514 | NM_002946 | replication protein A2 (32kD) | co-1st | [(2412)*0.903 - (2648)*0.431] <= 0.1909 |
| | | 510 | NM_004510 | interferon-induced protein 75 | co-1st | [(2412)*0.903 - (2648)*0.431] <= 0.1909 |
| Model I 3 | 0.125 | 514 | NM_002946 | replication protein A2 (32kD) | co-1st | [(2412)*0.903 - (2648)*0.431] <= 0.1909 |
| | | 510 | NM_004510 | interferon-induced protein 75 | co-1st | [(2412)*0.903 - (2648)*0.431] <= 0.1909 |
| | | 509 | BC002409 | actin, beta (ACTB) | 2nd | (G1435) > 0.0868 |
| Model II 1 | 0.512 | 504 | W16552 | PKR | 1st | (5087) > 0.1030 |
| Model II 3 | 0.686 | 504 | W16552 | PKR | 1st | (5087) > 0.1030 |
| | | 875 | AK024758 | hypothetical protein FLJ21103 | 2nd | (G1025) <= 0.3968 |
| | | 876 | AK024969 | hypothetical protein DKFZp586I133 | 3rd | (G1035) <= 0.0073 |
| Model II 5 | 0.745 | 504 | W16552 | PKR | 1st | (5087) > 0.1030 |
| | | 874 | AK024240 | cDNA FLJ14178 fis | 2nd | (G1003) > 0.2105 |
| | | 875 | AK024758 | hypothetical protein FLJ21103 | 2nd | (G1025) <= 0.3968 |
| | | 873 | AK024202 | heat shock 90kD protein 1, alpha | 3rd | (G1051) <= -0.3107 |
| | | 876 | AK024969 | hypothetical protein DKFZp586I133 | 3rd | (G1035) <= 0.0073 |

D.

| | Model | Sensitivity | Specificity | Relative Cost |
|---|---|---|---|---|
| Training Set | Model 1 (2 genes) | 100 | 94 | |
| | Model 1 (3 genes) | 100 | 100 | |
| 10-fold Cross Validation | Model 1 (2 genes) | 100 | 88 | 0.118 |
| | Model 1 (3 genes) | 93 | 94 | 0.125 |

FIGURE 5
E
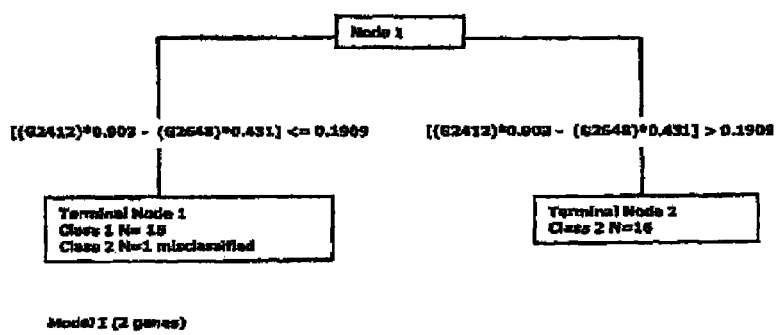
Model I (2 genes)
F.
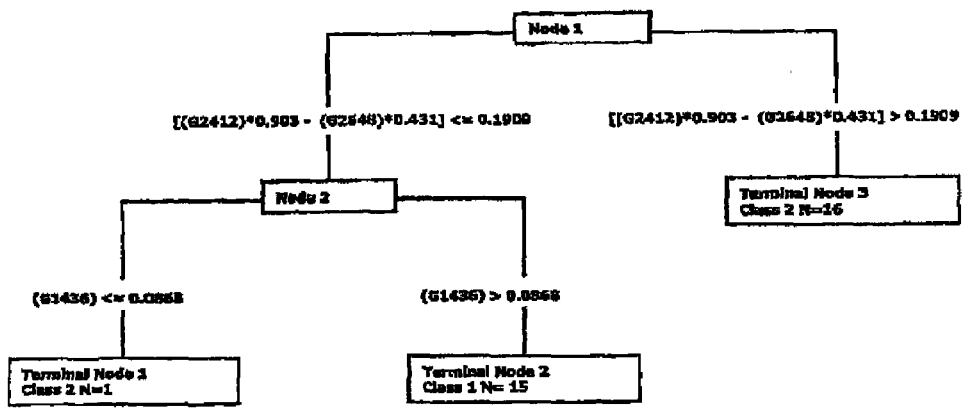
Model 1 (3 genes)

Figure 6. Endpoint testing of PCR primers
A.
B.
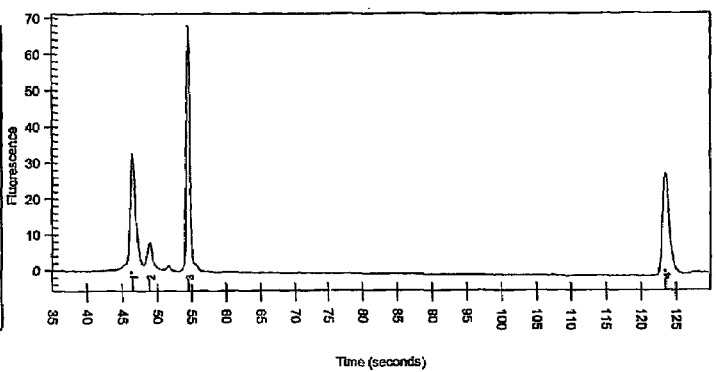
C.
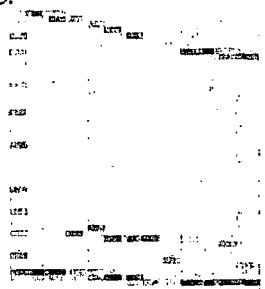
D.
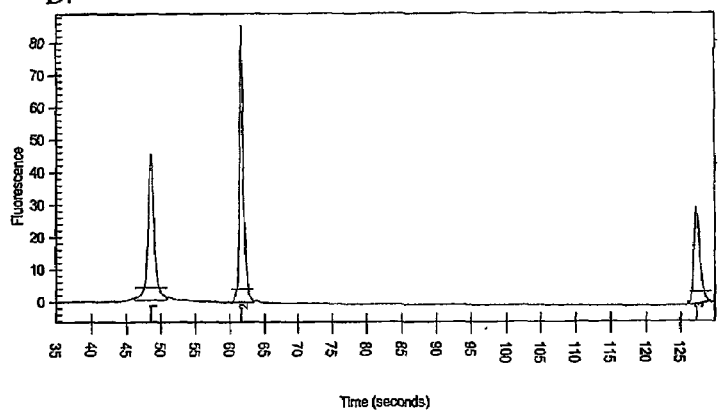

Figure 7: Validation of differential expression of Granzyme B in CMV patients using Real-time PCR
A.
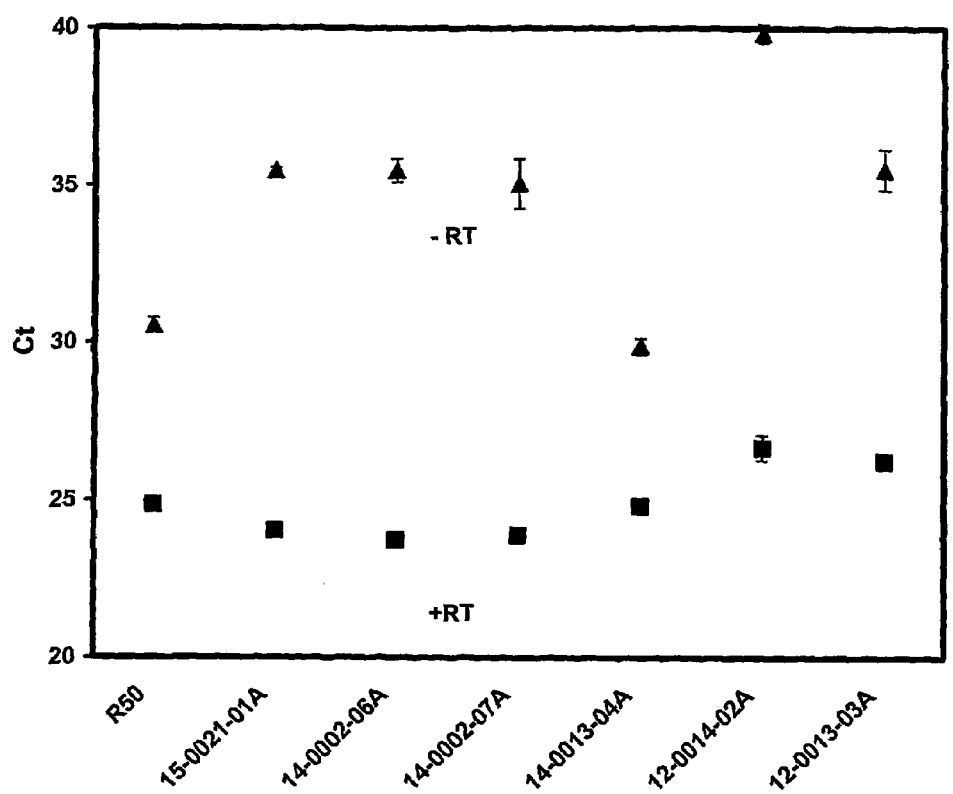

Figure 8
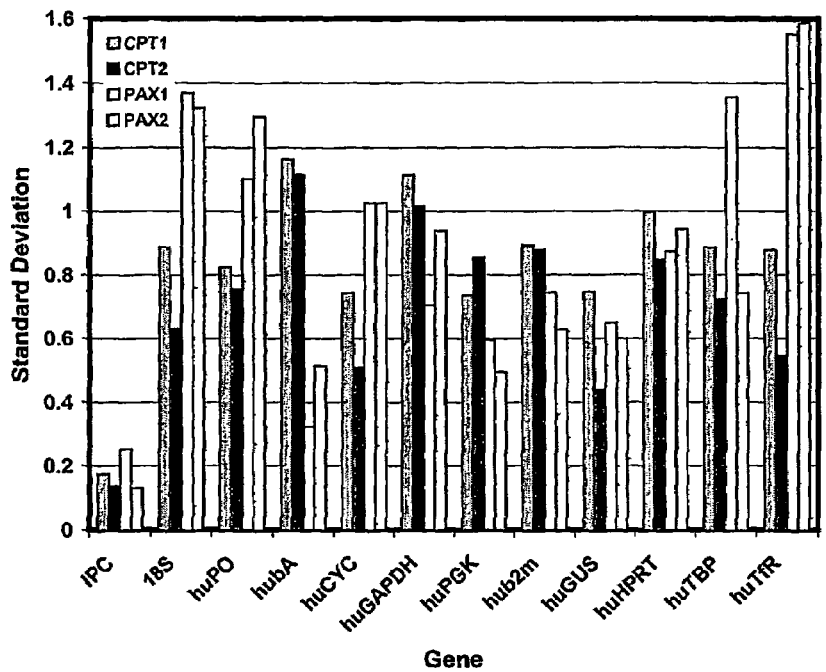
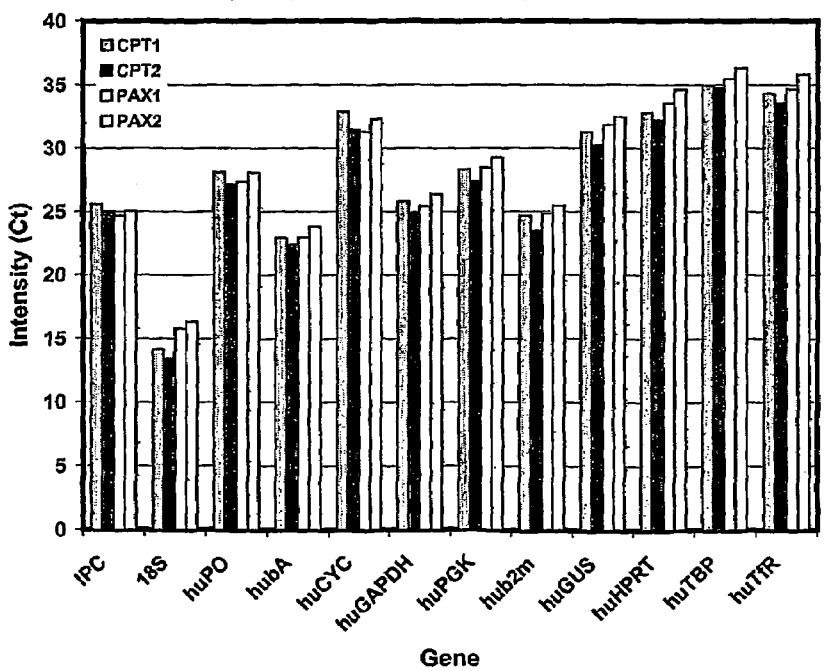

METHODS AND COMPOSITIONS FOR DIAGNOSIS AND MONITORING AUTO IMMUNE AND CHRONIC INFLAMMATORY DISEASES

RELATED APPLICATIONS

This application is a U.S. National Phase Application of International PCT/US03/13015, filed Apr. 24, 2003, which claims priority to U.S. patent application Ser. No. 10/131,827, filed Apr. 24, 2002, now U.S. Pat. No. 6,905,827, which is a continuation-in-part of U.S. application Ser. No. 10/006,290, filed Oct. 22, 2001, now abandoned, all of which are hereby incorporated by reference in their entirety.

FIELD OF THE INVENTION

This application is in the field of chronic inflammatory diseases. In particular, this invention relates to methods and compositions for diagnosing or monitoring chronic inflammatory diseases.

BACKGROUND OF THE INVENTION

Many of the current shortcomings in diagnosis, prognosis, risk stratification and treatment of disease can be approached through the identification of the molecular mechanisms underlying a disease and through the discovery of nucleotide sequences (or sets of nucleotide sequences) whose expression patterns predict the occurrence or progression of disease states, or predict a patient's response to a particular therapeutic intervention. In particular, identification of nucleotide sequences and sets of nucleotide sequences with such predictive value from cells and tissues that are readily accessible would be extremely valuable. For example, peripheral blood is attainable from all patients and can easily be obtained at multiple time points at low cost. This is a desirable contrast to most other cell and tissue types, which are less readily accessible, or accessible only through invasive and aversive procedures. In addition, the various cell types present in circulating blood are ideal for expression profiling experiments as the many cell types in the blood specimen can be easily separated if desired prior to analysis of gene expression. While blood provides a very attractive substrate for the study of diseases using expression profiling techniques, and for the development of diagnostic technologies and the identification of therapeutic targets, the value of expression profiling in blood samples rests on the degree to which changes in gene expression in these cell types are associated with a predisposition to, and pathogenesis and progression of a disease.

There is an extensive literature supporting the role of leukocytes, e.g., T- and B-lymphocytes, monocytes and granulocytes, including neutrophils, in a wide range of disease processes, including such broad classes as cardiovascular diseases, inflammatory, autoimmune and rheumatic diseases, infectious diseases, transplant rejection, cancer and malignancy, and endocrine diseases.

Of particular interest is the role of leukocytes and leukocyte gene expression in chronic inflammatory diseases such as Systemic Lupus Erythematosis and Rheumatoid Arthritis. Systemic lupus erythematosis (SLE) and Rheumatoid Arthritis (RA) are chronic autoimmune and inflammatory disorders characterized by dysregulation of the immune system, which causes damage to a variety of organs. These diseases clearly involve differential expression of genes in leukocytes. Diagnostic and disease monitoring tools are severely lacking for these patients and their physicians. Leukocyte expression profiling can be applied to discover expression markers for SLE and RA and apply them as patient management tools in the clinical setting. In addition, osteoarthritis is a degenerative joint disease that can be confused with RA. This disease also involves leukocytes and expression profiling of leukocytes associated with osteoarthritis may lead to the discovery of new diagnostic and therapeutic approaches to the disease.

SLE in particular is a chronic, usually life-long, potentially fatal autoimmune disease characterized by unpredictable exacerbations and remissions with protean clinical manifestations. SLE is notable for unpredictable exacerbations and remissions and a predilection for clinical involvement of the joints, skin, kidney, brain, serosa, lung, heart, and gastrointestinal tract. The pathologic hallmark of the disease is recurrent, widespread, and diverse vascular lesions.

SLE is not a rare disorder. Although reported at both extremes of life (e.g. diagnosed in infants and in the tenth decade of life) chiefly it affects women of child bearing age. Among children, SLE occurs three times more commonly in females than in males. In the 60% of SLE patients who experience onset of their disease between puberty and the fourth decade of life the female to male ratio is 9:1. Thereafter, the female preponderance again falls to that observed in prepubescents.

The disorder is three times more common in African American blacks than American caucasians. SLE is also more common in Asians and in China may be more common than Rheumatoid Arthritis. The ethnic group at greatest risk is African Caribbean blacks. The annual incidence of SLE ranges from six to 35 new cases per 100,000 population in relatively low-risk to high-risk groups. The prevalence of SLE in the United States is an issue of some debate. Prevalence estimates of between 250,000 to 500,000 are contradicted by a recent nationwide telephone poll suggesting a prevalence of between one and two million.

The prognosis for patients with SLE has greatly improved over the last few decades with at least 80-90% of all patients surviving ten years. Thereafter life expectancy approximates that of age matched controls. This improvement reflects the general advancements in health care (i.e. dialysis, antibiotics, antihypertensives, newer immunosuppressives with more favorable efficacy to toxicity ration) but also the specialized care available for patients with SLE.

Such specialized medical care includes care by experienced clinicians with access to state of the art diagnostic and therapeutic measures will result in improved outcomes and the most cost-effective utilization of resources. Expert care of patients with SLE leads to fewer hospitalizations secondary to uncontrolled disease exacerbation, less severe renal disease with fewer patients experiencing end stage renal disease requiring chronic dialysis, fewer episodes of avascular necrosis requiring total joint replacement, and less severe osteoporosis and fractures. In addition, more judicious use of steroids and steroid sparing agents can also reduce the severity of atherosclerosis and resulting incidence of myocardial infarctions and cerebral vascular accidents, which now complicate the natural history of SLE. Improved monitoring, diagnosis and prognosis of SLE should aid clinicians in determining appropriate care for SLE patients, including which drugs to use and at what amounts.

At a molecular level, SLE is an autoimmune disease characterized by immune dysregulation resulting in the production of antinuclear antibodies (ANA), generation of circulating immune complexes, and activation of the complement system. SLE is further characterized by end organ damage that results from deposition of circulating autoantibodies and subsequent complement- and Fc receptor-mediated inflammation. In addition, extensive immune system abnormalities, including altered T lymphocyte function and spontaneous apoptosis, contribute to the lymphopenia and increased susceptibility to infection that confer considerable morbidity.

The clinical features of SLE are protean and may mimic infectious mononucleosis, lymphoma, or other systemic disease. Therefore, the American College of Rheumatology developed criteria to include patients with SLE and exclude those with other disorders. These criteria are best used to insure the appropriateness of subjects for epidemiological or research studies. Although many patients do not fulfill the rigid criteria at first encounter most will when followed over periods of time.

The etiology of SLE remains unknown. A genetic predisposition, sex hormones, and environmental trigger(s) likely result in the disordered immune response that typifies the disease.

A role for genetics is suggested by the increased percentage of two histocompatibility antigens in patients with SLE, HLA-DR2 and HLA-DR3. In addition, there is an increased frequency of the extended haplotype HLA-A1, B8, DR3. The role for heredity is further supported by the concordance for this illness among monozygotic twins. The polygenic nature, however, of this genetic predisposition as well as the contribution of environmental factors is suggested by the only moderate concordance rate which is reported to be between 25 and 60%.

The origin of autoantibody production in SLE is unclear but a role has been suggested for an antigen driven process, spontaneous B-cell hyper-responsiveness, or impaired immune regulation. Regardless of the etiology of autoantibody production, SLE is associated with the impaired clearance of circulating immune complexes secondary to decreased CR1 expression, defective Fc receptor function, or deficiencies of early complement components such as C4A.

More is known about the pathogenic cellular and molecular events that are responsible for vascular lesions in SLE than the origins of autoimmunity. Disease manifestations result from recurrent vascular injury due to immune complex deposition, leukothrombosis, or thrombosis. Additionally, cytotoxic antibodies can mediate autoimmune hemolytic anemia and thrombocytopenia, while antibodies to specific cellular antigens can disrupt cellular function. An example of the latter, is the association between anti-neuronal antibodies and neuropsychiatric SLE.

The health status of a patient with SLE is related not only to disease activity, but to the damage that results from recurrent episodes of disease flare (i.e. deforming arthropathy, shrinking lung, end stage renal disease, organic mental syndrome, etc.), as well as the adverse effects of treatment (i.e. avascular necrosis of bone, infections, and precocious atherosclerosis, etc.).

The accuracy of technologies based on expression profiling for the diagnosis, prognosis, and monitoring of disease would be dramatically increased if numerous differentially expressed nucleotide sequences, each with a measure of sensitivity and specificity for a disease in question, could be identified and assayed in a concerted manner. Using the expression of multiple genes (gene sets) for diagnostic applications helps overcome assay and population variability. PCT application WO 02/057414 "LEUKOCYTE EXPRESSION PROFILING" to Wohlgemuth identifies a set of differentially expressed nucleotides.

In order to achieve this improved accuracy, the appropriate sets of nucleotide sequences once identified need to be validated against numerous samples in combination with relevant clinical data.

SUMMARY OF THE INVENTION

In order to meet these needs, the present invention identifies genes and gene sets that have clinical utility as diagnostic tools for the management of lupus patients and patients with a variety of chronic inflammatory and autoimmune diseases. The present invention is thus directed to a method of diagnosing or monitoring chronic autoimmune or inflammatory disease in a patient. The method of the invention involves detecting in a patient expression of one or more genes such as those genes depicted in Table 2E and surrogates derived therefrom. Exemplary surrogates are provided in Table 2D. The present invention is further directed to a method of diagnosing or monitoring an autoimmune or chronic inflammatory disease in a patient by detecting the expression level of one or more genes or surrogates derived therefrom in said patient to diagnose or monitor the autoimmune or chronic inflammatory disease in the patient wherein said genes include a nucleotide sequence selected from SEQ ID NO:503, SEQ ID NO:504, SEQ ID NO:505, SEQ ID NO:506, SEQ ID NO:507, SEQ ID NO:508, SEQ ID NO:509, SEQ ID NO:510, SEQ ID NO:511, SEQ ID NO:512, SEQ ID NO:513, SEQ ID NO:514, SEQ ID NO:515, SEQ ID NO:516, SEQ ID NO:517, SEQ ID NO:518, SEQ ID NO:519, SEQ ID NO:520, SEQ ID NO:521, SEQ ID NO:522, SEQ ID NO:523, SEQ ID NO:524, SEQ ID NO:525, SEQ ID NO:526, SEQ ID NO:527, SEQ ID NO:528, SEQ ID NO:529, SEQ ID NO:530, SEQ ID NO:531, SEQ ID NO:532, SEQ ID NO:533, SEQ ID NO:534, SEQ ID NO:535, SEQ ID NO:536, SEQ ID NO:537, SEQ ID NO:538, SEQ ID NO:539, SEQ ID NO:540, SEQ ID NO:541, SEQ ID NO:542, SEQ ID NO:543, SEQ ID NO:544, SEQ ID NO:545, SEQ ID NO:546, SEQ ID NO:547, SEQ ID NO:548, SEQ ID NO:549, SEQ ID NO:550, SEQ ID NO:551, SEQ ID NO:552, SEQ ID NO:553, SEQ ID NO:554, SEQ ID NO:555, SEQ ID NO:556, SEQ ID NO:557, SEQ ID NO:558, SEQ ID NO:559, SEQ ID NO:560, SEQ ID NO:561, SEQ ID NO:562, SEQ ID NO:563, SEQ ID NO:564, SEQ ID NO:565, SEQ ID NO:566, SEQ ID NO:567, SEQ ID NO:568, SEQ ID NO:569, SEQ ID NO:570, SEQ ID NO:571, SEQ ID NO:572, SEQ ID NO:573, SEQ ID NO:574, SEQ ID NO:575, SEQ ID NO:576, SEQ ID NO:577, SEQ ID NO:578, SEQ ID NO:579, SEQ ID NO:580, SEQ ID NO:581, SEQ ID NO:582, SEQ ID NO:583, SEQ ID NO:584, SEQ ID NO:585, SEQ ID NO:586, SEQ ID NO:587, SEQ ID NO:588, SEQ ID NO:589, SEQ ID NO:590, SEQ ID NO:591, SEQ ID NO:592, SEQ ID NO:593, SEQ ID NO:594, SEQ ID NO:595, SEQ ID NO:596, SEQ ID NO:597, SEQ ID NO:598, SEQ ID NO:599, SEQ ID NO:600, SEQ ID NO:601, SEQ ID NO:602, SEQ ID NO:603, SEQ ID NO:604, SEQ ID NO:605, SEQ ID NO:606, SEQ ID NO:607, SEQ ID NO:608, SEQ ID NO:609, SEQ ID NO:610, SEQ ID NO:611, SEQ ID NO:612, SEQ ID NO:613, SEQ ID NO:614, SEQ ID NO:615, SEQ ID NO:616, SEQ ID NO:617, SEQ ID NO:618, SEQ ID NO:619, SEQ ID NO:620, SEQ ID NO:621, SEQ ID NO:622, SEQ ID NO:623, SEQ ID NO:624, SEQ ID NO:625, SEQ ID NO:626, SEQ ID NO:627, SEQ ID NO:628, SEQ ID NO:629, SEQ ID NO:630, SEQ ID NO:631, SEQ ID NO:632, SEQ ID NO:633, SEQ ID NO:634, SEQ ID NO:635, SEQ ID NO:636, SEQ ID NO:637, SEQ ID NO:638, SEQ ID NO:639, SEQ ID NO:640, SEQ ID NO:641, SEQ ID NO:642, SEQ ID NO:643, SEQ ID NO:644, SEQ ID NO:645, SEQ ID NO:646, SEQ ID NO:647, SEQ ID NO:648, SEQ ID NO:649, SEQ ID NO:650, SEQ ID
NO:651, SEQ ID NO:652, SEQ ID NO:653, SEQ ID
NO:654, SEQ ID NO:655, SEQ ID NO:656, SEQ ID
NO:657, SEQ ID NO:658, SEQ ID NO:659, SEQ ID
NO:660, SEQ ID NO:661, SEQ ID NO:662, SEQ ID
NO:663, SEQ ID NO:664, SEQ ID NO:665, SEQ ID
NO:666, SEQ ID NO:667, SEQ ID NO:668, SEQ ID
NO:669, SEQ ID NO:670, SEQ ID NO:671, SEQ ID
NO:672, SEQ ID NO:673, SEQ ID NO:674, SEQ ID
NO:675, SEQ ID NO:676, SEQ ID NO:677, SEQ ID
NO:678, SEQ ID NO:679, SEQ ID NO:680, SEQ ID
NO:681, SEQ ID NO:682, SEQ ID NO:683, SEQ ID
NO:684, SEQ ID NO:685, SEQ ID NO:686, SEQ ID
NO:687, SEQ ID NO:688, SEQ ID NO:689, SEQ ID
NO:690, SEQ ID NO:691, SEQ ID NO:692, SEQ ID
NO:693, SEQ ID NO:694, SEQ ID NO:695, SEQ ID
NO:696, SEQ ID NO:697, SEQ ID NO:698, SEQ ID
NO:699, SEQ ID NO:700, SEQ ID NO:701, SEQ ID
NO:702, SEQ ID NO:703, SEQ ID NO:704, SEQ ID
NO:705, SEQ ID NO:706, SEQ ID NO:707, SEQ ID
NO:708, SEQ ID NO:709, SEQ ID NO:710, SEQ ID
NO:711, SEQ ID NO:712, SEQ ID NO:713, SEQ ID
NO:714, SEQ ID NO:715, SEQ ID NO:716, SEQ ID
NO:717, SEQ ID NO:718, SEQ ID NO:719, SEQ ID
NO:720, SEQ ID NO:721, SEQ ID NO:722, SEQ ID
NO:723, SEQ ID NO:724, SEQ ID NO:725, SEQ ID
NO:726, SEQ ID NO:727, SEQ ID NO:728, SEQ ID
NO:729, SEQ ID NO:730, SEQ ID NO:731, SEQ ID
NO:732, SEQ ID NO:733, SEQ ID NO:734, SEQ ID
NO:735, SEQ ID NO:736, SEQ ID NO:737, SEQ ID
NO:738, SEQ ID NO:739, SEQ ID NO:740, SEQ ID
NO:741, SEQ ID NO:742, SEQ ID NO:743, SEQ ID
NO:744, SEQ ID NO:745, SEQ ID NO:746, SEQ ID
NO:747, SEQ ID NO:748, SEQ ID NO:749, SEQ ID
NO:750, SEQ ID NO:751, SEQ ID NO:752, SEQ ID
NO:753, SEQ ID NO:754, SEQ ID NO:755, SEQ ID
NO:756, SEQ ID NO:757, SEQ ID NO:758, SEQ ID
NO:759, SEQ ID NO:760, SEQ ID NO:761, SEQ ID
NO:762, SEQ ID NO:763, SEQ ID NO:764, SEQ ID
NO:765, SEQ ID NO:766, SEQ ID NO:767, SEQ ID
NO:768, SEQ ID NO:769, SEQ ID NO:770, SEQ ID
NO:771, SEQ ID NO:772, SEQ ID NO:773, SEQ ID
NO:774, SEQ ID NO:775, SEQ ID NO:776, SEQ ID
NO:777, SEQ ID NO:778, SEQ ID NO:779, SEQ ID
NO:780, SEQ ID NO:781, SEQ ID NO:782, SEQ ID
NO:783, SEQ ID NO:784, SEQ ID NO:785, SEQ ID
NO:786, SEQ ID NO:787, SEQ ID NO:788, SEQ ID
NO:789, SEQ ID NO:790, SEQ ID NO:791, SEQ ID
NO:792, SEQ ID NO:793, SEQ ID NO:794, SEQ ID
NO:795, SEQ ID NO:796, SEQ ID NO:797, SEQ ID
NO:798, SEQ ID NO:799, SEQ ID NO:800, SEQ ID
NO:801, SEQ ID NO:802, SEQ ID NO:803, SEQ ID
NO:804, SEQ ID NO:805, SEQ ID NO:806, SEQ ID
NO:807, SEQ ID NO:808, SEQ ID NO:809, SEQ ID
NO:810, SEQ ID NO:811, SEQ ID NO:812, SEQ ID
NO:813, SEQ ID NO:814, SEQ ID NO:815, SEQ ID
NO:816, SEQ ID NO:817, SEQ ID NO:818, SEQ ID
NO:819, SEQ ID NO:820, SEQ ID NO:821, SEQ ID
NO:822, SEQ ID NO:823, SEQ ID NO:824, SEQ ID
NO:825, SEQ ID NO:826, SEQ ID NO:827, SEQ ID
NO:828, SEQ ID NO:829, SEQ ID NO:830, SEQ ID
NO:831, SEQ ID NO:832, SEQ ID NO:833, SEQ ID
NO:834, SEQ ID NO:835, SEQ ID NO:836, SEQ ID
NO:837, SEQ ID NO:838, SEQ ID NO:839, SEQ ID
NO:840, SEQ ID NO:841, SEQ ID NO:842, SEQ ID
NO:843, SEQ ID NO:844, SEQ ID NO:845, SEQ ID
NO:846, SEQ ID NO:847, SEQ ID NO:848, SEQ ID
NO:849, SEQ ID NO:850, SEQ ID NO:851, SEQ ID
NO:852, SEQ ID NO:853, SEQ ID NO:854, SEQ ID
NO:855, SEQ ID NO:856, SEQ ID NO:857, SEQ ID
NO:858, SEQ ID NO:859, SEQ ID NO:860, SEQ ID
NO:861, SEQ ID NO:862, SEQ ID NO:863, SEQ ID
NO:864, SEQ ID NO:865, SEQ ID NO:866, SEQ ID
NO:867, SEQ ID NO:868, SEQ ID NO:869, SEQ ID
NO:870, SEQ ID NO:871, SEQ ID NO:872, SEQ ID
NO:873, SEQ ID NO:874, SEQ ID NO:875, SEQ ID
NO:876, SEQ ID NO:877, SEQ ID NO:878, SEQ ID
NO:879, SEQ ID NO:880, SEQ ID NO:881, SEQ ID
NO:882, SEQ ID NO:883, SEQ ID NO:884, SEQ ID
NO:885, SEQ ID NO:886, SEQ ID NO:887, SEQ ID
NO:888, SEQ ID NO:889, SEQ ID NO:890, SEQ ID
NO:891, SEQ ID NO:892, SEQ ID NO:893, SEQ ID
NO:894, SEQ ID NO:895, SEQ ID NO:896, SEQ ID
NO:897, SEQ ID NO:898, SEQ ID NO:899, SEQ ID
NO:900, SEQ ID NO:901, SEQ ID NO:902, SEQ ID
NO:903, SEQ ID NO:904, SEQ ID NO:905, SEQ ID
NO:906, SEQ ID NO:907, SEQ ID NO:908, SEQ ID
NO:909, SEQ ID NO:910, SEQ ID NO:911, SEQ ID
NO:912, SEQ ID NO:913, SEQ ID NO:914, SEQ ID
NO:915, SEQ ID NO:916, SEQ ID NO:917, SEQ ID
NO:918, SEQ ID NO:919, SEQ ID NO:920, SEQ ID
NO:921, SEQ ID NO:922, SEQ ID NO:923, SEQ ID
NO:924, SEQ ID NO:925, SEQ ID NO:926, SEQ ID
NO:927, SEQ ID NO:928, SEQ ID NO:929, SEQ ID
NO:930, SEQ ID NO:931, SEQ ID NO:932, SEQ ID
NO:933, SEQ ID NO:934, SEQ ID NO:935, SEQ ID
NO:936, SEQ ID NO:937, SEQ ID NO:938, SEQ ID
NO:939, SEQ ID NO:940, SEQ ID NO:941, SEQ ID
NO:942, SEQ ID NO:943, SEQ ID NO:944, SEQ ID
NO:945, SEQ ID NO:946, SEQ ID NO:947, SEQ ID
NO:948, SEQ ID NO:949, SEQ ID NO:950, SEQ ID
NO:951, SEQ ID NO:952, SEQ ID NO:953, SEQ ID
NO:954, SEQ ID NO:955, SEQ ID NO:956, SEQ ID
NO:957, SEQ ID NO:958, SEQ ID NO:959, SEQ ID
NO:960, SEQ ID NO:961, SEQ ID NO:962, SEQ ID
NO:963, SEQ ID NO:964, SEQ ID NO:965, SEQ ID
NO:966, SEQ ID NO:967, SEQ ID NO:968, SEQ ID
NO:969, SEQ ID NO:970, SEQ ID NO:971, SEQ ID
NO:972, SEQ ID NO:973, SEQ ID NO:974, SEQ ID
NO:975, SEQ ID NO:976, SEQ ID NO:977, SEQ ID
NO:978, SEQ ID NO:979, SEQ ID NO:980, SEQ ID
NO:981, SEQ ID NO:982, SEQ ID NO:983, SEQ ID
NO:984, SEQ ID NO:985, SEQ ID NO:986, SEQ ID
NO:987, SEQ ID NO:988, SEQ ID NO:989, SEQ ID
NO:990, SEQ ID NO:991, SEQ ID NO:992, SEQ ID
NO:993, SEQ ID NO:994, SEQ ID NO:995, SEQ ID
NO:996, SEQ ID NO:997, SEQ ID NO:998, SEQ ID
NO:999, SEQ ID NO:1000, SEQ ID NO:1001, SEQ ID
NO:1002, SEQ ID NO:1003, SEQ ID NO:1004.

In the method of the invention, the diagnosing of monitoring may be performed by detecting the expression level of two or more genes, three or more genes, four or more genes, five or more genes, six or more genes, seven or more genes, eight or more genes, nine or more genes, ten or more genes, fifteen or more genes, twenty or more genes, thirty or more genes, fifty or more genes, one hundred or more genes, two hundred or more genes, or all five hundred and two of the genes.

The methods of the invention also includes diagnosing or monitoring auto immune and chronic inflammatory diseases in a patient by detecting the expression level of one or more genes in said patient to diagnose or monitor auto immune and chronic inflammatory diseases in said patient wherein said one or more genes identified by a nucleotide sequence selected from the following group: SEQ ID NO:503, SEQ ID NO:505, SEQ ID NO:506, SEQ ID NO:508, SEQ ID NO:509, SEQ ID NO:510, SEQ ID NO:511, SEQ ID NO:512, SEQ ID NO:513, SEQ ID NO:514, SEQ ID NO:515, SEQ ID NO:516, SEQ ID NO:517, SEQ ID NO:518, SEQ ID NO:519, SEQ ID NO:520, SEQ ID NO:521, SEQ ID NO:522, SEQ ID NO:523, SEQ ID NO:524, SEQ ID NO:525, SEQ ID NO:526, SEQ ID NO:527, SEQ ID NO:528, SEQ ID NO:529, SEQ ID NO:530, SEQ ID NO:531, SEQ ID NO:532, SEQ ID NO:533, SEQ ID NO:534, SEQ ID NO:535, SEQ ID NO:536, SEQ ID NO:537, SEQ ID NO:538, SEQ ID NO:539, SEQ ID NO:540, SEQ ID NO:541, SEQ ID NO:542, SEQ ID NO:543, SEQ ID NO:544, SEQ ID NO:545, SEQ ID NO:546, SEQ ID NO:547, SEQ ID NO:548, SEQ ID NO:549, SEQ ID NO:550, SEQ ID NO:551, SEQ ID NO:552, SEQ ID NO:553, SEQ ID NO:554, SEQ ID NO:555, SEQ ID NO:556, SEQ ID NO:5.57, SEQ ID NO:558, SEQ ID NO:559, SEQ ID NO:560, SEQ ID NO:561, SEQ ID NO:562, SEQ ID NO:563, SEQ ID NO:564, SEQ ID NO:565, SEQ ID NO:566, SEQ ID NO:567, SEQ ID NO:568, SEQ ID NO:569, SEQ ID NO:570, SEQ ID NO:571, SEQ ID NO:572, SEQ ID NO:573, SEQ ID NO:574, SEQ ID NO:575, SEQ ID NO:576, SEQ ID NO:577, SEQ ID NO:578, SEQ ID NO:579, SEQ ID NO:580, SEQ ID NO:581, SEQ ID NO:582, SEQ ID NO:583, SEQ ID NO:584, SEQ ID NO:585, SEQ ID NO:586, SEQ ID NO:587, SEQ ID NO:588, SEQ ID NO:589, SEQ ID NO:590, SEQ ID NO:591, SEQ ID NO:592, SEQ ID NO:593, SEQ ID NO:594, SEQ ID NO:595, SEQ ID NO:596, SEQ ID NO:597, SEQ ID NO:598, SEQ ID NO:599, SEQ ID NO:600, SEQ ID NO:601, SEQ ID NO:602, SEQ ID NO:604, SEQ ID NO:605, SEQ ID NO:606, SEQ ID NO:607, SEQ ID NO:608, SEQ ID NO:609, SEQ ID NO:610, SEQ ID NO:611, SEQ ID NO:612, SEQ ID NO:613, SEQ ID NO:614, SEQ ID NO:615, SEQ ID NO:616, SEQ ID NO:617, SEQ ID NO:618, SEQ ID NO:619, SEQ ID NO:620, SEQ ID NO:621, SEQ ID NO:622, SEQ ID NO:623, SEQ ID NO:624, SEQ ID NO:625, SEQ ID NO:626, SEQ ID NO:627, SEQ ID NO:628, SEQ ID NO:629, SEQ ID NO:630, SEQ ID NO:631, SEQ ID NO:632, SEQ ID NO:633, SEQ ID NO:634, SEQ ID NO:635, SEQ ID NO:636, SEQ ID NO:637, SEQ ID NO:638, SEQ ID NO:639, SEQ ID NO:640, SEQ ID NO:641, SEQ ID NO:642, SEQ ID NO:643, SEQ ID NO:644, SEQ ID NO:645, SEQ ID NO:646, SEQ ID NO:647, SEQ ID NO:648, SEQ ID NO:649, SEQ ID NO:650, SEQ ID NO:651, SEQ ID NO:652, SEQ ID NO:653, SEQ ID NO:654, SEQ ID NO:655, SEQ ID NO:656, SEQ ID NO:657, SEQ ID NO:658, SEQ ID NO:659, SEQ ID NO:660, SEQ ID NO:661, SEQ ID NO:662, SEQ ID NO:663, SEQ ID NO:664, SEQ ID NO:665, SEQ ID NO:666, SEQ ID NO:667, SEQ ID NO:668, SEQ ID NO:669, SEQ ID NO:670, SEQ ID NO:671, SEQ ID NO:672, SEQ ID NO:673, SEQ ID NO:674, SEQ ID NO:675, SEQ ID NO:676, SEQ ID NO:677, SEQ ID NO:678, SEQ ID NO:679, SEQ ID NO:680, SEQ ID NO:681, SEQ ID NO:682, SEQ ID NO:683, SEQ ID NO:684, SEQ ID NO:685, SEQ ID NO:686, SEQ ID NO:687, SEQ ID NO:688, SEQ ID NO:689, SEQ ID NO:690, SEQ ID NO:691, SEQ ID NO:692, SEQ ID NO:693, SEQ ID NO:694, SEQ ID NO:695, SEQ ID NO:696, SEQ ID NO:697, SEQ ID NO:698, SEQ ID NO:699, SEQ ID NO:700, SEQ ID NO:701, SEQ ID NO:702, SEQ ID NO:703, SEQ ID NO:704, SEQ ID NO:705, SEQ ID NO:706, SEQ ID NO:707, SEQ ID NO:708, SEQ ID NO:709, SEQ ID NO:710, SEQ ID NO:711, SEQ ID NO:712, SEQ ID NO:713, SEQ ID NO:714, SEQ ID NO:715, SEQ ID NO:716, SEQ ID NO:717, SEQ ID NO:718, SEQ ID NO:719, SEQ ID NO:720, SEQ ID NO:721, SEQ ID NO:722, SEQ ID NO:723, SEQ ID NO:724, SEQ ID NO:725, SEQ ID NO:726, SEQ ID NO:727, SEQ ID NO:728, SEQ ID NO:729, SEQ ID NO:730, SEQ ID NO:731, SEQ ID NO:732, SEQ ID NO:733, SEQ ID NO:734, SEQ ID NO:735, SEQ ID NO:736, SEQ ID NO:737, SEQ ID NO:738, SEQ ID NO:739, SEQ ID NO:741, SEQ ID NO:742, SEQ ID NO:743, SEQ ID NO:744, SEQ ID NO:745, SEQ ID NO:746, SEQ ID NO:747, SEQ ID NO:748, SEQ ID NO:7-49, SEQ ID NO:750, SEQ ID NO:751, SEQ ID NO:752, SEQ ID NO:753, SEQ ID NO:754, SEQ ID NO:755, SEQ ID NO:756, SEQ ID NO:757, SEQ ID NO:758, SEQ ID NO:759, SEQ ID NO:760, SEQ ID NO:761, SEQ ID NO:762, SEQ ID NO:763, SEQ ID NO:764, SEQ ID NO:765, SEQ ID NO:766, SEQ ID NO:767, SEQ ID NO:768, SEQ ID NO:769, SEQ ID NO:770, SEQ ID NO:771, SEQ ID NO:772, SEQ ID NO:773, SEQ ID NO:774, SEQ ID NO:775, SEQ ID NO:776, SEQ ID NO:777, SEQ ID NO:778, SEQ ID NO:779, SEQ ID NO:780, SEQ ID NO:781, SEQ ID NO:782, SEQ ID NO:783, SEQ ID NO:784, SEQ ID NO:785, SEQ ID NO:786, SEQ ID NO:787, SEQ ID NO:788, SEQ ID NO:789, SEQ ID NO:790, SEQ ID NO:791, SEQ ID NO:792, SEQ ID NO:793, SEQ ID NO:794, SEQ ID NO:795, SEQ ID NO:796, SEQ ID NO:797, SEQ ID NO:798, SEQ ID NO:799, SEQ ID NO:800, SEQ ID NO:801, SEQ ID NO:802, SEQ ID NO:803, SEQ ID NO:804, SEQ ID NO:805, SEQ ID NO:806, SEQ ID NO:807, SEQ ID NO:808, SEQ ID NO:809, SEQ ID NO:810, SEQ ID NO:813, SEQ ID NO:814, SEQ ID NO:815, SEQ ID NO:816, SEQ ID NO:817, SEQ ID NO:818, SEQ ID NO:819, SEQ ID NO:820, SEQ ID NO:821, SEQ ID NO:822, SEQ ID NO:823, SEQ ID NO:824, SEQ ID NO:825, SEQ ID NO:826, SEQ ID NO:827, SEQ ID NO:828, SEQ ID NO:829, SEQ ID NO:830, SEQ ID NO:831, SEQ ID NO:832, SEQ ID NO:833, SEQ ID NO:834, SEQ ID NO:835, SEQ ID NO:836, SEQ ID NO:837, SEQ ID NO:838, SEQ ID NO:839, SEQ ID NO:840, SEQ ID NO:841, SEQ ID NO:842, SEQ ID NO:843, SEQ ID NO:844, SEQ ID NO:845, SEQ ID NO:846, SEQ ID NO:847, SEQ ID NO:848, SEQ ID NO:849, SEQ ID NO:850, SEQ ID NO:851, SEQ ID NO:852, SEQ ID NO:853, SEQ ID NO:855, SEQ ID NO:856, SEQ ID NO:857, SEQ ID NO:858, SEQ ID NO:859, SEQ ID NO:860, SEQ ID NO:861, SEQ ID NO:862, SEQ ID NO:863, SEQ ID NO:864, SEQ ID NO:865, SEQ ID NO:866, SEQ ID NO:868, SEQ ID NO:869, SEQ ID NO:870, SEQ ID NO:871, SEQ ID NO:872, SEQ ID NO:873, SEQ ID NO:874, SEQ ID NO:875, SEQ ID NO:876, SEQ ID NO:877, SEQ ID NO:878, SEQ ID NO:879, SEQ ID NO:880, SEQ ID NO:881, SEQ ID NO:882, SEQ ID NO:883, SEQ ID NO:884, SEQ ID NO:885, SEQ ID NO:886, SEQ ID NO:887, SEQ ID NO:888, SEQ ID NO:889, SEQ ID NO:890, SEQ ID NO:891, SEQ ID NO:892, SEQ ID NO:893, SEQ ID NO:894, SEQ ID NO:895, SEQ ID NO:896, SEQ ID NO:897, SEQ ID NO:898, SEQ ID NO:899, SEQ ID NO:900, SEQ ID NO:901, SEQ ID NO:902, SEQ ID NO:903, SEQ ID NO:904, SEQ ID NO:905, SEQ ID NO:906, SEQ ID NO:907, SEQ ID NO:908, SEQ ID NO:909, SEQ ID NO:910, SEQ ID NO:911, SEQ ID NO:913, SEQ ID NO:914, SEQ ID NO:915, SEQ ID NO:916, SEQ ID NO:917, SEQ ID NO:918, SEQ ID NO:919, SEQ ID NO:920, SEQ ID NO:921, SEQ ID NO:923, SEQ ID NO:924, SEQ ID NO:925, SEQ ID NO:926, SEQ ID NO:927, SEQ ID NO:928, SEQ ID NO:929, SEQ ID NO:930, SEQ ID NO:931, SEQ ID NO:932, SEQ ID NO:933, SEQ ID NO:934, SEQ ID NO:935, SEQ ID NO:936, SEQ ID NO:937, SEQ ID NO:938, SEQ ID NO:939, SEQ ID NO:940, SEQ ID NO:941, SEQ ID NO:942, SEQ ID NO:943, SEQ ID NO:944, SEQ ID NO:945, SEQ ID NO:946, SEQ ID NO:947, SEQ ID NO:948, SEQ ID NO:949, SEQ ID NO:951, SEQ ID NO:952, SEQ ID NO:953, SEQ ID NO:954, SEQ ID NO:955, SEQ ID NO:956, SEQ ID NO:957, SEQ ID NO:958, SEQ ID NO:959, SEQ ID NO:960, SEQ ID NO:961, SEQ ID NO:962, SEQ ID NO:963, SEQ ID NO:964, SEQ ID NO:965, SEQ ID NO:966, SEQ ID NO:967, SEQ ID NO:968, SEQ ID NO:969, SEQ ID NO:970, SEQ ID NO:972, SEQ ID NO:973, SEQ ID NO:974, SEQ ID NO:975, SEQ ID NO:976, SEQ ID NO:977, SEQ ID NO:978, SEQ ID NO:979, SEQ ID NO:980, SEQ ID NO:981, SEQ ID NO:982, SEQ ID NO:983, SEQ ID NO:984, SEQ ID NO:985, SEQ ID NO:986, SEQ ID NO:987, SEQ ID NO:988, SEQ ID NO:989, SEQ ID NO:990, SEQ ID NO:991, SEQ ID NO:992, SEQ ID NO:993, SEQ ID NO:994, SEQ ID NO:995, SEQ ID NO:996, SEQ ID NO:997, SEQ ID NO:998, SEQ ID NO:999, SEQ ID NO:1000, SEQ ID NO:1001, SEQ ID NO:1002, SEQ ID NO:1003, SEQ ID NO:1004.

The methods of the invention may further include detecting the expression level of one or more additional genes in said patient to diagnose or monitor auto immune and chronic inflammatory diseases in a patient, wherein said one or more additional genes identified by a nucleotide sequence selected from the following group: SEQ ID NO:504, SEQ ID NO:507, SEQ ID NO:603, SEQ ID NO:740, SEQ ID NO:811, SEQ ID NO:812, SEQ ID NO:854, SEQ ID NO:867, SEQ ID NO:912, SEQ ID NO:922, SEQ ID NO:950, SEQ ID NO:971.

In the method of the invention, the chronic inflammatory disease or autoimmune disease may be systemic lupus erythematosis (SLE), Rheumatoid Arthritis, Cholecystitis, Sjogrens Disease, CREST syndrome, Scleroderma, Ankylosing Spondylitis, Crohn's, Ulcerative Colitis, Primary Sclerosing Cholangitis, Appendicitis, Diverticulitis, Primary Biliary Sclerosis, Wegener's Granulomatosis, Polyarteritis nodosa, Whipple's Disease, Psoriasis, Microscopic Polyanngiitis, Takayasu's Disease, Kawasaki's Disease, Autoimmune hepatitis, Asthma, Churg-Strauss Disease, Beurger's Disease, Raynaud's Disease, or Cholecystitis.

In one format, expression is detecting by measuring RNA levels or protein levels from the genes. Example of detecting of such detection include measuring protein in serum, measuring cell surface proteins, measuring using a a fluorescent activated cell sorter.

In the method of the invention, RNA may be isolated from the patient prior to detecting expression of a gene such as those depicted in Table 2E. RNA levels may be detected by PCR or hybridization. The nucleotide sequence may include comprises DNA, cDNA, PNA, genomic DNA, or synthetic oligonucleotides. The hybridization methods of the present invention may include high stringency, moderate stringency, or low stringency hybridization conditions.

In the methods of the invention, the RNA may be detected by hybridization to an oligonucleotide having a nucleotide sequence selected from SEQ ID NO:503, SEQ ID NO:504, SEQ ID NO:505, SEQ ID NO:506, SEQ ID NO:507, SEQ ID NO:508, SEQ ID NO:509, SEQ ID NO:510, SEQ ID NO:511, SEQ ID NO:512, SEQ ID NO:513, SEQ ID NO:514, SEQ ID NO:515, SEQ ID NO:516, SEQ ID NO:517, SEQ ID NO:518, SEQ ID NO:519, SEQ ID NO:520, SEQ ID NO:521, SEQ ID NO:522, SEQ ID NO:523, SEQ ID NO:524, SEQ ID NO:525, SEQ ID NO:526, SEQ ID NO:527, SEQ ID NO:528, SEQ ID NO:529, SEQ ID NO:530, SEQ ID NO:531, SEQ ID NO:532, SEQ ID NO:533, SEQ ID NO:534, SEQ ID NO:535, SEQ ID NO:536, SEQ ID NO:537, SEQ ID NO:538, SEQ ID NO:539, SEQ ID NO:540, SEQ ID NO:541, SEQ ID NO:542, SEQ ID NO:543, SEQ ID NO:544, SEQ ID NO:545, SEQ ID NO:546, SEQ ID NO:547, SEQ ID NO:548, SEQ ID NO:549, SEQ ID NO:550, SEQ ID NO:551, SEQ ID NO:552, SEQ ID NO:553, SEQ ID NO:554, SEQ ID NO:555, SEQ ID NO:556, SEQ ID NO:557, SEQ ID NO:558, SEQ ID NO:559, SEQ ID NO:560, SEQ ID NO:561, SEQ ID NO:562, SEQ ID NO:563, SEQ ID NO:564, SEQ ID NO:565, SEQ ID NO:566, SEQ ID NO:567, SEQ ID NO:568, SEQ ID NO:569, SEQ ID NO:570, SEQ ID NO:571, SEQ ID NO:572, SEQ ID NO:573, SEQ ID NO:574, SEQ ID NO:575, SEQ ID NO:576, SEQ ID NO:577, SEQ ID NO:578, SEQ ID NO:579, SEQ ID NO:580, SEQ ID NO:581, SEQ ID NO:582, SEQ ID NO:583, SEQ ID NO:584, SEQ ID NO:585, SEQ ID NO:586, SEQ ID NO:587, SEQ ID NO:588, SEQ ID NO:589, SEQ ID NO:590, SEQ ID NO:591, SEQ ID NO:592, SEQ ID NO:593, SEQ ID NO:594, SEQ ID NO:595, SEQ ID NO:596, SEQ ID NO:597, SEQ ID NO:598, SEQ ID NO:599, SEQ ID NO:600, SEQ ID NO:601, SEQ ID NO:602, SEQ ID NO:603, SEQ ID NO:604, SEQ ID NO:605, SEQ ID NO:606, SEQ ID NO:607, SEQ ID NO:608, SEQ ID NO:609, SEQ ID NO:610, SEQ ID NO:611, SEQ ID NO:612, SEQ ID NO:613, SEQ ID NO:614, SEQ ID NO:615, SEQ ID NO:616, SEQ ID NO:617, SEQ ID NO:618, SEQ ID NO:619, SEQ ID NO:620, SEQ ID NO:621, SEQ ID NO:622, SEQ ID NO:623, SEQ ID NO:624, SEQ ID NO:625, SEQ ID NO:626, SEQ ID NO:627, SEQ ID NO:628, SEQ ID NO:629, SEQ ID NO:630, SEQ ID NO:631, SEQ ID NO:632, SEQ ID NO:633, SEQ ID NO:634, SEQ ID NO:635, SEQ ID NO:636, SEQ ID NO:637, SEQ ID NO:638, SEQ ID NO:639, SEQ ID NO:640, SEQ ID NO:641, SEQ ID NO:642, SEQ ID NO:643, SEQ ID NO:644, SEQ ID NO:645, SEQ ID NO:646, SEQ ID NO:647, SEQ ID NO:648, SEQ ID NO:649, SEQ ID NO:650, SEQ ID NO:651, SEQ ID NO:652, SEQ ID NO:653, SEQ ID NO:654, SEQ ID NO:655, SEQ ID NO:656, SEQ ID NO:657, SEQ ID NO:658, SEQ ID NO:659, SEQ ID NO:660, SEQ ID NO:661, SEQ ID NO:662, SEQ ID NO:663, SEQ ID NO:664, SEQ ID NO:665, SEQ ID NO:666, SEQ ID NO:667, SEQ ID NO:668, SEQ ID NO:669, SEQ ID NO:670, SEQ ID NO:671, SEQ ID NO:672, SEQ ID NO:673, SEQ ID NO:674, SEQ ID NO:675, SEQ ID NO:676, SEQ ID NO:677, SEQ ID NO:678, SEQ ID NO:679, SEQ ID NO:680, SEQ ID NO:681, SEQ ID NO:682, SEQ ID NO:683, SEQ ID NO:684, SEQ ID NO:685, SEQ ID NO:686, SEQ ID NO:687, SEQ ID NO:688, SEQ ID NO:689, SEQ ID NO:690, SEQ ID NO:691, SEQ ID NO:692, SEQ ID NO:693, SEQ ID NO:694, SEQ ID NO:695, SEQ ID NO:696, SEQ ID NO:697, SEQ ID NO:698, SEQ ID NO:699, SEQ ID NO:700, SEQ ID NO:701, SEQ ID NO:702, SEQ ID NO:703, SEQ ID NO:704, SEQ ID NO:705, SEQ ID NO:706, SEQ ID NO:707, SEQ ID NO:708, SEQ ID NO:709, SEQ ID NO:710, SEQ ID NO:711, SEQ ID NO:712, SEQ ID NO:713, SEQ ID NO:714, SEQ ID NO:715, SEQ ID NO:716, SEQ ID NO:717, SEQ ID NO:718, SEQ ID NO:719, SEQ ID NO:720, SEQ ID NO:721, SEQ ID NO:722, SEQ ID NO:723, SEQ ID NO:724, SEQ ID NO:725, SEQ ID NO:726, SEQ ID NO:727, SEQ ID NO:728, SEQ ID NO:729, SEQ ID NO:730, SEQ ID NO:731, SEQ ID NO:732, SEQ ID NO:733, SEQ ID NO:734, SEQ ID NO:735, SEQ ID NO:736, SEQ ID NO:737, SEQ ID NO:738, SEQ ID NO:739, SEQ ID NO:740, SEQ ID NO:741, SEQ ID NO:742, SEQ ID NO:743, SEQ ID NO:744, SEQ ID NO:745, SEQ ID NO:746, SEQ ID NO:747, SEQ ID NO:748, SEQ ID NO:749, SEQ ID NO:750, SEQ ID NO:751, SEQ ID NO:752, SEQ ID NO:753, SEQ ID NO:754, SEQ ID NO:755, SEQ ID NO:756, SEQ ID NO:757, SEQ ID NO:758, SEQ ID NO:759, SEQ ID NO:760, SEQ ID NO:761, SEQ ID NO:762, SEQ ID NO:763, SEQ ID NO:764, SEQ ID NO:765, SEQ ID NO:766, SEQ ID NO:767, SEQ ID NO:768, SEQ ID NO:769, SEQ ID NO:770, SEQ ID NO:771, SEQ ID NO:772, SEQ ID NO:773, SEQ ID NO:774, SEQ ID NO:775, SEQ ID NO:776, SEQ ID NO:777, SEQ ID NO:778, SEQ ID NO:779, SEQ ID NO:780, SEQ ID NO:781, SEQ ID NO:782, SEQ ID NO:783, SEQ ID NO:784, SEQ ID NO:785, SEQ ID NO:786, SEQ ID NO:787, SEQ ID NO:788, SEQ ID NO:789, SEQ ID NO:790, SEQ ID NO:791, SEQ ID NO:792, SEQ ID NO:793, SEQ ID NO:794, SEQ ID NO:795, SEQ ID NO:796, SEQ ID NO:797, SEQ ID NO:798, SEQ ID NO:799, SEQ ID NO:800, SEQ ID NO:801, SEQ ID NO:802, SEQ ID NO:803, SEQ ID NO:804, SEQ ID NO:805, SEQ ID NO:806, SEQ ID NO:807, SEQ ID NO:808, SEQ ID NO:809, SEQ ID NO:810, SEQ ID NO:811, SEQ ID NO:812, SEQ ID NO:813, SEQ ID NO:814, SEQ ID NO:815, SEQ ID NO:816, SEQ ID NO:817, SEQ ID NO:818, SEQ ID NO:819, SEQ ID NO:820, SEQ ID NO:821, SEQ ID NO:822, SEQ ID NO:823, SEQ ID NO:824, SEQ ID NO:825, SEQ ID NO:826, SEQ ID NO:827) SEQ ID NO:828, SEQ ID NO:829, SEQ ID NO:830, SEQ ID NO:831, SEQ ID NO:832, SEQ ID NO:833, SEQ ID NO:834, SEQ ID NO:835, SEQ ID NO:836, SEQ ID NO:837, SEQ ID NO:838, SEQ ID NO:839, SEQ ID NO:840, SEQ ID NO:841, SEQ ID NO:842, SEQ ID NO:843, SEQ ID NO:844, SEQ ID NO:845, SEQ ID NO:846, SEQ ID NO:847, SEQ ID NO:848, SEQ ID NO:849, SEQ ID NO:850, SEQ ID NO:851, SEQ ID NO:852, SEQ ID NO:853, SEQ ID NO:854, SEQ ID NO:855, SEQ ID NO:856, SEQ ID NO:857, SEQ ID NO:858, SEQ ID NO:859, SEQ ID NO:860, SEQ ID NO:861, SEQ ID NO:862, SEQ ID NO:863, SEQ ID NO:864, SEQ ID NO:865, SEQ ID NO:866, SEQ ID NO:867, SEQ ID NO:868, SEQ ID NO:869, SEQ ID NO:870, SEQ ID NO:871, SEQ ID NO:872, SEQ ID NO:873, SEQ ID NO:874, SEQ ID NO:875, SEQ ID NO:876, SEQ ID NO:877, SEQ ID NO:878, SEQ ID NO:879, SEQ ID NO:880, SEQ ID NO:881, SEQ ID NO:882, SEQ ID NO:883, SEQ ID NO:884, SEQ ID NO:885, SEQ ID NO:886, SEQ ID NO:887, SEQ ID NO:888, SEQ ID NO:889, SEQ ID NO:890, SEQ ID NO:891, SEQ ID NO:892, SEQ ID NO:893, SEQ ID NO:894, SEQ ID NO:895, SEQ ID NO:896, SEQ ID NO:897, SEQ ID NO:898, SEQ ID NO:899, SEQ ID NO:900, SEQ ID NO:901, SEQ ID NO:902, SEQ ID NO:903, SEQ ID NO:904, SEQ ID NO:905, SEQ ID NO:906, SEQ ID NO:907, SEQ ID NO:908, SEQ ID NO:909, SEQ ID NO:910, SEQ ID NO:911, SEQ ID NO:912, SEQ ID NO:913, SEQ ID NO:914, SEQ ID NO:915, SEQ ID NO:916, SEQ ID NO:917, SEQ ID NO:918, SEQ ID NO:919, SEQ ID NO:920, SEQ ID NO:921, SEQ ID NO:922, SEQ ID NO:923, SEQ ID NO:924, SEQ ID NO:925, SEQ ID NO:926, SEQ ID NO:927, SEQ ID NO:928, SEQ ID NO:929, SEQ ID NO:930, SEQ ID NO:931, SEQ ID NO:932, SEQ ID NO:933, SEQ ID NO:934, SEQ ID NO:935, SEQ ID NO:936, SEQ ID NO:937, SEQ ID NO:938, SEQ ID NO:939, SEQ ID NO:940, SEQ ID NO:941, SEQ ID NO:942, SEQ ID NO:943, SEQ ID NO:944, SEQ ID NO:945, SEQ ID NO:946, SEQ ID NO:947, SEQ ID NO:948, SEQ ID NO:949, SEQ ID NO:950, SEQ ID NO:951, SEQ ID NO:952, SEQ ID NO:953, SEQ ID NO:954, SEQ ID NO:955, SEQ ID NO:956, SEQ ID NO:957, SEQ ID NO:958, SEQ ID NO:959, SEQ ID NO:960, SEQ ID NO:961, SEQ ID NO:962, SEQ ID NO:963, SEQ ID NO:964, SEQ ID NO:965, SEQ ID NO:966, SEQ ID NO:967, SEQ ID NO:968, SEQ ID NO:969, SEQ ID NO:970, SEQ ID NO:971, SEQ ID NO:972, SEQ ID NO:973, SEQ ID NO:974, SEQ ID NO:975, SEQ ID NO:976, SEQ ID NO:977, SEQ ID NO:978, SEQ ID NO:979, SEQ ID NO:980, SEQ ID NO:981, SEQ ID NO:982, SEQ ID NO:983, SEQ ID NO:984, SEQ ID NO:985, SEQ ID NO:986, SEQ ID NO:987, SEQ ID NO:988, SEQ ID NO:989, SEQ ID NO:990, SEQ ID NO:991, SEQ ID NO:992, SEQ ID NO:993, SEQ ID NO:994, SEQ ID NO:995, SEQ ID NO:996, SEQ ID NO:997, SEQ ID NO:998, SEQ ID NO:999, SEQ ID NO:1000, SEQ ID NO:1001, SEQ ID NO:1002, SEQ ID NO:1003, SEQ ID NO:1004.

The methods of the present invention further includes detection of proteins expressed by one or more genes with an amino acid sequence encoded by a nucleotide sequence selected from the following group SEQ ID NO:1, SEQ ID NO:3, SEQ ID NO:4, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, SEQ ID NO:111, SEQ ID NO:112, SEQ ID NO:113, SEQ ID NO:114, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124, SEQ ID NO:125, SEQ ID NO:126, SEQ ID NO:127, SEQ ID NO:128, SEQ ID NO:129, SEQ ID NO:130, SEQ ID NO:131, SEQ ID NO:132, SEQ ID NO:133, SEQ ID NO:134, SEQ ID NO:135, SEQ ID NO:136, SEQ ID NO:137, SEQ ID NO:138, SEQ ID NO:139, SEQ ID NO:140, SEQ ID NO:141, SEQ ID NO:142, SEQ ID NO:143, SEQ ID NO:144, SEQ ID NO:145, SEQ ID NO:146, SEQ ID NO:147, SEQ ID NO:148, SEQ ID NO:149, SEQ ID NO:150, SEQ ID NO:151, SEQ ID NO:152, SEQ ID NO:153, SEQ ID NO:154, SEQ ID NO:155, SEQ ID NO:156, SEQ ID NO:157, SEQ ID NO:158, SEQ ID NO:159, SEQ ID NO:160, SEQ ID NO:161, SEQ ID NO:162, SEQ ID NO:163, SEQ ID NO:164, SEQ ID NO:165, SEQ ID NO:166, SEQ ID NO:167, SEQ ID NO:168, SEQ ID NO:169, SEQ ID NO:170, SEQ ID NO:171, SEQ ID NO:172, SEQ ID NO:173, SEQ ID NO:174, SEQ ID NO:175, SEQ ID NO:176, SEQ ID NO:177, SEQ ID NO:178, SEQ ID NO:179, SEQ ID NO:180, SEQ ID NO:181, SEQ ID NO:182, SEQ ID NO:183, SEQ ID NO:184, SEQ ID NO:185, SEQ ID NO:186, SEQ ID NO:187, SEQ ID NO:188, SEQ ID NO:189, SEQ ID NO:190, SEQ ID NO:191, SEQ ID NO:192, SEQ ID NO:193, SEQ ID NO:194, SEQ ID NO:195, SEQ ID NO:196, SEQ ID NO:197, SEQ ID NO:198, SEQ ID NO:199, SEQ ID NO:200, SEQ ID NO:201, SEQ ID NO:202, SEQ ID NO:203, SEQ ID NO:204, SEQ ID NO:205, SEQ ID NO:206, SEQ ID NO:207, SEQ ID NO:208, SEQ ID NO:209, SEQ ID NO:210, SEQ ID NO:211, SEQ ID NO:212, SEQ ID NO:213, SEQ ID NO:214, SEQ ID NO:215, SEQ ID NO:216, SEQ ID NO:217, SEQ ID NO:218, SEQ ID NO:219, SEQ ID NO:220, SEQ ID NO:221, SEQ ID NO:222, SEQ ID NO:223, SEQ ID NO:224, SEQ ID NO:225, SEQ ID NO:226, SEQ ID NO:227, SEQ ID NO:228, SEQ ID NO:229, SEQ ID NO:230, SEQ ID NO:231, SEQ ID NO:232, SEQ ID NO:233, SEQ ID NO:234, SEQ ID NO:235, SEQ ID NO:236, SEQ ID NO:237, SEQ ID NO:239, SEQ ID NO:240, SEQ ID NO:241, SEQ ID NO:242, SEQ ID NO:243, SEQ ID NO:244, SEQ ID NO:245, SEQ ID NO:246, SEQ ID NO:247, SEQ ID NO:248, SEQ ID NO:249, SEQ ID NO:250, SEQ ID NO:251, SEQ ID NO:252, SEQ ID NO:253, SEQ ID NO:254, SEQ ID NO:255, SEQ ID NO:256, SEQ ID NO:257, SEQ ID NO:258, SEQ ID NO:259, SEQ ID NO:260, SEQ ID NO:261, SEQ ID NO:262, SEQ ID NO:263, SEQ ID NO:264, SEQ ID NO:265, SEQ ID NO:266, SEQ ID NO:267, SEQ ID NO:268, SEQ ID NO:269, SEQ ID NO:270, SEQ ID NO:271, SEQ ID NO:272, SEQ ID NO:273, SEQ ID NO:274, SEQ ID NO:275, SEQ ID NO:276, SEQ ID NO:277, SEQ ID NO:278, SEQ ID NO:279, SEQ ID NO:280, SEQ ID NO:281, SEQ ID NO:282, SEQ ID NO:283, SEQ ID NO:284, SEQ ID NO:285, SEQ ID NO:286, SEQ ID NO:287, SEQ ID NO:288, SEQ ID NO:289, SEQ ID NO:290, SEQ ID NO:291, SEQ ID NO:292, SEQ ID NO:293, SEQ ID NO:294, SEQ ID NO:295, SEQ ID NO:296, SEQ ID NO:297, SEQ ID NO:298, SEQ ID NO:299, SEQ ID NO:300, SEQ ID NO:301, SEQ ID NO:302, SEQ ID NO:303, SEQ ID NO:304, SEQ ID NO:305, SEQ ID NO:306, SEQ ID NO:307, SEQ ID NO:308, SEQ ID NO:311, SEQ ID NO:312, SEQ ID NO:313, SEQ ID NO:314, SEQ ID NO:315, SEQ ID NO:316, SEQ ID NO:317, SEQ ID NO:318, SEQ ID NO:319, SEQ ID NO:320, SEQ ID NO:321, SEQ ID NO:322, SEQ ID NO:323, SEQ ID NO:324, SEQ ID NO:325, SEQ ID NO:326, SEQ ID NO:327, SEQ ID NO:328, SEQ ID NO:329, SEQ ID NO:330, SEQ ID NO:331, SEQ ID NO:332, SEQ ID NO:333, SEQ ID NO:334, SEQ ID NO:335, SEQ ID NO:336, SEQ ID NO:337, SEQ ID NO:338, SEQ ID NO:339, SEQ ID NO:340, SEQ ID NO:341, SEQ ID NO:342, SEQ ID NO:343, SEQ ID NO:344, SEQ ID NO:345, SEQ ID NO:346, SEQ ID NO:347, SEQ ID NO:348, SEQ ID NO:349, SEQ ID NO:350, SEQ ID NO:351, SEQ ID NO:353, SEQ ID NO:354, SEQ ID NO:355, SEQ ID NO:356, SEQ ID NO:357, SEQ ID NO:358, SEQ ID NO:359, SEQ ID NO:360, SEQ ID NO:361, SEQ ID NO:362, SEQ ID NO:363, SEQ ID NO:364, SEQ ID NO:366, SEQ ID NO:367, SEQ ID NO:368, SEQ ID NO:369, SEQ ID NO:370, SEQ ID NO:371, SEQ ID NO:372, SEQ ID NO:373, SEQ ID NO:374, SEQ ID NO:375, SEQ ID NO:376, SEQ ID NO:377, SEQ ID NO:378, SEQ ID NO:379, SEQ ID NO:380, SEQ ID NO:381, SEQ ID NO:382, SEQ ID NO:383, SEQ ID NO:384, SEQ ID NO:385, SEQ ID NO:386, SEQ ID NO:387, SEQ ID NO:388, SEQ ID NO:389, SEQ ID NO:390, SEQ ID NO:391, SEQ ID NO:392, SEQ ID NO:393, SEQ ID NO:394, SEQ ID NO:395, SEQ ID NO:396, SEQ ID NO:397, SEQ ID NO:398, SEQ ID NO:399, SEQ ID NO:400, SEQ ID NO:401, SEQ ID NO:402, SEQ ID NO:403, SEQ ID NO:404, SEQ ID NO:405, SEQ ID NO:406, SEQ ID NO:407, SEQ ID NO:408, SEQ ID NO:409, SEQ ID NO:411, SEQ ID NO:412, SEQ ID NO:413, SEQ ID NO:414, SEQ ID NO:415, SEQ ID NO:416, SEQ ID NO:417, SEQ ID NO:418, SEQ ID NO:419, SEQ ID NO:421, SEQ ID NO:422, SEQ ID NO:423, SEQ ID NO:424, SEQ ID NO:425, SEQ ID NO:426, SEQ ID NO:427, SEQ ID NO:428, SEQ ID NO:429, SEQ ID NO:430, SEQ ID NO:431, SEQ ID NO:432, SEQ ID NO:433, SEQ ID NO:434, SEQ ID NO:435, SEQ ID NO:436, SEQ ID NO:437, SEQ ID NO:438, SEQ ID NO:439, SEQ ID NO:440, SEQ ID NO:441, SEQ ID NO:442, SEQ ID NO:443, SEQ ID NO:444, SEQ ID NO:445, SEQ ID NO:446, SEQ ID NO:447, SEQ ID NO:449, SEQ ID NO:450, SEQ ID NO:451, SEQ ID NO:452, SEQ ID NO:453, SEQ ID NO:454, SEQ ID NO:455, SEQ ID NO:456, SEQ ID NO:457, SEQ ID NO:458, SEQ ID NO:459, SEQ ID NO:460, SEQ ID NO:461, SEQ ID NO:462, SEQ ID NO:463, SEQ ID NO:464, SEQ ID NO:465, SEQ ID NO:466, SEQ ID NO:467, SEQ ID NO:468, SEQ ID NO:470, SEQ ID NO:471, SEQ ID NO:472, SEQ ID NO:473, SEQ ID NO:474, SEQ ID NO:475, SEQ ID NO:476, SEQ ID NO:477, SEQ ID NO:478, SEQ ID NO:479, SEQ ID NO:480, SEQ ID NO:481, SEQ ID NO:482, SEQ ID NO:483, SEQ ID NO:484, SEQ ID NO:485, SEQ ID NO:486, SEQ ID NO:487, SEQ ID NO:488, SEQ ID NO:489, SEQ ID NO:490, SEQ ID NO:491, SEQ ID NO:492, SEQ ID NO:493, SEQ ID NO:494, SEQ ID NO:495, SEQ ID NO:496, SEQ ID NO:497, SEQ ID NO:498, SEQ ID NO:499, SEQ ID NO:500, SEQ ID NO:501, SEQ ID NO:502.

The methods of the present invention further include detection of one or more proteins expressed by one or more additional genes with an amino acid sequence encoded by a nucleotide sequence selected from the following group SEQ ID NO:2, SEQ ID NO:5, SEQ ID NO:101, SEQ ID NO:238, SEQ ID NO:309, SEQ ID NO:310, SEQ ID NO:352, SEQ ID NO:365, SEQ ID NO:410, SEQ ID NO:420, SEQ ID NO:448, SEQ ID NO:469.

The present invention is further directed to a diagnostic oligonucleotide for detecting chronic or inflammatory disease wherein the oligonucleotide has a nucleotide sequence selected from SEQ ID NO:503, SEQ ID NO:504, SEQ ID NO:505, SEQ ID NO:506, SEQ ID NO:507, SEQ ID NO:508, SEQ ID NO:509, SEQ ID NO:510, SEQ ID NO:511, SEQ ID NO:512, SEQ ID NO:513, SEQ ID NO:514, SEQ ID NO:515, SEQ ID NO:516, SEQ ID NO:517, SEQ ID NO:518, SEQ ID NO:519, SEQ ID NO:520, SEQ ID NO:521, SEQ ID NO:522, SEQ ID NO:523, SEQ ID NO:524, SEQ ID NO:525, SEQ ID NO:526, SEQ ID NO:527, SEQ ID NO:528, SEQ ID NO:529, SEQ ID NO:530, SEQ ID NO:531, SEQ ID NO:532, SEQ ID NO:533, SEQ ID NO:534, SEQ ID NO:535, SEQ ID NO:536, SEQ ID NO:537, SEQ ID NO:538, SEQ ID NO:539, SEQ ID NO:540, SEQ ID NO:541, SEQ ID NO:542, SEQ ID NO:543, SEQ ID NO:544, SEQ ID NO:545, SEQ ID NO:546, SEQ ID NO:547, SEQ ID NO:548, SEQ ID NO:549, SEQ ID NO:550, SEQ ID NO:551, SEQ ID NO:552, SEQ ID NO:553, SEQ ID NO:554, SEQ ID NO:555, SEQ ID NO:556, SEQ ID NO:557, SEQ ID NO:558, SEQ ID NO:559, SEQ ID NO:560, SEQ ID NO:561, SEQ ID NO:562, SEQ ID NO:563, SEQ ID NO:564, SEQ ID NO:565, SEQ ID NO:566, SEQ ID NO:567, SEQ ID NO:568, SEQ ID NO:569, SEQ ID NO:570, SEQ ID NO:571, SEQ ID NO:572, SEQ ID NO:573, SEQ ID NO:574, SEQ ID NO:575, SEQ ID NO:576, SEQ ID NO:577, SEQ ID NO:578, SEQ ID NO:579, SEQ ID NO:580, SEQ ID NO:581, SEQ ID NO:582, SEQ ID NO:583, SEQ ID NO:584, SEQ ID NO:585, SEQ ID NO:586, SEQ ID NO:587, SEQ ID NO:588, SEQ ID NO:589, SEQ ID NO:590, SEQ ID NO:591, SEQ ID NO:592, SEQ ID NO:593, SEQ ID NO:594, SEQ ID NO:595, SEQ ID NO:596, SEQ ID NO:597, SEQ ID NO:598, SEQ ID NO:599, SEQ ID NO:600, SEQ ID NO:601, SEQ ID NO:602, SEQ ID NO:603, SEQ ID NO:604, SEQ ID NO:605, SEQ ID NO:606, SEQ ID NO:607, SEQ ID NO:608, SEQ ID NO:609, SEQ ID NO:610, SEQ ID NO:611, SEQ ID NO:612, SEQ ID NO:613, SEQ ID NO:614, SEQ ID NO:615, SEQ ID NO:616, SEQ ID NO:617, SEQ ID NO:618, SEQ ID NO:619, SEQ ID NO:620, SEQ ID NO:621, SEQ ID NO:622, SEQ ID NO:623, SEQ ID NO:624, SEQ ID NO:625, SEQ ID NO:626, SEQ ID NO:627, SEQ ID NO:628, SEQ ID NO:629, SEQ ID NO:630, SEQ ID NO:631, SEQ ID NO:632, SEQ ID NO:633, SEQ ID NO:634, SEQ ID NO:635, SEQ ID NO:636, SEQ ID NO:637, SEQ ID NO:638, SEQ ID NO:639, SEQ ID NO:640, SEQ ID NO:641, SEQ ID NO:642, SEQ ID NO:643, SEQ ID NO:644, SEQ ID NO:645, SEQ ID NO:646, SEQ ID NO:647, SEQ ID NO:648, SEQ ID NO:649, SEQ ID NO:650, SEQ ID NO:651, SEQ ID NO:652, SEQ ID NO:653, SEQ ID NO:654, SEQ ID NO:655, SEQ ID NO:656, SEQ ID NO:657, SEQ ID NO:658, SEQ ID NO:659, SEQ ID NO:660, SEQ ID NO:661, SEQ ID NO:662, SEQ ID NO:663, SEQ ID NO:664, SEQ ID NO:665, SEQ ID NO:666, SEQ ID NO:667, SEQ ID NO:668, SEQ ID NO:669, SEQ ID NO:670, SEQ ID NO:671, SEQ ID NO:672, SEQ ID NO:673, SEQ ID NO:674, SEQ ID NO:675, SEQ ID NO:676, SEQ ID NO:677, SEQ ID NO:678, SEQ ID NO:679, SEQ ID NO:680, SEQ ID NO:681, SEQ ID NO:682, SEQ ID NO:683, SEQ ID NO:684, SEQ ID NO:685, SEQ ID NO:686, SEQ ID NO:687, SEQ ID NO:688, SEQ ID NO:689, SEQ ID NO:690, SEQ ID NO:691, SEQ ID NO:692, SEQ ID NO:693, SEQ ID NO:694, SEQ ID NO:695, SEQ ID NO:696, SEQ ID NO:697, SEQ ID NO:698, SEQ ID NO:699, SEQ ID NO:700, SEQ ID NO:701, SEQ ID NO:702, SEQ ID NO:703, SEQ ID NO:704, SEQ ID NO:705, SEQ ID NO:706, SEQ ID NO:707, SEQ ID NO:708, SEQ ID NO:709, SEQ ID NO:710, SEQ ID NO:711, SEQ ID NO:712, SEQ ID NO:713, SEQ ID NO:714, SEQ ID NO:715, SEQ ID NO:716, SEQ ID NO:717, SEQ ID NO:718, SEQ ID NO:719, SEQ ID NO:720, SEQ ID NO:721, SEQ ID NO:722, SEQ ID NO:723, SEQ ID NO:724, SEQ ID NO:725, SEQ ID NO:726, SEQ ID NO:727, SEQ ID NO:728, SEQ ID NO:729, SEQ ID NO:730, SEQ ID NO:731, SEQ ID NO:732, SEQ ID NO:733, SEQ ID NO:734, SEQ ID NO:735, SEQ ID NO:736, SEQ ID NO:737, SEQ ID NO:738, SEQ ID NO:739, SEQ ID NO:740, SEQ ID NO:741, SEQ ID NO:742, SEQ ID NO:743, SEQ ID NO:744, SEQ ID NO:745, SEQ ID NO:746, SEQ ID NO:747, SEQ ID NO:748, SEQ ID NO:749, SEQ ID NO:750, SEQ ID NO:751, SEQ ID NO:752, SEQ ID NO:753, SEQ ID NO:754, SEQ ID NO:755, SEQ ID NO:756, SEQ ID NO:757, SEQ ID NO:758, SEQ ID NO:759, SEQ ID NO:760, SEQ ID NO:761, SEQ ID NO:762, SEQ ID NO:763, SEQ ID NO:764, SEQ ID NO:765, SEQ ID NO:766, SEQ ID NO:767, SEQ ID NO:768, SEQ ID NO:769, SEQ ID NO:770, SEQ ID NO:771, SEQ ID NO:772, SEQ ID NO:773, SEQ ID NO:774, SEQ ID NO:775, SEQ ID NO:776, SEQ ID NO:777, SEQ ID NO:778, SEQ ID NO:779, SEQ ID NO:780, SEQ ID NO:781, SEQ ID NO:782, SEQ ID NO:783, SEQ ID NO:784, SEQ ID NO:785, SEQ ID NO:786, SEQ ID NO:787, SEQ ID NO:788, SEQ ID NO:789, SEQ ID NO:790, SEQ ID NO:791, SEQ ID NO:792, SEQ ID NO:793, SEQ ID NO:794, SEQ ID NO:795, SEQ ID NO:796, SEQ ID NO:797, SEQ ID NO:798, SEQ ID NO:799, SEQ ID NO:800, SEQ ID NO:801, SEQ ID NO:802, SEQ ID NO:803, SEQ ID NO:804, SEQ ID NO:805, SEQ ID NO:806, SEQ ID NO:807, SEQ ID NO:808, SEQ ID NO:809, SEQ ID NO:810, SEQ ID NO:811, SEQ ID NO:812, SEQ ID NO:813, SEQ ID NO:814, SEQ ID NO:815, SEQ ID NO:816, SEQ ID NO:817, SEQ ID NO:818, SEQ ID NO:819, SEQ ID NO:820, SEQ ID NO:821, SEQ ID NO:822, SEQ ID NO:823, SEQ ID NO:824, SEQ ID NO:825, SEQ ID NO:826, SEQ ID NO:827, SEQ ID NO:828, SEQ ID NO:829, SEQ ID NO:830, SEQ ID NO:831, SEQ ID NO:832, SEQ ID NO:833, SEQ ID NO:834, SEQ ID NO:835, SEQ ID NO:836, SEQ ID NO:837, SEQ ID NO:838, SEQ ID NO:839, SEQ ID NO:840, SEQ ID NO:841, SEQ ID NO:842, SEQ ID NO:843, SEQ ID NO:844, SEQ ID NO:845, SEQ ID NO:846, SEQ ID NO:847, SEQ ID NO:848, SEQ ID NO:849, SEQ ID NO:850, SEQ ID NO:851, SEQ ID NO:852, SEQ ID NO:853, SEQ ID NO:854, SEQ ID NO:855, SEQ ID NO:856, SEQ ID NO:857, SEQ ID NO:858, SEQ ID NO:859, SEQ ID NO:860, SEQ ID NO:861, SEQ ID NO:862, SEQ ID NO:863, SEQ ID NO:864, SEQ ID NO:865, SEQ ID NO:866, SEQ ID NO:867, SEQ ID NO:868, SEQ ID NO:869, SEQ ID NO:870, SEQ ID NO:871, SEQ ID NO:872, SEQ ID NO:873, SEQ ID NO:874, SEQ ID NO:875, SEQ ID NO:876, SEQ ID NO:877, SEQ ID NO:878, SEQ ID NO:879, SEQ ID NO:880, SEQ ID NO:881, SEQ ID NO:882, SEQ ID NO:883, SEQ ID NO:884, SEQ ID NO:885, SEQ ID NO:886, SEQ ID NO:887, SEQ ID NO:888, SEQ ID NO:889, SEQ ID NO:890, SEQ ID NO:891, SEQ ID NO:892, SEQ ID NO:893, SEQ ID NO:894, SEQ ID NO:895, SEQ ID NO:896, SEQ ID NO:897, SEQ ID NO:898, SEQ ID NO:899, SEQ ID NO:900, SEQ ID NO:901, SEQ ID NO:902, SEQ ID NO:903, SEQ ID NO:904, SEQ ID NO:905, SEQ ID NO:906, SEQ ID NO:907, SEQ ID NO:908, SEQ ID NO:909, SEQ ID NO:910, SEQ ID NO:911, SEQ ID NO:912, SEQ ID NO:913, SEQ ID NO:914, SEQ ID NO:915, SEQ ID NO:916, SEQ ID NO:917, SEQ ID NO:918, SEQ ID NO:919, SEQ ID NO:920, SEQ ID NO:921, SEQ ID NO:922, SEQ ID NO:923, SEQ ID NO:924, SEQ ID NO:925, SEQ ID NO:926, SEQ ID NO:927, SEQ ID NO:928, SEQ ID NO:929, SEQ ID NO:930, SEQ ID NO:931, SEQ ID NO:932, SEQ ID NO:933, SEQ ID NO:934, SEQ ID NO:935, SEQ ID NO:936, SEQ ID NO:937, SEQ ID NO:938, SEQ ID NO:939, SEQ ID NO:940, SEQ ID NO:941, SEQ ID NO:942, SEQ ID NO:943, SEQ ID NO:944, SEQ ID NO:945, SEQ ID NO:946, SEQ ID NO:947, SEQ ID NO:948, SEQ ID NO:949, SEQ ID NO:950, SEQ ID NO:951, SEQ ID NO:952, SEQ ID NO:953, SEQ ID NO:954, SEQ ID NO:955, SEQ ID NO:956, SEQ ID NO:957, SEQ ID NO:958, SEQ ID NO:959, SEQ ID NO:960, SEQ ID NO:961, SEQ ID NO:962, SEQ ID NO:963, SEQ ID NO:964, SEQ ID NO:965, SEQ ID NO:966, SEQ ID NO:967, SEQ ID NO:968, SEQ ID NO:969, SEQ ID NO:970, SEQ ID NO:971, SEQ ID NO:972, SEQ ID NO:973, SEQ ID NO:974, SEQ ID NO:975, SEQ ID NO:976, SEQ ID NO:977, SEQ ID NO:978, SEQ ID NO:979, SEQ ID NO:980, SEQ ID NO:981, SEQ ID NO:982, SEQ ID NO:983, SEQ ID NO:984, SEQ ID NO:985, SEQ ID NO:986, SEQ ID NO:987, SEQ ID NO:988, SEQ ID NO:989, SEQ ID NO:990, SEQ ID NO:991, SEQ ID NO:992, SEQ ID NO:993, SEQ ID NO:994, SEQ ID NO:995, SEQ ID NO:996, SEQ ID NO:997, SEQ ID NO:998, SEQ ID NO:999, SEQ ID NO:1000, SEQ ID NO:1001, SEQ ID NO:1002, SEQ ID NO:1003, SEQ ID NO:1004. The diagnostic oligonucleotide of may include DNA, cDNA, PNA, genomic DNA, or synthetic oligonucleotides.

The method of the present invention may further comprise selecting an appropriate therapy based upon the diagnosis and or monitoring. Such therapies may include administering appropriate drugs such as drugs that target alpha-interferon.

The methods of the present invention may be applied to bodily fluids from or in a patient, including peripheral blood and urine.

The present invention is further directed to a system or kit for diagnosing or monitoring chronic inflammatory or autoimmune disease in a patient comprising an isolated DNA molecule wherein the isolated DNA molecule detects expression of a gene listed in Table 2E. In the system of the invention, the DNA molecules may be synthetic DNA, genomic DNA, PNA or cDNA. The isolated DNA molecule may be immobilized on an array. Such arrays may include a chip array, a plate array, a bead array, a pin array, a membrane array, a solid surface array, a liquid array, an oligonucleotide array, polynucleotide array or a cDNA array, a microtiter plate, a membrane and a chip.

The present invention is further directed to a system or detecting differential gene expression. In one format, the system has one or more isolated DNA molecules wherein each isolated DNA molecule detects expression of a gene selected from the group of genes corresponding to the oligonucleotides depicted in the Sequence Listing. It is understood that the DNA sequences and oligonucleotides of the invention may have slightly different sequences than those identified herein. Such sequence variations are understood to those of ordinary skill in the art to be variations in the sequence which do not significantly affect the ability of the sequences to detect gene expression.

The sequences encompassed by the invention have at least 40-50, 50-60, 70-80, 80-85, 85-90, 90-95 or 95-100% sequence identity to the sequences disclosed herein. In some embodiments, DNA molecules are less than about any of the following lengths (in bases or base pairs): 10,000; 5,000; 2500; 2000; 1500; 1250; 1000; 750; 500; 300; 250; 200; 175; 150; 125; 100; 75; 50; 25; 10. In some embodiments, DNA molecule is greater than about any of the following lengths (in bases or base pairs): 10; 15; 20; 25; 30; 40; 50; 60; 75; 100; 125; 150; 175; 200; 250; 300; 350; 400; 500; 750; 1000; 2000; 5000; 7500; 10000; 20000; 50000. Alternately, a DNA molecule can be any of a range of sizes having an upper limit of 10,000; 5,000; 2500; 2000; 1500; 1250; 1000; 750; 500; 300; 250; 200; 175; 150; 125; 100; 75; 50; 25; or 10 and an independently selected lower limit of 10; 15; 20; 25; 30; 40; 50; 60; 75; 100; 125; 150; 175; 200; 250; 300; 350; 400; 500; 750; 1000; 2000; 5000; 7500 wherein the lower limit is less than the upper limit.

The gene expression system may be a candidate library, a diagnostic agent, a diagnostic oligonucleotide set or a diagnostic probe set. The DNA molecules may be genomic DNA, protein nucleic acid (PNA), cDNA or synthetic oligonucleotides.

In one format, the gene expression system is immobilized on an array. The array may be a chip array, a plate array, a bead array, a pin array, a membrane array, a solid surface array, a liquid array, an oligonucleotide array, a polynucleotide array, a cDNA array, a microfilter plate, a membrane or a chip.

Brief Description of the Sequence Listing

A brief description of the sequence listing is given below. There are 1065 entries. The Sequence Listing presents 50mer oligonucleotide sequences derived from human leukocyte, plant and viral genes. These are listed as SEQ IDs 503-1004. The 50mer sequences and the corresponding gene sequences are also listed Table 2. Most of these 50mers were designed from sequences of genes in Table 2 and the Sequence listing.
SEQ ID's 1-502 represent mRNA sequences of genes those expression was altered in persons with SLE.
SEQ ID's 2-1004 are 50 nucleotide oligonucleotides used as probes to monitor RNA expression in blood.
SEQ ID's 1005-1037 are PCR primers and probes used to monitor expression of selected genes from 1-502
SEQ ID's 1038-1065 are sequences discussed in the Examples.

BRIEF DESCRIPTION OF THE FIGURES

FIG. 1: FIG. 1 is a schematic flow chart illustrating an instruction set for characterization of the nucleotide sequence and/or the predicted protein sequence of novel nucleotide sequences.
FIG. 2: FIG. 2 shows PCR Primer efficiency testing. A standard curve of Ct versus log of the starting RNA amount is shown for 2 genes.
FIG. 3: FIG. 3 describes kits useful for the practice of the invention. FIG. 3A describes the contents of a kit useful for the discovery of diagnostic nucleotide sets using microarrays. FIG. 3B describes the contents of a kit useful for the application of diagnostic nucleotide sets using microarrays.

FIG. 3C describes contents of a kit useful for the application of diagnostic nucleotide sets using real-time PCR.

FIG. 4 depicts a graph comparing the median background subtracted expression signals for various leukocyte reference RNAs.

FIG. 5: FIG. 5 depicts Diagnostic genes, gene sets and diagnostic algorithms for Systemic Lupus Erythematosis are identified. FIG. 5A shows the relative expression level of oligonucleotide and SEQ ID #16 (Sialyltransferase 4A) between Lupus and control samples is shown. The gene is identified as having a false detection rate for differential expression from the SAM algorithm of 0.5%.

FIG. 5B shows the scaled ratios (non log) for Sialyltransferase (SEQ ID #16) are given for the samples in the analysis. The average ratio of each group along with the standard deviation of the ratio is shown. The average fold change from control to Lupus is 1.48. FIG. 5C shows CART gene expression models for diagnosis of SLE. For each model, the number of genes used, the relative cost with 10 fold cross validation, the SEQ ID, Locus accession number, the name and the position and values in the CART model are given. The CART values given are the expression level thresholds for classification of the sample as SLE after the node. For example, in the single gene model II, the first node of the decision tree asks if expression of gene SEQ ID NO 2 is >0.103. If yes, the sample is placed in the lupus class. FIG. 5D shows the sensitivity and specificity of Model 1. The sensitivity and specificity are given for both the 2 and 3 gene models and both the training set and on cross validation. The relative cost is given for cross-validation. FIG. 5E shows the CART Model I, 2 genes. The model uses 2 genes in a single node to classify samples as Lupus (Class 1) or non-Lupus (Class 2). FIG. 5F shows CART Model I, 3 genes. The model uses a second node to classify all samples correctly as lupus (class 1) or non-lupus (class 2) for the training set. G2412=SEQ ID 514, G2648=SEQ ID 510, G1436=SEQ ID 509.

FIG. 6: FIG. 6 shows endpoint testing of PCR primers. Electrophoresis and microfluidics are used to assess the product of gene specific PCR primers. FIG. 6A is a β-GUS gel image. Lane 3 is the image for GUS primers. Lanes 2 and 1 correspond to the no-template control and −RT control, respectively. FIG. 6B shows the electropherogram of β-GUS primers, a graphical representation of Lane 3 from the gel image. FIG. 6C shows a β-Actin gel image. Lane 3 is the image for endpoint testing of actin primers. Lanes 2 and 1 correspond to the no-template control and −RT control, respectively. FIG. 6D shows the electropherogram of β-Actin primers, a graphical representation of Lave 3 from the gel image.

FIG. 7 shows the validation of differential expression of a gene discovered using microarrays using Real-time PCR. FIG. 7A shows the Ct for each patient sample on multiple assays is shown along with the Ct in the R50 control RNA. Triangles represent −RT (reverse transcriptase) controls. FIG. 7B shows the fold difference between the expression of Granzyme B and an Actin reference is shown for 3 samples from patients with and without CMV disease.

FIG. 8: Real-time PCR control gene analysis. 11 candidate control genes were tested using real-time PCR on 6 whole blood samples (PAX) paired with 6 mononuclear samples (CPT) from the same patient. Each sample was tested twice. For each gene, the variability of the gene across the samples is shown on the vertical axis (top graph). The average Ct value for each gene is also shown (bottom graph). 2 μg RNA was used for PAX samples and 0.5 μg total RNA was used for the mononuclear samples (CPT)

BRIEF DESCRIPTION OF THE TABLES

Figure 4:
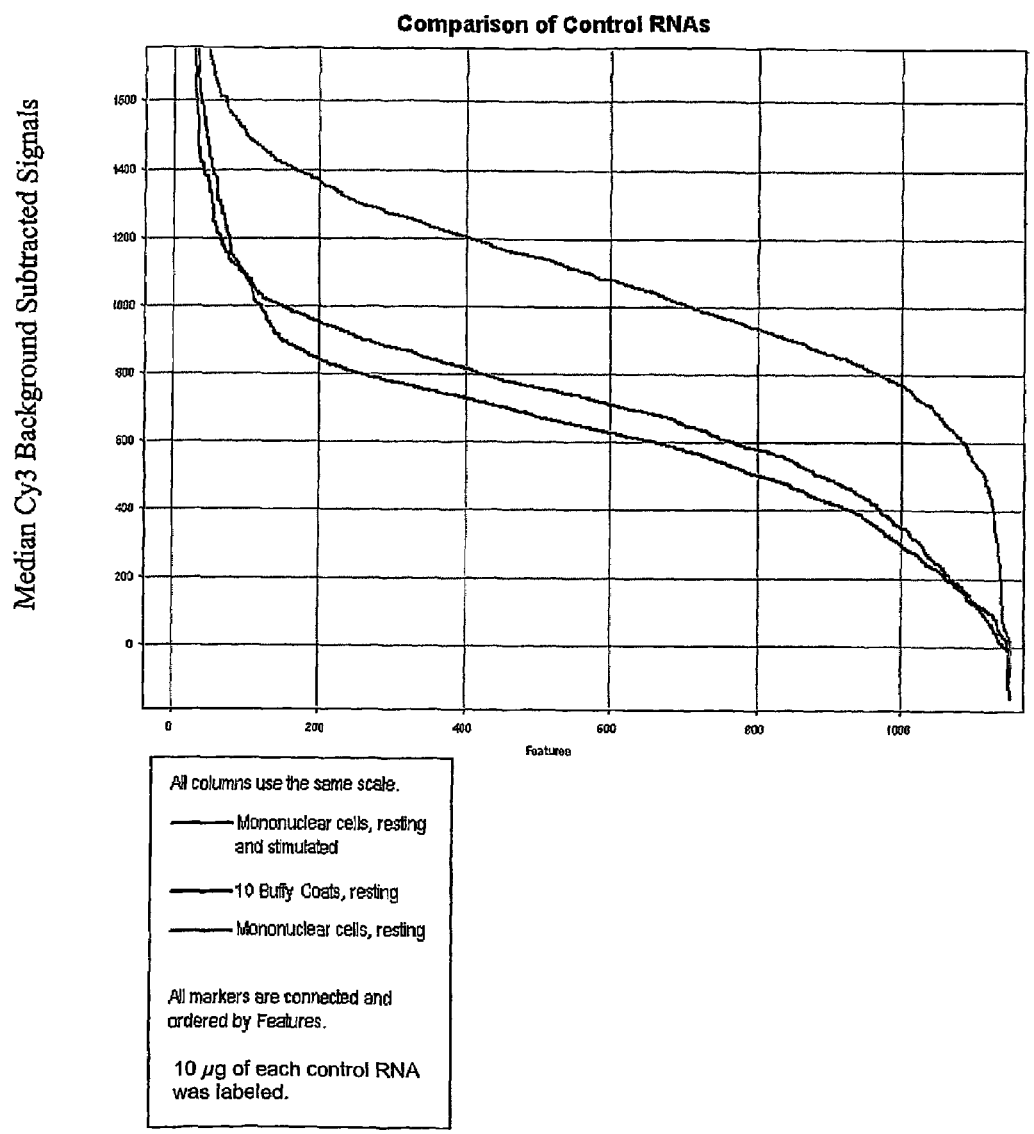
FIG. 4.
Figure 7:
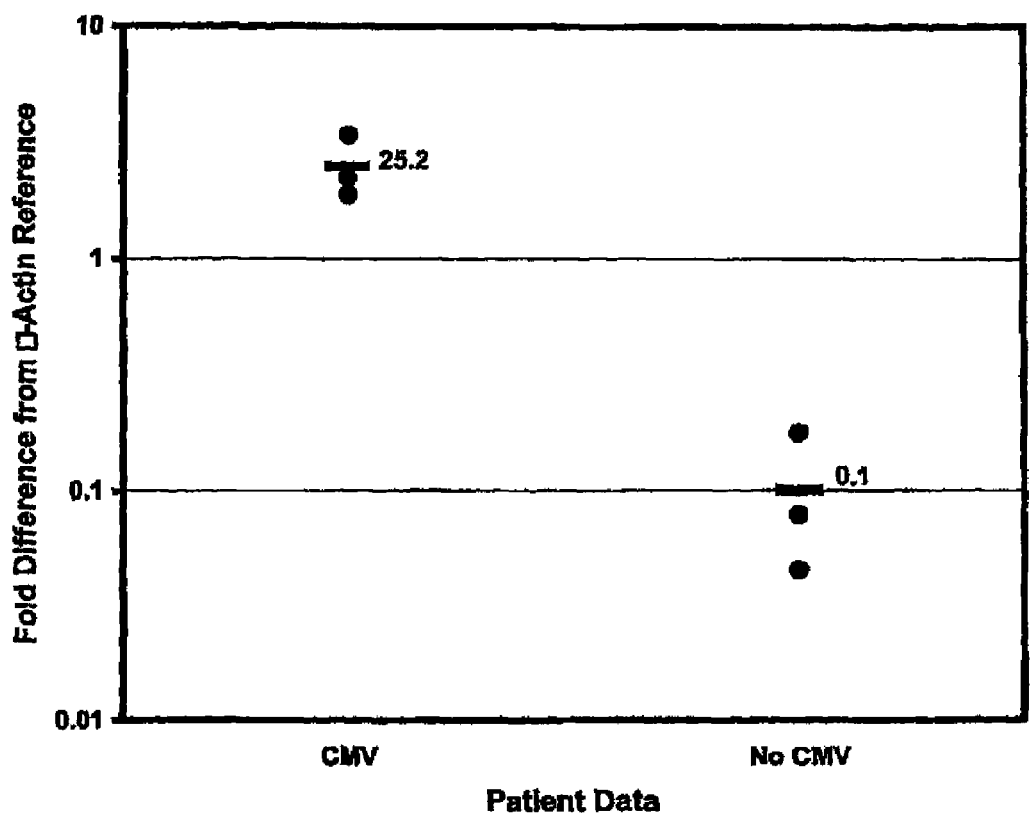
FIG. 7.

Table 1: Samples Used in Array and PCR Expression Profiling Experiments.

Samples were obtained from patients at a single medical center with appropriate IRB approval and informed consent. For each patient the primary clinical diagnosis is given according to American College of Rheumatology criteria (SLE=Systemic Lupus Erythematosis, RA=Rheumatoid Arthritis, C=Healthy control, OA=Osteoarthritis). Dependent variables were defined for analysis from the patient clinical diagnoses; For Dx1, patients were classified as Lupus (1) or no Lupus (0). For Dx2, patients with either quiescent, uncertain or recently treated Lupus were removed from the analysis (2). PCR was done on the set of samples marked with an x.

Table 2: Gene Expression Markers for SLE and Autoimmune Disease

A: Significance analysis for Microarrays (SAM), Lupus/Autoimmune merkers. Each gene is identified by an oligonucleotide (SEQ ID 50 mer), Genbank accession number from VERSION (ACC), a full length (or longest known) RNA transcript (SEQ ID FL), and a unigene number VERSION (HS). Results for microarray analysis of blood gene expression (Example 11) are given as the false detection rate (SAM FDR) and a direction of expression change in Lupus patients/controls (SAM Up/Down).

B. Real-time PCR gene expression analysis. Real-time PCR was used to validate and quantify expression behavior of marker genes as described in Example 11. Each gene is identified by an oligonucleotide (SEQ ID 50 mer), Genbank accession number from VERSION (ACC), a full length (or longest known) RNA transcript (SEQ ID FL), and a unigene number VERSION(HS). The fold change between Lupus patients and controls (PCR fold) and results of an unpaired t-test (PCR p-value) are given.

C. Multiple Additive Regression Trees analysis of Microarray Data. The MART algorithm was used to identify marker genes and gene sets as described in Example 11. Each gene is identified by an oligonucleotide (SEQ ID 50 mer), Genbank accession number from VERSION (ACC), a full length (or longest known) RNA transcript (SEQ ID FL), and a unigene number VERSION(HS). The importance of the gene in the MART model (MART Importance), the error rate of the model that identified the gene (MART error) and the ratio of those 2 variables (Imp/error) are given.

D. Identification of pathways and pathway genes with hierarchical clustering. Genes are identified by close coexpression to significant genes from the microarray or PCR analysis (Hierarchical Cluster SEQ ID). This analysis identifies distinct pathways of gene expression.

Table 3: Table 3 lists some of the diseases or conditions amenable to study by leukocyte profiling.

Table 4: Real-time PCR assay reporter and quencher dyes. Various combinations of reporter and quencher dyes are useful for real-time PCR assays. Reporter and quencher dyes work optimally in specific combinations defined by their spectra. For each reporter, appropriate choices for quencher dyes are given.

DETAILED DESCRIPTION OF THE INVENTION

Definitions

Unless defined otherwise, all scientific and technical terms are understood to have the same meaning as commonly used in the art to which they pertain. For the purpose of the present invention, the following terms are defined below.

In the context of the invention, the term "gene expression system" refers to any system, device or means to detect gene expression and includes diagnostic agents, candidate libraries oligonucleotide, oligonucleotide sets or probe sets.

The terms "diagnostic oligonucleotide" or "diagnostic oligonucleotide set" generally refers to an oligonucleotide or to a set of two or more oligonucleotides that, when evaluated for differential expression their corresponding diagnostic genes, collectively yields predictive data. Such predictive data typically relates to diagnosis, prognosis, monitoring of therapeutic outcomes, and the like. In general, the components of a diagnostic oligonucleotide or a diagnostic oligonucleotide set are distinguished from oligonucleotide sequences that are evaluated by analysis of the DNA to directly determine the genotype of an individual as it correlates with a specified trait or phenotype, such as a disease, in that it is the pattern of expression of the components of the diagnostic oligonucleotide set, rather than mutation or polymorphism of the DNA sequence that provides predictive value. It will be understood that a particular component (or member) of a diagnostic oligonucleotide set can, in some cases, also present one or more mutations, or polymorphisms that are amenable to direct genotyping by any of a variety of well known analysis methods, e.g., Southern blotting, RFLP, AFLP, SSCP, SNP, and the like.

A "diagnostic gene" is a gene whose expression is detected by a diagnostic oligonucleotide or diagnostic oligonucleotide set.

A "disease specific target oligonucleotide sequence" is a gene or other oligonucleotide that encodes a polypeptide, most typically a protein, or a subunit of a multi-subunit protein that is a therapeutic target for a disease, or group of diseases.

A "candidate library" or a "candidate oligonucleotide library" refers to a collection of oligonucleotide sequences (or gene sequences) that by one or more criteria have an increased probability of being associated with a particular disease or group of diseases. The criteria can be, for example, a differential expression pattern in a disease state or in activated or resting leukocytes in vitro as reported in the scientific or technical literature, tissue specific expression as reported in a sequence database, differential expression in a tissue or cell type of interest, or the like. Typically, a candidate library has at least 2 members or components; more typically, the library has in excess of about 10, or about 100, or about 1000, or even more, members or components.

The term "disease criterion" is used herein to designate an indicator of a disease, such as a diagnostic factor, a prognostic factor, a factor indicated by a medical or family history, a genetic factor, or a symptom, as well as an overt or confirmed diagnosis of a disease associated with several indicators such as those selected from the above list. A disease criterion includes data describing a patient's health status, including retrospective or prospective health data, e.g. in the form of the patient's medical history, laboratory test results, diagnostic test result, clinical events, medications, lists, response(s) to treatment and risk factors, etc.

An autoimmune disorder is defined as a disease state in which a patient's immune system recognizes an antigen in that patient's organs or tissues as foreign and becomes activated. The activated immune cells can then cause damage to the inciting organ or tissue or can damage other organs or tissues. In some cases, the disorder may be caused by a dysregulation of the immune system cells, rather than by the recognition as a self-antigen as foreign. Dysregulated immune cells can secrete inflammatory cytokines that cause systemic inflammation or they can recognize self-antigens as foreign.

Examples of autoimmune diseases include: Autoimmune hepatitis, Multiple Sclerosis, Myasthenia Gravis, Type I diabetes, Rheumatoid Arthritis, Psoriasis, Systemic Lupus Erythematosis, Hashimoto's Thyroiditis, Grave's disease, Ankylosing Spondylitis Sjogrens Disease, CREST syndrome, Scleroderma and many more.

Most of the autoimmune diseases are also chronic inflammatory diseases. This is defined as a disease process associated with long-term (>6 months) activation of inflammatory cells (leukocytes). The chronic inflammation leads to damage of patient organs or tissues. Many diseases are chronic inflammatory disorders, but are not know to have an autoimmune basis. For example, Atherosclerosis, Congestive Heart Failure, Crohn's disease, Ulcerative Colitis, Polyarteritis nodosa, Whipple's Disease, Primary Sclerosing Cholangitis and many more.

The terms "molecular signature" or "expression profile" refers to the collection of expression values for a plurality (e.g., at least 2, but frequently about 10, about 100, about 1000, or more) of members of a candidate library. In many cases, the molecular signature represents the expression pattern for all of the nucleotide sequences in a library or array of candidate or diagnostic nucleotide sequences or genes. Alternatively, the molecular signature represents the expression pattern for one or more subsets of the candidate library. The term "oligonucleotide" refers to two or more nucleotides. Nucleotides may be DNA or RNA, naturally occurring or synthetic.

The term "healthy individual," as used herein, is relative to a specified disease or disease criterion. That is, the individual does not exhibit the specified disease criterion or is not diagnosed with the specified disease. It will be understood, that the individual in question, can, of course, exhibit symptoms, or possess various indicator factors for another disease.

Similarly, an "individual diagnosed with a disease" refers to an individual diagnosed with a specified disease (or disease criterion). Such an individual may, or may not, also exhibit a disease criterion associated with, or be diagnosed with another (related or unrelated) disease.

The term "monitoring" is used herein to describe the use of gene sets to provide useful information about an individual or an individual's health or disease status. "Monitoring" can include, determination of prognosis, risk-stratification, selection of drug therapy, assessment of ongoing drug therapy, prediction of outcomes, determining response to therapy, diagnosis of a disease or disease complication, following progression of a disease or providing any information relating to a patients health status over time, selecting patients most likely to benefit from experimental therapies with known molecular mechanisms of action, selecting patients most likely to benefit from approved drugs with known molecular mechanisms where that mechanism may be important in a small subset of a disease for which the medication may not have a label, screening a patient population to help decide on a more invasive/expensive test, for example a cascade of tests from a non-invasive blood test to a more invasive option such as biopsy, or testing to assess side effects of drugs used to treat another indication.

An "array" is a spatially or logically organized collection, e.g., of oligonucleotide sequences or nucleotide sequence products such as RNA or proteins encoded by an oligonucleotide sequence. In some embodiments, an array includes antibodies or other binding reagents specific for products of a candidate library.

When referring to a pattern of expression, a "qualitative" difference in gene expression refers to a difference that is not assigned a relative value. That is, such a difference is designated by an "all or nothing" valuation. Such an all or nothing variation can be, for example, expression above or below a threshold of detection (an on/off pattern of expression). Alternatively, a qualitative difference can refer to expression of different types of expression products, e.g., different alleles (e.g., a mutant or polymorphic allele), variants (including sequence variants as well as post-translationally modified variants), etc.

In contrast, a "quantitative" difference, when referring to a pattern of gene expression, refers to a difference in expression that can be assigned a value on a graduated scale, (e.g., a 0-5 or 1-10 scale, a+–+++scale, a grade 1-grade 5 scale, or the like; it will be understood that the numbers selected for illustration are entirely arbitrary and in no-way are meant to be interpreted to limit the invention).

Gene Expression Systems and Methods of Detecting Gene Expression

The invention is directed to methods of detecting gene expression with a gene expression system having one or more DNA molecules wherein the one or more DNA molecules has a nucleotide sequence which detects expression of a gene corresponding to the oligonucleotides depicted in the Sequence Listing. In one format, the oligonucleotide detects expression of a gene that is differentially expressed in leukocytes. The gene expression system may be a candidate library, a diagnostic agent, a diagnostic oligonucleotide set or a diagnostic probe set. The DNA molecules may be genomic DNA, RNA, protein nucleic acid (PNA), cDNA or synthetic oligonucleotides. Following the procedures taught herein, one can identify sequences of interest for analyzing gene expression in leukocytes. Such sequences may be predictive of a disease state.

Diagnostic Oligonucleotides of the Invention

The invention relates to diagnostic oligonucleotides and diagnostic oligonucleotide set(s) comprising members of the leukocyte candidate library listed in Table 2 and the Sequence Listing, for which a correlation exists between the health status of an individual, and the individual's expression of RNA or protein products corresponding to the nucleotide sequence. In some instances, only one oligonucleotide is necessary for such detection. Members of a diagnostic oligonucleotide set may be identified by any means capable of detecting expression of RNA or protein products, including but not limited to differential expression screening, PCR, RT-PCR, SAGE analysis, high-throughput sequencing, microarrays, liquid or other arrays, protein-based methods (e.g., western blotting, proteomics, and other methods described herein), and data mining methods, as further described herein.

In one embodiment, a diagnostic oligonucleotide set comprises at least two oligonucleotide sequences listed in Table 2 or the Sequence Listing which are differentially expressed in leukocytes in an individual with at least one disease criterion for at least one leukocyte-implicated disease relative to the expression in individual without the at least one disease criterion, wherein expression of the two or more nucleotide sequences is correlated with at least one disease criterion, as described below.

In another embodiment, a diagnostic oligonucleotide set comprises at least one oligonucleotide having an oligonucleotide sequence listed in Table 2 or the Sequence Listing which is differentially expressed, and further wherein the differential expression/correlation has not previously been described. In some embodiments, the diagnostic oligonucleotide set is immobilized on an array.

In another embodiment, diagnostic oligonucleotides (or oligonucleotide sets) are related to the members of the leukocyte candidate library listed in Table 2 and in the Sequence Listing, for which a correlation exists between the health status (or disease criterion) of an individual. The diagnostic oligonucleotides are partially or totally contained in (or derived from) full-length gene sequences (or predicted full-length gene sequences) for the members of the candidate library listed in Table 2 and the Sequence Listing.

The diagnostic oligonucleotides may also be derived from other genes that are coexpressed with the correlated sequence or full-length gene. Genes may share expression patterns because they are regulated in the same molecular pathway. Because of the similarity of expression, behavior genes are identified as surrogates in that they can substitute for a diagnostic gene in a diagnostic gene set. Example 4 demonstrates the discovery of surrogates from the data. Surrogate oligonucleotide and surrogate oligonucleotide sets can be utilized to detect expression of surrogate genes and thereby diagnose or monitor patients with a disease.

As used herein the term "gene cluster" or "cluster" refers to a group of genes related by expression pattern. In other words, a cluster of genes is a group of genes with similar regulation across different conditions, such as a patient having a chronic autoimmune or inflammatory disease or a patient without chronic autoimmune or inflammatory disease. The expression profile for each gene in a cluster should be correlated with the expression profile of at least one other gene in that cluster. Correlation may be evaluated using a variety of statistical methods. As used herein the term "surrogate" refers to a gene with an expression profile such that it can substitute for a diagnostic gene in a diagnostic assay. Such genes are often members of the same gene cluster as the diagnostic gene. For each member of a diagnostic gene set, a set of potential surrogates can be identified through identification of genes with similar expression patterns as described below.

Many statistical analyses produce a correlation coefficient to describe the relatedness between two gene expression patterns. Patterns may be considered correlated if the correlation coefficient is greater than or equal to 0.8. In preferred embodiments, the correlation coefficient should be greater than 0.85, 0.9 or 0.95. Other statistical methods produce a measure of mutual information to describe the relatedness between two gene expression patterns. Patterns may be considered correlated if the normalized mutual information value is greater than or equal to 0.7. In preferred embodiments, the normalized mutual information value should be greater than 0.8, 0.9 or 0.95. Patterns may also be considered similar if they cluster closely upon hierarchical clustering of gene expression data (Eisen et al. 1998). Similar patterns may be those genes that are among the 1, 2, 5, 10, 20, 50 or 100 nearest neighbors in a hierarchical clustering or have a similarity score (Eisen et al. 1998) of >0.5, 0.7, 0.8, 0.9, 0.95 or 0.99. Similar patterns may also be identified as those genes found to be surrogates in a classification tree by CART (Breiman et al. 1994). Often, but not always, members of a gene cluster have similar biological functions in addition to similar gene expression patterns.

Correlated genes, clusters and surrogates are identified for the diagnostic genes of the invention. These surrogates may be used as diagnostic genes in an assay instead of, or in addition to, the diagnostic genes for which they are surrogates.

The invention also provides diagnostic probe sets. It is understood that a probe includes any reagent capable of specifically identifying a nucleotide sequence of the diagnostic nucleotide set, including but not limited to amplified DNA, amplified RNA, cDNA, synthetic oligonucleotide, partial or full-length nucleic acid sequences. In addition, the probe may identify the protein product of a diagnostic nucleotide sequence, including, for example, antibodies and other affinity reagents.

It is also understood that each probe can correspond to one gene, or multiple probes can correspond to one gene, or both, or one probe can correspond to more than one gene.

Homologs and variants of the disclosed nucleic acid molecules may be used in the present invention. Homologs and variants of these nucleic acid molecules will possess a relatively high degree of sequence identity when aligned using standard methods. The sequences encompassed by the invention have at least 40-50, 50-60, 70-80, 80-85, 85-90, 90-95 or 95-100% sequence identity to the sequences disclosed herein.

It is understood that for expression profiling, variations in the disclosed sequences will still permit detection of gene expression. The degree of sequence identity required to detect gene expression varies depending on the length of the oligomer. For a 60 mer, (an oligonucleotide with 60 nucleotides) 6-8 random mutations or 6-8 random deletions in a 60 mer do not affect gene expression detection. Hughes, T R, et al. "Expression profiling using microarrays fabricated by an ink-jet oligonucleotide synthesizer. Nature Biotechnology, 19:343-347 (2001). As the length of the DNA sequence is increased, the number of mutations or deletions permitted while still allowing gene expression detection is increased.

As will be appreciated by those skilled in the art, the sequences of the present invention may contain sequencing errors. That is, there may be incorrect nucleotides, frame-shifts, unknown nucleotides, or other types of sequencing errors in any of the sequences; however, the correct sequences will fall within the homology and stringency definitions herein.

The minimum length of an oligonucleotide probe necessary for specific hybridization in the human genome can be estimated using two approaches. The first method uses a statistical argument that the probe will be unique in the human genome by chance. Briefly, the number of independent perfect matches (Po) expected for an oligonucleotide of length L in a genome of complexity C can be calculated from the equation (Laird C D, Chromosoma 32:378 (1971):

$$Po = (¼)^L * 2C$$

In the case of mammalian genomes, $2C = \sim 3.6 \times 10^9$, and an oligonucleotide of 14-15 nucleotides is expected to be represented only once in the genome. However, the distribution of nucleotides in the coding sequence of mammalian genomes is nonrandom (Lathe, R. J. Mol. Biol. 183:1 (1985) and longer oligonucleotides may be preferred in order to in increase the specificity of hybridization. In practical terms, this works out to probes that are 19-40 nucleotides long (Sambrook J et al., infra). The second method for estimating the length of a specific probe is to use a probe long enough to hybridize under the chosen conditions and use a computer to search for that sequence or close matches to the sequence in the human genome and choose a unique match. Probe sequences are chosen based on the desired hybridization properties as described in Chapter 11 of Sambrook et al, infra. The PRIMER3 program is useful for designing these probes (S. Rozen and H. Skaletsky 1996, 1997; Primer3 code available at genome.wi.mit.edu/genome_software/other/primer3.html, the website). The sequences of these probes are then compared pair wise against a database of the human genome sequences using a program such as BLAST or MEGABLAST (Madden, T. L et al. (1996) Meth. Enzymol. 266:131-141). Since most of the human genome is now contained in the database, the number of matches will be determined. Probe sequences are chosen that are unique to the desired target sequence.

In some embodiments, a diagnostic oligonucleotide or oligonucleotide probe set is immobilized on an array. The array is optionally comprises one or more of: a chip array, a plate array, a bead array, a pin array, a membrane array, a solid surface array, a liquid array, an oligonucleotide array, a polynucleotide array or a cDNA array, a microtiter plate, a pin array, a bead array, a membrane or a chip.

In some embodiments, the leukocyte-implicated disease is selected from the diseases listed in Table 3. In other embodiments, the disease is chronic autoimmune and inflammatory diseases, systemic lupus erythematosis (SLE) and rheumatoid arthritis.

In some embodiments, diagnostic oligonucleotides of the invention are used as a diagnostic gene set in combination with genes that are know to be associated with a disease state ("known markers"). The use of the diagnostic oligonucleotides in combination with the known markers can provide information that is not obtainable through the known markers alone. The known markers include those identified by the prior art listing provided.

General Molecular Biology References

In the context of the invention, nucleic acids and/or proteins are manipulated according to well known molecular biology techniques. Detailed protocols for numerous such procedures are described in, e.g., in Ausubel et al. *Current Protocols in Molecular Biology* (supplemented through 2000) John Wiley & Sons, New York ("Ausubel"); Sambrook et al. *Molecular Cloning—A Laboratory Manual* (2nd Ed.), Vol. 1-3, Cold Spring Harbor Laboratory, Cold Spring Harbor, N.Y., 1989 ("Sambrook"), and Berger and Kimmel *Guide to Molecular Cloning Techniques, Methods in Enzymology* volume 152 Academic Press, Inc., San Diego, Calif. ("Berger").

In addition to the above references, protocols for in vitro amplification techniques, such as the polymerase chain reaction (PCR), the ligase chain reaction (LCR), Q-replicase amplification, and other RNA polymerase mediated techniques (e.g., NASBA), useful e.g., for amplifying cDNA probes of the invention, are found in Mullis et al. (1987) U.S. Pat. No. 4,683,202; *PCR Protocols A Guide to Methods and Applications* (Innis et al. eds) Academic Press Inc. San Diego, Calif. (1990) ("Innis"); Arnheim and Levinson (1990) *C&EN* 36; *The Journal Of NIH Research* (1991) 3:81; Kwoh et al. (1989) *Proc Natl Acad Sci USA* 86, 1173; Guatelli et al. (1990) *Proc Natl Acad Sci USA* 87:1874; Lomell et al. (1989) *J Clin Chem* 35:1826; Landegren et al. (1988) *Science* 241: 1077; Van Brunt (1990) *Biotechnology* 8:291; Wu and Wallace (1989) *Gene* 4: 560; Barringer et al. (1990) *Gene* 89:117, and Sooknanan and Malek (1995) *Biotechnology* 13:563. Additional methods, useful for cloning nucleic acids in the context of the present invention, include Wallace et al. U.S. Pat. No. 5,426,039. Improved methods of amplifying large nucleic acids by PCR are summarized in Cheng et al. (1994) *Nature* 369:684 and the references therein.

Certain polynucleotides of the invention, e.g., oligonucleotides can be synthesized utilizing various solid-phase strategies involving mononucleotide- and/or trinucleotide-based phosphoramidite coupling chemistry. For example, nucleic acid sequences can be synthesized by the sequential addition of activated monomers and/or trimers to an elongating polynucleotide chain. See e.g., Caruthers, M. H. et al. (1992) *Meth Enzymol* 211:3.

In lieu of synthesizing the desired sequences, essentially any nucleic acid can be custom ordered from any of a variety of commercial sources, such as The Midland Certified Reagent Company (mcrc@oligos.com), The Great American Gene Company (genco.com), ExpressGen, Inc. (expressgen.com), Operon Technologies, Inc. (operon.com), and many others.

Similarly, commercial sources for nucleic acid and protein microarrays are available, and include, e.g., Agilent Technologies, Palo Alto, Calif. and Affymetrix, Santa Clara, Calif.

One area of relevance to the present invention is hybridization of oligonucleotides. Those of skill in the art differentiate hybridization conditions based upon the stringency of hybridization. For example, highly stringent conditions could include hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3). Moderate stringency conditions could include, e.g., washing in 0.2×SSC/0.1% SDS at 42° C. (Ausubel et al., 1989, supra).

The invention also includes nucleic acid molecules, preferably DNA molecules, that hybridize to, and are therefore the complements of, the DNA sequences of the present invention. Such hybridization conditions may be highly stringent or less highly stringent, as described above. In instances wherein the nucleic acid molecules are deoxyoligonucleotides ("oligos"), highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may act as target nucleotide sequence antisense molecules, useful, for example, in target nucleotide sequence regulation and/or as antisense primers in amplification reactions of target nucleotide sequence nucleic acid sequences. Further, such sequences may be used as part of ribozyme and/or triple helix sequences, also useful for target nucleotide sequence regulation. Still further, such molecules may be used as components of diagnostic methods whereby the presence of a disease-causing allele, may be detected.

Candidate Library

Libraries of candidate genes that are differentially expressed in leukocytes are substrates for the identification and evaluation of diagnostic oligonucleotides and oligonucleotide sets and disease specific target nucleotide sequences.

The term leukocyte is used generically to refer to any nucleated blood cell that is not a nucleated erythrocyte. More specifically, leukocytes can be subdivided into two broad classes. The first class includes granulocytes, including, most prevalently, neutrophils, as well as eosinophils and basophils at low frequency. The second class, the non-granular or mononuclear leukocytes, includes monocytes and lymphocytes (e.g., T cells and B cells). There is an extensive literature in the art implicating leukocytes, e.g., neutrophils, monocytes and lymphocytes in a wide variety of disease processes, including inflammatory and rheumatic diseases, neurodegenerative diseases (such as Alzheimer's dementia), cardiovascular disease, endocrine diseases, transplant rejection, malignancy and infectious diseases, and other diseases listed in Table 3. Mononuclear cells are involved in the chronic immune response, while granulocytes, which make up approximately 60% of the leukocytes, have a non-specific and stereotyped response to acute inflammatory stimuli and often have a life span of only 24 hours.

In addition to their widespread involvement and/or implication in numerous disease related processes, leukocytes are particularly attractive substrates for clinical and experimental evaluation for a variety of reasons. Most importantly, they are readily accessible at low cost from essentially every potential subject. Collection is minimally invasive and associated with little pain, disability or recovery time. Collection can be performed by minimally trained personnel (e.g., phlebotomists, medical technicians, etc.) in a variety of clinical and non-clinical settings without significant technological expenditure. Additionally, leukocytes are renewable, and thus available at multiple time points for a single subject.

Assembly of an Initial Candidate Library

The initial candidate library was assembled from a combination of "mining" publication and sequence databases and construction of a differential expression library. Candidate oligonucleotide sequences in the library may be represented by a full-length or partial nucleic acid sequence, deoxyribonucleic acid (DNA) sequence, cDNA sequence, RNA sequence, synthetic oligonucleotides, etc. The nucleic acid sequence can be at least 19 nucleotides in length, at least 25 nucleotides, at least 40 nucleotides, at least 100 nucleotides, or larger. Alternatively, the protein product of a candidate nucleotide sequence may be represented in a candidate library using standard methods, as further described below. In selecting and validating diagnostic oligonucleotides, an initial library of 8,031 candidate oligonucleotide sequences using nucleic acid sequences of 50 nucleotides in length was constructed as described below.

Candidate Nucleotide Library

We identified members of an initial candidate nucleotide library that are differentially expressed in activated leukocytes and resting leukocytes. From that initial candidate nucleotide library, a pool of 502 candidates were selected. Accordingly, the invention provides the candidate leukocyte nucleotide library comprising the nucleotide sequences listed in Table 2 and in the Sequence Listing. In another embodiment, the invention provides a candidate library comprising at least two nucleotide sequences listed in Table 2 and the Sequence Listing. In another embodiment, at least two nucleotide sequences are 18 nucleotides in length, at least 35 nucleotides, at least 40 nucleotides or at least 100 nucleotides. In some embodiments, the nucleotide sequences comprises deoxyribonucleic acid (DNA) sequence, ribonucleic acid (RNA) sequence, synthetic oligonucleotide sequence, or genomic DNA sequence. It is understood that the nucleotide sequences may each correspond to one gene, or that several nucleotide sequences may correspond to one gene, or that a single nucleotide sequence may correspond to multiple genes.

The invention also provides probes to the candidate nucleotide library. In one embodiment of the invention, the probes comprise at least two nucleotide sequences listed in Table 2 or the Sequence Listing which are differentially expressed in leukocytes in an individual with a least one disease criterion for at least one leukocyte-related disease and in leukocytes in an individual without the at least one disease criterion, wherein expression of the two or more nucleotide sequences is correlated with at least one disease criterion. It is understood that a probe may detect either the RNA expression or protein product expression of the candidate nucleotide library. Alternatively, or in addition, a probe can detect a genotype associated with a candidate nucleotide sequence, as further described below. In another embodiment, the probes for the candidate nucleotide library are immobilized on an array.

The candidate nucleotide library of the invention is useful in identifying diagnostic nucleotide sets of the invention and is itself a diagnostic nucleotide set of the invention, as described below. The candidate nucleotide sequences may be further characterized, and may be identified as a disease target nucleotide sequence, as described below. The candidate nucleotide sequences may also be suitable for use as imaging reagents, as described below.

Generation of Expression Patterns

RNA, DNA or Protein Sample Procurement

Following identification or assembly of a library of differentially expressed candidate nucleotide sequences, leukocyte expression profiles corresponding to multiple members of the candidate library are obtained. Leukocyte samples from one or more subjects are obtained by standard methods. Most typically, these methods involve trans-cutaneous venous sampling of peripheral blood. While sampling of circulating leukocytes from whole blood from the peripheral vasculature is generally the simplest, least invasive, and lowest cost alternative, it will be appreciated that numerous alternative sampling procedures exist, and are favorably employed in some circumstances. No pertinent distinction exists, in fact, between leukocytes sampled from the peripheral vasculature, and those obtained, e.g., from a central line, from a central artery, or indeed from a cardiac catheter, or during a surgical procedure which accesses the central vasculature. In addition, other body fluids and tissues that are, at least in part, composed of leukocytes are also desirable leukocyte samples. For example, fluid samples obtained from the lung during bronchoscopy may be rich in leukocytes, and amenable to expression profiling in the context of the invention, e.g., for the diagnosis, prognosis, or monitoring of lung transplant rejection, inflammatory lung diseases or infectious lung disease. Fluid samples from other tissues, e.g., obtained by endoscopy of the colon, sinuses, esophagus, stomach, small bowel, pancreatic duct, biliary tree, bladder, ureter, vagina, cervix or uterus, etc., are also suitable. Samples may also be obtained other sources containing leukocytes, e.g., from urine, bile, cerebrospinal fluid, feces, gastric or intestinal secretions, semen, or solid organ or joint biopsies.

Most frequently, mixed populations of leukocytes, such as are found in whole blood are utilized in the methods of the present invention. A crude separation, e.g., of mixed leukocytes from red blood cells, and/or concentration, e.g., over a sucrose, percoll or ficoll gradient, or by other methods known in the art, can be employed to facilitate the recovery of RNA or protein expression products at sufficient concentrations, and to reduce non-specific background. In some instances, it can be desirable to purify sub-populations of leukocytes, and methods for doing so, such as density or affinity gradients, flow cytometry, Fluorescence Activated Cell Sorting (FACS), immuno-magnetic separation, "panning," and the like, are described in the available literature and below.

Obtaining DNA, RNA and Protein Samples for Expression Profiling

A variety of techniques are available for the isolation of RNA from whole blood. Any technique that allows isolation of mRNA from cells (in the presence or absence of rRNA and tRNA) can be utilized. In brief, one method that allows reliable isolation of total RNA suitable for subsequent gene expression analysis is described as follows. Peripheral blood (either venous or arterial) is drawn from a subject, into one or more sterile, endotoxin free, tubes containing an anticoagulant (e.g., EDTA, citrate, heparin, etc.). Typically, the sample is divided into at least two portions. One portion, e.g., of 5-8 ml of whole blood is frozen and stored for future analysis, e.g., of DNA or protein. A second portion, e.g., of approximately 8 ml whole blood is processed for isolation of total RNA by any of a variety of techniques as described in, e.g, Sambook, Ausubel, below, as well as U.S. Pat. Nos. 5,728, 822 and 4,843,155.

Typically, a subject sample of mononuclear leukocytes obtained from about 8 ml of whole blood, a quantity readily available from an adult human subject under most circumstances, yields 5-20 μg of total RNA. This amount is ample, e.g., for labeling and hybridization to at least two probe arrays. Labeled probes for analysis of expression patterns of nucleotides of the candidate libraries are prepared from the subject's sample of RNA using standard methods. In many cases, cDNA is synthesized from total RNA using a polyT primer and labeled, e.g., radioactive or fluorescent, nucleotides. The resulting labeled cDNA is then hybridized to probes corresponding to members of the candidate nucleotide library, and expression data is obtained for each nucleotide sequence in the library. RNA isolated from subject samples (e.g., peripheral blood leukocytes, or leukocytes obtained from other biological fluids and samples) is next used for analysis of expression patterns of nucleotides of the candidate libraries.

In some cases, however, the amount of RNA that is extracted from the leukocyte sample is limiting, and amplification of the RNA is desirable. Amplification may be accomplished by increasing the efficiency of probe labeling, or by amplifying the RNA sample prior to labeling. It is appreciated that care must be taken to select an amplification procedure that does not introduce any bias (with respect to gene expression levels) during the amplification process.

Several methods are available that increase the signal from limiting amounts of RNA, e.g. use of the Clontech (Glass Fluorescent Labeling Kit) or Stratagene (Fairplay Microarray Labeling Kit), or the Micromax kit (New England Nuclear, Inc.). Alternatively, cDNA is synthesized from RNA using a T7-polyT primer, in the absence of label, and DNA dendrimers from Genisphere (3DNA Submicro) are hybridized to the poly T sequence on the primer, or to a different "capture sequence" which is complementary to a fluorescently labeled sequence. Each 3DNA molecule has 250 fluorescent molecules and therefore can strongly label each cDNA.

Alternatively, the RNA sample is amplified prior to labeling. For example, linear amplification may be performed, as described in U.S. Pat. No. 6,132,997. A T7-polyT primer is used to generate the cDNA copy of the RNA. A second DNA strand is then made to complete the substrate for amplification. The T7 promoter incorporated into the primer is used by a T7 polymerase to produce numerous antisense copies of the original RNA. Fluorescent dye labeled nucleotides are directly incorporated into the RNA. Alternatively, amino allyl labeled nucleotides are incorporated into the RNA, and then fluorescent dyes are chemically coupled to the amino allyl groups, as described in Hughes et al. 2001. Other exemplary methods for amplification are described below.

It is appreciated that the RNA isolated must contain RNA derived from leukocytes, but may also contain RNA from other cell types to a variable degree. Additionally, the isolated RNA may come from subsets of leukocytes, e.g. monocytes and/or T-lymphocytes, as described above. Such consideration of cell type used for the derivation of RNA depends on the method of expression profiling used. Subsets of leukocytes can be obtained by fluorescence activated cell sorting (FACS), microfluidics cell separation systems or a variety of other methods. Cell sorting may be necessary for the discovery of diagnostic gene sets, for the implementation of gene sets as products or both. Cell sorting can be achieved with a variety of technologies (See Galbraith et al. 1999, Cantor et al. 1975, see also the technology of Guava Technologies, Hayward, Calif.).

DNA samples may be obtained for analysis of the presence of DNA mutations, single nucleotide polymorphisms (SNPs), or other polymorphisms. DNA is isolated using standard techniques, e.g. Maniatus, supra.

Expression of products of candidate nucleotides may also be assessed using proteomics. Protein(s) are detected in samples of patient serum or from leukocyte cellular protein. Serum is prepared by centrifugation of whole blood, using standard methods. Proteins present in the serum may have been produced from any of a variety of leukocytes and non-leukocyte cells, and may include secreted proteins from leukocytes. Alternatively, leukocytes or a desired sub-population of leukocytes are prepared as described above. Cellular protein is prepared from leukocyte samples using methods well known in the art, e.g., Trizol (Invitrogen Life Technologies, cat #15596108; Chomczynski, P. and Sacchi, N. (1987) Anal. Biochem. 162, 156; Simms, D., Cizdziel, P. E., and Chomczynski, P. (1993) Focus® 15, 99; Chomczynski, P., Bowers-Finn, R., and Sabatini, L. (1987) J. of NIH Res. 6, 83; Chomczynski, P. (1993) Bio/Techniques 15, 532; Bracete, A. M., Fox, D. K., and Simms, D. (1998) Focus 20, 82; Sewall, A. and McRae, S. (1998) Focus 20, 36; Anal Biochem 1984 April; 138(1):141-3, A method for the quantitative recovery of protein in dilute solution in the presence of detergents and lipids; Wessel D, Flugge UI. (1984) Anal Biochem. 1984 April; 138(1):141-143.

The assay itself may be a cell sorting assay in which cells are sorted and/or counted based on cell surface expression of a protein marker. (See Cantor et al. 1975, Galbraith et al. 1999)

Obtaining Expression Patterns

Expression patterns, or profiles, of a plurality of nucleotides corresponding to members of the candidate library are then evaluated in one or more samples of leukocytes. Typically, the leukocytes are derived from patient peripheral blood samples, although, as indicated above, many other sample sources are also suitable. These expression patterns constitute a set of relative or absolute expression values for some number of RNAs or protein products corresponding to the plurality of nucleotide sequences evaluated, which is referred to herein as the subject's "expression profile" for those nucleotide sequences. While expression patterns for as few as one independent member of the candidate library can be obtained, it is generally preferable to obtain expression patterns corresponding to a larger number of nucleotide sequences, e.g., about 2, about 5, about 10, about 20, about 50, about 100, about 200, about 500, or about 1000, or more. The expression pattern for each differentially expressed component member of the library provides a finite specificity and sensitivity with respect to predictive value, e.g., for diagnosis, prognosis, monitoring, and the like.

Clinical Studies, Data and Patient Groups

For the purpose of discussion, the term subject, or subject sample of leukocytes, refers to an individual regardless of health and/or disease status. A subject can be a patient, a study participant, a control subject, a screening subject, or any other class of individual from whom a leukocyte sample is obtained and assessed in the context of the invention. Accordingly, a subject can be diagnosed with a disease, can present with one or more symptom of a disease, or a predisposing factor, such as a family (genetic) or medical history (medical) factor, for a disease, or the like. Alternatively, a subject can be healthy with respect to any of the aforementioned factors or criteria. It will be appreciated that the term "healthy" as used herein, is relative to a specified disease, or disease factor, or disease criterion, as the term "healthy" cannot be defined to correspond to any absolute evaluation or status. Thus, an individual defined as healthy with reference to any specified disease or disease criterion, can in fact be diagnosed with any other one or more disease, or exhibit any other one or more disease criterion.

Furthermore, while the discussion of the invention focuses, and is exemplified using human sequences and samples, the invention is equally applicable, through construction or selection of appropriate candidate libraries, to non-human animals, such as laboratory animals, e.g., mice, rats, guinea pigs, rabbits; domesticated livestock, e.g., cows, horses, goats, sheep, chicken, etc.; and companion animals, e.g., dogs, cats, etc.

Methods for Obtaining Expression Data

Numerous methods for obtaining expression data are known, and any one or more of these techniques, singly or in combination, are suitable for determining expression profiles in the context of the present invention. For example, expression patterns can be evaluated by northern analysis, PCR, RT-PCR, Taq Man analysis, FRET detection, monitoring one or more molecular beacon, hybridization to an oligonucleotide array, hybridization to a cDNA array, hybridization to a polynucleotide array, hybridization to a liquid microarray, hybridization to a microelectric array, molecular beacons, cDNA sequencing, clone hybridization, cDNA fragment fingerprinting, serial analysis of gene expression (SAGE), subtractive hybridization, differential display and/or differential screening (see, e.g., Lockhart and Winzeler (2000) *Nature* 405:827-836, and references cited therein).

For example, specific PCR primers are designed to a member(s) of a candidate nucleotide library. cDNA is prepared from subject sample RNA by reverse transcription from a poly-dT oligonucleotide primer, and subjected to PCR. Double stranded cDNA may be prepared using primers suitable for reverse transcription of the PCR product, followed by amplification of the cDNA using in vitro transcription. The product of in vitro transcription is a sense-RNA corresponding to the original member(s) of the candidate library. PCR product may be also be evaluated in a number of ways known in the art, including real-time assessment using detection of labeled primers, e.g. TaqMan or molecular beacon probes. Technology platforms suitable for analysis of PCR products include the ABI 7700, 5700, or 7000 Sequence Detection Systems (Applied Biosystems, Foster City, Calif.), the MJ Research Opticon (MJ Research, Waltham, Mass.), the Roche Light Cycler (Roche Diagnostics, Indianapolis, Ind.), the Stratagene MX4000 (Stratagene, La Jolla, Calif.), and the Bio-Rad iCycler (Bio-Rad Laboratories, Hercules, Calif.). Alternatively, molecular beacons are used to detect presence of a nucleic acid sequence in an unamplified RNA or cDNA sample, or following amplification of the sequence using any method, e.g. IVT (In Vitro transcription) or NASBA (nucleic acid sequence based amplification). Molecular beacons are designed with sequences complementary to member(s) of a candidate nucleotide library, and are linked to fluorescent labels. Each probe has a different fluorescent label with non-overlapping emission wavelengths. For example, expression of ten genes may be assessed using ten different sequence-specific molecular beacons.

Alternatively, or in addition, molecular beacons are used to assess expression of multiple nucleotide sequences at once. Molecular beacons with sequence complimentary to the members of a diagnostic nucleotide set are designed and linked to fluorescent labels. Each fluorescent label used must have a non-overlapping emission wavelength. For example, 10 nucleotide sequences can be assessed by hybridizing 10 sequence specific molecular beacons (each labeled with a different fluorescent molecule) to an amplified or un-amplified RNA or cDNA sample. Such an assay bypasses the need for sample labeling procedures.

Alternatively, or in addition bead arrays can be used to assess expression of multiple sequences at once (See, e.g, LabMAP 100, Luminex Corp, Austin, Tex.). Alternatively, or in addition electric arrays are used to assess expression of multiple sequences, as exemplified by the e-Sensor technology of Motorola (Chicago, Ill.) or Nanochip technology of Nanogen (San Diego, Calif.)

Of course, the particular method elected will be dependent on such factors as quantity of RNA recovered, practitioner preference, available reagents and equipment, detectors, and the like. Typically, however, the elected method(s) will be appropriate for processing the number of samples and probes of interest. Methods for high-throughput expression analysis are discussed below.

Alternatively, expression at the level of protein products of gene expression is performed. For example, protein expression, in a sample of leukocytes, can be evaluated by one or more method selected from among: western analysis, two-dimensional gel analysis, chromatographic separation, mass spectrometric detection, protein-fusion reporter constructs, calorimetric assays, binding to a protein array and characterization of polysomal mRNA. One particularly favorable approach involves binding of labeled protein expression products to an array of antibodies specific for members of the candidate library. Methods for producing and, evaluating antibodies are widespread in the art, see, e.g., Coligan, supra; and Harlow and Lane (1989) *Antibodies: A Laboratory Manual*, Cold Spring Harbor Press, NY ("Harlow and Lane"). Additional details regarding a variety of immunological and immunoassay procedures adaptable to the present invention by selection of antibody reagents specific for the products of candidate nucleotide sequences can be found in, e.g., Stites and Terr (eds.) (1991) *Basic and Clinical Immunology* 7th ed., and Paul, supra. Another approach uses systems for performing desorption spectrometry. Commercially available systems, e.g., from Ciphergen Biosystems, Inc. (Fremont, Calif.) are particularly well suited to quantitative analysis of protein expression. Indeed, Protein Chip® arrays (see, e.g., the website, ciphergen.com) used in desorption spectrometry approaches provide arrays for detection of protein expression. Alternatively, affinity reagents, (e.g., antibodies, small molecules, etc.) are developed that recognize epitopes of the protein product. Affinity assays are used in protein array assays, e.g. to detect the presence or absence of particular proteins. Alternatively, affinity reagents are used to detect expression using the methods described above. In the case of a protein that is expressed on the cell surface of leukocytes, labeled affinity reagents are bound to populations of leukocytes, and leukocytes expressing the protein are identified and counted using fluorescent activated cell sorting (FACS).

It is appreciated that the methods of expression evaluation discussed herein, although discussed in the context of discovery of diagnostic nucleotide sets, are also applicable for expression evaluation when using diagnostic nucleotide sets for, e.g. diagnosis of diseases, as further discussed below.

High Throughput Expression Assays

A number of suitable high throughput formats exist for evaluating gene expression. Typically, the term high throughput refers to a format that performs at least about 100 assays, or at least about 500 assays, or at least about 1000 assays, or at least about 5000 assays, or at least about 10,000 assays, or more per day. When enumerating assays, either the number of samples or the number of candidate nucleotide sequences evaluated can be considered. For example, a northern analysis of, e.g., about 100 samples performed in a gridded array, e.g., a dot blot, using a single probe corresponding to a candidate nucleotide sequence can be considered a high throughput assay. More typically, however, such an assay is performed as a series of duplicate blots, each evaluated with a distinct probe corresponding to a different member of the candidate library. Alternatively, methods that simultaneously evaluate expression of about 100 or more candidate nucleotide sequences in one or more samples, or in multiple samples, are considered high throughput.

Numerous technological platforms for performing high throughput expression analysis are known. Generally, such methods involve a logical or physical array of either the subject samples, or the candidate library, or both. Common array formats include both liquid and solid phase arrays. For example, assays employing liquid phase arrays, e.g., for hybridization of nucleic acids, binding of antibodies or other receptors to ligand, etc., can be performed in multiwell, or microtiter, plates. Microtiter plates with 96, 384 or 1536 wells are widely available, and even higher numbers of wells, e.g, 3456 and 9600 can be used. In general, the choice of microtiter plates is determined by the methods and equipment, e.g., robotic handling and loading systems, used for sample preparation and analysis. Exemplary systems include, e.g., the ORCA™ system from Beckman-Coulter, Inc. (Fullerton, Calif.) and the Zymate systems from Zymark Corporation (Hopkinton, Mass.).

Alternatively, a variety of solid phase arrays can favorably be employed in to determine expression patterns in the context of the invention. Exemplary formats include membrane or filter arrays (e.g, nitrocellulose, nylon), pin arrays, and bead arrays (e.g., in a liquid "slurry"). Typically, probes corresponding to nucleic acid or protein reagents that specifically interact with (e.g., hybridize to or bind to) an expression product corresponding to a member of the candidate library are immobilized, for example by direct or indirect cross-linking, to the solid support. Essentially any solid support capable of withstanding the reagents and conditions necessary for performing the particular expression assay can be utilized. For example, functionalized glass, silicon, silicon dioxide, modified silicon, any of a variety of polymers, such as (poly)tetrafluoroethylene, (poly)vinylidenedifluoride, polystyrene, polycarbonate, or combinations thereof can all serve as the substrate for a solid phase array.

In a preferred embodiment, the array is a "chip" composed, e.g., of one of the above-specified materials. Polynucleotide probes, e.g., RNA or DNA, such as cDNA, synthetic oligonucleotides, and the like, or binding proteins such as antibodies, that specifically interact with expression products of individual components of the candidate library are affixed to the chip in a logically ordered manner, i.e., in an array. In addition, any molecule with a specific affinity for either the sense or anti-sense sequence of the marker nucleotide sequence (depending on the design of the sample labeling), can be fixed to the array surface without loss of specific affinity for the marker and can be obtained and produced for array production, for example, proteins that specifically recognize the specific nucleic acid sequence of the marker, ribozymes, peptide nucleic acids (PNA), or other chemicals or molecules with specific affinity.

Detailed discussion of methods for linking nucleic acids and proteins to a chip substrate, are found in, e.g., U.S. Pat. No. 5,143,854 "Large Scale Photolithographic Solid Phase Synthesis Of Polypeptides And Receptor Binding Screening Thereof" to Pirrung et al., issued, Sep. 1, 1992; U.S. Pat. No. 5,837,832 "Arrays Of Nucleic Acid Probes On Biological Chips" to Chee et al., issued Nov. 17, 1998; U.S. Pat. No. 6,087,112 "Arrays With Modified Oligonucleotide And Polynucleotide Compositions" to Dale, issued Jul. 11, 2000; U.S. Pat. No. 5,215,882 "Method Of Immobilizing Nucleic Acid On A Solid Substrate For Use In Nucleic Acid Hybridization Assays" to Bahl et al., issued Jun. 1, 1993; U.S. Pat. No. 5,707,807 "Molecular Indexing For Expressed Gene Analysis" to Kato, issued Jan. 13, 1998; U.S. Pat. No. 5,807,522 "Methods For Fabricating Microarrays Of Biological Samples" to Brown et al., issued Sep. 15, 1998; U.S. Pat. No. 5,958,342 "Jet Droplet Device" to Gamble et al., issued Sep. 28, 1999; U.S. Pat. No. 5,994,076 "Methods Of Assaying Differential Expression" to Chenchik et al., issued Nov. 30, 1999; U.S. Pat. No. 6,004,755 "Quantitative Microarray Hybridization Assays" to Wang, issued Dec. 21, 1999; U.S. Pat. No. 6,048,695 "Chemically Modified Nucleic Acids And Method For Coupling Nucleic Acids To Solid Support" to Bradley et al., issued Apr. 11, 2000; U.S. Pat. No. 6,060,240 "Methods For Measuring Relative Amounts Of Nucleic Acids In A Complex Mixture And Retrieval Of Specific Sequences Therefrom" to Kamb et al., issued May 9, 2000; U.S. Pat. No. 6,090,556 "Method For Quantitatively Determining The Expression Of A Gene" to Kato, issued Jul. 18, 2000; and U.S. Pat. No. 6,040,138 "Expression Monitoring By Hybridization To High Density Oligonucleotide Arrays" to Lockhart et al., issued Mar. 21, 2000 each of which are hereby incorporated by reference in their entirety.

For example, cDNA inserts corresponding to candidate nucleotide sequences, in a standard TA cloning vector are amplified by a polymerase chain reaction for approximately 30-40 cycles. The amplified PCR products are then arrayed onto a glass support by any of a variety of well-known techniques, e.g., the VSLIPS™ technology described in U.S. Pat. No. 5,143,854. RNA, or cDNA corresponding to RNA, isolated from a subject sample of leukocytes is labeled, e.g., with a fluorescent tag, and a solution containing the RNA (or cDNA) is incubated under conditions favorable for hybridization, with the "probe" chip. Following incubation, and washing to eliminate non-specific hybridization, the labeled nucleic acid bound to the chip is detected qualitatively or quantitatively, and the resulting expression profile for the corresponding candidate nucleotide sequences is recorded. It is appreciated that the probe used for diagnostic purposes may be identical to the probe used during diagnostic nucleotide sequence discovery and validation. Alternatively, the probe sequence may be different than the sequence used in diagnostic nucleotide sequence discovery and validation. Multiple cDNAs from a nucleotide sequence that are non-overlapping or partially overlapping may also be used.

In another approach, oligonucleotides corresponding to members of a candidate nucleotide library are synthesized and spotted onto an array. Alternatively, oligonucleotides are synthesized onto the array using methods known in the art, e.g. Hughes, et al. supra. The oligonucleotide is designed to be complementary to any portion of the candidate nucleotide sequence. In addition, in the context of expression analysis for, e.g. diagnostic use of diagnostic nucleotide sets, an oligonucleotide can be designed to exhibit particular hybridization characteristics, or to exhibit a particular specificity and/or sensitivity, as further described below.

Hybridization signal may be amplified using methods known in the art, and as described herein, for example use of the Clontech kit (Glass Fluorescent Labeling Kit), Stratagene kit (Fairplay Microarray Labeling Kit), the Micromax kit (New England Nuclear, Inc.), the Genisphere kit (3DNA Submicro), linear amplification, e.g. as described in U.S. Pat. No. 6,132,997 or described in Hughes, T R, et al., Nature Biotechnology, 19:343-347 (2001) and/or Westin et al. *Nat. Biotech.* 18:199-204. In some cases, amplification techniques do not increase signal intensity, but allow assays to be done with small amounts of RNA.

Alternatively, fluorescently labeled cDNA are hybridized directly to the microarray using methods known in the art. For example, labeled cDNA are generated by reverse transcription using Cy3- and Cy5-conjugated deoxynucleotides, and the reaction products purified using standard methods. It is appreciated that the methods for signal amplification of expression data useful for identifying diagnostic nucleotide sets are also useful for amplification of expression data for diagnostic purposes.

Microarray expression may be detected by scanning the microarray with a variety of laser or CCD-based scanners, and extracting features with numerous software packages, for example, Imagene (Biodiscovery), Feature Extraction Software (Agilent), Scanalyze (Eisen, M. 1999. SCANALYZE User Manual; Stanford Univ., Stanford, Calif. Ver 2.32), GenePix (Axon Instruments).

In another approach, hybridization to microelectric arrays is performed, e.g. as described in Umek et al (2001) *J Mol. Diagn.* 3:74-84. An affinity probe, e.g. DNA, is deposited on a metal surface. The metal surface underlying each probe is connected to a metal wire and electrical signal detection system. Unlabelled RNA or cDNA is hybridized to the array, or alternatively, RNA or cDNA sample is amplified before hybridization, e.g. by PCR. Specific hybridization of sample RNA or cDNA results in generation of an electrical signal, which is transmitted to a detector. See Westin (2000) *Nat. Biotech.* 18:199-204 (describing anchored multiplex amplification of a microelectronic chip array); Edman (1997) *NAR* 25:4907-14; Vignali (2000) *J Immunol Methods* 243:243-55.

In another approach, a microfluidics chip is used for RNA sample preparation and analysis. This approach increases efficiency because sample preparation and analysis are streamlined. Briefly, microfluidics may be used to sort specific leukocyte sub-populations prior to RNA preparation and analysis. Microfluidics chips are also useful for, e.g., RNA preparation, and reactions involving RNA (reverse transcription, RT-PCR). Briefly, a small volume of whole, anti-coagulated blood is loaded onto a microfluidics chip, for example chips available from Caliper (Mountain View, Calif.) or Nanogen (San Diego, Calif.) A microfluidics chip may contain channels and reservoirs in which cells are moved and reactions are performed. Mechanical, electrical, magnetic, gravitational, centrifugal or other forces are used to move the cells and to expose them to reagents. For example, cells of whole blood are moved into a chamber containing hypotonic saline, which results in selective lysis of red blood cells after a 20-minute incubation. Next, the remaining cells (leukocytes) are moved into a wash chamber and finally, moved into a chamber containing a lysis buffer such as guanidine isothyocyanate. The leukocyte cell lysate is further processed for RNA isolation in the chip, or is then removed for further processing, for example, RNA extraction by standard methods. Alternatively, the microfluidics chip is a circular disk containing ficoll or another density reagent. The blood sample is injected into the center of the disc, the disc is rotated at a speed that generates a centrifugal force appropriate for density gradient separation of mononuclear cells, and the separated mononuclear cells are then harvested for further analysis or processing.

It is understood that the methods of expression evaluation, above, although discussed in the context of discovery of diagnostic nucleotide sets, are also applicable for expression evaluation when using diagnostic nucleotide sets for, e.g. diagnosis of diseases, as further discussed below.

Evaluation of Expression Patterns

Expression patterns can be evaluated by qualitative and/or quantitative measures. Certain of the above described techniques for evaluating gene expression (as RNA or protein products) yield data that are predominantly qualitative in nature. That is, the methods detect differences in expression that classify expression into distinct modes without providing significant information regarding quantitative aspects of expression. For example, a technique can be described as a qualitative technique if it detects the presence or absence of expression of a candidate nucleotide sequence, i.e., an on/off pattern of expression. Alternatively, a qualitative technique measures the presence (and/or absence) of different alleles, or variants, of a gene product.

In contrast, some methods provide data that characterize expression in a quantitative manner. That is, the methods relate expression on a numerical scale, e.g., a scale of 0-5, a scale of 1-10, a scale of +-+++, from grade 1 to grade 5, a grade from a to z, or the like. It will be understood that the numerical, and symbolic examples provided are arbitrary, and that any graduated scale (or any symbolic representation of a graduated scale) can be employed in the context of the present invention to describe quantitative differences in nucleotide sequence expression. Typically, such methods yield information corresponding to a relative increase or decrease in expression.

Any method that yields either quantitative or qualitative expression data is suitable for evaluating expression of candidate nucleotide sequence in a subject sample of leukocytes. In some cases, e.g., when multiple methods are employed to determine expression patterns for a plurality of candidate nucleotide sequences, the recovered data, e.g., the expression profile, for the nucleotide sequences is a combination of quantitative and qualitative data.

In some applications, expression of the plurality of candidate nucleotide sequences is evaluated sequentially. This is typically the case for methods that can be characterized as low- to moderate-throughput. In contrast, as the throughput of the elected assay increases, expression for the plurality of candidate nucleotide sequences in a sample or multiple samples of leukocytes, is assayed simultaneously. Again, the methods (and throughput) are largely determined by the individual practitioner, although, typically, it is preferable to employ methods that permit rapid, e.g. automated or partially automated, preparation and detection, on a scale that is time-efficient and cost-effective.

It is understood that the preceding discussion, while directed at the assessment of expression of the members of candidate libraries, is also applies to the assessment of the expression of members of diagnostic nucleotide sets, as further discussed below.

Genotyping

In addition to, or in conjunction with the correlation of expression profiles and clinical data, it is often desirable to correlate expression patterns with the subject's genotype at one or more genetic loci or to correlate both expression profiles and genetic loci data with clinical data. The selected loci can be, for example, chromosomal loci corresponding to one or more member of the candidate library, polymorphic alleles for marker loci, or alternative disease related loci (not contributing to the candidate library) known to be, or putatively associated with, a disease (or disease criterion). Indeed, it will be appreciated, that where a (polymorphic) allele at a locus is linked to a disease (or to a predisposition to a disease), the presence of the allele can itself be a disease criterion.

Numerous well known methods exist for evaluating the genotype of an individual, including southern analysis, restriction fragment length polymorphism (RFLP) analysis, polymerase chain reaction (PCR), amplification length polymorphism (AFLP) analysis, single stranded conformation polymorphism (SSCP) analysis, single nucleotide polymorphism (SNP) analysis (e.g., via PCR, Taqman or molecular beacons), among many other useful methods. Many such procedures are readily adaptable to high throughput and/or automated (or semi-automated) sample preparation and analysis methods. Most, can be performed on nucleic acid samples recovered via simple procedures from the same sample of leukocytes as yielded the material for expression profiling. Exemplary techniques are described in, e.g., Sambrook, and Ausubel, supra.

Identification of the Diagnostic Oligonucleotides and Oligonucleotide Sets of the Invention Identification of diagnostic nucleotides and nucleotide sets and disease specific target nucleotide sequence proceeds by correlating the leukocyte expression profiles with data regarding the subject's health status to produce a data set designated a "molecular signature." Examples of data regarding a patient's health status, also termed "disease criteria(ion)", is described below and in the Section titled "selected diseases," below. Methods useful for correlation analysis are further described elsewhere in the specification.

Generally, relevant data regarding the subject's health status includes retrospective or prospective health data, e.g., in the form of the subject's medical history, as provided by the subject, physician or third party, such as, medical diagnoses, laboratory test results, diagnostic test results, clinical events, or medication lists, as further described below. Such data may include information regarding a patient's response to treatment and/or a particular medication and data regarding the presence of previously characterized "risk factors." For example, cigarette smoking and obesity are previously identified risk factors for heart disease. Further examples of health status information, including diseases and disease criteria, is described in the section titled Selected diseases, below.

Typically, the data describes prior events and evaluations (i.e., retrospective data). However, it is envisioned that data collected subsequent to the sampling (i.e., prospective data) can also be correlated with the expression profile. The tissue sampled, e.g., peripheral blood, bronchial lavage, etc., can be obtained at one or more multiple time points and subject data is considered retrospective or prospective with respect to the time of sample procurement.

Data collected at multiple time points, called "longitudinal data", is often useful, and thus, the invention encompasses the analysis of patient data collected from the same patient at different time points. Analysis of paired samples, such as samples from a patient at different times, allows identification of differences that are specifically related to the disease state since the genetic variability specific to the patient is controlled for by the comparison. Additionally, other variables that exist between patients may be controlled for in this way, for example, the presence or absence of inflammatory diseases (e.g., rheumatoid arthritis) the use of medications that may effect leukocyte gene expression, the presence or absence of co-morbid conditions, etc. Methods for analysis of paired samples are further described below. Moreover, the analysis of a pattern of expression profiles (generated by collecting multiple expression profiles) provides information relating to changes in expression level over time, and may permit the determination of a rate of change, a trajectory, or an expression curve. Two longitudinal samples may provide information on the change in expression of a gene over time, while three longitudinal samples may be necessary to determine the "trajectory" of expression of a gene. Such information may be relevant to the diagnosis of a disease. For example, the expression of a gene may vary from individual to individual, but a clinical event, for example, a heart attack, may cause the level of expression to double in each patient. In this example, clinically interesting information is gleaned from the change in expression level, as opposed to the absolute level of expression in each individual.

When a single patient sample is obtained, it may still be desirable to compare the expression profile of that sample to some reference expression profile. In this case, one can determine the change of expression between the patient's sample and a reference expression profile that is appropriate for that patient and the medical condition in question. For example, a reference expression profile can be determined for all patients without the disease criterion in question who have similar characteristics, such as age, sex, race, diagnoses etc.

Generally, small sample sizes of 10-40 samples from 10-20 individuals are used to identify a diagnostic nucleotide set. Larger sample sizes are generally necessary to validate the diagnostic nucleotide set for use in large and varied patient populations, as further described below. For example, extension of gene expression correlations to varied ethnic groups, demographic groups, nations, peoples or races may require expression correlation experiments on the population of interest.

Expression Reference Standards

Expression profiles derived from a patient (i.e., subjects diagnosed with, or exhibiting symptoms of, or exhibiting a disease criterion, or under a doctor's care for a disease) sample are compared to a control or standard expression RNA to facilitate comparison of expression profiles (e.g. of a set of candidate nucleotide sequences) from a group of patients relative to each other (i.e., from one patient in the group to other patients in the group, or to patients in another group).

The reference RNA used should have desirable features of low cost and simplicity of production on a large scale. Additionally, the reference RNA should contain measurable amounts of as many of the genes of the candidate library as possible.

For example, in one approach to identifying diagnostic nucleotide sets, expression profiles derived from patient samples are compared to a expression reference "standard." Standard expression reference can be, for example, RNA derived from resting cultured leukocytes or commercially available reference RNA, such as Universal reference RNA from Stratagene. See Nature, V406, 8-17-00, p. 747-752. Use of an expression reference standard is particularly useful when the expression of large numbers of nucleotide sequences is assayed, e.g. in an array, and in certain other applications, e.g. qualitative PCR, RT-PCR, etc., where it is desirable to compare a sample profile to a standard profile, and/or when large numbers of expression profiles, e.g. a patient population, are to be compared. Generally, an expression reference standard should be available in large quantities, should be a good substrate for amplification and labeling reactions, and should be capable of detecting a large percentage of candidate nucleic acids using suitable expression profiling technology.

Alternatively, or in addition, the expression profile derived from a patient sample is compared with the expression of an internal reference control gene, for example, β-actin or CD4. The relative expression of the profiled genes and the internal reference control gene (from the same individual) is obtained.

An internal reference control may also be used with a reference RNA. For example, an expression profile for "gene 1" and the gene encoding CD4 can be determined in a patient sample and in a reference RNA. The expression of each gene can be expressed as the "relative" ratio of expression the gene in the patient sample compared with expression of the gene in the reference RNA. The expression ratio (sample/reference) for gene 1 may be divided by the expression ration for CD4 (sample/reference) and thus the relative expression of gene 1 to CD4 is obtained.

The invention also provides a buffy coat control RNA useful for expression profiling, and a method of using control RNA produced from a population of buffy coat cells, the white blood cell layer derived from the centrifugation of whole blood. Buffy coat contains all white blood cells, including granulocytes, mononuclear cells and platelets. The invention also provides a method of preparing control RNA from buffy coat cells for use in expression profile analysis of leukocytes. Buffy coat fractions are obtained, e.g. from a blood bank or directly from individuals, preferably from a large number of individuals such that bias from individual samples is avoided and so that the RNA sample represents an average expression of a healthy population. Buffy coat fractions from about 50 or about 100, or more individuals are preferred. 10 ml buffy coat from each individual is used. Buffy coat samples are treated with an erthythrocyte lysis buffer, so that erthythrocytes are selectively removed. The leukocytes of the buffy coat layer are collected by centrifugation. Alternatively, the buffy cell sample can be further enriched for a particular leukocyte sub-populations, e.g. mononuclear cells, T-lymphocytes, etc. To enrich for mononuclear cells, the buffy cell pellet, above, is diluted in PBS (phosphate buffered saline) and loaded onto a non-polystyrene tube containing a polysucrose and sodium diatrizoate solution adjusted to a density of 1.077+/−0.001 g/ml. To enrich for T-lymphocytes, 45 ml of whole blood is treated with RosetteSep (Stem Cell Technologies), and incubated at room temperature for 20 minutes. The mixture is diluted with an equal volume of PBS plus 2% FBS and mixed by inversion. 30 ml of diluted mixture is layered on top of 15 ml DML medium (Stem Cell Technologies). The tube is centrifuged at 1200×g, and the enriched cell layer at the plasma: medium interface is removed, washed with PBS+2% FBS, and cells collected by centrifugation at 1200×g. The cell pellet is treated with 5 ml of erythrocyte lysis buffer (EL buffer, Qiagen) for 10 minutes on ice, and enriched T-lymphoctes are collected by centrifugation.

In addition or alternatively, the buffy cells (whole buffy coat or sub-population, e.g. mononuclear fraction) can be cultured in vitro and subjected to stimulation with cytokines or activating chemicals such as phorbol esters or ionomycin. Such stimuli may increase expression of nucleotide sequences that are expressed in activated immune cells and might be of interest for leukocyte expression profiling experiments.

Following sub-population selection and/or further treatment, e.g. stimulation as described above, RNA is prepared using standard methods. For example, cells are pelleted and lysed with a phenol/guanidinium thiocyanate and RNA is prepared. RNA can also be isolated using a silica gel-based purification column or the column method can be used on RNA isolated by the phenol/guanidinium thiocyanate method. RNA from individual buffy coat samples can be pooled during this process, so that the resulting reference RNA represents the RNA of many individuals and individual bias is minimized or eliminated. In addition, a new batch of buffy coat reference RNA can be directly compared to the last batch to ensure similar expression pattern from one batch to another, using methods of collecting and comparing expression profiles described above/below. One or more expression reference controls are used in an experiment. For example, RNA derived from one or more of the following sources can be used as controls for an experiment: stimulated or unstimulated whole buffy coat, stimulated or unstimulated peripheral mononuclear cells, or stimulated or unstimulated T-lymphocytes.

Alternatively, the expression reference standard can be derived from any subject or class of subjects including healthy subjects or subjects diagnosed with the same or a different disease or disease criterion. Expression profiles from subjects in two or more distinct classes are compared to determine which subset of nucleotide sequences in the candidate library can best distinguish between the subject classes, as further discussed below. It will be appreciated that in the present context, the term "distinct classes" is relevant to at least one distinguishable criterion relevant to a disease of interest, a "disease criterion." The classes can, of course, demonstrate significant overlap (or identity) with respect to other disease criteria, or with respect to disease diagnoses, prognoses, or the like. The mode of discovery involves, e.g., comparing the molecular signature of different subject classes to each other (such as patient to control, patients with a first diagnosis to patients with a second diagnosis, etc.) or by comparing the molecular signatures of a single individual taken at different time points. The invention can be applied to a broad range of diseases, disease criteria, conditions and other clinical and/or epidemiological questions, as further discussed above/below.

It is appreciated that while the present discussion pertains to the use of expression reference controls while identifying diagnostic nucleotide sets, expression reference controls are also useful during use of diagnostic nucleotide sets, e.g. use of a diagnostic nucleotide set for diagnosis of a disease, as further described below.

Analysis of Expression Profiles

In order to facilitate ready access, e.g., for comparison, review, recovery, and/or modification, the molecular signatures/expression profiles are typically recorded in a database. Most typically, the database is a relational database accessible by a computational device, although other formats, e.g., manually accessible indexed files of expression profiles as photographs, analogue or digital imaging readouts, spreadsheets, etc. can be used. Further details regarding preferred embodiments are provided below. Regardless of whether the expression patterns initially recorded are analog or digital in nature and/or whether they represent quantitative or qualitative differences in expression, the expression patterns, expression profiles (collective expression patterns), and molecular signatures (correlated expression patterns) are stored digitally and accessed via a database. Typically, the database is compiled and maintained at a central facility, with access being available locally and/or remotely.

As additional samples are obtained, and their expression profiles determined and correlated with relevant subject data, the ensuing molecular signatures are likewise recorded in the database. However, rather than each subsequent addition being added in an essentially passive manner in which the data from one sample has little relation to data from a second (prior or subsequent) sample, the algorithms optionally additionally query additional samples against the existing database to further refine the association between a molecular signature and disease criterion. Furthermore, the data set comprising the one (or more) molecular signatures is optionally queried against an expanding set of additional or other disease criteria. The use of the database in integrated systems and web embodiments is further described below.

Analysis of Expression Profile Data from Arrays

Expression data is analyzed using methods well known in the art, including the software packages Imagene (Biodiscovery, Marina del Rey, Calif.), Feature Extraction Software (Agilent, Palo Alto, Calif.), and Scanalyze (Stanford University). In the discussion that follows, a "feature" refers to an individual spot of DNA on an array. Each gene may be represented by more than one feature. For example, hybridized microarrays are scanned and analyzed on an Axon Instruments scanner using GenePix 3.0 software (Axon Instruments, Union City, Calif.). The data extracted by GenePix is used for all downstream quality control and expression evaluation. The data is derived as follows. The data for all features flagged as "not found" by the software is removed from the dataset for individual hybridizations. The "not found" flag by GenePix indicates that the software was unable to discriminate the feature from the background. Each feature is examined to determine the value of its signal. The median pixel intensity of the background ($B_n$) is subtracted from the median pixel intensity of the feature ($F_n$) to produce the background-subtracted signal (hereinafter, "BGSS"). The BGSS is divided by the standard deviation of the background pixels to provide the signal-to-noise ratio (hereinafter, "S/N"). Features with a S/N of three or greater in both the Cy3 channel (corresponding to the sample RNA) and Cy5 channel (corresponding to the reference RNA) are used for further analysis (hereinafter denoted "useable features"). Alternatively, different S/Ns are used for selecting expression data for an analysis. For example, only expression data with signal to noise ratios >3 might be used in an analysis. Alternatively, features with S/N values <3 may be flagged as such and included in the analysis. Such flagged data sets include more values and may allow one to discover expression markers that would be missed otherwise. However, such data sets may have a higher variability than filtered data, which may decrease significance of findings or performance of correlation statistics.

For each usable feature (i), the expression level (e) is expressed as the logarithm of the ratio (R) of the Background Subtracted Signal (hereinafter "BGSS") for the Cy3 (sample RNA) channel divided by the BGSS for the Cy5 channel (reference RNA). This "log ratio" value is used for comparison to other experiments.

$$R_i = \frac{BGSS_{sample}}{BGSS_{reference}} \quad (0.1)$$

$$e_i = \log r_i \quad (0.2)$$

Variation in signal across hybridizations may be caused by a number of factors affecting hybridization, DNA spotting, wash conditions, and labeling efficiency.

A single reference RNA may be used with all of the experimental RNAs, permitting multiple comparisons in addition to individual comparisons. By comparing sample RNAs to the same reference, the gene expression levels from each sample are compared across arrays, permitting the use of a consistent denominator for our experimental ratios. Alternative methods of analyzing the data may involve 1) using the sample channel without normalization by the reference channel, 2) using an intensity-dependent normalization based on the reference which provides a greater correction when the signal in the reference channel is large, 3) using the data without background subtraction or subtracting an empirically derived function of the background intensity rather than the background itself.

Scaling

The data may be scaled (normalized) to control for labeling and hybridization variability within the experiment, using methods known in the art. Scaling is desirable because it facilitates the comparison of data between different experiments, patients, etc. Generally the BGSS are scaled to a factor such as the median, the mean, the trimmed mean, and percentile. Additional methods of scaling include: to scale between 0 and 1, to subtract the mean, or to subtract the median.

Scaling is also performed by comparison to expression patterns obtained using a common reference RNA, as described in greater detail above. As with other scaling methods, the reference RNA facilitates multiple comparisons of the expression data, e.g., between patients, between samples, etc. Use of a reference RNA provides a consistent denominator for experimental ratios.

In addition to the use of a reference RNA, individual expression levels may be adjusted to correct for differences in labeling efficiency between different hybridization experiments, allowing direct comparison between experiments with different overall signal intensities, for example. A scaling factor ($\alpha$) may be used to adjust individual expression levels as follows. The median of the scaling factor ($\alpha$), for example, BGSS, is determined for the set of all features with a S/N greater than three. Next, the $BGSS_i$ (the BGSS for each feature "i") is divided by the median for all features ($\alpha$), generating a scaled ratio. The scaled ration is used to determine the expression value for the feature ($e_i$), or the log ratio.

$$S_i = \frac{BGSS_i}{a} \quad (0.3)$$

$$e_i = \log\left(\frac{Cy3S_i}{Cy5S_i}\right). \quad (0.4)$$

In addition, or alternatively, control features are used to normalize the data for labeling and hybridization variability within the experiment. Control feature may be cDNA for genes from the plant, *Arabidopsis thaliana*, that are included when spotting the mini-array. Equal amounts of RNA complementary to control cDNAs are added to each of the samples before they were labeled. Using the signal from these control genes, a normalization constant (L) is determined according to the following formula:

$$L_j = \frac{\sum\limits_{i=1}^{N} BGSS_{j,i}}{\sum\limits_{j=1}^{K} \frac{\sum\limits_{i=1}^{N} BGSS_{j,i}}{N}},$$

where $BGSS_i$ is the signal for a specific feature, N is the number of *A. thaliana* control features, K is the number of hybridizations, and $L_j$ is the normalization constant for each individual hybridization.

Using the formula above, the mean for all control features of a particular hybridization and dye (e.g., Cy3) is calculated. The control feature means for all Cy3 hybridizations are averaged, and the control feature mean in one hybridization divided by the average of all hybridizations to generate a normalization constant for that particular Cy3 hybridization ($L_j$), which is used as $\alpha$ in equation (0.3). The same normalization steps may be performed for Cy3 and Cy5 values.

An alternative scaling method can also be used. The log of the ratio of Green/Red is determined for all features. The median log ratio value for all features is determined. The feature values are then scaled using the following formula: Log_Scaled_Feature_Ratio=Log_Feature_Ratio−Median_Log_Ratio.

Many additional methods for normalization exist and can be applied to the data. In one method, the average ratio of Cy3 BGSS/Cy5 BGSS is determined for all features on an array. This ratio is then scaled to some arbitrary number, such as 1 or some other number. The ratio for each probe is then multiplied by the scaling factor required to bring the average ratio to the chosen level. This is performed for each array in an analysis. Alternatively, the ratios are normalized to the average ratio across all arrays in an analysis. Other methods of normalization include forcing the distribution of signal strengths of the various arrays into greater agreement by transforming them to match certain points (quartiles, or deciles, etc.) in a standard distribution, or in the most extreme case using the rank of the signal of each oligonucleotide relative to the other oligonucleotides on the array.

If multiple features are used per gene sequence or oligonucleotide, these repeats can be used to derive an average expression value for each gene. If some of the replicate features are of poor quality and don't meet requirements for analysis, the remaining features can be used to represent the gene or gene sequence.

Correlation Analysis

Correlation analysis is performed to determine which array probes have expression behavior that best distinguishes or serves as markers for relevant groups of samples representing a particular clinical condition. Correlation analysis, or comparison among samples representing different disease criteria (e.g., clinical conditions), is performed using standard statistical methods. Numerous algorithms are useful for correlation analysis of expression data, and the selection of algorithms depends in part on the data analysis to be performed. For example, algorithms can be used to identify the single most informative gene with expression behavior that reliably classifies samples, or to identify all the genes useful to classify samples. Alternatively, algorithms can be applied that determine which set of 2 or more genes have collective expression behavior that accurately classifies samples. The use of multiple expression markers for diagnostics may overcome the variability in expression of a gene between individuals, or overcome the variability intrinsic to the assay. Multiple expression markers may include redundant markers (surrogates), in that two or more genes or probes may provide the same information with respect to diagnosis. This may occur, for example, when two or more genes or gene probes are coordinately expressed. For diagnostic application, it may be appropriate to utilize a gene and one or more of its surrogates in the assay. This redundancy may overcome failures (technical or biological) of a single marker to distinguish samples. Alternatively, one or more surrogates may have properties that make them more suitable for assay development, such as a higher baseline level of expression, better cell specificity, a higher fold change between sample groups or more specific sequence for the design of PCR primers or complimentary probes. It will be appreciated that while the discussion above pertains to the analysis of RNA expression profiles the discussion is equally applicable to the analysis of profiles of proteins or other molecular markers.

Prior to analysis, expression profile data may be formatted or prepared for analysis using methods known in the art. For example, often the log ratio of scaled expression data for every array probe is calculated using the following formula:

log(Cy 3 BGSS/Cy5 BGSS), where Cy 3 signal corresponds to the expression of the gene in the clinical sample, and Cy5 signal corresponds to expression of the gene in the reference RNA.

Data may be further filtered depending on the specific analysis to be done as noted below. For example, filtering may be aimed at selecting only samples with expression above a certain level, or probes with variability above a certain level between sample sets.

The following non-limiting discussion consider several statistical methods known in the art. Briefly, the t-test and ANOVA are used to identify single genes with expression differences between or among populations, respectively. Multivariate methods are used to identify a set of two or more genes for which expression discriminates between two disease states more specifically than expression of any single gene.

t-Test

The simplest measure of a difference between two groups is the Student's t test. See, e.g., Welsh et al. (2001) *Proc Natl Acad Sci USA* 98:1176-81 (demonstrating the use of an unpaired Student's t-test for the discovery of differential gene expression in ovarian cancer samples and control tissue samples). The t-test assumes equal variance and normally distributed data. This test identifies the probability that there is a difference in expression of a single gene between two groups of samples. The number of samples within each group that is required to achieve statistical significance is dependent upon the variation among the samples within each group. The standard formula for a t-test is:

$$t(e_i) = \frac{\overline{e}_{i,c} - \overline{e}_{i,t}}{\sqrt{(s_{i,c}^2/n_c) + (s_{i,t}^2/n_t)}}, \quad (0.5)$$

where $\overline{e}_i$ is the difference between the mean expression level of gene i in groups c and t, $s_{i,c}$ is the variance of gene x in group c and $s_{i,t}$ is the variance of gene x in group t. $n_c$ and $n_t$ are the numbers of samples in groups c and t.

The combination of the t statistic and the degrees of freedom $[\min(n_t, n_c)-1]$ provides a p value, the probability of rejecting the null hypothesis. A p-value of $\leq 0.01$, signifying a 99 percent probability the mean expression levels are different between the two groups (a 1% chance that the mean expression levels are in fact not different and that the observed difference occurred by statistical chance), is often considered acceptable.

When performing tests on a large scale, for example, on a large dataset of about 8000 genes, a correction factor must be included to adjust for the number of individual tests being performed. The most common and simplest correction is the Bonferroni correction for multiple tests, which divides the p-value by the number of tests run. Using this test on an 8000 member dataset indicates that a p value of $\leq 0.00000125$ is required to identify genes that are likely to be truly different between the two test conditions.

Significance Analysis for Microarrays (SAM)

Significance analysis for microarrays (SAM) (Tusher 2001) is a method through which genes with a correlation between their expression values and the response vector are statistically discovered and assigned a statistical significance. The ratio of false significant to significant genes is the False Discovery Rate (FDR). This means that for each threshold there are a set of genes which are called significant, and the FDR gives a confidence level for this claim. If a gene is called differentially expressed between 2 classes by SAM, with a FDR of 5%, there is a 95% chance that the gene is actually differentially expressed between the classes. SAM takes into account the variability and large number of variables of microarrays. SAM will identity genes that are most globally differentially expressed between the classes. Thus, important genes for identifying and classifying outlier samples or patients may not be identified by SAM.

Non-Parametric Tests

Wilcoxon's signed ranks method is one example of a non-parametric test and is utilized for paired comparisons. See e.g., Sokal and Rohlf (1987) *Introduction to Biostatistics* $2^{nd}$ edition, WH Freeman, New York. At least 6 pairs are necessary to apply this statistic. This test is useful for analysis of paired expression data (for example, a set of patients who have had samples taken before and after administration of a pharmacologic agent). The Fisher Exact Test with a threshold and the Mann-Whitney Test are other non-parametric tests that may be used

ANOVA

Differences in gene expression across multiple related groups may be assessed using an Analysis of Variance (ANOVA), a method well known in the art (Michelson and Schofield, 1996).

Multivariate Analysis

Many algorithms suitable for multivariate analysis are known in the art (Katz 1999). Generally, a set of two or more genes for which expression discriminates between two disease states more specifically than expression of any single gene is identified by searching through the possible combinations of genes using a criterion for discrimination, for example the expression of gene X must increase from normal 300 percent, while the expression of genes Y and Z must decrease from normal by 75 percent. Ordinarily, the search starts with a single gene, then adds the next best fit at each step of the search. Alternatively, the search starts with all of the genes and genes that do not aid in the discrimination are eliminated step-wise.

Paired Samples

Paired samples, or samples collected at different time-points from the same patient, are often useful, as described above. For example, use of paired samples permits the reduction of variation due to genetic variation among individuals. In addition, the use of paired samples has a statistical significance in that data derived from paired samples can be calculated in a different manner that recognizes the reduced variability. For example, the formula for a t-test for paired samples is:

$$t(e_x) = \frac{\overline{D}_{\overline{e}_x}}{\sqrt{\frac{\sum D^2 - (\sum D)^2/b}{b-1}}} \quad (0.5)$$

where D is the difference between each set of paired samples and b is the number of sample pairs. $\overline{D}$ is the mean of the differences between the members of the pairs. In this test, only the differences between the paired samples are considered, then grouped together (as opposed to taking all possible differences between groups, as would be the case with an ordinary t-test). Additional statistical tests useful with paired data, e.g., ANOVA and Wilcoxon's signed rank test, are discussed above.

Diagnostic Classification

Once a discriminating set of genes is identified, the diagnostic classifier (a mathematical function that assigns samples to diagnostic categories based on expression data) is applied to unknown sample expression levels.

Methods that can be used for this analysis include the following non-limiting list:

CLEAVER is an algorithm used for classification of useful expression profile data. See Raychaudhuri et al. (2001) *Trends Biotechnol* 19:189-193. CLEAVER uses positive training samples (e.g., expression profiles from samples known to be derived from a particular patient or sample diagnostic category, disease or disease criteria), negative training samples (e.g., expression profiles from samples known not to be derived from a particular patient or sample diagnostic category, disease or disease criteria) and test samples (e.g., expression profiles obtained from a patient), and determines whether the test sample correlates with the particular disease or disease criteria, or does not correlate with a particular disease or disease criteria. CLEAVER also generates a list of the 20 most predictive genes for classification.

Artificial neural networks (hereinafter, "ANN") can be used to recognize patterns in complex data sets and can discover expression criteria that classify samples into more than 2 groups. The use of artificial neural networks for discovery of gene expression diagnostics for cancers using expression data generated by oligonucleotide expression microarrays is demonstrated by Khan et al. (2001) *Nature Med.* 7:673-9. Khan found that 96 genes provided 0% error rate in classification of the tumors. The most important of these genes for classification was then determined by measuring the sensitivity of the classification to a change in expression of each gene. Hierarchical clustering using the 96 genes results in correct grouping of the cancers into diagnostic categories.

Golub uses cDNA microarrays and a distinction calculation to identify genes with expression behavior that distinguishes myeloid and lymphoid leukemias. See Golub et al. (1999) *Science* 286:531-7. Self organizing maps were used for new class discovery. Cross validation was done with a "leave one out" analysis. 50 genes were identified as useful markers. This was reduced to as few as 10 genes with equivalent diagnostic accuracy.

Hierarchical and non-hierarchical clustering methods are also useful for identifying groups of genes that correlate with a subset of clinical samples such as those with and without Lupus. Alizadeh used hierarchical clustering as the primary tool to distinguish different types of diffuse B-cell lymphomas based on gene expression profile data. See Alizadeh et al. (2000) *Nature* 403:503-11. Alizadeh used hierarchical clustering as the primary tool to distinguish different types of diffuse B-cell lymphomas based on gene expression profile data. A cDNA array carrying 17856 probes was used for these experiments, 96 samples were assessed on 128 arrays, and a set of 380 genes was identified as being useful for sample classification.

Perou demonstrates the use of hierarchical clustering for the molecular classification of breast tumor samples based on expression profile data. See Perou et al. (2000) *Nature* 406: 747-52. In this work, a cDNA array carrying 8102 gene probes was used. 1753 of these genes were found to have high variation between breast tumors and were used for the analysis.

Hastie describes the use of gene shaving for discovery of expression markers. Hastie et al. (2000) *Genome Biol.* 1(2): RESEARCH 0003.1-0003.21. The gene shaving algorithm identifies sets of genes with similar or coherent expression patterns, but large variation across conditions (RNA samples, sample classes, patient classes). In this manner, genes with a tight expression pattern within a diagnostic group, but also with high variability across the diagnoses are grouped together. The algorithm takes advantage of both characteristics in one grouping step. For example, gene shaving can identify useful marker genes with co-regulated expression. Sets of useful marker genes can be reduced to a smaller set, with each gene providing some non-redundant value in classification. This algorithm was used on the data set described in Alizadeh et al., supra, and the set of 380 informative gene markers was reduced to 234.

Supervised harvesting of expression trees (Hastie 2001) identifies genes or clusters that best distinguish one class from all the others on the data set. The method is used to identify the genes/clusters that can best separate one class versus all the others for datasets that include two or more classes or all classes from each other. This algorithm can be used for discovery or testing of a diagnostic gene set.

CART is a decision tree classification algorithm (Breiman 1984). From gene expression and or other data, CART can develop a decision tree for the classification of samples. Each node on the decision tree involves a query about the expression level of one or more genes or variables. Samples that are above the threshold go down one branch of the decision tree and samples that are not go down the other branch. See examples 10 and 16 for further description of its use in classification analysis and examples of its usefulness in discovering and implementing a diagnostic gene set. CART identifies surrogates for each splitter (genes that are the next best substitute for a useful gene in classification.

Multiple Additive Regression Trees (Friedman, J H 1999, MART) is similar to CART in that it is a classification algorithm that builds decision trees to distinguish groups. MART builds numerous trees for any classification problem and the resulting model involves a combination of the multiple trees. MART can select variables as it build models and thus can be used on large data sets, such as those derived from an 8000 gene microarray. Because MART uses a combination of many trees and does not take too much information from any one tree, it resists over training. MART identifies a set of genes and an algorithm for their use as a classifier.

A Nearest Shrunken Centroids Classifier can be applied to microarray or other data sets by the methods described by Tibshirani et al. 2002. This algorithms also identified gene sets for classification and determines their 10 fold cross validation error rates for each class of samples. The algorithm determines the error rates for models of any size, from one gene to all genes in the set. The error rates for either or both sample classes can are minimized when a particular number of genes are used. When this gene number is determined, the algorithm associated with the selected genes can be identified and employed as a classifier on prospective sample.

Once a set of genes and expression criteria for those genes have been established for classification, cross validation is done. There are many approaches, including a 10 fold cross validation analysis in which 10% of the training samples are left out of the analysis and the classification algorithm is built with the remaining 90%. The 10% are then used as a test set for the algorithm. The process is repeated 10 times with 10% of the samples being left out as a test set each time. Through this analysis, one can derive a cross validation error which helps estimate the robustness of the algorithm for use on prospective (test) samples.

Clinical data are gathered for every patient sample used for expression analysis. Clinical variables can be quantitative or non-quantitative. A clinical variable that is quantitative can be used as a variable for significance or classification analysis. Non-quantitative clinical variables, such as the sex of the patient, can also be used in a significance analysis or classification analysis with some statistical tool. It is appreciated that the most useful diagnostic gene set for a condition may be optimal when considered along with one or more predictive clinical variables. Clinical data can also be used as supervising vectors for a correlation analysis. That is to say that the clinical data associated with each sample can be used to divide the samples into meaningful diagnostic categories for analysis. For example, samples can be divided into 2 or more groups based on the presence or absence of some diagnostic criterion (a). In addition, clinical data can be utilized to select patients for a correlation analysis or to exclude them based on some undesirable characteristic, such as an ongoing infection, a medicine or some other issue. Clinical data can also be used to assess the pre-test probability of an outcome. For example, patients who are female are much more likely to be diagnosed as having systemic lupus erythematosis than patients who are male.

Once a set of genes are identified that classify samples with acceptable accuracy. These genes are validated as a set using new samples that were not used to discover the gene set. These samples can be taken from frozen archieves from the discovery clinical study or can be taken from new patients prospectively. Validation using a "test set" of samples can be done using expression profiling of the gene set with microarrays or using real-time PCR for each gene on the test set samples. Alternatively, a different expression profiling technology can be used.

Validation and Accuracy of Diagnostic Nucleotide Sets

Prior to widespread application of the diagnostic probe sets of the invention the predictive value of the probe set is validated. When the diagnostic probe set is discovered by microarray based expression analysis, the differential expression of the member genes may be validated by a less variable and more quantitative and accurate technology such as real time PCR. In this type of experiment the amplification product is measured during the PCR reaction. This enables the researcher to observe the amplification before any reagent becomes rate limiting for amplification. In kinetic PCR the measurement is of $C_T$ (threshold cycle) or $C_P$ (crossing point). This measurement ($C_T=C_P$) is the point at which an amplification curve crosses a threshold fluorescence value. The threshold is set to a point within the area where all of the reactions were in their linear phase of amplification. When measuring $C_T$, a lower $C_T$ value is indicative of a higher amount of starting material since an earlier cycle number means the threshold was crossed more quickly.

Several fluorescence methodologies are available to measure amplification product in real-time PCR. Taqman (Applied BioSystems, Foster City, Calif.) uses fluorescence resonance energy transfer (FRET) to inhibit signal from a probe until the probe is degraded by the sequence specific binding and Taq 3' exonuclease activity. Molecular Beacons (Stratagene, La Jolla, Calif.) also use FRET technology, whereby the fluorescence is measured when a hairpin structure is relaxed by the specific probe binding to the amplified DNA. The third commonly used chemistry is Sybr Green, a DNA-binding dye (Molecular Probes, Eugene, Oreg.). The more amplified product that is produced, the higher the signal. The Sybr Green method is sensitive to non-specific amplification products, increasing the importance of primer design and selection. Other detection chemistries can also been used, such as ethedium bromide or other DNA-binding dyes and many modifications of the fluorescent dye/quencher dye Taqman chemistry, for example scorpions.

Real-time PCR validation can be done as described in Example 8.

Typically, the oligonucleotide sequence of each probe is confirmed, e.g. by DNA sequencing using an oligonucleotide-specific primer. Partial sequence obtained is generally sufficient to confirm the identity of the oligonucleotide probe. Alternatively, a complementary polynucleotide is fluorescently labeled and hybridized to the array, or to a different array containing a resynthesized version of the oligo nucleotide probe, and detection of the correct probe is confirmed.

Typically, validation is performed by statistically evaluating the accuracy of the correspondence between the molecular signature for a diagnostic probe set and a selected indicator. For example, the expression differential for a nucleotide sequence between two subject classes can be expressed as a simple ratio of relative expression. The expression of the nucleotide sequence in subjects with selected indicator can be compared to the expression of that nucleotide sequence in subjects without the indicator, as described in the following equations.

$$\Sigma E_x ai/N = E_x A$$

the average expression of nucleotide sequence x in the members of group A;

$$\Sigma E_x bi/M = E_x B$$

the average expression of nucleotide sequence x in the members of group B;

$$\Sigma E_x A/ExB = \Delta E_x AB$$

the average differential expression of nucleotide sequence x between groups A and B:

where $\Sigma$ indicates a sum; Ex is the expression of nucleotide sequence x relative to a standard; ai are the individual members of group A, group A has N members; bi are the individual members of group B, group B has M members.

Individual components of a diagnostic probe set each have a defined sensitivity and specificity for distinguishing between subject groups. Such individual nucleotide sequences can be employed in concert as a diagnostic probe set to increase the sensitivity and specificity of the evaluation. The database of molecular signatures is queried by algorithms to identify the set of nucleotide sequences (i.e., corresponding to members of the probe set) with the highest average differential expression between subject groups. Typically, as the number of nucleotide sequences in the diagnostic probe set increases, so does the predictive value, that is, the sensitivity and specificity of the probe set. When the probe sets are defined they may be used for diagnosis and patient monitoring as discussed below. The diagnostic sensitivity and specificity of the probe sets for the defined use can be determined for a given probe set with specified expression levels as demonstrated above. By altering the expression threshold required for the use of each nucleotide sequence as a diagnostic, the sensitivity and specificity of the probe set can be altered by the practitioner. For example, by lowering the magnitude of the expression differential threshold for each nucleotide sequence in the set, the sensitivity of the test will increase, but the specificity will decrease. As is apparent from the foregoing discussion, sensitivity and specificity are inversely related and the predictive accuracy of the probe set is continuous and dependent on the expression threshold set for each nucleotide sequence. Although sensitivity and specificity tend to have an inverse relationship when expression thresholds are altered, both parameters can be increased as nucleotide sequences with predictive value are added to the diagnostic nucleotide set. In addition a single or a few markers may not be reliable expression markers across a population of patients. This is because of the variability in expression and measurement of expression that exists between measurements, individuals and individuals over time. Inclusion of a large number of candidate nucleotide sequences or large numbers of nucleotide sequences in a diagnostic nucleotide set allows for this variability as not all nucleotide sequences need to meet a threshold for diagnosis. Generally, more markers are better than a single marker. If many markers are used to make a diagnosis, the likelihood that all expression markers will not meet some thresholds based upon random variability is low and thus the test will give fewer false negatives. Surrogate markers are useful for these purposes. These are markers or genes that are coordinately expressed. Surrogate markers essential provide redundant information, but this redundancy can improve accuracy by decreasing errors due to assay variability.

It is appreciated that the desired diagnostic sensitivity and specificity of the diagnostic nucleotide set may vary depending on the intended use of the set. For example, in certain uses, high specificity and high sensitivity are desired. For example, a diagnostic nucleotide set for predicting which patient population may experience side effects may require high sensitivity so as to avoid treating such patients. In other settings, high sensitivity is desired, while reduced specificity may be tolerated. For example, in the case of a beneficial treatment with few side effects, it may be important to identify as many patients as possible (high sensitivity) who will respond to the drug, and treatment of some patients who will not respond is tolerated. In other settings, high specificity is desired and reduced sensitivity may be tolerated. For example, when identifying patients for an early-phase clinical trial, it is important to identify patients who may respond to the particular treatment. Lower sensitivity is tolerated in this setting as it merely results in reduced patients who enroll in the study or requires that more patients are screened for enrollment.

To discover and validate a gene set that can be applied to accurately diagnose or classify patients across the country or around the world, it is necessary to ensure that the gene set was developed and validated using samples that represent the types of patients that will be encountered in the clinical setting. For example, diverse ethnicity, drug usage and clinical practice patterns must all be represented in the discovery and validation to ensure that the test works on this variety of patients.

Immune Monitoring

Leukocyte gene expression can be used to monitor the immune system. Immune monitoring examines both the level of gene expression for a set of genes in a given cell type and for genes which are expressed in a cell type selective manner gene expression monitoring will also detect the presence or absence of new cell types, progenitor cells, differentiation of cells and the like. Gene expression patterns may be associated with activation or the resting state of cells of the immune system that are responsible for or responsive to a disease state. For example, in the process of lupus and other autoimmune diseases, cells of the immune system are activated by self-antigens. Genes and gene sets that monitor and diagnose this process are providing a measure of the level and type of activation of the immune system. Genes and gene sets that are useful in monitoring the immune system may be useful for diagnosis and monitoring of all diseases that involve the immune system. Some examples are rheumatoid arthritis, lupus, inflammatory bowel diseases, multiple sclerosis, HIV/AIDS, and viral, bacterial and fungal infection. All disorders and diseases disclosed herein are contemplated. Genes and gene sets that monitor immune activation are useful for monitoring response to immunosuppressive drug therapy, which is used to decrease immune activation. Genes are found to correlate with immune activation by correlation of expression patterns to the known presence of immune activation or quiescence in a sample as determined by some other test.

Selected Diseases

In principle, individual oligonucleotides and diagnostic oligonucleotide sets of the invention may be developed and applied to essentially any disease, or disease criterion, as long as at least one subset of oligonucleotide sequences is differentially expressed in samples derived from one or more individuals with a disease criteria or disease and one or more individuals without the disease criteria or disease, wherein the individual may be the same individual sampled at different points in time, or the individuals may be different individuals (or populations of individuals). For example, the subset of oligonucleotide sequences may be differentially expressed in the sampled tissues of subjects with the disease or disease criterion (e.g., a patient with a disease or disease criteria) as compared to subjects without the disease or disease criterion (e.g., patients without a disease (control patients)). Alternatively, or in addition, the subset of oligonucleotide sequence(s) may be differentially expressed in different samples taken from the same patient, e.g at different points in time, at different disease stages, before and after a treatment, in the presence or absence of a risk factor, etc.

Expression profiles corresponding to oligonucleotides and sets of oligonucleotide sequences that correlate not with a diagnosis, but rather with a particular aspect of a disease can also be used to identify the diagnostic oligonucleotide sets and disease specific target oligonucleotide sequences of the invention. For example, such an aspect, or disease criterion, can relate to a subject's medical or family history, e.g., occurrence of an autoimmune disease, childhood illness, cause of death of a parent or other relative, prior surgery or other intervention, medications, laboratory values and results of diagnostic testing (radiology, pathology, etc.), symptoms (including onset and/or duration of symptoms), etc. Alternatively, the disease criterion can relate to a diagnosis, e.g., chronic inflammatory disease such as lupus, rheumatoid arthritis, osteoarthritis, or prognosis (e.g., prediction of future diagnoses, events or complications), e.g., renal failure from lupus, joint replacement surgery for rheumatoid arthritis, rheumatoid arthritis or systemic lupus erythematosis disease activity or the like. In other cases, the disease criterion corresponds to a therapeutic outcome, e.g., response to a medication, response to a surgery or physical therapy for a joint. Alternatively, the disease criteria correspond with previously identified or classic risk factors and may correspond to prognosis or future disease diagnosis. As indicated above, a disease criterion can also correspond to genotype for one or more loci. Disease criteria (including patient data) may be collected (and compared) from the same patient at different points in time, from different patients, between patients with a disease (criterion) and patients representing a control population, etc. Longitudinal data, i.e., data collected at different time points from an individual (or group of individuals) may be used for comparisons of samples obtained from an individual (group of individuals) at different points in time, to permit identification of differences specifically related to the disease state, and to obtain information relating to the change in expression over time, including a rate of change or trajectory of expression over time. The usefulness of longitudinal data is further discussed in the section titled "Identification of diagnostic nucleotide sets of the invention".

It is further understood that diagnostic oligonucleotides and oligonucleotide sets may be developed for use in diagnosing conditions for which there is no present means of diagnosis. For example, in rheumatoid arthritis, joint destruction is often well under way before a patient experience symptoms of the condition. A diagnostic nucleotide or nucleotide set may be developed that diagnoses rheumatic joint destruction at an earlier stage than would be possible using present means of diagnosis, which rely in part on the presentation of symptoms by a patient. Diagnostic nucleotide sets may also be developed to replace or augment current diagnostic procedures. For example, the use of a diagnostic nucleotide or nucleotide set to diagnose lupus may replace or supplement the current diagnostic tests and strategies:

It is understood that the following discussion of diseases is exemplary and non-limiting, and further that the general criteria discussed above, e.g. use of family medical history, are generally applicable to the specific diseases discussed below.

In addition to leukocytes, as described throughout, the general method is applicable to oligonucleotide sequences that are differentially expressed in any subject tissue or cell type, by the collection and assessment of samples of that tissue or cell type. However, in many cases, collection of such samples presents significant technical or medical problems given the current state of the art.

Systemic Lupus Erythematosis (SLE)

SLE is a chronic, systemic inflammatory disease characterized by dysregulation of the immune system, which effects up to 2 million patients in the US. Symptoms of SLE include rashes, joint pain, abnormal blood counts, renal dysfunction and damage, infections, CNS disorders, arthralgias and autoimmunity. Patients may also have early onset atherosclerosis. The diagnosis of SLE is difficult to make with certainty using current diagnostic tests and algorithms. Antibody tests can be specific for the disease, but often lack sensitivity. Clinical diagnosis may lack both high sensitivity and specificity. SLE is a disease that clearly involves differential gene expression in leukocytes compared to patients without the disease.

Diagnostic oligonucleotides and oligonucleotide sets are identified and validated for use in diagnosis and monitoring of SLE activity and progression. Disease criteria correspond to clinical data, e.g. symptom rash, joint pain, malaise, rashes, blood counts (white and red), tests of renal function e.g. creatinine, blood urea nitrogen (hereinafter, "bun") creative clearance, data obtained from laboratory tests, including complete blood counts with differentials, CRP, ESR, ANA, Serum IL6, Soluble CD40 ligand, LDL, HDL, Anti-DNA antibodies, rheumatoid factor, C3, C4, serum creatinine and any medication levels, the need for pain medications, cumulative doses or immunosuppressive therapy, symptoms or any manifestation of carotid atherosclerosis (e.g. ultrasound diagnosis or any other manifestations of the disease), data from surgical procedures such as gross operative findings and pathological evaluation of resected tissues and biopsies (e.g., renal, CNS), information on pharmacological therapy and treatment changes, clinical diagnoses of disease "flare", hospitalizations, death, response to medications, quantitative joint exams, results from health assessment questionnaires (HAQs), and other clinical measures of patient symptoms and disability. In addition, disease criteria correspond to the clinical score known as SLEDAI (Bombadier C, Gladman D D, Urowitz M B, Caron D, Chang C H and the Committee on Prognosis Studies in SLE: Derivation of the SLEDAI for Lupus Patients. *Arthritis Rheum* 35:630-640, 1992). Diagnostic nucleotide sets may be useful for diagnosis of SLE, monitoring disease progression including progressive renal dysfunction, carotid atherosclerosis and CNS dysfunction, and predicting occurrence of side-effects, for example.

Rheumatoid Arthritis

Rheumatoid arthritis (RA) effects about two million patients in the US and is a chronic and debilitating inflammatory arthritis, particularly involving pain and destruction of the joints. RA often goes undiagnosed because patients may have no pain, but the disease is actively destroying the joint. Other patients are known to have RA, and are treated to alleviate symptoms, but the rate of progression of joint destruction can't easily be monitored. Drug therapy is available, but the most effective medicines are toxic (e.g., steroids, methotrexate) and thus need to be used with caution. A new class of medications (TNF blockers) is very effective, but the drugs are expensive, have side effects, and not all patients respond. Side-effects are common and include immune suppression, toxicity to organ systems, allergy and metabolic disturbances.

Diagnostic oligonucleotides and oligonucleotide sets of the invention are developed and validated for use in diagnosis and treatment of RA. Disease criteria correspond to disease symptoms (e.g., joint pain, joint swelling and joint stiffness and any of the American College for Rheumatology criteria for the diagnosis of RA, see Arnett et al (1988) *Arthr. Rheum.* 31:315-24), progression of joint destruction (e.g. as measured by serial hand radiographs, assessment of joint function and mobility), surgery, need for medication, additional diagnoses of inflammatory and non-inflammatory conditions, and clinical laboratory measurements including complete blood counts with differentials, CRP, ESR, ANA, Serum IL6, Soluble CD40 ligand, LDL, HDL, Anti-DNA antibodies, rheumatoid factor, C3, C4, serum creatinine, death, hospitalization and disability due to joint destruction. In addition, or alternatively, disease criteria correspond to response to drug therapy and presence or absence of side-effects or measures of improvement exemplified by the American College of Rheumatology "20%" and "50%" response/improvement rates. See Felson et al (1995) *Arthr Rheum* 38:531-37. Diagnostic nucleotide sets are identified that monitor and predict disease progression including flaring (acute worsening of disease accompanied by joint pain or other symptoms), response to drug treatment and likelihood of side-effects.

In addition to peripheral leukocytes, surgical specimens of rheumatoid joints can be used for leukocyte expression profiling experiments. Members of diagnostic nucleotide sets are candidates for leukocyte target nucleotide sequences, e.g. as a candidate drug target for rheumatoid arthritis. Synovial specimens can be used for expression profiling or cells derived and sorted from that tissue (such as subsets of leukocytes) can be used. Cells can be separated by fluorescence activated cell sorting or magnetic affinity reagent techniques or some other technique. Synovial specimens and blood can be obtained from the same patient and gene expression can be compared between these 2 sample types.

Osteoarthritis 20-40 million patients in the US have osteoarthritis. Patient groups are heterogeneous, with a subset of patients having earlier onset, more aggressive joint damage, involving more inflammation (leukocyte infiltration). Leukocyte diagnostics can be used to distinguish osteoarthritis from rheumatoid arthritis and other differential diagnoses, define likelihood and degree of response to NSAID therapy (non-steroidal anti-inflammatory drugs) or other anti-inflammatory therapies. Rate of progression of joint damage can also be assessed. Diagnostic nucleotide sets may be developed for use in selection and titration of treatment therapies. Disease criteria correspond to response to therapy, and disease progression using certain therapies, response to medications, need for joint surgery, joint pain and disability.

In addition to peripheral leukocytes, surgical specimens of osteoarthritic joints can be used for leukocyte expression profiling experiments. Diagnostic oligonucleotides and diagnostic oligonucleotide sets are candidates for leukocyte target nucleotide sequences, e.g. as a candidate drug target for osteoarthritis. Synovial specimens can be used for expression profiling or cells derived and sorted from that tissue (such as subsets of leukocytes) can be used. Cells can be separated by fluorescence activated cell sorting or magnetic affinity reagent techniques or some other technique. Synovial specimens and blood can be obtained from the same patient and gene expression can be compared between these 2 sample types.

In another example, diagnostic nucleotide sets are developed and validated for use in diagnosis and therapy of peri-prosthetic osteolysis. In this disease, a prosthetic joint such as a knee or hip is found to loosen over time and requires repeat surgery. Loosening may occur in some patients due to an inflammatory response incited by the foreign material of the prosthesis. Disease criteria include joint loosening, radiographic evidence of peri-prosthetic osteolysis, need for repeat surgery, response to pharmacological therapy, and/or histological (from biopsy or surgery) or biochemical (markers of bone metabolism such as alkaline phosphatase) evidence of osteolysis. Tissues used for expression profiling can include peripheral leukocytes or leukocyte subsets, periprosthetic tissue, or synovial fluid. In addition, gene sets can be discovered using an in vitro model of the disease in which immune cells are exposed to prosthesis materials such as cement or titanium.

Pharmacogenomics

Pharmacogenomics is the study of the individual propensity to respond to a particular drug therapy (combination of therapies). In this context, response can mean whether a particular drug will work on a particular patient, e.g. some patients respond to one drug but not to another drug. One example of this would be prediction of a patient's response to drugs that target IFNs. Response can also refer to the likelihood of successful treatment or the assessment of progress in treatment. Titration of drug therapy to a particular patient is also included in this description, e.g. different patients can respond to different doses of a given medication. This aspect may be important when drugs with side-effects or interactions with other drug therapies are contemplated.

Diagnostic oligonucleotides and oligonucleotide sets are developed and validated for use in assessing whether a patient will respond to a particular therapy and/or monitoring response of a patient to drug therapy (therapies). Disease criteria correspond to presence or absence of clinical symptoms or clinical endpoints, presence of side-effects or interaction with other drug(s). The diagnostic nucleotide set may further comprise nucleotide sequences that are targets of drug treatment or markers of active disease.

Diagnostic oligonucleotides and oligonucleotide sets are developed and validated for use in assessing whether a patient has a particular drug toxicity or toxicity due to an environmental, work-related or other agent. Such exposures of the patient may also be related to biological or biochemical agents used in warfare. Diagnostic oligonucleotides and oligonucleotide sets may allow early diagnosis of a toxicity or exposure or may monitor the severity and course of toxic responses.

Methods of using diagnostic oligonucleotides and oligonucleotide sets.

The invention also provide methods of using the diagnostic oligonucleotides and oligonucleotide sets to: diagnose or monitor disease; assess severity of disease; predict future occurrence of disease; predict future complications of disease; determine disease prognosis; evaluate the patient's risk, or "stratify" a group of patients; assess response to current drug therapy; assess response to current non-pharmacological therapy; determine the most appropriate medication or treatment for the patient; predict whether a patient is likely to respond to a particular drug; and determine most appropriate additional diagnostic testing for the patient, among other clinically and epidemiologically relevant applications.

The oligonucleotides and oligonucleotide sets of the invention can be utilized for a variety of purposes by physicians, healthcare workers, hospitals, laboratories, patients, companies and other institutions. As indicated previously, essentially any disease, condition, or status for which at least one nucleotide sequence is differentially expressed in leukocyte populations (or sub-populations) can be evaluated, e.g., diagnosed, monitored, etc. using the diagnostic nucleotide sets and methods of the invention. In addition to assessing health status at an individual level, the diagnostic nucleotide sets of the present invention are suitable for evaluating subjects at a "population level," e.g., for epidemiological studies, or for population screening for a condition or disease.

Collection and Preparation of Sample

RNA, protein and/or DNA are prepared using methods well-known in the art, as further described herein. It is appreciated that subject samples collected for use in the methods of the invention are generally collected in a clinical setting, where delays may be introduced before RNA samples are prepared from the subject samples of whole blood, e.g. the blood sample may not be promptly delivered to the clinical lab for further processing. Further delay may be introduced in the clinical lab setting where multiple samples are generally being processed at any given time. For this reason, methods that feature lengthy incubations of intact leukocytes at room temperature are not preferred, because the expression profile of the leukocytes may change during this extended time period. For example, RNA can be isolated from whole blood using a phenol/guanidine isothiocyanate reagent or another direct whole-blood lysis method, as described in, e.g., U.S. Pat. Nos. 5,346,994 and 4,843,155. This method may be less preferred under certain circumstances because the large majority of the RNA recovered from whole blood RNA extraction comes from erythrocytes since these cells outnumber leukocytes 1000:1. Care must be taken to ensure that the presence of erythrocyte RNA and protein does not introduce bias in the RNA expression profile data or lead to inadequate sensitivity or specificity of probes.

Alternatively, intact leukocytes may be collected from whole blood using a lysis buffer that selectively lyses erythrocytes, but not leukocytes, as described, e.g., in (U.S. Pat. Nos. 5,973,137, and 6,020,186). Intact leukocytes are then collected by centrifugation, and leukocyte RNA is isolated using standard protocols, as described herein. However, this method does not allow isolation of sub-populations of leukocytes, e.g. mononuclear cells, which may be desired. In addition, the expression profile may change during the lengthy incubation in lysis buffer, especially in a busy clinical lab where large numbers of samples are being prepared at any given time.

Alternatively, specific leukocyte cell types can be separated using density gradient reagents (Boyum, A, 1968). For example, mononuclear cells may be separated from whole blood using density gradient centrifugation, as described, e.g., in U.S. Pat. Nos. 4,190,535, 4,350,593, 4,751,001, 4,818,418, and 5,053,134. Blood is drawn directly into a tube containing an anticoagulant and a density reagent (such as Ficoll or Percoll). Centrifugation of this tube results in separation of blood into an erythrocyte and granulocyte layer, a mononuclear cell suspension, and a plasma layer. The mononuclear cell layer is easily removed and the cells can be collected by centrifugation, lysed, and frozen. Frozen samples are stable until RNA can be isolated. Density centrifugation, however, must be conducted at room temperature, and if processing is unduly lengthy, such as in a busy clinical lab, the expression profile may change.

Alternatively, cells can be separated using fluorescence activated cell sorting (FACS) or some other technique, which divides cells into subsets based on gene or protein expression. This may be desirable to enrich the sample for cells of interest, but it may also introduce cell manipulations and time delays, which result in alteration of gene expression profiles (Cantor et al. 1975; Galbraith et al. 1999).

The quality and quantity of each clinical RNA sample is desirably checked before amplification and labeling for array hybridization, using methods known in the art. For example, one microliter of each sample may be analyzed on a Bioanalyzer (Agilent 2100 Palo Alto, Calif. USA) using an RNA 6000 nano LabChip (Caliper, Mountain View, Calif. USA). Degraded RNA is identified by the reduction of the 28S to 18S ribosomal RNA ratio and/or the presence of large quantities of RNA in the 25-100 nucleotide range.

It is appreciated that the RNA sample for use with a diagnostic oligonucleotide or oligonucleotide set may be produced from the same or a different cell population, sub-population and/or cell type as used to identify the diagnostic nucleotide set. For example, a diagnostic oligonucleotide or oligonucleotide set identified using RNA extracted from mononuclear cells may be suitable for analysis of RNA extracted from whole blood or mononuclear cells, depending on the particular characteristics of the members of the diagnostic nucleotide set. Generally, diagnostic oligonucleotides or oligonucleotide sets must be tested and validated when used with RNA derived from a different cell population, sub-population or cell type than that used when obtaining the diagnostic gene set. Factors such as the cell-specific gene expression of diagnostic nucleotide set members, redundancy of the information provided by members of the diagnostic nucleotide set, expression level of the member of the diagnostic nucleotide set, and cell-specific alteration of expression of a member of the diagnostic nucleotide set will contribute to the usefulness of a different RNA source than that used when identifying the members of the diagnostic nucleotide set. It is appreciated that it may be desirable to assay RNA derived from whole blood, obviating the need to isolate particular cell types from the blood.

Rapid Method of RNA Extraction Suitable for Production in a Clinical Setting of High Quality RNA for Expression Profiling In a clinical setting, obtaining high quality RNA preparations suitable for expression profiling, from a desired population of leukocytes poses certain technical challenges, including: the lack of capacity for rapid, high-throughput sample processing in the clinical setting, and the possibility that delay in processing (in a busy lab or in the clinical setting) may adversely affect RNA quality, e.g. by a permitting the expression profile of certain nucleotide sequences to shift. Also, use of toxic and expensive reagents, such as phenol, may be disfavored in the clinical setting due to the added expense associated with shipping and handling such reagents.

A useful method for RNA isolation for leukocyte expression profiling would allow the isolation of monocyte and lymphocyte RNA in a timely manner, while preserving the expression profiles of the cells, and allowing inexpensive production of reproducible high-quality RNA samples. Accordingly, the invention provides a method of adding inhibitor(s) of RNA transcription and/or inhibitor(s) of protein synthesis, such that the expression profile is "frozen" and RNA degradation is reduced. A desired leukocyte population or sub-population is then isolated, and the sample may be frozen or lysed before further processing to extract the RNA. Blood is drawn from subject population and exposed to ActinomycinD (to a final concentration of 10 ug/ml) to inhibit transcription, and cycloheximide (to a final concentration of 10 ug/ml) to inhibit protein synthesis. The inhibitor(s) can be injected into the blood collection tube in liquid form as soon as the blood is drawn, or the tube can be manufactured to contain either lyophilized inhibitors or inhibitors that are in solution with the anticoagulant. At this point, the blood sample can be stored at room temperature until the desired leukocyte population or sub-population is isolated, as described elsewhere. RNA is isolated using standard methods, e.g., as described above, or a cell pellet or extract can be frozen until further processing of RNA is convenient.

The invention also provides a method of using a low-temperature density gradient for separation of a desired leukocyte sample. In another embodiment, the invention provides the combination of use of a low-temperature density gradient and the use of transcriptional and/or protein synthesis inhibitor(s). A desired leukocyte population is separated using a density gradient solution for cell separation that maintains the required density and viscosity for cell separation at 0-4□C. Blood is drawn into a tube containing this solution and may be refrigerated before and during processing as the low temperatures slow cellular processes and minimize expression profile changes. Leukocytes are separated, and RNA is isolated using standard methods. Alternately, a cell pellet or extract is frozen until further processing of RNA is convenient. Care must be taken to avoid rewarming the sample during further processing steps.

Alternatively, the invention provides a method of using low-temperature density gradient separation, combined with the use of actinomycin A and cyclohexamide, as described above.

Assessing Expression for Diagnostics

Expression profiles for the oligonucleotides or the set of diagnostic oligonucleotide sequences in a subject sample can be evaluated by any technique that determines the expression of each component oligonucleotide sequence. Methods suitable for expression analysis are known in the art, and numerous examples are discussed in the Sections titled "Methods of obtaining expression data" and "high throughput expression Assays", above.

In many cases, evaluation of expression profiles is most efficiently, and cost effectively, performed by analyzing RNA expression. Alternatively, the proteins encoded by each component of the diagnostic nucleotide set are detected for diagnostic purposes by any technique capable of determining protein expression, e.g., as described above. Expression profiles can be assessed in subject leukocyte sample using the same or different techniques as those used to identify and validate the diagnostic oligonucleotide or oligonucleotide set. For example, a diagnostic nucleotide set identified as a subset of sequences on a cDNA microarray can be utilized for diagnostic (or prognostic, or monitoring, etc.) purposes on the same array from which they were identified. Alternatively, the diagnostic nucleotide sets for a given disease or condition can be organized onto a dedicated sub-array for the indicated purpose. It is important to note that if diagnostic nucleotide sets are discovered using one technology, e.g. RNA expression profiling, but applied as a diagnostic using another technology, e.g. protein expression profiling, the nucleotide (or gene, or protein) sets must generally be validated for diagnostic purposes with the new technology. In addition, it is appreciated that diagnostic nucleotide sets that are developed for one use, e.g. to diagnose a particular disease, may later be found to be useful for a different application, e.g. to predict the likelihood that the particular disease will occur. Generally, the diagnostic nucleotide set will need to be validated for use in the second circumstance. As discussed herein, the sequence of diagnostic nucleotide set members may be amplified from RNA or cDNA using methods known in the art providing specific amplification of the nucleotide sequences.

General Protein Methods

Protein products of the nucleotide sequences of the invention may include proteins that represent functionally equivalent gene products. Such an equivalent gene product may contain deletions, additions or substitutions of amino acid residues within the amino acid sequence encoded by the nucleotide sequences described, above, but which result in a silent change, thus producing a functionally equivalent nucleotide sequence product. Amino acid substitutions may be made on the basis of similarity in polarity, charge, solubility, hydrophobicity, hydrophilicity, and/or the amphipathic nature of the residues involved.

For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. "Functionally equivalent", as utilized herein, refers to a protein capable of exhibiting a substantially similar in vivo activity as the endogenous gene products encoded by the nucleotides described herein.

The gene products (protein products of the nucleotide sequences) may be produced by recombinant DNA technology using techniques well known in the art. Methods which are well known to those skilled in the art can be used to construct expression vectors containing novel nucleotide sequence protein coding sequences and appropriate transcriptional/translational control signals. These methods include, for example, in vitro recombinant DNA techniques, synthetic techniques and in vivo recombination/genetic recombination. See, for example, the techniques described in Sambrook et al., 1989, supra, and Ausubel et al., 1989, supra. Alternatively, RNA capable of encoding novel nucleotide sequence protein sequences may be chemically synthesized using, for example, synthesizers. See, for example, the techniques described in. "Oligonucleotide Synthesis", 1984, Gait, M. J. ed., IRL Press, Oxford, which is incorporated by reference herein in its entirety.

A variety of host-expression vector systems may be utilized to express the nucleotide sequence coding sequences of the invention. Such host-expression systems represent vehicles by which the coding sequences of interest may be produced and subsequently purified, but also represent cells which may, when transformed or transfected with the appropriate nucleotide coding sequences, exhibit the protein encoded by the nucleotide sequence of the invention in situ. These include but are not limited to microorganisms such as bacteria (e.g., *E. coli, B. subtilis*) transformed with recombinant bacteriophage DNA, plasmid DNA or cosmid DNA expression vectors containing nucleotide sequence protein coding sequences; yeast (e.g. *Saccharomyces, Pichia*) transformed with recombinant yeast expression vectors containing the nucleotide sequence protein coding sequences; insect cell systems infected with recombinant virus expression vectors (e.g., baculovirus) containing the nucleotide sequence protein coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing nucleotide sequence protein coding sequences; or mammalian cell systems (e.g. COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5 K promoter).

In bacterial systems, a number of expression vectors may be advantageously selected depending upon the use intended for the nucleotide sequence protein being expressed. For example, when a large quantity of such a protein is to be produced, for the generation of antibodies or to screen peptide libraries, for example, vectors which direct the expression of high levels of fusion protein products that are readily purified may be desirable. Such vectors include, but are not limited to, the *E. coli* expression vector pUR278 (Ruther et al., 1983, EMBO J. 2:1791), in which the nucleotide sequence protein coding sequence may be ligated individually into the vector in frame with the lac Z coding region so that a fusion protein is produced; pIN vectors (Inouye & Inouye, 1985, Nucleic Acids Res. 13:3101-3109; Van Heeke & Schuster, 1989, J. Biol. Chem. 264:5503-5509); and the likes of pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target nucleotide sequence protein can be released from the GST moiety. Other systems useful in the invention include use of the FLAG epitope or the 6-HIS systems.

In an insect system, *Autographa californica* nuclear polyhedrosis virus (AcNPV) is used as a vector to express foreign nucleotide sequences. The virus grows in *Spodoptera frugiperda* cells. The nucleotide sequence coding sequence may be cloned individually into non-essential regions (for example the polyhedrin gene) of the virus and placed under control of an AcNPV promoter (for example the polyhedrin promoter). Successful insertion of nucleotide sequence coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted nucleotide sequence is expressed. (E.g., see Smith et al., 1983, J. Virol. 46: 584; Smith, U.S. Pat. No. 4,215,051).

In mammalian host cells, a number of viral-based expression systems may be utilized. In cases where an adenovirus is used as an expression vector, the nucleotide sequence coding sequence of interest may be ligated to an adenovirus transcription/translation control complex, e.g., the late promoter and tripartite leader sequence. This chimeric nucleotide sequence may then be inserted in the adenovirus genome by in vitro or in vivo recombination. Insertion in a non-essential region of the viral genome (e.g., region E1 or E3) will result in a recombinant virus that is viable and capable of expressing nucleotide sequence encoded protein in infected hosts. (E.g., See Logan & Shenk, 1984, Proc. Natl. Acad. Sci. USA 81:3655-3659). Specific initiation signals may also be required for efficient translation of inserted nucleotide sequence coding sequences. These signals include the ATG initiation codon and adjacent sequences. In cases where an entire nucleotide sequence, including its own initiation codon and adjacent sequences, is inserted into the appropriate expression vector, no additional translational control signals may be needed. However, in cases where only a portion of the nucleotide sequence coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:516-544).

In addition, a host cell strain may be chosen which modulates the expression of the inserted sequences, or modifies and processes the product of the nucleotide sequence in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, WI38, etc.

For long-term, high-yield production of recombinant proteins, stable expression is preferred. For example, cell lines which stably express the nucleotide sequence encoded protein may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express nucleotide sequence encoded protein. Such engineered cell lines may be particularly useful in screening and evaluation of compounds that affect the endogenous activity of the nucleotide sequence encoded protein.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk-, hgprt— or aprt—cells, respectively. Also, antimetabolite resistance can be used as the basis of selection for dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30: 147; 147) genes.

An alternative fusion protein system allows for the ready purification of non-denatured fusion proteins expressed in human cell lines (Janknecht, et al., 1991, Proc. Natl. Acad. Sci. USA 88: 8972-8976). In this system, the nucleotide sequence of interest is subcloned into a vaccinia recombination plasmid such that the nucleotide sequence's open reading frame is translationally fused to an amino-terminal tag consisting of six histidine residues. Extracts from cells infected with recombinant vaccinia virus are loaded onto Ni.sup.2+-nitriloacetic acid-agarose columns and histidine-tagged proteins are selectively eluted with imidazole-containing buffers.

Where recombinant DNA technology is used to produce the protein encoded by the nucleotide sequence for such assay systems, it may be advantageous to engineer fusion proteins that can facilitate labeling, immobilization and/or detection.

Antibodies

Indirect labeling involves the use of a protein, such as a labeled antibody, which specifically binds to the protein encoded by the nucleotide sequence. Such antibodies include but are not limited to polyclonal, monoclonal, chimeric, single chain, Fab fragments and fragments produced by an Fab expression library.

The invention also provides for antibodies to the protein encoded by the nucleotide sequences. Described herein are methods for the production of antibodies capable of specifically recognizing one or more nucleotide sequence epitopes. Such antibodies may include, but are not limited to polyclonal antibodies, monoclonal antibodies (mAbs), humanized or chimeric antibodies, single chain antibodies, Fab fragments, F(ab')2 fragments, fragments produced by a Fab expression library, anti-idiotypic (anti-Id) antibodies, and epitope-binding fragments of any of the above. Such antibodies may be used, for example, in the detection of a nucleotide sequence in a biological sample, or, alternatively, as a method for the inhibition of abnormal gene activity, for example, the inhibition of a disease target nucleotide sequence, as further described below. Thus, such antibodies may be utilized as part of cardiovascular or other disease treatment method, and/or may be used as part of diagnostic techniques whereby patients may be tested for abnormal levels of nucleotide sequence encoded proteins, or for the presence of abnormal forms of the such proteins.

For the production of antibodies to a nucleotide sequence, various host animals may be immunized by injection with a protein encoded by the nucleotide sequence, or a portion thereof. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Polyclonal antibodies are heterogeneous populations of antibody molecules derived from the sera of animals immunized with an antigen, such as gene product, or an antigenic functional derivative thereof. For the production of polyclonal antibodies, host animals such as those described above, may be immunized by injection with gene product supplemented with adjuvants as also described above.

Monoclonal antibodies, which are homogeneous populations of antibodies to a particular antigen, may be obtained by any technique which provides for the production of antibody molecules by continuous cell lines in culture. These include, but are not limited to the hybridoma technique of Kohler and Milstein, (1975, Nature 256:495-497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026-2030), and the EBV-hybridoma technique (Cole et al., 1985, Monoclonal Antibodies And Cancer Therapy, Alan R. Liss, Inc., pp. 77-96). Such antibodies may be of any immunoglobulin class including IgG, IgM, IgE, IgA, IgD and any subclass thereof. The hybridoma producing the mAb of this invention may be cultivated in vitro or in vivo.

In addition, techniques developed for the production of "chimeric antibodies" (Morrison et al., 1984, Proc. Natl. Acad. Sci., 81:6851-6855; Neuberger et al., 1984, Nature, 312:604-608; Takeda et al., 1985, Nature, 314:452-454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, 1988, Science 242:423-426; Huston et al., 1988, Proc. Natl. Acad. Sci. USA 85:5879-5883; and Ward et al., 1989, Nature 334: 544-546) can be adapted to produce nucleotide sequence-single chain antibodies. Single chain antibodies are formed by linking the heavy and light chain fragments of the Fv region via an amino acid bridge, resulting in a single chain polypeptide.

Antibody fragments which recognize specific epitopes may be generated by known techniques For example, such fragments include but are not limited to: the F(ab')2 fragments which can be produced by pepsin digestion of the antibody molecule and the Fab fragments which can be generated by reducing the disulfide bridges of the F(ab')2 fragments. Alternatively, Fab expression libraries may be constructed (Huse et al., 1989, Science, 246:1275-1281) to allow rapid and easy identification of monoclonal Fab fragments with the desired specificity.

Disease Specific Target Oligonucleotide Sequences

The invention also provides disease specific target oligonucleotide sequences, and sets of disease specific target oligonucleotide sequences. The diagnostic oligonucleotide sets, subsets thereof, novel oligonucleotide sequences, and individual members of the diagnostic oligonucleotide sets identified as described above are also disease specific target oligonucleotide sequences. In particular, individual oligonucleotide sequences that are differentially regulated or have predictive value that is strongly correlated with a disease or disease criterion are especially favorable as disease specific target oligonucleotide sequences. Sets of genes that are co-regulated may also be identified as disease specific target oligonucleotide sets. Such oligonucleotide sequences and/or oligonucleotide sequence products are targets for modulation by a variety of agents and techniques. For example, disease specific target oligonucleotide sequences (or the products of such oligonucleotide sequences, or sets of disease specific target oligonucleotide sequences) can be inhibited or activated by, e.g., target specific monoclonal antibodies or small molecule inhibitors, or delivery of the oligonucleotide sequence or gene product of the oligonucleotide sequence to patients. Also, sets of genes can be inhibited or activated by a variety of agents and techniques. The specific usefulness of the target oligonucleotide sequence(s) depends on the subject groups from which they were discovered, and the disease or disease criterion with which they correlate.

Identification of Nucleotide Sequence Involved in Leukocyte Adhesion

The invention also encompasses a method of identifying nucleotide sequences involved in leukocyte adhesion. The interaction between the endothelial cell and leukocyte is a fundamental mechanism of all inflammatory disorders, including the diseases listed in Table 3. For example, the first visible abnormality in atherosclerosis is the adhesion to the endothelium and diapedesis of mononuclear cells (e.g., T-cell and monocyte). Insults to the endothelium (for example, cytokines, tobacco, diabetes, hypertension and many more) lead to endothelial cell activation. The endothelium then expresses adhesion molecules, which have counter receptors on mononuclear cells. Once the leukocyte receptors have bound the endothelial adhesion molecules, they stick to the endothelium, roll a short distance, stop and transmigrate across the endothelium. A similar set of events occurs in both acute and chronic inflammation. When the leukocyte binds the endothelial adhesion molecule, or to soluble cytokines secreted by endothelial or other cells, a program of gene expression is activated in the leukocyte. This program of expression leads to leukocyte rolling, firm adhesion and transmigration into the vessel wall or tissue parenchyma. Inhibition of this process is highly desirable goal in anti-inflammatory drug development. In addition, leukocyte nucleotide sequences and epithelial cell nucleotide sequences, that are differentially expressed during this process may be disease-specific target nucleotide sequences.

Human endothelial cells, e.g. derived from human coronary arteries, human aorta, human pulmonary artery, human umbilical vein or microvascular endothelial cells, are cultured as a confluent monolayer, using standard methods. Some of the endothelial cells are then exposed to cytokines or another activating stimuli such as oxidized LDL, hyperglycemia, shear stress, or hypoxia (Moser et al. 1992). Some endothelial cells are not exposed to such stimuli and serve as controls. For example, the endothelial cell monolayer is incubated with culture medium containing 5 U/ml of human recombinant IL-1alpha or 10 ng/ml TNF (tumor necrosis factor), for a period of minutes to overnight. The culture medium composition is changed or the flask is sealed to induce hypoxia. In addition, tissue culture plate is rotated to induce sheer stress.

Human T-cells and/or monocytes are cultured in tissue culture flasks or plates, with LGM-3 media from Clonetics. Cells are incubated at 37 degree C., 5% CO2 and 95% humidity. These leukocytes are exposed to the activated or control endothelial layer by adding a suspension of leukocytes on to the endothelial cell monolayer. The endothelial cell monolayer is cultured on a tissue culture treated plate/flask or on a microporous membrane. After a variable duration of exposures, the endothelial cells and leukocytes are harvested separately by treating all cells with trypsin and then sorting the endothelial cells from the leukocytes by magnetic affinity reagents to an endothelial cell specific marker such as PECAM-1 (Stem Cell Technologies). RNA is extracted from the isolated cells by standard techniques. Leukocyte RNA is labeled as described above, and hybridized to leukocyte candidate nucleotide library. Epithelial cell RNA is also labeled and hybridized to the leukocyte candidate nucleotide library. Alternatively, the epithelial cell RNA is hybridized to a epithelial cell candidate nucleotide library, prepared according to the methods described for leukocyte candidate libraries, above.

Hybridization to candidate nucleotide libraries will reveal nucleotide sequences that are up-regulated or down-regulated in leukocyte and/or epithelial cells undergoing adhesion. The differentially regulated nucleotide sequences are further characterized, e.g. by isolating and sequencing the full-length sequence, analysis of the DNA and predicted protein sequence, and functional characterization of the protein product of the nucleotide sequence, as described above. Further characterization may result in the identification of leukocyte adhesion specific target nucleotide sequences, which may be candidate targets for regulation of the inflammatory process. Small molecule or antibody inhibitors can be developed to inhibit the target nucleotide sequence function. Such inhibitors are tested for their ability to inhibit leukocyte adhesion in the in vitro test described above.

Integrated Systems

Integrated systems for the collection and analysis of expression profiles, and molecular signatures, as well as for the compilation, storage and access of the databases of the invention, typically include a digital computer with software including an instruction set for sequence searching and analysis, and, optionally, high-throughput liquid control software, image analysis software, data interpretation software, a robotic control armature for transferring solutions from a source to a destination (such as a detection device) operably linked to the digital computer, an input device (e.g., a computer keyboard) for entering subject data to the digital computer, or to control analysis operations or high throughput sample transfer by the robotic control armature. Optionally, the integrated system further comprises an image scanner for digitizing label signals from labeled assay components, e.g., labeled nucleic acid hybridized to a candidate library microarray. The image scanner can interface with image analysis software to provide a measurement of the presence or intensity of the hybridized label, i.e., indicative of an on/off expression pattern or an increase or decrease in expression.

Readily available computational hardware resources using standard operating systems are fully adequate, e.g., a PC (Intel x86 or Pentium chip-compatible DOS,™ OS2,™ WINDOWS,™ WINDOWS NT,™ WINDOWS95,™ WINDOWS98,™ LINUX, or even Macintosh, Sun or PCs will suffice) for use in the integrated systems of the invention. Current art in software technology is similarly adequate (i.e., there are a multitude of mature programming languages and source code suppliers) for design, e.g., of an upgradeable open-architecture object-oriented heuristic algorithm, or instruction set for expression analysis, as described herein. For example, software for aligning or otherwise manipulating molecular signatures can be constructed by one of skill using a standard programming language such as Visual basic, Fortran, Basic, Java, or the like, according to the methods herein.

Various methods and algorithms, including genetic algorithms and neural networks, can be used to perform the data collection, correlation, and storage functions, as well as other desirable functions, as described herein. In addition, digital or analog systems such as digital or analog computer systems can control a variety of other functions such as the display and/or control of input and output files.

For example, standard desktop applications such as word processing software (e.g., Corel WordPerfect™ or Microsoft Word™) and database software (e.g., spreadsheet software such as Corel Quattro Pro™, Microsoft Excel™, or database programs such as Microsoft Access™ or Paradox™) can be adapted to the present invention by inputting one or more character string corresponding, e.g., to an expression pattern or profile, subject medical or historical data, molecular signature, or the like, into the software which is loaded into the memory of a digital system, and carrying out the operations indicated in an instruction set. For example, systems can include the foregoing software having the appropriate character string information, e.g., used in conjunction with a user interface in conjunction with a standard operating system such as a Windows, Macintosh or LINUX system. For example, an instruction set for manipulating strings of characters, either by programming the required operations into the applications or with the required operations performed manually by a user (or both). For example, specialized sequence alignment programs such as PILEUP or BLAST can also be incorporated into the systems of the invention, e.g., for alignment of nucleic acids or proteins (or corresponding character strings).

Software for performing the statistical methods required for the invention, e.g., to determine correlations between expression profiles and subsets of members of the diagnostic nucleotide libraries, such as programmed embodiments of the statistical methods described above, are also included in the computer systems of the invention. Alternatively, programming elements for performing such methods as principle component analysis (PCA) or least squares analysis can also be included in the digital system to identify relationships between data. Exemplary software for such methods is provided by Partek, Inc., St. Peter, Mo.; at the web site partek.com.

Any controller or computer optionally includes a monitor which can include, e.g., a flat panel display (e.g., active matrix liquid crystal display, liquid crystal display), a cathode ray tube ("CRT") display, or another display system which serves as a user interface, e.g., to output predictive data. Computer circuitry, including numerous integrated circuit chips, such as a microprocessor, memory, interface circuits, and the like, is often placed in a casing or box which optionally also includes a hard disk drive, a floppy disk drive, a high capacity removable drive such as a writeable CD-ROM, and other common peripheral elements.

Inputting devices such as a keyboard, mouse, or touch sensitive screen, optionally provide for input from a user and for user selection, e.g., of sequences or data sets to be compared or otherwise manipulated in the relevant computer system. The computer typically includes appropriate software for receiving user instructions, either in the form of user input into a set parameter or data fields (e.g., to input relevant subject data), or in the form of preprogrammed instructions, e.g., preprogrammed for a variety of different specific operations. The software then converts these instructions to appropriate language for instructing the system to carry out any desired operation.

The integrated system may also be embodied within the circuitry of an application specific integrated circuit (ASIC) or programmable logic device (PLD). In such a case, the invention is embodied in a computer readable descriptor language that can be used to create an ASIC or PLD. The integrated system can also be embodied within the circuitry or logic processors of a variety of other digital apparatus, such as PDAs, laptop computer systems, displays, image editing equipment, etc.

The digital system can comprise a learning component where expression profiles, and relevant subject data are compiled and monitored in conjunction with physical assays, and where correlations, e.g., molecular signatures with predictive value for a disease, are established or refined. Successful and unsuccessful combinations are optionally documented in a database to provide justification/preferences for user-base or digital system based selection of diagnostic nucleotide sets with high predictive accuracy for a specified disease or condition.

The integrated systems can also include an automated workstation. For example, such a workstation can prepare and analyze leukocyte RNA samples by performing a sequence of events including: preparing RNA from a human blood sample; labeling the RNA with an isotopic or non-isotopic label; hybridizing the labeled RNA to at least one array comprising all or part of the candidate library; and detecting the hybridization pattern. The hybridization pattern is digitized and recorded in the appropriate database.

Automated RNA Preparation Tool

The invention also includes an automated RNA preparation tool for the preparation of mononuclear cells from whole blood samples, and preparation of RNA from the mononuclear cells. In a preferred embodiment, the use of the RNA preparation tool is fully automated, so that the cell separation and RNA isolation would require no human manipulations. Full automation is advantageous because it minimizes delay, and standardizes sample preparation across different laboratories. This standardization increases the reproducibility of the results.

The processes performed by the RNA preparation tool of the invention are as follows. A primary component of the device is a centrifuge. Tubes of whole blood containing a density gradient solution, transcription/translation inhibitors, and a gel barrier that separates erythrocytes from mononuclear cells and serum after centrifugation are placed in the centrifuge. The barrier is permeable to erythrocytes and granulocytes during centrifugation, but does not allow mononuclear cells to pass through (or the barrier substance has a density such that mononuclear cells remain above the level of the barrier during the centrifugation). After centrifugation, the erythrocytes and granulocytes are trapped beneath the barrier, facilitating isolation of the mononuclear cell and serum layers. A mechanical arm removes the tube and inverts it to mix the mononuclear cell layer and the serum. The arm next pours the supernatant into a fresh tube, while the erythrocytes and granulocytes remained below the barrier. Alternatively, a needle is used to aspirate the supernatant and transfer it to a fresh tube. The mechanical arms of the device opens and closes lids, dispenses PBS to aid in the collection of the mononuclear cells by centrifugation, and moves the tubes in and out of the centrifuge. Following centrifugation, the supernatant is poured off or removed by a vacuum device, leaving an isolated mononuclear cell pellet. Purification of the RNA from the cells is performed automatically, with lysis buffer and other purification solutions automatically dispensed and removed before and after centrifugation steps. The result is a purified RNA solution. In another embodiment, RNA isolation is performed using a column or filter method. In yet another embodiment, the invention includes an on-board homogenizer for use in cell lysis.

Other Automated Systems

Automated and/or semi-automated methods for solid and liquid phase high-throughput sample preparation and evaluation are available, and supported by commercially available devices. For example, robotic devices for preparation of nucleic acids from bacterial colonies, e.g., to facilitate production and characterization of the candidate library include, for example, an automated colony picker (e.g., the Q-bot, Genetix, U.K.) capable of identifying, sampling, and inoculating up to 10,000/4 hrs different clones into 96 well microtiter dishes. Alternatively, or in addition, robotic systems for liquid handling are available from a variety of sources, e.g., automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Beckman Coulter, Inc. (Fullerton, Calif.)) which mimic the manual operations performed by a scientist. Any of the above devices are suitable for use with the present invention, e.g., for high-throughput analysis of library components or subject leukocyte samples. The nature and implementation of modifications to these devices (if any) so that they can operate as discussed herein will be apparent to persons skilled in the relevant art.

High throughput screening systems that automate entire procedures, e.g., sample and reagent pipetting, liquid dispensing, timed incubations, and final readings of the microplate in detector(s) appropriate for the relevant assay are commercially available. (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These configurable systems provide high throughput and rapid start up as well as a high degree of flexibility and customization. Similarly, arrays and array readers are available, e.g., from Affinetrix, PE Biosystems, and others.

The manufacturers of such systems provide detailed protocols the various high throughput. Thus, for example, Zymark Corp. provides technical bulletins describing screening systems for detecting the modulation of gene transcription, ligand binding, and the like.

A variety of commercially available peripheral equipment, including, e.g., optical and fluorescent detectors, optical and fluorescent microscopes, plate readers, CCD arrays, phosphorimagers, scintillation counters, phototubes, photodiodes, and the like, and software is available for digitizing, storing and analyzing a digitized video or digitized optical or other assay results, e.g., using PC (Intel x86 or pentium chip-compatible DOS™, OS2™ WINDOWS™, WINDOWS NT™ or WINDOWS95™ based machines), MACINTOSH™, or UNIX based (e.g., SUN™ work station) computers.

Embodiment in a Web Site.

The methods described above can be implemented in a localized or distributed computing environment. For example, if a localized computing environment is used, an array comprising a candidate nucleotide library, or diagnostic nucleotide set, is configured in proximity to a detector, which is, in turn, linked to a computational device equipped with user input and output features.

In a distributed environment, the methods can be implemented on a single computer with multiple processors or, alternatively, on multiple computers. The computers can be linked, e.g. through a shared bus, but more commonly, the computer(s) are nodes on a network. The network can be generalized or dedicated, at a local level or distributed over a wide geographic area. In certain embodiments, the computers are components of an intra-net or an internet.

The predictive data corresponding to subject molecular signatures (e.g., expression profiles, and related diagnostic, prognostic, or monitoring results) can be shared by a variety of parties. In particular, such information can be utilized by the subject, the subject's health care practitioner or provider, a company or other institution, or a scientist. An individual subject's data, a subset of the database or the entire database recorded in a computer readable medium can be accessed directly by a user by any method of communication, including, but not limited to, the internet. With appropriate computational devices, integrated systems, communications networks, users at remote locations, as well as users located in proximity to, e.g., at the same physical facility, the database can access the recorded information. Optionally, access to the database can be controlled using unique alphanumeric passwords that provide access to a subset of the data. Such provisions can be used, e.g., to ensure privacy, anonymity, etc.

Typically, a client (e.g., a patient, practitioner, provider, scientist, or the like) executes a Web browser and is linked to a server computer executing a Web server. The Web browser is, for example, a program such as IBM's Web Explorer, Internet explorer, NetScape or Mosaic, or the like. The Web server is typically, but not necessarily, a program such as IBM's HTTP Daemon or other WWW daemon (e.g., LINUX-based forms of the program). The client computer is bi-directionally coupled with the server computer over a line or via a wireless system. In turn, the server computer is bi-directionally coupled with a website (server hosting the website) providing access to software implementing the methods of this invention.

A user of a client connected to the Intranet or Internet may cause the client to request resources that are part of the web site(s) hosting the application(s) providing an implementation of the methods described herein. Server program(s) then process the request to return the specified resources (assuming they are currently available). A standard naming convention has been adopted, known as a Uniform Resource Locator ("URL"). This convention encompasses several types of location names, presently including subclasses such as Hypertext Transport Protocol ("http"), File Transport Protocol ("ftp"), gopher, and Wide Area Information Service ("WAIS"). When a resource is downloaded, it may include the URLs of additional resources. Thus, the user of the client can easily learn of the existence of new resources that he or she had not specifically requested.

Methods of implementing Intranet and/or Intranet embodiments of computational and/or data access processes are well known to those of skill in the art and are documented, e.g., in ACM Press, pp. 383-392; ISO-ANSI Working Draft, "Information Technology-Database Language SQL", Jim Melton, Editor, International Organization for Standardization and American National Standards Institute, July 1992; ISO Working Draft, "Database Language SQL-Part 2:Foundation (SQL/Foundation)", CD9075-2:199.chi.SQL, Sep. 11, 1997; and Cluer et al. (1992) A General Framework for the Optimization of Object-Oriented Queries, Proc SIGMOD International Conference on Management of Data, San Diego, Calif., Jun. 2-5, 1992, SIGMOD Record, vol. 21, Issue 2, June, 1992; Stonebraker, M., Editor. Other resources are available, e.g., from Microsoft, IBM, Sun and other software development companies.

Using the tools described above, users of the reagents, methods and database as discovery or diagnostic tools can query a centrally located database with expression and subject data. Each submission of data adds to the sum of expression and subject information in the database. As data is added, a new correlation statistical analysis is automatically run that incorporates the added clinical and expression data. Accordingly, the predictive accuracy and the types of correlations of the recorded molecular signatures increases as the database grows.

For example, subjects, such as patients, can access the results of the expression analysis of their leukocyte samples and any accrued knowledge regarding the likelihood of the patient's belonging to any specified diagnostic (or prognostic, or monitoring, or risk group), i.e., their expression profiles, and/or molecular signatures. Optionally, subjects can add to the predictive accuracy of the database by providing additional information to the database regarding diagnoses, test results, clinical or other related events that have occurred since the time of the expression profiling. Such information can be provided to the database via any form of communication, including, but not limited to, the internet. Such data can be used to continually define (and redefine) diagnostic groups. For example, if 1000 patients submit data regarding the occurrence of myocardial infarction over the 5 years since their expression profiling, and 300 of these patients report that they have experienced a myocardial infarction and 700 report that they have not, then the 300 patients define a new "group A." As the algorithm is used to continually query and revise the database, a new diagnostic nucleotide set that differentiates groups A and B (i.e., with and without myocardial infarction within a five year period) is identified. This newly defined nucleotide set is then be used (in the manner described above) as a test that predicts the occurrence of myocardial infarction over a five-year period. While submission directly by the patient is exemplified above, any individual with access and authority to submit the relevant data e.g., the patient's physician, a laboratory technician, a health care or study administrator, or the like, can do so.

As will be apparent from the above examples, transmission of information via the internet (or via an intranet) is optionally bi-directional. That is, for example, data regarding expression profiles, subject data, and the like are transmitted via a communication system to the database, while information regarding molecular signatures, predictive analysis, and the like, are transmitted from the database to the user. For example, using appropriate configurations of an integrated system including a microarray comprising a diagnostic nucleotide set, a detector linked to a computational device can directly transmit (locally or from a remote workstation at great distance, e.g., hundreds or thousands of miles distant from the database) expression profiles and a corresponding individual identifier to a central database for analysis according to the methods of the invention. According to, e.g., the algorithms described above, the individual identifier is assigned to one or more diagnostic (or prognostic, or monitoring, etc.) categories. The results of this classification are then relayed back, via, e.g., the same mode of communication, to a recipient at the same or different internet (or intranet) address.

Kits

The present invention is optionally provided to a user as a kit. Typically, a kit contains one or more diagnostic nucleotide sets of the invention. Alternatively, the kit contains the candidate nucleotide library of the invention. Most often, the kit contains a diagnostic nucleotide probe set, or other subset of a candidate library, (e.g., as a cDNA, oligonucleotide or antibody microarray or reagents for performing an assay on a diagnostic gene set using any expression profiling technology), packaged in a suitable container. The kit may further comprise, one or more additional reagents, e.g., substrates, labels, primers, for labeling expression products, tubes and/or other accessories, reagents for collecting blood samples, buffers, e.g., erythrocyte lysis buffer, leukocyte lysis buffer, hybridization chambers, cover slips, etc., as well as a software package, e.g., including the statistical methods of the invention, e.g., as described above, and a password and/or account number for accessing the compiled database. The kit optionally further comprises an instruction set or user manual detailing preferred methods of using the diagnostic nucleotide sets in the methods of the invention. In one embodiment, the kit may include contents useful for the discovery of diagnostic nucleotide sets using microarrays. The kit may include sterile, endotoxin and RNAse free blood collection tubes. The kit may also include alcohol swabs, tourniquet, blood collection set, and/or PBS (phosphate buffer saline; needed when method of example 8 is used to derived mononuclear RNA). The kit may also include cell lysis buffer. The kit may include RNA isolation kit, substrates for labeling of RNA (may vary for various expression profiling techniques). The kit may also include materials for fluorescence microarray expression profiling, including one or more of the following: reverse transcriptase and 10×RT buffer, T7(dT)24 primer (primer with T7 promoter at 5' end), DTT, deoxynucleotides, optionally 100 mM each, RNAse inhibitor, second strand cDNA buffer, DNA polymerase, Rnase H, T7 RNA polymerase ribonucleotides, in vitro transcription buffer, and/or Cy3 and Cy5 labeled ribonucleotides. The kit may also include microarrays containing candidate gene libraries, cover slips for slides, and/or hybridization chambers. The kit may further include software package for identification of diagnostic gene set from data, that contains statistical methods, and/or allows alteration in desired sensitivity and specificity of gene set. The software may further facilitate access to and data analysis by centrally a located database server. The software may further include a password and account number to access central database server. In addition, the kit may include a kit user manual.

In another embodiment, the kit may include contents useful for the application of diagnostic nucleotide sets using microarrays. The kit may include sterile, endotoxin and/or RNAse free blood collection tubes. The kit may also include, alcohol swabs, tourniquet, and/or a blood collection set. The kit may further include PBS (phosphate buffer saline; needed when method of example 7 is used to derived mononuclear RNA), cell lysis buffer, and/or an RNA isolation kit. In addition, the kit may include substrates for labeling of RNA (may vary for various expression profiling techniques). For fluorescence microarray expression profiling, components may include reverse transcriptase and 10×RT buffer, T7(dT)24 primer (primer with T7 promoter at 5' end), DTT, deoxynucleotides (optionally 100 mM each), RNAse inhibitor, second strand cDNA buffer, DNA polymerase, Rnase H, T7 RNA polymerase, ribonucleotides, in vitro transcription buffer, and/or Cy3 and Cy5 labeled ribonucleotides. The kit may further include microarrays containing candidate gene libraries. The kit may also include cover slips for slides, and/or hybridization chambers. The kit may include a software package for identification of diagnostic gene set from data. The software package may contain statistical methods, allow alteration in desired sensitivity and specificity of gene set, and/or facilitate access to and data analysis by centrally located database server. The software package may include a password and account number to access central database server. In addition, the kit may include a kit user manual.

In another embodiment, the kit may include contents useful for the application of diagnostic nucleotide sets using real-time PCR. This kit may include terile, endotoxin and/or RNAse free blood collection tubes. The kit may further include alcohol swabs, tourniquet, and/or a blood collection set. The kit may also include PBS (phosphate buffer saline; needed when method of example 7 is used to derived mononuclear RNA). In addition, the kit may include cell lysis buffer and/or an RNA isolation kit. The kit may also include substrates for real time RT-PCR, which may vary for various real-time PCR techniques, including poly dT primers, random hexamer primers, reverse Transcriptase and RT buffer, DTT, deoxynucleotides 100 mM, RNase H, primer pairs for diagnostic and control gene set, 10×PCR reaction buffer, and/or Taq DNA polymerase. The kit may also include fluorescent probes for diagnostic and control gene set (alternatively, fluorescent dye that binds to only double stranded DNA). The kit may further include reaction tubes with or without barcode for sample tracking, 96-well plates with barcode for sample identification, one barcode for entire set, or individual barcode per reaction tube in plate. The kit may also include a software package for identification of diagnostic gene set from data, and/or statistical methods. The software package may allow alteration in desired sensitivity and specificity of gene set, and/or facilitate access to and data analysis by centrally located database server. The kit may include a password and account number to access central database server. Finally, the kit may include a kit user manual.

This invention will be better understood by reference to the following non-limiting Examples:

EXAMPLES

Example 1: Preparation of RNA from mononuclear cells for expression profiling
Example 2: Preparation of Universal Control RNA for use in leukocyte expression profiling
Example 3: Identification of diagnostic oligonucleotide sets for use in diagnosis of rheumatoid arthritis.
Example 4: Identification of diagnostic oligonucleotide sets for diagnosis of Systemic Lupus Erythematosis
Example 5: Design of oligonucleotide probes.
Example 6: Production of an array of 8,000 spotted 50 mer oligonucleotides.
Example 7: Amplification, labeling, and hybridization of total RNA to an oligonucleotide microarray
Example 8: Real-time PCR validation of array expression results
Example 9: Correlation and Classification Analysis
Example 10: Assay Sample Preparation
Example 11: Identification and validation of gene expression markers for diagnosis and monitoring of lupus and autoimmune diseases.

EXAMPLES

Example 1

Preparation of RNA from Mononuclear Cells for Expression Profiling

Blood was isolated from the subject for leukocyte expression profiling using the following methods:

Two tubes were drawn per patient. Blood was drawn from either a standard peripheral venous blood draw or directly from a large-bore intra-arterial or intravenous catheter inserted in the femoral artery, femoral vein, subclavian vein or internal jugular vein. Care was taken to avoid sample contamination with heparin from the intravascular catheters, as heparin can interfere with subsequent RNA reactions.

For each tube, 8 ml of whole blood was drawn into a tube (CPT, Becton-Dickinson order #362753) containing the anticoagulant Citrate, 25° C. density gradient solution (e.g. Ficoll, Percoll) and a polyester gel barrier that upon centrifugation was permeable to RBCs and granulocytes but not to mononuclear cells. The tube was inverted several times to mix the blood with the anticoagulant. The tubes were centrifuged at 1750×g in a swing-out rotor at room temperature for 20 minutes. The tubes were removed from the centrifuge and inverted 5-10 times to mix the plasma with the mononuclear cells, while trapping the RBCs and the granulocytes beneath the gel barrier. The plasma/mononuclear cell mix was decanted into a 15 ml tube and 5 ml of phosphate-buffered saline (PBS) is added. The 15 ml tubes were spun for 5 minutes at 1750×g to pellet the cells. The supernatant was discarded and 1.8 ml of RLT lysis buffer is added to the mononuclear cell pellet. The buffer and cells were pipetted up and down to ensure complete lysis of the pellet. The cell lysate was frozen and stored until it is convenient to proceed with isolation of total RNA.

Total RNA was purified from the lysed mononuclear cells using the Qiagen Rneasy Miniprep kit, as directed by the manufacturer (10/99 version) for total RNA isolation, including homogenization (Qiashredder columns) and on-column DNase treatment. The purified RNA was eluted in 50 ul of water.

Some samples were prepared by a different protocol, as follows:

Two 8 ml blood samples were drawn from a peripheral vein into a tube (CPT, Becton-Dickinson order #362753) containing anticoagulant (Citrate), 25° C. density gradient solution (Ficoll) and a polyester gel barrier that upon centrifugation is permeable to RBCs and granulocytes but not to mononuclear cells. The mononuclear cells and plasma remained above the barrier while the RBCs and granulocytes were trapped below. The tube was inverted several times to mix the blood with the anticoagulant, and the tubes were subjected to centrifugation at 1750×g in a swing-out rotor at room temperature for 20 min. The tubes were removed from the centrifuge, and the clear plasma layer above the cloudy mononuclear cell layer was aspirated and discarded. The cloudy mononuclear cell layer was aspirated, with care taken to rinse all of the mononuclear cells from the surface of the gel barrier with PBS (phosphate buffered saline). Approximately 2 mls of mononuclear cell suspension was transferred to a 2 ml microcentrifuge tube, and centrifuged for 3 min. at 16,000 rpm in a microcentrifuge to pellet the cells. The supernatant was discarded and 1.8 ml of RLT lysis buffer (Qiagen) were added to the mononuclear cell pellet, which lysed the cells and inactivated Rnases. The cells and lysis buffer were pipetted up and down to ensure complete lysis of the pellet. Cell lysate was frozen and stored until it was convenient to proceed with isolation of total RNA.

RNA samples were isolated from 8 mL of whole blood. Yields ranged from 2 µg to 20 µg total RNA for 8 mL blood. A260/A280 spectrophotometric ratios were between 1.6 and 2.0, indicating purity of sample. 2 ul of each sample were run on an agarose gel in the presence of ethidium bromide. No degradation of the RNA sample and no DNA contamination were visible.

In some cases, specific subsets of mononuclear cells were isolated from peripheral blood of human subjects. When this was done, the StemSep cell separation kits (manual version 6.0.0) were used from StemCell Technologies (Vancouver, Canada). This same protocol can be applied to the isolation of T cells, CD4 T cells, CD8 T cells, B cells, monocytes, NK cells and other cells. Isolation of cell types using negative selection with antibodies may be desirable to avoid activation of target cells by antibodies.

Example 2

Preparation of Universal Control RNA for Use in Leukocyte Expression Profiling

Control RNA was prepared using total RNA from Buffy coats and/or total RNA from enriched mononuclear cells isolated from Buffy coats, both with and without stimulation with ionomycin and PMA. The following control RNAs were prepared:

Control 1: Buffy Coat Total RNA
Control 2: Mononuclear cell Total RNA
Control 3: Stimulated buffy coat Total RNA
Control 4: Stimulated mononuclear Total RNA
Control 5: 50% Buffy coat Total RNA/50% Stimulated buffy coat Total RNA
Control 6: 50% Mononuclear cell Total RNA/50% Stimulated Mononuclear Total RNA.

Some samples were prepared using the following protocol: Buffy coats from 38 individuals were obtained from Stanford Blood Center. Each buffy coat is derived from ~350 mL whole blood from one individual. 10 ml buffy coat was removed from the bag, and placed into a 50 ml tube. 40 ml of Buffer EL (Qiagen) was added, the tube was mixed and placed on ice for 15 minutes, then cells were pelleted by centrifugation at 2000×g for 10 minutes at 4° C. The supernatant was decanted and the cell pellet was re-suspended in 10 ml of Qiagen Buffer EL. The tube was then centrifuged at 2000×g for 10 minutes at 4° C. The cell pellet was then re-suspended in 20 ml TRIZOL (GibcoBRL) per Buffy coat sample, the mixture was shredded using a rotary homogenizer, and the lysate was then frozen at −80° C. prior to proceeding to RNA isolation.

Other control RNAs were prepared from enriched mononuclear cells prepared from Buffy coats. Buffy coats from Stanford Blood Center were obtained, as described above. 10 ml buffy coat was added to a 50 ml polypropylene tube, and 10 ml of phosphate buffer saline (PBS) was added to each tube. A polysucrose (5.7 g/dL) and sodium diatrizoate (9.0 g/dL) solution at a 1.077+/−0.0001 g/ml density solution of equal volume to diluted sample was prepared (Histopaque 1077, Sigma cat. no 1077-1). This and all subsequent steps were performed at room temperature. 15 ml of diluted buffy coat/PBS was layered on top of 15 ml of the histopaque solution in a 50 ml tube. The tube was centrifuged at 400×g for 30 minutes at room temperature. After centrifugation, the upper layer of the solution to within 0.5 cm of the opaque interface containing the mononuclear cells was discarded. The opaque interface was transferred into a clean centrifuge tube. An equal volume of PBS was added to each tube and centrifuged at 350×g for 10 minutes at room temperature. The supernatant was discarded. 5 ml of Buffer EL (Qiagen) was used to resuspend the remaining cell pellet and the tube was centrifuged at 2000×g for 10 minutes at room temperature. The supernatant was discarded. The pellet was resuspended in 20 ml of TRIZOL (GibcoBRL) for each individual buffy coat that was processed. The sample was homogenized using a rotary homogenizer and frozen at −80 C until RNA was isolated.

RNA was isolated from frozen lysed Buffy coat samples as follows: frozen samples were thawed, and 4 ml of chloroform was added to each buffy coat sample. The sample was mixed by vortexing and centrifuged at 2000×g for 5 minutes. The aqueous layer was moved to new tube and then repurified by using the RNeasy Maxi RNA clean up kit, according to the manufacturer's instruction (Qiagen, PN 75162). The yield, purity and integrity were assessed by spectrophotometer and gel electrophoresis.

Some samples were prepared by a different protocol, as follows. The further use of RNA prepared using this protocol is described in Example 7.

50 whole blood samples were randomly selected from consented blood donors at the Stanford Medical School Blood Center. Each buffy coat sample was produced from ~350 mL of an individual's donated blood. The whole blood sample was centrifuged at ~4,400×g for 8 minutes at room temperature, resulting in three distinct layers: a top layer of plasma, a second layer of buffy coat, and a third layer of red blood cells. 25 ml of the buffy coat fraction was obtained and diluted with an equal volume of PBS (phosphate buffered saline). 30 ml of diluted buffy coat was layered onto 15 ml of sodium diatrizoate solution adjusted to a density of 1.077+/−0.001 g/ml (Histopaque 1077, Sigma) in a 50 mL plastic tube. The tube was spun at 800 g for 10 minutes at room temperature. The plasma layer was removed to the 30 ml mark on the tube, and the mononuclear cell layer removed into a new tube and washed with an equal volume of PBS, and collected by centrifugation at 2000 g for 10 minutes at room temperature. The cell pellet was resuspended in 10 ml of Buffer EL (Qiagen) by vortexing and incubated on ice for 10 minutes to remove any remaining erthythrocytes. The mononuclear cells were spun at 2000 g for 10 minutes at 4 degrees Celsius. The cell pellet was lysed in 25 ml of a phenol/guanidinium thiocyanate solution (TRIZOL Reagent, Invitrogen). The sample was homogenized using a PowerGene 5 rotary homogenizer (Fisher Scientific) and Omini disposable generator probes (Fisher Scientific). The Trizol lysate was frozen at −80 degrees C. until the next step.

The samples were thawed out and incubated at room temperature for 5 minutes. 5 ml chloroform was added to each sample, mixed by vortexing, and incubated at room temperature for 3 minutes. The aqueous layers were transferred to new 50 ml tubes. The aqueous layer containing total RNA was further purified using the Qiagen RNeasy Maxi kit (PN 75162), per the manufacturer's protocol (October 1999). The columns were eluted twice with 1 ml Rnase-free water, with a minute incubation before each spin. Quantity and quality of RNA was assessed using standard methods. Generally, RNA was isolated from batches of 10 buffy coats at a time, with an average yield per buffy coat of 870 μg, and an estimated total yield of 43.5 mg total RNA with a 260/280 ratio of 1.56 and a 28S/18S ratio of 1.78.

Quality of the RNA was tested using the Agilent 2100 Bioanalyzer using RNA 6000 microfluidics chips. Analysis of the electrophorgrams from the Bioanalyzer for five different batches demonstrated the reproducibility in quality between the batches.

Total RNA from all five batches were combined and mixed in a 50 ml tube, then aliquoted as follows: 2×10 ml aliquots in 15 ml tubes, and the rest in 100 μl aliquots in 1.5 ml microcentrifuge tubes. The aliquots gave highly reproducible results with respect to RNA purity, size and integrity. The RNA was stored at −80° C.

Test hybridization of Reference RNA.

When compared with BC38 and Stimulated mononuclear reference samples, the R50 performed as well, if not better than the other reference samples as shown in FIG. 4.

In an analysis of hybridizations, where the R50 targets were fluorescently labeled with Cy-5 using methods described herein and the amplified and labeled aRNA was hybridized (as in example 7) to the oligonucleotide array described in example 6. The R50 detected 97.3% of probes with a Signal to Noise ratio (S/N) of greater than three and 99.9% of probes with S/N greater one.

Example 3

Identification of Diagnostic Oligonucleotides and Oligonucleotide Sets for Use in Monitoring Treatment and/or Progression of Rheumatoid Arthritis Rheumatoid arthritis (hereinafter, "RA") is a chronic and debilitating inflammatory arthritis. The diagnosis of RA is made by clinical criteria and radiographs. A new class of medication, TNF blockers, are effective, but the drugs are expensive, have side effects and not all patients respond to treatment. In addition, relief of disease symptoms does not always correlate with inhibition of joint destruction. For these reasons, an alternative mechanism for the titration of therapy is needed.

An observational study was conducted in which a cohort of patients meeting American College of Rheumatology (hereinafter "ARC") criteria for the diagnosis of RA was identified. Arnett et al. (1988) *Arthritis Rheum* 31:315-24. Patients gave informed consent and a peripheral blood mononuclear cell RNA sample was obtained by the methods as described herein. When available, RNA samples were also obtained from surgical specimens of bone or synovium from effected joints, and synovial fluid. Also, T-cells were isolated from the peripheral blood for some patients for expression analysis. This was done using the protocol given in Example 1.

From each patient, the following clinical information was obtained if available: Demographic information; information relating to the ACR criteria for RA; presence or absence of additional diagnoses of inflammatory and non-inflammatory conditions; data from laboratory test, including complete blood counts with differentials, CRP, ESR, ANA, Serum IL6, Soluble CD40 ligand, LDL, HDL, Anti-DNA antibodies, rheumatoid factor, C3, C4, serum creatinine and any medication levels; data from surgical procedures such as gross operative findings and pathological evaluation of resected tissues and biopsies; information on pharmacological therapy and treatment changes; clinical diagnoses of disease "flare"; hospitalizations; quantitative joint exams; results from health assessment questionnaires (HAQs); other clinical measures of patient symptoms and disability; physical examination results and radiographic data assessing joint involvement, synovial thickening, bone loss and erosion and joint space narrowing and deformity. In some cases, data includes pathological evaluation of synovial membranes and joint tissues from RA and control patients. Pathology scoring systems were used to determine disease category, inflammation, type of inflammatory infiltrate, cellular and makeup of the synovial inflammation.

For some specimens of synovium, mononuclear cells or subsets of mononuclear cells (such as T cells) can be isolated for expression profiling. The relative number of lymphocyte subsets for some specimens can be determined by fluorescence activated cell sorting. Examples are determination of the CD4/CD8 T-cell ratio for a specimen. This information can be used as a variable to correlate to other outcomes or as an outcome for correlation analysis.

From these data, measures of improvement in RA are derived as exemplified by the ACR 20% and 50% response/improvement rates (Felson et al. 1996). Measures of disease activity over some period of time is derived from these data as are measures of disease progression. Serial radiography of effected joints is used for objective determination of progression (e.g., joint space narrowing, peri-articular osteoporosis, synovial thickening). Disease activity is determined from the clinical scores, medical history, physical exam, lab studies, surgical and pathological findings.

The collected clinical data (disease criteria) is used to define patient or sample groups for correlation of expression data. Patient groups are identified for comparison, for example, a patient group that possesses a useful or interesting clinical distinction, verses a patient group that does not possess the distinction. Examples of useful and interesting patient distinctions that can be made on the basis of collected clinical data are listed here:

Samples from patients during a clinically diagnosed RA flare versus samples from these same or different patients while they are asymptomatic.

Samples from patients who subsequently have high measures of disease activity versus samples from those same or different patients who have low subsequent disease activity.

Samples from patients who subsequently have high measures of disease progression versus samples from those same or different patients who have low subsequent disease progression.

Samples from patients who subsequently respond to a given medication or treatment regimen versus samples from those same or different patients who subsequently do not respond to a given medication or treatment regimen (for example, TNF pathway blocking medications).

Samples from patients with a diagnosis of osteoarthritis versus patients with rheumatoid arthritis.

Samples from patients with tissue biopsy results showing a high degree of inflammation versus samples from patients with lesser degrees of histological evidence of inflammation on biopsy.

Expression profiles correlating with progression of RA are identified. Subsets of the candidate library (or a previously identified diagnostic nucleotide set) are identified, according to the above procedures, that have predictive value for the progression of RA.

Diagnostic nucleotide set(s) are identified which predict respond to TNF blockade. Patients are profiled before and during treatment with these medications. Patients are followed for relief of symptoms, side effects and progression of joint destruction, e.g., as measured by hand radiographs. Expression profiles correlating with response to TNF blockade are identified. Subsets of the candidate library (or a previously identified diagnostic nucleotide set) are identified, according to the above procedures that have predictive value for response to TNF blockade.

Example 4

Identification of Diagnostic Oligonucleotide and Oligonucleotide Sets for Diagnosis of Systemic Lupus Erythematosis SLE is a chronic, systemic inflammatory disease characterized by dysregulation of the immune system. Clinical manifestations affect every organ system and include skin rash, renal dysfunction, CNS disorders, arthralgias and hematologic abnormalities. SLE clinical manifestations tend to both recur intermittently (or "flare") and progress over time, leading to permanent end-organ damage.

An observational study was conducted in which a cohort of patients meeting American College of Rheumatology (hereinafter "ACR") criteria for the diagnosis of SLE were identified. See Tan et al. (1982) *Arthritis Rheum* 25:1271-7. Patients gave informed consent and a peripheral blood mononuclear cell RNA sample or a peripheral T cell sample was obtained by the methods as described in example 1.

From each patient, the following clinical information was obtained if available: Demographic information, ACR criteria for SLE, additional diagnoses of inflammatory and non-inflammatory conditions, data from laboratory testing including complete blood counts with differentials, CRP, ESR, ANA, Serum IL6, Soluble CD40 ligand, LDL, HDL, Anti-DNA antibodies, rheumatoid factor, C3, C4, serum creatinine (and other measures of renal dysfunction), medication levels, data from surgical procedures such as gross operative findings and pathological evaluation of resected tissues and biopsies (e.g., renal, CNS), information on pharmacological therapy and treatment changes, clinical diagnoses of disease "flare", hospitalizations, quantitative joint exams, results from health assessment questionnaires (HAQs), SLEDAIs (a clinical score for SLE activity that assess many clinical variables; Bombadier C, Gladman D D, Urowitz M B, Caron D, Chang C H and the Committee on Prognosis Studies in SLE: Derivation of the SLEDAI for Lupus Patients. *Arthritis Rheum* 35:630-640, 1992), other clinical measures of patient symptoms and disability, physical examination results and carotid ultrasonography.

The collected clinical data (disease criteria) is used to define patient or sample groups for correlation of expression data. Patient groups are identified for comparison, for example, a patient group that possesses a useful or interesting clinical distinction, verses a patient group that does not possess the distinction. Measures of disease activity in SLE are derived from the clinical data described above to divide patients (and patient samples) into groups with higher and lower disease activity over some period of time or at any one point in time. Such data are SLEDAI scores and other clinical scores, levels of inflammatory markers or complement, number of hospitalizations, medication use and changes, biopsy results and data measuring progression of end-organ damage or end-organ damage, including progressive renal failure, carotid atherosclerosis, and CNS dysfunction.

Expression profiles correlating with progression of SLE are identified, including expression profiles corresponding to end-organ damage and progression of end-organ damage. Expression profiles are identified predicting disease progression or disease "flare", response to treatment or likelihood of response to treatment, predict likelihood of "low" or "high" disease measures (optionally described using the SLEDAI score), and presence or likelihood of developing premature carotid atherosclerosis. Subsets of the candidate library (or a previously identified diagnostic nucleotide set) are identified, according to the above procedures that have predictive value for the progression of SLE.

Further examples of useful and interesting patient distinctions that can be made on the basis of collected clinical data are listed here. Samples can be grouped and groups are compared to discover diagnostic gene sets:

1. Samples from patients during a clinically diagnosed SLE flare versus samples from these same or different patients while they are asymptomatic or while they have a documented infection.
2. Samples from patients who subsequently have high measures of disease activity versus samples from those same or different patients who have low subsequent disease activity.

3. Samples from patients who subsequently have high measures of disease progression versus samples from those same or different patients who have low subsequent disease progression.
4. Samples from patients who subsequently respond to a given medication or treatment regimen versus samples from those same or different patients who subsequently do not respond to a given medication or treatment regimen.
5. Samples from patients with premature carotid atherosclerosis on ultrasonography versus patients with SLE without premature atherosclerosis.

Identification of a Diagnostic Oligonucleotide or Oligonucleotide Set for Diagnosis of Lupus Mononuclear RNA samples were collected from patients with SLE and patients with Rheumatoid or Osteoarthritis (RA and OA) or controls using the protocol described in example 1. The patient diagnoses were determined using standard diagnostic algorithms such as those that are employed by the American College of Rheumatology (see example See Tan et al. (1982) *Arthritis Rheum* 25:1271-7; Arnett et al. (1988) *Arthritis Rheum* 31:315-24).

32 samples were included in the analysis. 15 samples were derived from patients with a clinical diagnosis of SLE and the remainder were derived from patients with RA (9), OA (4) and subjects without known disease (4) who served as controls. Samples from patients with SLE or RA were classified as "Active" or "Controlled" (with respect to disease activity) by the patient's physician based on objective and subjective criteria, such as patient history, physical exam and lab studies. An attempt was made to match SLE patients and controls with respect to important variables such as medication use, sex, age and secondary diagnoses.

After preparation of RNA (example 1), amplification, labeling, hybridization, scanning, feature extraction and data processing were done as described in Example 7 using the oligonucleotide microarrays described in Example 6. The resulting log ratio of expression of Cy3 (patient sample)/Cy5 (R50 reference RNA) was used for analysis.

Initially, significance analysis for microarrays (SAM, Tusher 2001, Example 9) was used to discover that were differentially expressed between 7 of the Lupus samples and 17 control samples. 1 gene was identified that was expressed at a higher level in the lupus patients than in all controls. This gene had a 0.5% false detection rate using SAM. This means that there is statistically, a 99.5% chance that the gene is truly differentially expressed between the Lupus and control samples. This gene was oligonucleotide and SEQ ID #518. The oligonucleotide:

GCCTCTTGCTTGGCGTGATAACCCTGT-CATCTTCCCAAAGCTCATTTATG detects a specific human gene: sialyltransferase (SIAT4A), Unigene: Hs.301698

Locus: NM_003033, GI: 4506950. Expression ratios for the gene are given for each sample in FIG. 5A-B. The average fold change in expression between SLE and controls was 1.48.

When a larger data set was used, 15 SLE samples were compared to 17 controls. Using SAM, genes were identified as significantly differentially expressed between Lupus and controls. Supervised harvesting classification (X-Mine, Brisbane, Calif.) and CART (Salford Systems, San Diego Calif.) were also used on the same data to determine which set of genes best distinguish SLE from control samples (Example 9).

CART was used to build a decision tree for classification of samples as lupus or not lupus using the gene expression data from the arrays. The analysis identities sets of genes that can be used together to accurately identify samples derived from lupus patients. The set of genes and the identified threshold expression levels for the decision tree are referred to as "models". Multiple models for diagnosis of Lupus were derived by using different settings and parameters for the CART algorithm and using different sets of genes in the analysis. When using CART, it may be desirable to limit the number of independent variables. In the case of the genes on the arrays, a subset of ~8000 can be selected for analysis in CART based on significant differential expression discovered by using SAM or some other algorithm.

Model I was based on a data set consisting of thirty-two samples (fifteen SLE and seventeen non-SLE). These samples were used to derive the model and are referred to a the "training set". Model I used the expression values for twenty-nine genes, which were found to be most significant in differentiating SLE and non-SLE samples in the analysis using SAM described above. SLE samples were designated as Class 1 and non-SLE samples were designated as Class 2. For this analysis, the following settings were used in the MODEL SETUP (CART, Salford Systems, San Diego, Calif.). In the Model settings, the tree type selected for the analysis was classification. In the Categorical settings, the default values were used. In the Testing settings, V-fold cross-validation was selected with a value of 10. In the Select Cases settings, the default values were used. In the Best Tree settings, the default values were used. In the Combine settings, the default values were used. In the Method settings, Symmetric Gini was selected as the type of classification tree and Linear combinations for splitting was also selected. The default values were used for the linear combinations. In the Advance Settings, the default values were used. In the Costs settings, the default values were used. In the Priors settings, Equal was selected as the priors for Class. In the penalty settings, the default values were used.

From this analysis, CART built two models, a two-gene model and a three-gene model (FIGS. 5C-E). The sensitivity and specificity for the identification of lupus in the training set samples of the two genes model were 100% and 94%, respectively. The sensitivity and specificity for the 10-fold cross validation set of the two-gene model were 100% and 88%, respectively, with a relative cost of 0.118. The sensitivity and specificity for the training set of the three genes model were 100% and 100%, respectively. The sensitivity and specificity for the 10-fold cross validation set of the three genes model were 93% and 94%, respectively, with a relative cost of 0.125.

Model II was based on a data set consisted of thirty-two samples, fifteen SLE and seventeen non-SLE (training set) and six thousand forty-four genes with expression values for at least 80% of the samples. The MODEL SETUP for the analysis of this data set was the same as for the analysis above, except for the following correction. In the Method settings, Linear combination for splitting was unchecked after the analysis yielded no classification tree. The change in the linear combination setting resulted in the following.

The sensitivity and specificity for the training set of the one gene model were 87% and 82%, respectively. The sensitivity and specificity for the 10-fold cross validation set of the one gene model were 80% and 59%, respectively, with a relative cost of 0.612. The sensitivity and specificity for the training set of the three genes model were 100% and 88%, respectively. The sensitivity and specificity for the 10-fold cross validation set of the three genes model were 67% and 65%, respectively, with a relative cost of 0.686. The sensitivity and specificity for the training set of the five genes model were 100% and 94%, respectively. The sensitivity and specificity for the 10-fold cross validation set of the five genes model were 67% and 59%, respectively, with a relative cost of 0.745. Results and models are summarized in FIGS. 5 C and F.

Those genes that were found to be useful for classification are noted in Table 2.

These genes can be used alone or in association with other genes or variables to build a diagnostic gene set or a classification algorithm. These genes can be used in association with known gene markers for lupus (such as those identified in the prior art) to provide a diagnostic algorithm.

Primers for real-time PCR validation were designed for some of the genes as described in Example 8 and are listed in Table 2B.

Surrogates for some of the most useful genes were identified. Surrogates can be used in addition to or in place of a diagnostic gene in a method of detecting lupus or in diagnostic gene set. For genes that were splitters in CART, surrogates were identified and reported by the software. In these cases, the best available surrogates are listed. For other genes, hierarchical clustering of the data was performed with default settings (x-miner, X-mine, Brisbane, Calif.) and members of gene expression clusters were noted. A cluster was selected that included the gene of interest and the members of that cluster were recorded in Table 2D.

Example 5

Design of Oligonucleotide Probes

By way of example, this section describes the design of four oligonucleotide probes using Array Designer Ver 1.1 (Premier Biosoft International, Palo Alto, Calif.). The major steps in the process are given first.

1) Obtain best possible sequence of mRNA from GenBank. If a full-length sequence reference sequence is not available, a partial sequence is used, with preference for the 3' end over the 5' end. When the sequence is known to represent the antisense strand, the reverse complement of the sequence is used for probe design. For sequences represented in the subtracted leukocyte expression library that have no significant match in GenBank at the time of probe design, our sequence is used.
2) Mask low complexity regions and repetitive elements in the sequence using an algorithm such as RepeatMasker.
3) Use probe design software, such as Array Designer, version 1.1, to select a sequence of 50 residues with specified physical and chemical properties. The 50 residues nearest the 3' end constitute a search frame. The residues it contains are tested for suitability. If they don't meet the specified criteria, the search frame is moved one residue closer to the 5' end, and the 50 residues it now contains are tested. The process is repeated until a suitable 50-mer is found.
4) If no such 50-mer occurs in the sequence, the physical and chemical criteria are adjusted until a suitable 50-mer is found.
5) Compare the probe to dbEST, the UniGene cluster set, and the assembled human genome using the BLASTn search tool at NCBI to obtain the pertinent identifying information and to verify that the probe does not have significant similarity to more than one known gene.

Clone 40H12

Clone 40H12 was sequenced and compared to the nr, dbEST, and UniGene databases at NCBI using the BLAST search tool. The sequence matched accession number NM_002310, a 'curated RefSeq project' sequence, see Pruitt et al. (2000) *Trends Genet.* 16:44-47, encoding leukemia inhibitory factor receptor (LIFR) mRNA with a reported E value of zero. An E value of zero indicates there is, for all practical purposes, no chance that the similarity was random based on the length of the sequence and the composition and size of the database. This sequence, cataloged by accession number NM_002310, is much longer than the sequence of clone 40H12 and has a poly-A tail. This indicated that the sequence cataloged by accession number NM_002310 is the sense strand and a more complete representation of the mRNA than the sequence of clone 40H12, especially at the 3' end. Accession number "NM_002310" was included in a text file of accession numbers representing sense strand mRNAs, and sequences for the sense strand mRNAs were obtained by uploading a text file containing desired accession numbers as an Entrez search query using the Batch Entrez web interface and saving the results locally as a FASTA file. The following sequence was obtained, and the region of alignment of clone 40H12 is outlined:

(SEQ ID NO:1039)
CTCTCTCCCAGAACGTGTCTCTGCTGCAAGGCACCGGGCCCTTTCGCTCTGCAGAACTGCACTTGCAAGA

CCATTATCAACTCCTAATCCCAGCTCAGAAAGGGAGCCTCTGCGACTCATTCATCGCCCTCCAGGACTGA

CTGCATTGCACAGATGATGGATATTTACGTATGTTTGAAACGACCATCCTGGATGGTGGACAATAAAAGA

ATGAGGACTGCTTCAAATTTCCAGTGGCTGTTATCAACATTTATTCTTCTATATCTAATGAATCAAGTAA

ATAGCCAGAAAAAGGGGGCTCCTCATGATTTGAAGTGTGTAACTAACAATTTGCAAGTGTGGAACTGTTC

TTGGAAAGCACCCTCTGGAACAGGCCGTGGTACTGATTATGAAGTTTGCATTGAAAACAGGTCCCGTTCT

TGTTATCAGTTGGAGAAAACCAGTATTAAAATTCCAGCTCTTTCACATGGTGATTATGAAATAACAATAA

ATTCTCTACATGATTTTGGAAGTTCTACAAGTAAATTCACACTAAATGAACAAAACGTTTCCTTAATTCC

AGATACTCCAGAGATCTTGAATTTGTCTGCTGATTTCTCAACCTCTACATTATACCTAAAGTGGAACGAC

AGGGGTTCAGTTTTTCCACACCGCTCAAATGTTATCTGGGAAATTAAAGTTCTACGTAAAGAGAGTATGG

AGCTCGTAAAATTAGTGACCCACAACACAACTCTGAATGGCAAAGATACACTTCATCACTGGAGTTGGGC

CTCAGATATGCCCTTGGAATGTGCCATTCATTTTGTGGAAATTAGATGCTACATTGACAATCTTCATTTT

TCTGGTCTCGAAGAGTGGAGTGACTGGAGCCCTGTGAAGAACATTTCTTGGATACCTGATTCTCAGACTA

AGGTTTTTCCTCAAGATAAAGTGATACTTGTAGGCTCAGACATAACATTTTGTTGTGTGAGTCAAGAAAA

AGTGTTATCAGCACTGATTGGCCATACAAACTGCCCCTTGATCCATCTTGATGGGGAAAATGTTGCAATC

-continued

```
AAGATTCGTAATATTTCTGTTTCTGCAAGTAGTGGAACAAATGTAGTTTTTACAACCGAAGATAACATAT

TTGGAACCGTTATTTTTGCTGGATATCCACCAGATACTCCTCAACAACTGAATTGTGAGACACATGATTT

AAAAGAAATTATATGTAGTTGGAATCCAGGAAGGGTGACAGCGTTGGTGGGCCCACGTGCTACAAGCTAC

ACTTTAGTTGAAAGTTTTTCAGGAAAATATGTTAGACTTAAAAGAGCTGAAGCACCTACAAACGAAAGCT

ATCAATTATTATTTCAAATGCTTCCAAATCAAGAAATATATAATTTTACTTTGAATGCTCACAATCCGCT

GGGTCGATCACAATCAACAATTTTAGTTAATATAACTGAAAAAGTTTATCCCCATACTCCTACTTCATTC

AAAGTGAAGGATATTAATTCAACAGCTGTTAAACTTTCTTGGCATTTACCAGGCAACTTTGCAAAGATTA

ATTTTTTATGTGAAATTGAAATTAAGAAATCTAATTCAGTACAAGAGCAGCGGAATGTCACAATCAAGG

AGTAGAAAATTCAAGTTATCTTGTTGCTCTGGACAAGTTAAATCCATACACTCTATATACTTTTCGGATT

CGTTCTTCTACTGAAACTTTCTGGAAATGGAGCAAATGGAGCAATAAAAAACAACATTTAACAACAGAAG

CCAGTCCTTCAAAGGGGCCTGATACTTGGAGAGAGTGGAGTTCTGATGGAAAAAATTTAATAATCTATTG

GAAGCCTTTACCCATTAATGAAGCTAATGGAAAAATACTTTCCTACAATGTATCGTGTTCATCAGATGAG

GAAACACAGTCCCTTTCTGAAATCCCTGATCCTCAGCACAAAGCAGAGATACGACTTGATAAGAATGACT

ACATCATCAGCGTAGTGGCTAAAAATTCTGTGGGCTCATCACCACCTTCCAAAATAGCGAGTATGGAAAT

TCCAAATGATGATCTCAAAATAGAACAAGTTGTTGGGATGGGAAGGGGATTCTCCTCACCTGGCATTAC

GACCCCAACATGACTTGCGACTACGTCATTAAGTGGTGTAACTCGTCTCGGTCGGAACCATGCCTTATGG

ACTGGAGAAAAGTTCCCTCAAACAGCACTGAAACTGTAATAGAATCTGATGAGTTTCGACCAGGTATAAG

ATATAATTTTTTCCTGTATGGATGCAGAAATCAAGGATATCAATTATTACGCTCCATGATTGGATATATA

GAAGAATTGGCTCCCATTGTTGCACCAAATTTTACTGTTGAGGATACTTCTGCAGATTCGATATTAGTAA

AATGGGAAGACATTCCTGTGGAAGAACTTAGAGGCTTTTTAAGAGGATATTTGTTTTACTTTGGAAAAGG

AGAAAGAGACACATCTAAGATGAGGGTTTTAGAATCAGGTCGTTCTGACATAAAAGTTAAGAATATTACT

GACATATCCCAGAAGACACTGAGAATTGCTGATCTTCAAGGTAAAACAAGTTACCACCTGGTCTTGCGAG

CCTATACAGATGGTGGAGTGGGCCCGGAGAAGAGTATGTATGTGGTGACAAAGGAAAATTCTGTGGGATT

AATTATTGCCATTCTCATCCCAGTGGCAGTGGCTGTCATTGTTGGAGTGGTGACAAGTATCCTTTGCTAT

CGGAAACGAGAATGGATTAAAGAAACCTTCTACCCTGATATTCCAAATCCAGAAAACTGTAAAGCATTAC

AGTTTCAAAAGAGTGTCTGTGAGGGAAGCAGTGCTCTTAAAACATTGGAAATGAATCCTTGTACCCCAAA

TAATGTTGAGGTTCTGGAAACTCGATCAGCATTTCCTAAAATAGAAGATACAGAAATAATTTCCCCAGTA

GCTGAGCGTCCTGAAGATCGCTCTGATGCAGAGCCTGAAACCATGTGGTTGTGTCCTATTGTCCACCCA

TCATTGAGGAAGAAATACCAAACCCAGCCGCAGATGAAGCTGGAGGGACTGCACAGGTTATTTACATTGA

TGTTCAGTCGATGTATCAGCCTCAAGCAAAACCAGAAGAAGAACAAGAAAATGACCCTGTAGGAGGGCA

GGCTATAAGCCACAGATGCACCTCCCCATTAATTCTACTGTGGAAGATATAGCTGCAGAAGAGGACTTAG

ATAAAACTGCGGGTTACAGACCTCAGGCCAATGTAAATACATGGAATTTAGTGTCTCCAGACTCTCCTAG

ATCCATAGACAGCAACAGTGAGATTGTCTCATTTGGAAGTCCATGCTCCATTAATTCCCGACAATTTTTG

ATTCCTCCTAAAGATGAAGACTCTCCTAAATCTAATGGAGGAGGGTGGTCCTTTACAAACTTTTTTCAGA

ACAAACCAAACGATTAACAGTGTCACCGTGTCACTTCAGTCAGCCATCTCAATAAGCTCTTACTGCTAGT

GTTGCTACATCAGCACTGGGCATTCTTGGAGGGATCCTGTGAAGTATTGTTAGGAGGTGAACTTCACTAC

ATGTTAAGTTACACTGAAAGTTCATGTGCTTTTAATGTAGTCTAAAAGCCAAAGTATAGTGACTCAGAAT

CCTCAATCCACAAAACTCAAGATTGGGAGCTCTTTGTGATCAAGCCAAAGAATTCTCATGTACTCTACCT

TCAAGAAGCATTTCAAGGCTAATACCTACTTGTACGTACATGTAAAACAAATCCCGCCGCAACTGTTTTC

TGTTCTGTTGTTTGTGGTTTTCTCATATGTATACTTGGTGGAATTGTAAGTGGATTTGCAGGCCAGGGAG
```

-continued

```
AAAATGTCCAAGTAACAGGTGAAGTTTATTTGCCTGACGTTTACTCCTTTCTAGATGAAAACCAAGCACA
GATTTTAAAACTTCTAAGATTATTCTCCTCTATCCACAGCATTCACAAAAATTAATATAATTTTTAATGT
AGTGACAGCGATTTAGTGTTTTGTTTGATAAAGTATGCTTATTTCTGTGCCTACTGTATAATGGTTATCA
AACAGTTGTCTCAGGGGTACAAACTTTGAAAACAAGTGTGACACTGACCAGCCCAAATCATAATCATGTT
TTCTTGCTGTGATAGGTTTTGCTTGCCTTTTCATTATTTTTAGCTTTTATGCTTGCTTCCATTATTTCA
GTTGGTTGCCCTAATATTTAAAATTTACACTTCTAAGACTAGAGACCCACATTTTTTAAAAATCATTTTA
TTTTGTGATACAGTGACAGCTTTATATGAGCAAATTCAATATTATTCATAAGCATGTAATTCCAGTGACT
TACTATGTGAGATGACTACTAAGCAATATCTAGCAGCGTTAGTTCCATATAGTTCTGATTGGATTTCGTT
CCTCCTGAGGAGACCATGCCGTTGAGCTTGGCTACCCAGGCAGTGGTGATCTTTGACACCTTCTGGTGGA
TGTTCCTCCCACTCATGAGTCTTTTCATCATGCCACATTATCTGATCCAGTCCTCACATTTTTAAATATA
AAACTAAAGAGAGAATGCTTCTTACAGGAACAGTTACCCAAGGGCTGTTTCTTAGTAACTGTCATAAACT
GATCTGGATCCATGGGCATACCTGTGTTCGAGGTGCAGCAATTGCTTGGTGAGCTGTGCAGAATTGATTG
CCTTCAGCACAGCATCCTCTGCCCACCCTTGTTTCTCATAAGCGATGTCTGGAGTGATTGTGGTTCTTGG
AAAAGCAGAAGGAAAAACTAAAAAGTGTATCTTGTATTTTCCCTGCCCTCAGGTTGCCTATGTATTTTAC
CTTTTCATATTTAAGGCAAAAGTACTTGAAAATTTTAAGTGTCCGAATAAGATATGTCTTTTTTGTTTGT
TTTTTTTGGTTGGTTGTTTGTTTTTTATCATCTGAGATTCTGTAATGTATTTGCAAATAATGGATCAATT
AATTTTTTTGAAGCTCATATTGTATCTTTTTAAAAACCATGTTGTGGAAAAAAGCCAGAGTGACAAGTG
ACAAAATCTATTTAGGAACTCTGTGTATGAATCCTGATTTTAACTGCTAGGATTCAGCTAAATTTCTGAG
CTTTATGATCTGTGGAAATTTGGAATGAAATCGAATTCATTTTGTACATACATAGTATATTAAAACTATA
TAATAGTTCATAGAAATGTTCAGTAATGAAAAAATATATCCAATCAGAGCCATCCCGAAAAAAAAAAAA
AA
```

The FASTA file, including the sequence of NM_002310, was masked using the RepeatMasker web interface (Smit, AFA & Green, P RepeatMasker at genome.washington.edu/RM/RepeatMasker.html, Smit and Green). Specifically, during masking, the following types of sequences were replaced with 'N's: SINE/MIR & LINE/L2, LINE/L1, LTR/MaLR, LTR/Retroviral, Alu, and other low informational content sequences such as simple repeats. Below is the sequence following masking:

```
                                                    (SEQ ID NO:1040)
CTCTCTCCCAGAACGTGTCTCTGCTGCAAGGCACCGGGCCCTTTCGCTCTGCAGAACTGCACTTGCAAGA
CCATTATCAACTCCTAATCCCAGCTCAGAAAGGGAGCCTCTGCGACTCATTCATCGCCCTCCAGGACTGA
CTGCATTGCACAGATGATGGATATTTACGTATGTTTGAAACGACCATCCTGGATGGTGGACAATAAAAGA
ATGAGGACTGCTTCAAATTTCCAGTGGCTGTTATCAACATTTATTCTTCTATATCTAATGAATCAAGTAA
ATAGCCAGAAAAAGGGGGCTCCTCATGATTTGAAGTGTGTAACTAACAATTTGCAAGTGTGGAACTGTTC
TTGGAAAGCACCCTCTGGAACAGGCCGTGGTACTGATTATGAAGTTTGCATTGAAAACAGGTCCCGTTCT
TGTTATCAGTTGGAGAAAACCAGTATTAAAATTCCAGCTCTTTCACATGGTGATTATGAAATAACAATAA
ATTCTCTACATGATTTTGGAAGTTCTACAAGTAAATTCACACTAAATGAACAAAACGTTTCCTTAATTCC
```

```
AGATACTCCAGAGATCTTGAATTTGTCTGCTGATTTCTCAACCTCTACATTATACCTAAAGTGGAACGAC
AGGGGTTCAGTTTTTCCACACCGCTCAAATGTTATCTGGGAAATTAAAGTTCTACGTAAAGAGAGTATGG
AGCTCGTAAAATTAGTGACCCACAACACAACTCTGAATGGCAAAGATACACTTCATCACTGGAGTTGGGC
CTCAGATATGCCCTTGGAATGTGCCATTCATTTTGTGGAAATTAGATGCTACATTGACAATCTTCATTTT
TCTGGTCTCGAAGAGTGGAGTGACTGGAGCCCTGTGAAGAACATTTCTTGGATACCTGATTCTCAGACTA
AGGTTTTTCCTCAAGATAAAGTGATACTTGTAGGCTCAGACATAACATTTTGTTGTGTGAGTCAAGAAAA
AGTGTTATCAGCACTGATTGGCCATACAAACTGCCCCTTGATCCATCTTGATGGGAAAATGTTGCAATC
AAGATTCGTAATATTTCTGTTTCTGCAAGTAGTGGAACAAATGTAGTTTTTACAACCGAAGATAACATAT
TTGGAACCGTTATTTTTGCTGGATATCCACCAGATACTCCTCAACAACTGAATTGTGAGACACATGATTT
AAAAGAAATTATATGTAGTTGGAATCCAGGAAGGGTGACAGCGTTGGTGGGCCCACGTGCTACAAGCTAC
ACTTTAGTTGAAAGTTTTTCAGGAAAATATGTTAGACTTAAAAGAGCTGAAGCACCTACAAACGAAAGCT
ATCAATTATTATTTCAAATGCTTCCAAATCAAGAAATATATAATTTTACTTTGAATGCTCACAATCCGCT
GGGTCGATCACAATCAACAATTTTAGTTAATATAACTGAAAAAGTTTATCCCCATACTCCTACTTCATTC
AAAGTGAAGGATATTAATTCAACAGCTGTTAAACTTTCTTGGCATTTACCAGGCAACTTTGCAAAGATTA
ATTTTTTATGTGAAATTGAAATTAAGAAATCTAATTCAGTACAAGAGCAGCGGAATGTCACAATCAAAGG
AGTAGAAAATTCAAGTTATCTTGTTGCTCTGGACAAGTTAAATCCATACACTCTATATACTTTTCGGATT
CGTTCTTCTACTGAAACTTTCTGGAAATGGAGCAAATGGAGCAATAAAAAACAACATTTAACAACAGAAG
CCAGTCCTTCAAAGGGGCCTGATACTTGGAGAGAGTGGAGTTCTGATGGAAAAAATTTAATAATCTATTG
GAAGCCTTTACCCATTAATGAAGCTAATGGAAAAATACTTTCCTACAATGTATCGTGTTCATCAGATGAG
GAAACACAGTCCCTTTCTGAAATCCCTGATCCTCAGCACAAAGCAGAGATACGACTTGATAAGAATGACT
ACATCATCAGCGTAGTGGCTAAAAATTCTGTGGGCTCATCACCACCTTCCAAAATAGCGAGTATGGAAAT
TCCAAATGATGATCTCAAAATAGAACAAGTTGTTGGGATGGGAAAGGGGATTCTCCTCACCTGGCATTAC
GACCCCAACATGACTTGCGACTACGTCATTAAGTGGTGTAACTCGTCTCGGTCGGAACCATGCCTTATGG
ACTGGAGAAAAGTTCCCTCAAACAGCACTGAAACTGTAATAGAATCTGATGAGTTTCGACCAGGTATAAG
ATATAATTTTTTCCTGTATGGATGCAGAAATCAAGGATATCAATTATTACGCTCCATGATTGGATATATA
GAAGAATTGGCTCCCATTGTTGCACCAAATTTTACTGTTGAGGATACTTCTGCAGATTCGATATTAGTAA
AATGGGAAGACATTCCTGTGGAAGAACTTAGAGGCTTTTTAAGAGGATATTTGTTTTACTTTGGAAAAGG
AGAAAGAGACACATCTAAGATGAGGGTTTTAGAATCAGGTCGTTCTGACATAAAAGTTAAGAATATTACT
GACATATCCCAGAAGACACTGAGAATTGCTGATCTTCAAGGTAAAACAAGTTACCACCTGGTCTTGCGAG
CCTATACAGATGGTGGAGTGGGCCCGGAGAAGAGTATGTATGTGGTGACAAAGGAAAATTCTGTGGGATT
AATTATTGCCATTCTCATCCCAGTGGCAGTGGCTGTCATTGTTGGAGTGGTGACAAGTATCCTTTGCTAT
CGGAAACGAGAATGGATTAAAGAAACCTTCTACCCTGATATTCCAAATCCAGAAAACTGTAAAGCATTAC
AGTTTCAAAAGAGTGTCTGTGAGGGAAGCAGTGCTCTTAAAACATTGGAAATGAATCCTTGTACCCCAAA
TAATGTTGAGGTTCTGGAAACTCGATCAGCATTTCCTAAAATAGAAGATACAGAAATAATTTCCCCAGTA
GCTGAGCGTCCTGAAGATCGCTCTGATGCAGAGCCTGAAACCATGTGGTTGTGTCCTATTGTCCACCCA
TCATTGAGGAAGAAATACCAAACCCAGCCGCAGATGAAGCTGGAGGGACTGCACAGGTTATTTACATTGA
TGTTCAGTCGATGTATCAGCCTCAAGCAAAACCAGAAGAAGAACAAGAAAATGACCCTGTAGGAGGGGCA
GGCTATAAGCCACAGATGCACCTCCCCATTAATTCTACTGTGGAAGATATAGCTGCAGAAGAGGACTTAG
ATAAAACTGCGGGTTACAGACCTCAGGCCAATGTAAATACATGGAATTTAGTGTCTCCAGACTCTCCTAG
ATCCATAGACAGCAACAGTGAGATTGTCTCATTTGGAAGTCCATGCTCCATTAATTCCCGACAATTTTTG
```

-continued
```
ATTCCTCCTAAAGATGAAGACTCTCCTAAATCTAATGGAGGAGGGTGGTCCTTTACAAACTTTTTTCAGA

ACAAACCAAACGATTAACAGTGTCACCGTGTCACTTCAGTCAGCCATCTCAATAAGCTCTTACTGCTAGT

GTTGCTACATCAGCACTGGGCATTCTTGGAGGGATCCTGTGAAGTATTGTTAGGAGGTGAACTTCACTAC

ATGTTAAGTTACACTGAAAGTTCATGTGCTTTTAATGTAGTCTAAAAGCCAAAGTATAGTGACTCAGAAT

CCTCAATCCACAAAACTCAAGATTGGGAGCTCTTTGTGATCAAGCCAAAGAATTCTCATGTACTCTACCT

TCAAGAAGCATTTCAAGGCTAATACCTACTTGTACGTACATGTAAAACAAATCCCGCCGCAACTGTTTTC

TGTTCTGTTGTTTGTGGTTTTCTCATATGTATACTTGGTGGAATTGTAAGTGGATTTGCAGGCCAGGGAG

AAAATGTCCAAGTAACAGGTGAAGTTTATTTGCCTGACGTTTACTCCTTTCTAGATGAAAACCAAGCACA

GATTTTAAAACTTCTAAGATTATTCTCCTCTATCCACAGCATTCACNNNNNNNNNNNNNNNNNNNNNNGT

AGTGACAGCGATTTAGTGTTTTGTTTGATAAAGTATGCTTATTTCTGTGCCTACTGTATAATGGTTATCA

AACAGTTGTCTCAGGGGTACAAACTTTGAAAACAAGTGTGACACTGACCAGCCCAAAT|CATAATCATGTT

TTCTTGCTGTGATAGGTTTTGCTTGCCTTTTCATTATTTTTTAGCTTTTATGCTTGCTTCCATTATTTCA|

|GTTGGTTGCCCTAATATTTAAAATTTACACTTCTAAGACTAGAGACCCACATTTTTTAAAAATCATTTTA|

|TTTTGTGATACAGTGACAGCTTTATATGAGCAAATTCAATATTATTCATAAGCATGTAATTCCAGTGACT|

|TACTATGTGAGATGACTACTAAGCAATATCTAGCAGCGTTAGTTCCATATAGTTCTGATTGGATTTCGTT|

|CCTCCTGAGGAGACCATGCCGTTGAGCTTGGCTACCCAGGCAGTGGTGATCTTTGACACCTTCTGGTGGA|

|TGTTCCTCCCACTCATGAGTCTTTTCATCATGCCACATTATCTGATCCAGTCCTCACATTTTTAAATATA|

|AAACTAAAGAGAGAATGCTTCTTACAGGAACAGTTACCCAAGGGCTGTTTCTTAGTAACTGTCATAAACT|

|GATCTGGATCCATGGGCATACCTGTGTTCGAGGTGCAGCAATTGCTTGGTGAGCTGTGCAGAATTGATTG|

|CCTTCAGCACAGCATCCTCTGCCCACCCTTGTTTCTCATAAGCGATGTCTGGAGTGATTGTGGTTCTTGG|

|AAAAGCAGAAGGAAAAACTAAAAAGTGTATCTTGTATTTTCCCTGCC|CTCAGGTTGCCTATGTATTTTAC

CTTTTCATATTTAAGGCAAAAGTACTTGAAAATTTTAAGTGTCCGAATAAGATATGTCTTTTTGTTTGT

TTTTTTGGTTGGTTGTTTGTTTTTTATCATCTGAGATTCTGTAATGTATTTGCAAATAATGGATCAATT

AATTTTTTTTGAAGCTCATATTGTATCTTTTTAAAAACCATGTTGTGGAAAAAAGCCAGAGTGACAAGTG

ACAAAATCTATTTAGGAACTCTGTGTATGAATCCTGATTTTAACTGCTAGGATTCAGCTAAATTTCTGAG

CTTTATGATCTGTGGAAATTTGGAATGAAATCGAATTCATTTTGTACATACATAGTATATTAAAACTATA

TAATAGTTCATAGAAATGTTCAGTAATGAAAAAATATATCCAATCAGAGCCATCCCGAAAAAAAAAAAA
```
AA.

The length of this sequence was determined using batch, automated computational methods and the sequence, as sense strand, its length, and the desired location of the probe sequence near the 3' end of the mRNA was submitted to Array Designer Ver 1.1 (Premier Biosoft International, Palo Alto, Calif.). Search quality was set at 100%, number of best probes set at 1, length range set at 50 base pairs, Target Tm set at 75 C. degrees plus or minus 5 degrees, Hairpin max deltaG at 6.0-kcal/mol., Self dimmer max deltaG at 6.0-kcal/mol, Run/repeat (dinucleotide) max length set at 5, and Probe site minimum overlap set at 1. When none of the 49 possible probes met the criteria, the probe site would be moved 50 base pairs closer to the 5' end of the sequence and resubmitted to Array Designer for analysis. When no possible probes met the criteria, the variation on melting temperature was raised to plus and minus 8 degrees and the number of identical basepairs in a run increased to 6 so that a probe sequence was produced.

In the sequence above, using the criteria noted above, Array Designer Ver 1.1 designed a probe with the following sequence oligonucleotide SEQ ID NO:1041 and is indicated by underlining in the sequence above. It has a melting temperature of 68.4 degrees Celsius and a max run of 6 nucleotides and represents one of the cases where the criteria for probe design in Array Designer Ver 1.1 were relaxed in order to obtain an oligonucleotide near the 3' end of the mRNA (Low melting temperature was allowed).

Clone 463D12

Clone 463D12 was sequenced and compared to the nr, dbEST, and UniGene databases at NCBI using the BLAST search tool. The sequence matched accession number AI184553, an EST sequence with the definition line "qd60a05.x1 Soares_testis_NHT *Homo sapiens* cDNA clone IMAGE:1733840 3' similar to gb:M29550 PROTEIN PHOSPHATASE 2B CATALYTIC SUBUNIT 1 (HUMAN); mRNA sequence." The E value of the alignment was 1.00× $10^{-118}$. The GenBank sequence begins with a poly-T region, suggesting that it is the antisense strand, read 5' to 3'. The beginning of this sequence is complementary to the 3' end of the mRNA sense strand. The accession number for this sequence was included in a text file of accession numbers representing antisense sequences. Sequences for antisense strand mRNAs were obtained by uploading a text file containing desired accession numbers as an Entrez search query using the Batch Entrez web interface and saving the results locally as a FASTA file. The following sequence was obtained, and the region of alignment of clone 463D12 is outlined:

(SEQ ID NO:1042)
TTTTTTTTTTTTTCTTAAATAGCATTTATTTTCTCTCAAAAAGCCTATTATGTACTAACAAGTGTTCC

TCTAAATTAGAAAGGCATCACTACTAAAATTTTATACATATTTTTTATATAAGAGAAGGAATATTGGGT

TACAATCTGAATTTCTCTTTATGATTTCTCTTAAAGTATAGAACAGCTATTAAAATGACTAATATTGCT

AAAATGAAGGCTACTAAATTTCCCCAAGAATTTCGGTGGAATGCCCAAAAATGGTGTTAAGATATGCAG

AAGGGCCCATTTCAAGCAAAGCAATCTCTCCACCCCTTCATAAAAGATTTAAGCTAAAAAAAAAAAAAA

AAGAAGAAAATCCAACAGCTGAAGACATTGGGCTATTTATAAATCTTCTCCCAGTCCCCCAGACAGCCT

CACATGGGGCTGTAAACAGCTAACTAAAATATCTTTGAGACTCTTATGTCCACACCCACTGACACAAG

GAGAGCTGTAACCACAGTGAAACTAGACTTTGCTTTCCTTTAGCAAGTATGTGCCTATGATAGTAAACT

GGAGTAAATGTAACAGTAATAAAACAAATTTTTTTTAAAAATAAAAATTATACCTTTTTCTCCAACAAA

CGGTAAAGACCACGTGAAGACATCCATAAAATTAGGCAACCAGTAAAGATGTGGAGAACCAGTAAACTG

TCGAAATTCATCACATTATTTTCATACTTTAATACAGCAGCTTTAATTATTGGAGAACATCAAAGTAAT

TAGGTGCCGAAAAACATTGTTATTAATGAAGGGAACCCCTGACGTTTGACCTTTTCTGTACCATCTATA

GCCCTGGACTTGA

The FASTA file, including the sequence of AA184553, was then masked using the RepeatMasker web interface, as shown below. The region of alignment of clone 463D12 is outlined.

(SEQ ID NO:1043)
TTTTTTTTTTTTTCTTAAATAGCATTTATTTTCTCTCAAAAAGCCTATTATGTACTAACAAGTGTTCC

TCTAAATTAGAAAGGCATCACTACNNNNNNNNNNNNNNNNNNNNNNNNNNNNNNNNNNNNNGAGAAGGAATATTGGGT

TACAATCTGAATTTCTCTTTATGATTTCTCTTAAAGTATAGAACAGCTATTAAAATGACTAATAT<u>TGCT</u>

<u>AAAATGAAGGCTACTAAATTTCCCCAAGAATTTCGGTGGAATGCCC</u>AAAAATGGTGTTAAGATATGCAG

AAGGGCCCATTTCAAGCAAAGCAATCTCTCCACCCCTTCATAAAAGATTTAAGCTAAAAAAAAAAAAAA

AAGAAGAAAATCCAACAGCTGAAGACATTGGGCTATTTATAAATCTTCTCCCAGTCCCCCAGACAGCCT

CACATGGGGCTGTAAACAGCTAACTAAAATATCTTTGAGACTCTTATGTCCACACCCACTGACACAAG

GAGAGCTGTAACCACAGTGAAACTAGACTTTGCTTTCCTTTAGCAAGTATGTGCCTATGATAGTAAACT

GGAGTAAATGTAACAGNNNNNNNNNNNNNNNNNNNNNNNNNNNNNNNNNNNNNNNNNNCCTTTTTCTCCAACAAA

CGGTAAAGACCACGTGAAGACATCCATAAAATTAGGCAACCAGTAAAGATGTGGAGAACCAGTAAACTG

TCGAAATTCATCACATTATTTTCATACTTTAATACAGCAGCTTTAATTATTGGAGAACATCAAAGTAAT

-continued

```
TAGGTGCCGAAAAACATTGTTATTAATGAAGGGAACCCCTGACGTTTGACCTTTTCTGTACCATCTATA

GCCCTGGACTTGA Masked version of 463D12 sequence.
```

The sequence was submitted to Array Designer as described above, however, the desired location of the probe was indicated at base pair 50 and if no probe met the criteria, moved in the 3' direction. The complementary sequence from Array Designer was used, because the original sequence was antisense. The oligonucleotide designed by Array Designer has the following sequence oligonucleotide SEQ ID NO:1044 and is complementary to the underlined sequence above. The probe has a melting temperature of 72.7 degrees centigrade and a max run of 4 nucleotides.

Clone 72D4

Clone 72D4 was sequenced and compared to the nr, dbEST, and UniGene databases at NCBI using the BLAST search tool. No significant matches were found in any of these databases. When compared to the human genome draft, significant alignments were found to three consecutive regions of the reference sequence NT_008060, as depicted below, suggesting that the insert contains three spliced exons of an unidentified gene.

Residue Numbers on Matching Residue

| clone 72D4 sequence | numbers on NT_008060 |
|---|---|
| 1-198 | 478646-478843 |
| 197-489 | 479876-480168 |
| 491-585 | 489271-489365 |

Because the reference sequence contains introns and may represent either the coding or noncoding strand for this gene, BioCardia's own sequence file was used to design the oligonucleotide. Two complementary probes were designed to ensure that the sense strand was represented. The sequence of the insert in clone 72D4 is shown below, with the three putative exons outlined.

(SEQ ID NO: 1045)
```
CAGGTCACACAGCACATCAGTGGCTACATGTGAGCTCAGACCTGGGTCT
GCTGCTGTCTGTCTTCCCAATATCCATGACCTTGACTGATGCAGGTGTC
TAGGGATACGTCCATCCCCGTCCTGCTGGAGCCCAGAGCACGGAAGCCT
GGCCCTCCGAGGAGACAGAAGGGAGTGTCGGACACCATGACGAGAGCTT
GGCAGAATAAATAACTTCTTTAAACAATTTTACGGCATGAAGAAATCTG
GACCAGTTTATTAAATGGGATTTCTGCCACAAACCTTGGAAGAATCACA
TCATCTTANNCCCAAGTGAAAACTGTGTTGCGTAACAAAGAACATGACT
GCGCTCCACACATACATCATTGCCCGGCGAGGCGGGACACAAGTCAACG
ACGGAACACTTGAGACAGGCCTACAACTGTGCACGGGTCAGAAGCAAGT
TTAAGCCATACTTGCTGCAGTGAGACTACATTTCTGTCTATAGAAGATA
CCTGACTTGATCTGTTTTCAGCTCCAGTTCCCAGATGTGCGTGTTGTC
GTCCCCAAGTATCACCTTCCAATTTCTGGGAGCAGTGCTCTGGCCGGAT
CCTTGCCGCGCGGATAAAAAC
```

The sequence was submitted to RepeatMasker, but no repetitive sequences were found. The sequence shown above was used to design the two 50-mer probes using Array Designer as described above. The probes are shown in bold typeface in the sequence depicted below. SEQ ID NO: 1046 and SEQ ID NO:1047

```
CAGGTCACACAGCACATCAGTGGCTACATGTGAGCTCAGACCTGGGTCTG

CTGCTGTCTGTCTTCCCAATATCCATGACCTTGACTGATGCAGGTGTCTA

GGGATACGTCCATCCCCGTCCTGCTGGAGCCCAGAGCACGGAAGCCTGGC

CCTCCGAGGAGACAGAAGGGAGTGTCGGACACCATGACGAGAGCTTGGCA

GAATAAATAACTTCTTTAAACAATTTTACGGCATGAAGAAATCTGGACCA

GTTTATTAAATGGGATTTCTGCCACAAACCTTGGAAGAATCACATCATCT

TANNCCCAAGTGAAAACTGTGTTGCGTAACAAAGAACATGACTGCGCTCC

ACACATACATCATTGCCCGGCGAGGCGGGACACAAGTCAACGACGGAACA

CTTGAGACAGGCCTACAACTGTGCACGGGTCAGAAGCAAGTTTAAGCCAT

ACTTGCTGCAGTGAGACTACATTTCTGTCTATAGAAGATACCTGACTTGA

TCTGTTTTTCAGC
TCCAGTTCCCAGATGTGC
                                                    ←----
GTCAAGGGTCTACACG

GTGTTGTGGTCCCCAAGTATCACCTTCCAATTTCTGGGAG--→

CACAACACCAGGGGTTCATAGTGGAAGGTTAAAG-5'

CAGTGCTCTGGCCGGATCCTTGCCGCGCGGATAAAAACT---→
```

Confirmation of Probe Sequence

Following probe design, each probe sequence was confirmed by comparing the sequence against dbEST, the UniGene cluster set, and the assembled human genome using BLASTn at NCBI. Alignments, accession numbers, gi numbers, UniGene cluster numbers and names were examined and the most common sequence used for the probe. The final probe set was compiled into Table 2. In this table, the sequence ID is given which corresponds to the sequence listing. The origin of the sequence for inclusion on the array is noted as coming from one of the cDNA libraries described in example 1, mining from databases as described in examples 2 and 11 or identification from the published literature. The unigene number, genebank accession and GI number are also given for each sequence when known. The name of the gene associated with the accession number is noted. Finally, the nucleotide sequence of each probe is also given.

Example 6

Production of an Array of 8000 Spotted 50mer Oligonucleotides

We produced an array of 8000 spotted 50mer oligonucleotides. Examples 11 and 12 exemplify the design and selection of probes for this array.

Sigma-Genosys (The Woodlands, Tex.) synthesized unmodified 50-mer oligonucleotides using standard phosphoramidite chemistry, with a starting scale of synthesis of 0.05 μmole (see, e.g., R. Meyers, ed. (1995) *Molecular Biology and Biotechnology: A Comprehensive Desk Reference*). Briefly, to begin synthesis, a 3' hydroxyl nucleoside with a dimethoxytrityl (DMT) group at the 5' end was attached to a solid support. The DMT group was removed with trichloroacetic acid (TCA) in order to free the 5'-hydroxyl for the coupling reaction. Next, tetrazole and a phosphoramidite derivative of the next nucleotide were added. The tetrazole protonates the nitrogen of the phosphoramidite, making it susceptible to nucleophilic attack. The DMT group at the 5'-end of the hydroxyl group blocks further addition of nucleotides in excess. Next, the inter-nucleotide linkage was converted to a phosphotriester bond in an oxidation step using an oxidizing agent and water as the oxygen donor. Excess nucleotides were filtered out and the cycle for the next nucleotide was started by the removal of the DMT protecting group. Following the synthesis, the oligo was cleaved from the solid support. The oligonucleotides were desalted, resuspended in water at a concentration of 100 or 200 μM, and placed in 96-deep well format. The oligonucleotides were re-arrayed into Whatman Uniplate 384-well polyproylene V bottom plates. The oligonucleotides were diluted to a final concentration 30 μM in 1× Micro Spotting Solution Plus (Telechem/arrayit.com, Sunnyvale, Calif.) in a total volume of 15 μl. In total, 8,031 oligonucleotides were arrayed into twenty-one 384-well plates.

Arrays were produced on Telechem/arrayit.com Super amine glass substrates (Telechem/arrayit.com), which were manufactured in 0.1 mm filtered clean room with exact dimensions of 25×76×0.96 mm. The arrays were printed using the Virtek Chipwriter with a Telechem 48 pin Micro Spotting Printhead. The Printhead was loaded with 48 Stealth SMP3B TeleChem Micro Spotting Pins, which were used to print oligonucleotides onto the slide with the spot size being 110-115 microns in diameter.

Example 7

Amplification, Labeling, and Hybridization of Total RNA to an Oligonucleotide Microarray Amplification, Labeling, Hybridization and Scanning Samples consisting of at least 0.5 to 2 μg of intact total RNA were further processed for array hybridization. When available, 2 μg of intact total RNA is used for amplification. Amplification and labeling of total RNA samples was performed in three successive enzymatic reactions. First, a single-stranded DNA copy of the RNA was made (hereinafter, "ss-cDNA"). Second, the ss-cDNA was used as a template for the complementary DNA strand, producing double-stranded cDNA (hereinafter, "ds-cDNA, or cDNA"). Third, linear amplification was performed by in vitro transcription from a bacterial $T_7$ promoter. During this step, fluorescent-conjugated nucleotides were incorporated into the amplified RNA (hereinafter, "aRNA").

The first strand cDNA was produced using the Invitrogen kit (Superscript II). The first strand cDNA was produced in a reaction composed of 50 mM Tris-HCl (pH 8.3), 75 mM KCl, and 3 mM $MgCl_2$ (1× First Strand Buffer, Invitrogen), 0.5 mM dGTP, 0.5 mM dTTP, 0.5 mM dTTP, 0.5 mM dCTP, 10 mM DTT, 200 U reverse transcriptase (Superscript II, Invitrogen, #18064014), 15 U RNase inhibitor (RNAGuard, Amersham Pharmacia, #27-0815-01), 5 μM T7T24 primer (5'-GGCCAGTGAATTGTAATACGACTCAC-TATAGGGAGGCGGTTTTTTTTTTTTTTTTTTTT TTT-3'), (SEQ ID NO:1048) and 0.5 to 2 μg of selected sample total RNA. Several purified, recombinant control mRNAs from the plant *Arabidopsis thaliana* were added to the reaction mixture: 2-20 pg of the following genes CAB, RCA, LTP4, NAC1, RCP1, XCP2, RBCL, LTP6, TIM, and PRKase (Stratagene, #252201, #252202, #252204, #252208, #252207, #252206, #252203, #252205, #252209, #252210 respectively). The control RNAs allow the estimate of copy numbers for individual mRNAs in the clinical sample because corresponding sense oligonucleotide probes for each of these plant genes are present on the microarray. The final reaction volume of 20 μl was incubated at 42° C. for 90 min.

For synthesis of the second cDNA strand, DNA polymerase and RNase were added to the previous reaction, bringing the final volume to 150 μl. The previous contents were diluted and new substrates were added to a final concentration of 20 mm Tris-HCl (pH 7.0) (Fisher Scientific, Pittsburgh, Pa. #BP1756-100), 90 mMKCl (Teknova, Half Moon Bay, Calif., #0313-500), 4.6 mM $MgCl_2$ (Teknova, Half Moon Bay, Calif., #0304-500), 10 mM $(NH_4)_2SO_4$ (Fisher Scientific #A702-500) (1× Second Strand buffer, Invitrogen), 0.266 mM dGTP, 0.266 mM dATP, 0.266 mM dTTP, 0.266 mM dCTP, 40 U *E. coli* DNA polymerase (Invitrogen, #18010-025), and 2 U RNaseH (Invitrogen, #18021-014). The second strand synthesis took place at 16° C. for 150 minutes.

Following second-strand synthesis, the ds-cDNA was purified from the enzymes, dNTPs, and buffers before proceeding to amplification, using phenol-chloroform extraction followed by ethanol precipitation of the cDNA in the presence of glycogen.

Alternatively, a silica-gel column is used to purify the cDNA (e.g. Qiaquick PCR cleanup from Qiagen, #28104). The volume of the column purified cDNA was reduced by ethanol precipitation in the presence of glycogen in which the cDNA was collected by centrifugation at >10,000×g for 30 minutes, the supernatant is aspirated, and 150 μl of 70% ethanol, 30% water was added to wash the DNA pellet. Following centrifugation, the supernatant was removed, and residual ethanol was evaporated at room temperature. Alternatively, the volume of the column purified cDNA is reduce in a vacuum evaporator where the supernatant is reduce to a final volume of 7.4 μl.

Linear amplification of the cDNA was performed by in vitro transcription of the cDNA. The cDNA pellet from the step described above was resuspended in 7.4 μl of water, and in vitro transcription reaction buffer was added to a final volume of 20 μl containing 7.5 mM GTP, 7.5 mM ATP, 7.5 mM TTP, 2.25 mM CTP, 1.025 mM Cy3-conjugated CTP (Perkin Elmer; Boston, Mass., #NEL-580), 1× reaction buffer (Ambion, Megascript Kit, Austin, Tex. and #1334) and 1% $T_7$ polymerase enzyme mix (Ambion, Megascript Kit, Austin, Tex. and #1334). This reaction was incubated at 37° C. overnight. Following in vitro transcription, the RNA was purified from the enzyme, buffers, and excess NTPs using the RNeasy kit from Qiagen (Valencia, Calif.; #74106) as described in the vendor's protocol. A second elution step was performed and the two eluates were combined for a final volume of 60 μl. RNA is quantified using an Agilent 2100 bioanalyzer with the RNA 6000 nano LabChip.

Reference RNA was prepared as described above, except Cy5-CTP was incorporated instead of Cy3CTP. Reference RNA from five reactions, each reaction started with 2 μg total RNA, was pooled together and quantitated as described above.

Hybridization to an Array

RNA was prepared for hybridization as follows: for an 18 mm×55 mm array, 20 µg of amplified RNA (aRNA) was combined with 20 µg of reference aRNA. The combined sample and reference aRNA was concentrated by evaporating the water to 10 µl in a vacuum evaporator. The sample was fragmented by heating the sample at 95° C. for 30 minutes to fragment the RNA into 50-200 bp pieces. Alternatively, the combined sample and reference aRNA was concentrated by evaporating the water to 5 µl in a vacuum evaporator. Five µl of 20 mM zinc acetate was added to the aRNA and the mix incubated at 60° C. for 10 minutes. Following fragmentation, 40 µl of hybridization buffer was added to achieve final concentrations of 5×SSC and 0.20% SDS with 0.1 µg/ul of Cot-1 DNA (Invitrogen) as a competitor DNA. The final hybridization mix was heated to 98° C., and then reduced to 50° C. at 0.1° C. per second.

Alternatively, formamide is included in the hybridization mixture to lower the hybridization temperature.

The hybridization mixture was applied to a pre-heated 65° C. microarray, surface, covered with a glass coverslip (Corning, #2935-246), and placed on a pre-heated 65° C. hybridization chamber (Telechem, AHC-10). 15 ul of 5×SSC was placed in each of the reservoir in the hybridization chamber and the chamber was sealed and placed in a water bath at 62° C. for overnight (16-20 hrs). Following incubation, the slides were washed in 2×SSC, 0.1% SDS for five minutes at 30° C., then in 2×SSC for five minutes at 30° C., then in 2×SSC for another five minutes at 30° C., then in 0.2×SSC for two minutes at room temperature. The arrays were spun at 1000×g for 2 minutes to dry them. The dry microarrays are then scanned by methods described above.

The microarrays were imaged on the Agilent (Palo Alto, Calif.) scanner G2565AA. The scan settings using the Agilent software were as follows: for the PMT Sensitivity (100% Red and 100% Green); Scan Resolution (10 microns); red and green dye channels; used the default scan region for all slides in the carousel; using the largest scan region; scan date for Instrument ID; and barcode for Slide ID. The fall image produced by the Agilent scanner was flipped, rotated, and split into two images (one for each signal channel) using TIFFSplitter (Agilent, Palo Alto, Calif.). The two channels are the output at 532 nm (Cy3-labeled sample) and 633 nm (Cy5-labeled R50). The individual images were loaded into GenePix 3.0 (Axon Instruments, Union City, Calif.) for feature extraction, each image was assigned an excitation wavelength corresponding the file opened; Red equals 633 nm and Green equals 532 nm. The setting file (gal) was opened and the grid was laid onto the image so that each spot in the grid overlapped with >50% of the feature. Then the GenePix software was used to find the features without setting minimum threshold value for a feature. For features with low signal intensity, GenePix reports "not found". For all features, the diameter setting was adjusted to include only the feature if necessary.

The GenePix software determined the median pixel intensity for each feature ($F_i$) and the median pixel intensity of the local background for each feature ($B_i$) in both channels. The standard deviation ($SDF_{i\ and}\ SDB_i$) for each is also determined. Features for which GenePix could not discriminate the feature from the background were "flagged" as described below.

Following feature extraction into a ".gpr" file, the header information of the .gpr file was changed to carry accurate information into the database. An Excel macro was written to include the following information: Name of the original .tif image file, SlideID, Version of the feature extraction software, GenePix Array List file, GenePix Settings file, ScanID, Name of person who scanned the slide, Green PMT setting, Red PMT setting, ExtractID (date .gpr file was created, formatted as yyyy.mm.dd-hh.mm.ss), Results file name (same as the .gpr file name), StorageCD, and Extraction comments.

Pre-Processing with Excel Templates

Following analysis of the image and extraction of the data, the data from each hybridization was pre-processed to extract data that was entered into the database and subsequently used for analysis. The complete GPR file produced by the feature extraction in GenePix was imported into an excel file pre-processing template or processed using a AWK script. Both programs used the same processing logic and produce identical results. The same excel template or AWK script was used to process each GPR file. The template performs a series of calculations on the data to differentiate poor features from others and to combine duplicate or triplicate feature data into a single data point for each probe.

The data columns used in the pre-processing were: Oligo ID, F633 Median (median value from all the pixels in the feature for the Cy5 dye), B633 Median (the median value of all the pixels in the local background of the selected feature for Cy5), B633 SD (the standard deviation of the values for the pixels in the local background of the selected feature for Cy5), F532 Median (median value from all the pixels in the feature for the Cy3 dye), B532 Median (the median value of all the pixels in the local background of the selected feature for Cy3), B532 SD (the standard deviation of the values for the pixels in the local background of the selected feature for Cy3), and Flags. The GenePix Flags column contains the flags set during feature extraction. "−75" indicates there were no features printed on the array in that position, "−50" indicates that GenePix could not differentiate the feature signal from the local background, and "−100" indicates that the user marked the feature as bad.

Once imported, the data associated with features with −75 flags was not used. Then the median of B633 SD and B532 SD were calculated over all features with a flag value of "0". The minimum values of B633 Median and B532 Median were identified, considering only those values associated with a flag value of "0". For each feature, the signal to noise ratio (S/N) was calculated for both dyes by taking the fluorescence signal minus the local background (BGSS) and dividing it by the standard deviation of the local background:

$$S/N = \frac{F_i - B_i}{SDB_i}$$

If the S/N was less than 3, then an adjusted background-subtracted signal was calculated as the fluorescence minus the minimum local background on the slide. An adjusted S/N was then calculated as the adjusted background subtracted signal divided by the median noise over all features for that channel. If the adjusted S/N was greater than three and the original S/N were less than three, a flag of 25 was set for the Cy5 channel, a flag of 23 was set for the Cy3 channel, and if both met these criteria, then a flag of 28 was set. If both the adjusted S/N and the original S/N were less than three, then a flag of 65 was set for Cy5, 63 set for Cy3, and 68 set if both dye channels had an adjusted S/N less than three. All signal to noise calculations, adjusted background-subtracted signal, and adjusted S/N were calculated for each dye channel. If the BGSS value was greater than or equal to 64000, a flag was set to indicate saturation; 55 for Cy5, 53 for Cy3, 58 for both.

The BGSS used for further calculations was the original BGSS if the original S/N was greater than or equal to three. If the original S/N ratio was less than three and the adjusted S/N ratio was greater than or equal to three, then the adjusted BGSS was used. If the adjusted S/N ratio was less than three, then the adjusted BGSS was used, but with knowledge of the flag status.

To facilitate comparison among arrays, the Cy3 and Cy5 data were scaled. The log of the ratio of Green/Red was determined for all features. The median log ratio value for good features (Flags 0, 23, 25, 28, 63) was determined. The feature values were scaled using the following formula:

Log_Scaled_Feature_Ratio=Log_Feature_Ratio−Median_Log_Ratio.

The flag setting for each feature was used to determine the expression ratio for each probe, a choice of one, two or three features. If all features had flag settings in the same category (categories=negatives, 0 to 28, 53-58, and 63-68), then the average of the three scaled, anti log feature ratios was calculated. If the three features did not have flags in the same category, then the feature or features with the best quality flags were used (0>25>23>28>55>53>58>65>63>68). Features with negative flags were never used. When the best flags were two or three features in the same category, the anti log average was used. If a single feature had a better flag category than the other two then the anti log of that feature ratio was used.

Once the probe expression ratios were calculated from the one, two, or three features, the log of the scaled, averaged ratios was taken as described below and stored for use in analyzing the data. Whichever features were used to calculate the probe value, the flag from those features was carried forward and stored as the flag value for that probe. 2 different data sets can be used for analysis. Flagged data uses all values, including those with flags. Filtered data sets are created by removing flagged data from the set before analysis.

Example 8

Real-Time PCR Validation of Array Expression Results

Leukocyte microarray gene expression was used to discover expression markers and diagnostic gene sets for clinical outcomes. It is desirable to validate the gene expression results for each gene using a more sensitive and quantitative technology such as real-time PCR. Further, it is possible for the diagnostic nucleotide sets to be implemented as a diagnostic test as a real-time PCR panel. Alternatively, the quantitative information provided by real-time PCR validation can be used to design a diagnostic test using any alternative quantitative or semi-quantitative gene expression technology.

To validate the results of the microarray experiments we used real-time, or kinetic, PCR. In this type of experiment the amplification product is measured during the PCR reaction. This enables the researcher to observe the amplification before any reagent becomes rate limiting for amplification. In kinetic PCR the measurement is of $C_T$ (threshold cycle) or $C_P$ (crossing point). This measurement ($C_T=C_P$) is the point at which an amplification curve crosses a threshold fluorescence value. The threshold is set to a point within the area where all of the reactions were in their linear phase of amplification. When measuring $C_T$, a lower $C_T$ value is indicative of a higher amount of starting material since an earlier cycle number means the threshold was crossed more quickly.

Several fluorescence methodologies are available to measure amplification product in real-time PCR. Taqman (Applied BioSystems, Foster City, Calif.) uses fluorescence resonance energy transfer (FRET) to inhibit signal from a probe until the probe is degraded by the sequence specific binding and Taq 3' exonuclease activity. Molecular Beacons (Stratagene, La Jolla, Calif.) also use FRET technology, whereby the fluorescence is measured when a hairpin structure is relaxed by the specific probe binding to the amplified DNA. The third commonly used chemistry is Sybr Green, a DNA-binding dye (Molecular Probes, Eugene, Oreg.). The more amplified product that is produced, the higher the signal. The Sybr Green method is sensitive to non-specific amplification products, increasing the importance of primer design and selection. Other detection chemistries can also been used, such as ethedium bromide or other DNA-binding dyes and many modifications of the fluorescent dye/quencher dye Taqman chemistry.

Sample Prep and cDNA Synthesis

The inputs for real time PCR reaction are gene-specific primers, cDNA from specific patient samples, and standard reagents. The cDNA was produced from mononuclear RNA (prepared as in example 1) by reverse transcription using Oligo dT primers (Invitrogen, 18418-012) and random hexamers (Invitrogen, 48190-011) at a final concentration of 0.5 ng/μl and 3 ng/μl respectively. For the first strand reaction mix, 0.5 μg of mononuclear total RNA or 2 μg of whole blood RNA and 1 μl of the Oligo dT/Random Hexamer Mix, were added to water to a final volume of 11.5 μl. The sample mix was then placed at 70° C. for 10 minutes. Following the 70° C. incubation, the samples were chilled on ice, spun down, and 88.5 μl of first strand buffer mix dispensed into the reaction tube. The final first strand buffer mix produced final concentrations of 1× first strand buffer (Invitrogen, Y00146, Carlsbad, Calif.), 10 mM DTT (Invitrogen, Y00147), 0.5 μM dATP (NEB, N0440S, Beverly, Mass.), 0.5 mM dGTP (NEB, N0442S), 0.5mM dTTP (NEB, N0443S), 0.5 mM dCTP (NEB, N0441S), 200 U of reverse transcriptase (Superscript II, Invitrogen, 18064-014), and 18 U of RNase inhibitor (RNAGuard Amersham Pharmacia, 27-0815-01, Piscataway, N.J.). The reaction was incubated at 42° C. for 90 minutes. After incubation the enzyme was heat inactivated at 70° C. for 15 minutes, 2 U of RNAse H added to the reaction tube, and incubated at 37° C. for 20 minutes.

Primer Design

Two methods were used to design primers. The first was to use the software, Primer Express™ and recommendations for primer design that are provided with the GeneAmp® 7700 Sequence Detection System supplied by Applied BioSystems (Foster City, Calif.). The second method used to design primers was the PRIMER3 ver 0.9 program that is available from the Whitehead Research Institute, Cambridge, Mass. at the web site genome.wi.mit.edu/genome_software/other/primer3.html. The program can also be accessed on the World Wide Web at the web site genome.wi.mit.edu/cgi-bin/primer/primer3_www.cgi. Primers and Taqman/hybridization probes were designed as described below using both programs.

The Primer Express literature explains that primers should be designed with a melting temperature between 58 and 60 degrees C. while the Taqman probes should have a melting temperature of 68 to 70 under the salt conditions of the supplied reagents. The salt concentration is fixed in the software. Primers should be between 15 and 30 basepairs long. The primers should produce and amplicon in size between 50 and 150 base pairs, have a C-G content between 20% and 80%, have no more than 4 identical base pairs next to one another, and no more than 2 C's and G's in the last 5 bases of the 3' end.

The probe cannot have a G on the 5' end and the strand with the fewest G's should be used for the probe.

Primer3 has a large number of parameters. The defaults were used for all except for melting temperature and the optimal size of the amplicon was set at 100 bases. One of the most critical is salt concentration as it affects the melting temperature of the probes and primers. In order to produce primers and probes with melting temperatures equivalent to Primer Express, a number of primers and probes designed by Primer Express were examined using PRIMER3. Using a salt concentration of 50 mM these primers had an average melting temperature of 3.7 degrees higher than predicted by Primer Express. In order to design primers and probes with equivalent melting temperatures as Primer Express using PRIMER3, a melting temperature of 62.7 plus/minus 1.0 degree was used in PRIMER3 for primers and 72.7 plus/minus 1.0 degrees for probes with a salt concentration of 50 mM.

The C source code for Primer3 was downloaded and complied on a Sun Enterprise 250 server using the GCC complier. The program was then used from the command line using a input file that contained the sequence for which we wanted to design primers and probes along with the input parameters as described by help files that accompany the software. Using scripting it was possible to input a number of sequences and automatically generate a number of possible probes and primers.

Primers for β-Actin (Beta Actin, Genbank Locus: NM_001101) and β-GUS: glucuronidase, beta, (GUSB, Genbank Locus: NM_000181), two reference genes, were designed using both methods and are shown here as examples:

The first step was to mask out repetitive sequences found in the mRNA sequences using RepeatMasker program that can be accessed at: the web site repeatmasker.genome.washington.edu/cgi-bin/RepeatMasker (Smit, AFA & Green, P "RepeatMasker" at the web site ftp.genome.washington.edu/RM/RepeatMasker.html).

The last 500 basepairs on the last 3' end of masked sequence was then submitted to PRIMER3 using the following exemplary input sequences:

```
                                        (SEQ ID NO:1049)
PRIMER_SEQUENCE_ID = > ACTB Beta Actin
SEQUENCE = TTGGCTTGACTCAGGATTTAAAAACTGGAACGGTGAAGG
TGACAGCAGTCGGTTGGACGAGCATCCCCCAAAGTTCACAATGTGGCCGA
GGACTTTGATTGCACATTGTTGTTTTTAATAGTCATTCCAAATATGAGA
TGCATTGTTACAGGAAGTCCCTTGCCATCCTAAAAGCACCCCACTTCTCT
CTAAGGAGAATGGCCCAGTCCTCTCCCAAGTCCACACAGGGGAGGGATAG
CATTGCTTTCGTGTAAATTATGTAATGCAAAATTTTTTTAATCTTCGCCT
TAATCTTTTTATTTTGTTTTATTTTGAATGATGAGCCTTCGTGCCCCCC
CTTCCCCCTTTTTTCCCCCAACTTGAGATGTATGAAGGCTTTTGGTCTCC
CTGGGAGTGGGTGGAGGCAGCCGGGCTTACCTGTACACTGACTTGAGACC
AGTTGAATAAAAGTGCACACCTTA
                                        (SEQ ID NO:1050)
PRIMER_SEQUENCE_ID = > GUSB
SEQUENCE = GAAGAGTACCAGAAAAGTCTGCTAGAGCAGTACCATCTG
GGTCTGGATCAAAAACGCAGAAAATATGTGGTTGGAGAGCTGATTTGGAA
TTTTGCCGATTTCATGACTGAACAGTCACCGACGAGAGTGCTGGGGAATA
AAAAGGGGATCTTCACTCGGCAGAGACAACCAAAAAGTGCAGCGTTCCTT
TTGCGAGAGAGATACTGGAAGATTGCCAATGAAACCAGGTATCCCCACTC
AGTAGCCAAGTCACAATGTTTGGAAAACAGCCCGTTTACTTGAGCAAGAC
TGATACCACCTGCGTGTCCCTTCCTCCCCGAGTCAGGGCGACTTCCACAG
CAGCAGAACAAGTGCCTCCTGGACTGTTCACGGCAGACCAGAACGTTTCT
GGCCTGGGTTTTGTGGTCATCTATTCTAGCAGGGAACACTAAAGGTGGAA
ATAAAAGATTTTCTATTATGGAAATAAAGAGTTGGCATGAAAGTCGCTAC
TG
```

After running PRIMER3, 100 sets of primers and probes were generated for ACTB and GUSB. From this set, nested primers were chosen based on whether both left primers could be paired with both right primers and a single Taqman probe could be used on an insert of the correct size. With more experience we have decided not use the mix and match approach to primer selection and just use several of the top pairs of predicted primers.

For ACTB this turned out to be:

```
Forward 75    CACAATGTGGCCGAGGACTT,  (SEQ ID NO:1051)
Forward 80    TGTGGCCGAGGACTTTGATT,  (SEQ ID NO:1052)
Reverse 178   TGGCTITTAGGATGGGAAGG,  (SEQ ID NO:1053)
and
Reverse 168   GGGGGCTTAGTTTGCTTCCT.  (SEQ ID NO:1054)
```

Upon testing, the F75 and R178 pair worked best.

For GUSB the following primers were chosen:

```
Forward 59    AAGTGCAGCGTTCCTTTTGC,  (SEQ ID NO:1055)
Forward 65    AGCGTTCCTTTTGCGAGAGA,  (SEQ ID NO:1056)
Reverse 158   CGGGCTGTTTTCCAAACATT,  (SEQ ID NO:1057)
and
Reverse 197   GAAGGGACACGCAGGTGGTA.  (SEQ ID NO:1058)
```

No combination of these GUSB pairs worked well.

In addition to the primer pairs above, Primer Express predicted the following primers for GUSB:

Forward 178 TACCACCTGCGTGTCCCTTC (SEQ ID NO:1059) and Reverse 242 GAGGCACTTGTTCTGCTGCTG (SEQ ID NO:1060). This pair of primers worked to amplify the GUSB mRNA.

The parameters used to predict these primers in Primer Express were:
Primer Tm: min 58, Max=60, opt 59, max difference=2 degrees
Primer GC: min=20% Max=80% no 3' G/C clamp
Primer: Length: min=9 max=40 opt=20
Amplicon: min Tm=0 max Tm=85
min=50 bp max=150 bp
Probe: Tm 10 degrees>primers, do not begin with a G on 5' end
Other: max base pair repeat=3 max number of ambiguous residues=0
secondary structure: max consecutive bp=4, max total bp=8
Uniqueness: max consecutive match=9
max % match=75
max 3' consecutive match=7

Granzyme B is a Marker of Transplant Rejection.

For Granzyme B the following sequence (NM_004131) (SEQ ID:1061) was used as input for Primer3:

GGGGACTCTGGAGGCCCTCTTGTGTGTAACAAGGTGGCCCAGGGCATTGT

CTCCTATGGACGAAACAATGGCATGCCTCCACGAGCCTGCACCAAAGTCT

CAAGCTTTGTACACTGGATAAAGAAAACCATGAAACGCTACTAACTACAG

GAAGCAAACTAAGCCCCGCTGTAATGAAACACCTTCTCTGGAGCCAAGT

CCAGATTTACACTGGGAGAGGTGCCAGCAACTGAATAAATACCTCTCCCA

GTGTAAATCTGGAGCCAAGTCCAGATTTACACTGGGAGAGGTGCCAGCAA

CTGAATAAATACCTCTTAGCTGAGTGG

For Granzyme B the following primers were chosen for testing:

```
Forward 81    ACGAGCCTGCACCAAAGTCT    (SEQ ID NO:1062)
Forward 63    AAACAATGGCATGCCTCCAC    (SEQ ID NO:1063)
Reverse 178   TCATTACAGCGGGGCTTAG     (SEQ ID NO:1064)
Reverse 168   GGGGGCTTAGTTTGCTTCCT    (SEQ ID NO:1065)
```

Testing demonstrated that F81 and R178 worked well.

Using this approach, primers were designed for all the genes that were shown to have expression patterns that correlated with allograft rejection. Primers can be designed from any region of a target gene using this approach.

Primer Endpoint Testing

Primers were first tested to examine whether they would produce the correct size product without non-specific amplification. The standard real-time PCR protocol was used without the Rox and Sybr green dyes. Each primer pair was tested on cDNA made from universal mononuclear leukocyte reference RNA that was produced from 50 individuals as described in Example 2 (R50).

The PCR reaction consisted of 1× RealTime PCR Buffer (Ambion, Austin, Tex.), 2 mM MgCl2 (Applied BioSystems, B02953), 0.2 mM dATP (NEB), 0.2mM dTTP (NEB), 0.2 mM dCTP (NEB), 0.2 mM dGTP (NEB), 0.625 U AmpliTaq Gold (Applied BioSystems, Foster City, Calif.), 0.3 µM of each primer to be used (Sigma Genosys, The Woodlands, Tex.), 5 µl of the R50 reverse-transcription reaction and water to a final volume of 190.

Following 40 cycles of PCR, 10 microliters of each product was combined with Sybr green at a final dilution of 1:72,000. Melt curves for each PCR product were determined on an ABI 7900 (Applied BioSystems, Foster City, Calif.), and primer pairs yielding a product with one clean peak were chosen for further analysis. One microliter of the product from these primer pairs was examined by agarose gel electrophoresis on an Agilent Bioanalyzer, DNA1000 chip (Palo Alto, Calif.). Results for 2 genes are shown in FIG. 6. From the primer design and the sequence of the target gene, one can calculate the expected size of the amplified DNA product. Only primer pairs with amplification of the desired product and minimal amplification of contaminants were used for real-time PCR. Primers that produced multiple products of different sizes are likely not specific for the gene of interest and may amplify multiple genes or chromosomal loci.

Primer Optimization/Efficiency

Once primers passed the end-point PCR, the primers were tested to determine the efficiency of the reaction in a real-time PCR reaction. cDNA was synthesized from starting total RNA as described above. A set of 5 serial dilutions of the R50 reverse-transcribed cDNA (as described above) were made in water: 1:10, 1:20, 1:40, 1:80, and 1:160.

The Sybr Green real-time PCR reaction was performed using the Taqman PCR Reagent kit (Applied BioSystems, Foster City, Calif., N808-0228). A master mix was made that consisted of all reagents except the primes and template. The final concentration of all ingredients in the reaction was 1× Taqman Buffer A (Applied BioSystems), 2 mM MgCl2 (Applied BioSystems), 200 µM dATP (Applied BioSystems), 200 µM dCTP (Applied BioSystems), 200 µM dGTP (Applied BioSystems), 400 µM dUTP (Applied BioSystems), 1:400,000 diluted Sybr Green dye (Molecular Probes), 1.25 U AmpliTaq Gold (Applied BioSystems). The PCR master mix was dispensed into two, light-tight tubes. Each β-Actin primer F75 and R178 (Sigma-Genosys, The Woodlands, Tex.), was added to one tube of PCR master mix and Each β-GUS primer F178 and R242 (Sigma-Genosys), was added to the other tube of PCR master mix to a final primer concentration of 300 nM. 45 µl of the β-Actin or β-GUS master mix was dispensed into wells, in a 96-well plate (Applied BioSystems). 5 µl of the template dilution series was dispensed into triplicate wells for each primer. The reaction was run on an ABI 7900 Sequence Detection System (Applied BioSystems) with the following conditions: 10 min. at 95° C.; 40 cycles of 95° C. for 15 sec, 60° C. for 1 min; followed by a disassociation curve starting at 50° C. and ending at 95° C.

The Sequence Detection System v2.0 software was used to analyze the fluorescent signal from each well. The high end of the baseline was adjusted to between 8 and 20 cycles to reduce the impact on any data curves, yet be as high as possible to reduce baseline drift. A threshold value was selected that allowed the majority of the amplification curves to cross the threshold during the linear phase of amplification. The disassociation curve for each well was compared to other wells for that marker. This comparison allowed identification of "bad" wells, those that did not amplify, that amplified the wrong size product, or that amplified multiple products. The cycle number at which each amplification curve crossed the threshold ($C_T$) was recorded and the file transferred to MS Excel for further analysis. The $C_T$ values for triplicate wells were averaged. The data were plotted as a function of the $\log_{10}$ of the calculated starting concentration of RNA. The starting RNA concentration for each cDNA dilution was determined based on the original amount of RNA used in the RT reaction, the dilution of the RT reaction, and the amount used (5 µl) in the real-time PCR reaction. For each gene, a linear regression line was plotted through all of the dilutions series points. The slope of the line was used to calculate the efficiency of the reaction for each primer set using the equation:

$$E=10^{(-1/slope)}-1$$

Using this equation (Pfaffl 2001, Applied Biosystems User Bulletin #2), the efficiency for these β-actin primers is 1.28 and the efficiency for these β-GUS primers is 1.14 (FIG. 6). This efficiency was used when comparing the expression levels among multiple genes and multiple samples. This same method was used to calculate reaction efficiency for primer pairs for each gene studied. A primer pair was considered successful if the efficiency was reproducibly determined to be between 0.7 and 2.4.

Sybr-Green Assays

Once markers passed the Primer Efficiency QPCR (as stated above), they were used in real-time PCR assays. Patient RNA samples were reverse-transcribed to cDNA (as described above) and 1:10 dilutions made in water. In addition to the patient samples, a no template control (NTC) and a pooled reference RNA (see example 2) described in were included on every plate.

The Sybr Green real-time PCR reaction was performed using the Taqman Core PCR Reagent kit (Applied BioSystems, Foster City, Calif., N808-0228). A master mix was made that consisted of all reagents except the primers and template. The final concentration of all ingredients in the reaction was 1× Taqman Buffer A (Applied BioSystems), 2 mM MgCl2 (Applied BioSystems), 200 µM dATP (Applied BioSystems), 200 µM dCTP (Applied BioSystems), 200 µM dGTP (Applied BioSystems), 400 µM dUTP (Applied BioSystems), 1:400,000 diluted Sybr Green dye (Molecular Probes), 1.25 U AmpliTaq Gold (Applied BioSystems). The PCR master mix was aliquotted into eight light-tight tubes, one for each marker to be examined across a set of samples. The optimized primer pair for each marker was then added to the PCR master mix to a final primer concentration of 300 nM. 181 µl of the each marker master mix was dispensed into wells in a 384 well plate (Applied BioSystems). 2 µl of the 1:10 diluted control or patient cDNA sample was dispensed into triplicate wells for each primer pair. The reaction was run on an ABI 7900 Sequence Detection System (Applied BioSystems) using the cycling conditions described above.

The Sequence Detection System v2.0 software (Applied BioSystems) was used to analyze the fluorescent signal from each well. The high end of the baseline was adjusted to between 8 and 20 cycles to reduce the impact on any data curves, yet be as high as possible to reduce baseline drift. A threshold value was selected that allowed the majority of the amplification curves to cross the threshold during the linear phase of amplification. The disassociation curve for each well was compared to other wells for that marker. This comparison allowed identification of "bad" wells, those that did not amplify, that amplified the wrong size product, or that amplified multiple products. The cycle number at which each amplification curve crossed the threshold ($C_T$) was recorded and the file transferred to MS Excel for further analysis. The $C_T$ value representing any well identified as bad by analysis of disassociation curves was deleted. The $C_T$ values for triplicate wells were averaged. A standard deviation (Stdev) and a coefficient of variation (CV) were calculated for the triplicate wells. If the CV was greater than 2, an outlier among the three wells was identified and deleted. Then the average was re-calculated. In each plate, $\Delta C_T$ was calculated for each marker-control combination by subtracting the average $C_T$ of the target marker from the average $C_T$ of the control (β-Actin or β-GUS). The expression relative to the control marker was calculated by taking two to the power of the $\Delta C_T$ of the target marker. For example, expression relative to β-Actin was calculated by the equation:

$$ErA = 2^{(C_{T,Actin} - C_{T,target})}$$

All plates were run in duplicate and analyzed in the same manner. The percent variation was determined for each sample-marker combination (relative expression) by taking the absolute value of the value of the RE for the second plate from the RE for the first plate, and dividing that by the average. If more than 25% of the variation calculations on a plate are greater than 50%, then a third plate was run.

Taqman Protocol

Real-time PCR assays were also done using Taqman PCR chemistry.

The Taqman real-time PCR reaction was performed using the Taqman Universal PCR Master Mix (Applied BioSystems, Foster City, Calif., #4324018). The master mix was aliquoted into eight, light-tight tubes, one for each marker. The optimized primer pair for each marker was then added to the correctly labeled tube of PCR master mix. A FAM/TAMRA dual-labeled Taqman probe (Biosearch Technologies, Navoto, Calif., DLO-FT-2) was then added to the correctly labeled tube of PCR master mix. Alternatively, different combinations of fluorescent reporter dyes and quenchers can be used such that the absorption wavelength for the quencher matches the emission wavelength for the reporter, as shown in table 4. 18 µl of the each marker master mix was dispensed into a 384 well plate (Applied BioSystems). 2 µl of the template sample was dispensed into triplicate wells for each primer pair. The final concentration of each reagent was: 1× TaqMan Universal PCR Master Mix, 300 nM each primer, 0.25 nM probe, 2 µl 1:10 diluted template. The reaction was run on an ABI 7900 Sequence Detection System (Applied Biosystems) using standard conditions (95° C. for 10 min., 40 cycles of 95° C. for 15 sec, 60° C. for 1 min.).

The Sequence Detector v2.0 software (Applied BioSystems) was used to analyze the fluorescent signal from each well. The high end of the baseline was adjusted to between 8 and 20 cycles to reduce the impact on any data curves, yet be as high as possible to reduce baseline drift. A threshold value was selected that allowed most of the amplification curves to cross the threshold during the linear phase of amplification. The cycle number at which each amplification curve crossed the threshold ($C_T$) was recorded and the file transferred to MS Excel for further analysis. The $C_T$ values for triplicate wells were averaged. The $C_T$ values for triplicate wells were averaged. A standard deviation (Stdev) and a coefficient of variation (CV) were calculated for the triplicate wells. If the CV was greater than 2, an outlier among the three wells was identified and deleted. Then the average was re-calculated. In each plate, $\Delta C_T$ was calculated for each marker-control combination by subtracting the average $C_T$ of the target marker from the average $C_T$ of the control (β-Actin or β-GUS). The expression relative to the control marker was calculated by taking two to the power of the $\Delta C_T$ of the target marker. All plates were run in duplicate and analyzed in the same manner. The percent variation was determined for each sample-marker combination (relative expression) by taking the absolute value of the value of the RE for the second plate from the RE for the first plate, and dividing that by the average. If more than 25% of the variation calculations on a plate are greater than 50%, then a third plate was run.

Bi-Plexing

Variation of real-time PCR assays can arise from unequal amounts of RNA starting material between reactions. In some assays, to reduce variation, the control gene amplification was included in the same reaction well as the target gene. To differentiate the signal from the two genes, different fluorescent dyes were used for the control gene. β-Actin was used as the control gene and the TaqMan probe used was labeled with the fluorescent dye VIC and the quencher TAMRA (Biosearch Technologies, Navoto, Calif., DLO-FT-2). Alternatively, other combinations of fluorescent reporter dyes and quenchers (table 4) can be used as long as the emission wavelength of the reporter for the control gene is sufficiently different from the wavelength of the reporter dye used for the target. The control gene primers and probe were used at limiting concentrations in the reaction (150 nM primers and 0.125 nM probe) to ensure that there were enough reagents to amplify the target marker. The plates were run under the same protocol and the data are analyzed in the same way, but with a separate baseline and threshold for the VIC signal. Outliers were removed as above from both the FAM and VIC signal channels. The expression relative to control was calculated as above, using the VIC signal from the control gene.

$$ErA=2^{(C_T,VIC-C_T,FAM)}$$

Absolute Quantitation

Instead of calculating the expression relative to a reference marker, an absolute quantitation can be performed using real-time PCR. To determine the absolute quantity of each marker, a standard curve is constructed using serial dilutions from a known amount of template for each marker on the plate. The standard curve may be made using cloned genes purified from bacteria or using synthetic complimentary oligonucleotides. In either case, a dilution series that covers the expected range of expression is used as template in a series of wells in the plate. From the average $C_T$ values for these known amounts of template a standard curve can be plotted. From this curve the $C_T$ values for the unknowns are used to identify the starting concentration of cDNA. These absolute quantities can be compared between disease classes (i.e. rejection vs. no-rejection) or can be taken as expression relative to a control gene to correct for variation among samples in sample collection, RNA purification and quantification, cDNA synthesis, and the PCR amplification.

Cell Type Specific Expression

Some markers are expressed only in specific types of cells. These markers may be useful markers for differentiation of rejection samples from no-rejection samples or may be used to identify differential expression of other markers in a single cell type. A specific marker for cytotoxic T-lymphocytes (such as CD8) can be used to identify differences in cell proportions in the sample. Other markers that are known to be expressed in this cell type can be compared to the level of CD8 to indicate differential gene expression within CD8 T-cells.

Control Genes for PCR

As discussed above, PCR expression measurements can be made as either absolute quantification of gene expression using a standard curve or relative expression of a gene of interest compared to a control gene. In the latter case, the gene of interest and the control gene are measured in the same sample. This can be done in separate reactions or in the same reaction (biplex format, see above). In either case, the final measurement for expression of a gene is expressed as a ratio of gene expression to control gene expression. It is important for a control gene to be constitutively expressed in the target tissue of interest and have minimal variation in expression on a per cell basis between individuals or between samples derived from an individual. If the gene has this type of expression behavior, the relative expression ratio will help correct for variability in the amount of sample RNA used in an assay. In addition, an ideal control gene has a high level of expression in the sample of interest compared to the genes being assayed. This is important if the gene of interest and control gene are used in a biplex format. The assay is set up so that the control gene reaches its threshold Ct value early and its amplification is limited by primers so that it does not compete for limiting reagents with the gene of interest.

To identify an ideal control gene for an assay, a number of genes were tested for variability between samples and expression in both mononuclear RNA samples and whole blood RNA samples using the RNA procurement and preparation methods and real-time PCR assays described above. 6 whole-blood and 6 mononuclear RNA samples from transplant recipients were tested. The intensity levels and variability of each gene in duplicate experiments on both sample types are shown in FIG. 8.

Based on criteria of low variability and high expression across samples, β-actin, 18s, GAPDH, b2microglobulin were found to be good examples of control genes for the PAX samples. A single control gene may be incorporated as an internal biplex control is assays.

Controlling for Variation in Real Time PCR

Due to differences in reagents, experimenters, and preparation methods, and the variability of pipetting steps, there is significant plate-to-plate variation in real-time PCR experiments. This variation can be reduced by automation (to reduce variability and error), reagent lot quality control, and optimal data handling. However, the results on replicate plates are still likely to be different since they are run in the machine at different times.

Variation can also enter in data extraction and analysis. Real-time PCR results are measured as the time (measured in PCR cycles) at which the fluorescence intensity (ΔRn in Applied Biosystems SDS v2.1 software) crosses a user-determined threshold (CT). When performing relative quantification, the CT value for the target gene is subtracted from the CT value for a control gene. This difference, called ΔCT, is the value compared among experiments to determine whether there is a difference between samples. Variation in setting the threshold can introduce additional error. This is especially true in the duplexed experimental format, where both the target gene and the control gene are measured in the same reaction tube. Duplexing is performed using dyes specific to each of the two genes. Since two different fluorescent dyes are used on the plate, two different thresholds are set. Both of these thresholds contribute to each ΔCT. Slight differences in the each dye's threshold settings (relative to the other dye) from one plate to the next can have significant effects on the ΔCT.

There are several methods for setting the threshold for a PCR plate. Older versions of SDS software (Applied Biosystems) determine the average baseline fluorescence for the plate and the standard deviation of the baseline. The threshold is set to 10× the standard deviation of the baseline. In SDS 2.0 the users must set the baseline by themselves. Software from other machine manufacturers either requires the user to set the threshold themselves or uses different algorithms. The latest version of the SDS software (SDS 2.1) contains Automatic baseline and threshold setting. The software sets the baseline separately for each well on the plate using the ΔRn at cycles preceding detectable levels.

Variability among plates is dependent on reproducible threshold setting. This requires a mathematical or experimental data driven threshold setting protocol. Reproducibly setting the threshold according to a standard formula will minimize variation that might be introduced in the threshold setting process.

Additionally, there may be experimental variation among plates that can be reduced by setting the threshold to a component of the data. We have developed a system that uses a set of reactions on each plate that are called the threshold calibrator (TCb). The TCb wells are used to set the threshold on all plates.

1. The TCb wells contain a template, primers, and probes that are common among all plates within an experiment.

2. The threshold is set within the minimum threshold and maximum threshold determined above.

3. The threshold is set to a value in this range that results in the average CT value for the TCb wells to be the same on all plates.

Example 9

Correlation and Classification Analysis

After generation and processing of expression data sets from microarrays as described in Example 7, a log ratio value is used for most subsequent analysis. This is the logarithm of the expression ratio for each gene between sample and universal reference. The processing algorithm assigns a number of flags to data that are of low signal to noise, saturated signal or are in some other way of low or uncertain quality. Correlation analysis can proceed with all the data (including the flagged data) or can be done on filtered data sets where the flagged data is removed from the set. Filtered data should have less variability and noise and may result in more significant or predictive results. Flagged data contains all information available and may allow discovery of genes that are missed with the filtered data set.

After filtering the data for quality as described above and in example 7, missing data are common in microarray data sets. Some algorithms don't require complete data sets and can thus tolerate missing values. Other algorithms are optimal with or require imputed values for missing data. Analysis of data sets with missing values can proceed by filtering all genes from the analysis that have more than 5%, 10%, 20%, 40%, 50%, 60% or other % of values missing across all samples in the analysis. Imputation of data for missing values can be done by a variety of methods such as using the row mean, the column mean, the nearest neighbor or some other calculated number. Except when noted, default settings for filtering and imputation were used to prepare the data for all analytical software packages.

In addition to expression data, clinical data are included in the analysis. Continuous variables, such as the ejection fraction of the heart measured by echocardiography or the white blood cell count can be used for correlation analysis. Any piece of clinical data collected on study subjects can be used in a correlation or classification analysis. In some cases, it may be desirable to take the logarithm of the values before analysis. These variables can be included in an analysis along with gene expression values, in which case they are treated as another "gene". Sets of markers can be discovered that work to diagnose a patient condition and these can include both genes and clinical parameters. Categorical variables such as male or female can also be used as variables for correlation analysis. For example, the sex of a patient may be an important splitter for a classification tree.

Clinical data are used as supervising vectors (dependent variables) for the significance or classification analysis of expression data. In this case, clinical data associated with the samples are used to divide samples in to clinically meaningful diagnostic categories for correlation or classification analysis. For example, pathologic specimens from kidney biopsies can be used to divide lupus patients into groups with and without kidney disease. A third or more categories can also be included (for example "unknown" or "not reported"). After generation of expression data and definition of supervising vectors, correlation, significance and classification analysis are used to determine which set of genes and set of genes are most appropriate for diagnosis and classification of patients and patient samples.

Two main types of expression data analyses are commonly performed on the expression data with differing results and purposes. The first is significance analyses or analyses of difference. In this case, the goal of the analysis is to identify genes that are differentially expressed between sample groups and to assign a statistical confidence to those genes that are identified. These genes may be markers of the disease process in question and are further studied and developed as diagnostic tools for the indication.

The second major type of analysis is classification analysis. While significance analysis identifies individual genes that are differentially expressed between sample groups, classification analysis identifies gene sets and an algorithm for their gene expression values that best distinguish sample (patient) groups. The resulting gene expression panel and algorithm can be used to create and implement a diagnostic test. The set of genes and the algorithm for their use as a diagnostic tool are often referred to herein as a "model". Individual markers can also be used to create a gene expression diagnostic model. However, multiple genes (or gene sets) are often more useful and accurate diagnostic tools.

Significance Analysis for Microarrays (SAM)

Significance analysis for microarrays (SAM) (Tusher 2001) is a method through which genes with a correlation between their expression values and the response vector are statistically discovered and assigned a statistical significance. The ratio of false significant to significant genes is the False Discovery Rate (FDR). This means that for each threshold there are some number of genes that are called significant, and the FDR gives a confidence level for this claim. If a gene is called differentially expressed between two classes by SAM, with a FDR of 5%, there is a 95% chance that the gene is actually differentially expressed between the classes. SAM will identify genes that are differentially expressed between the classes. The algorithm selects genes with low variance within a class and large variance between classes. The algorithm may not identify genes that are useful in classification, but are not differentially expressed in many of the samples. For example, a gene that is a useful marker for disease in women and not men, may not be a highly significant marker in a SAM analysis, but may be useful as part of a gene set for diagnosis of a multi-gene algorithm.

After generation of data from patient samples and definition of categories using clinical data as supervising vectors, SAM is used to detect genes that are likely to be differentially expressed between the groupings. Those genes with the highest significance can be validated by real-time PCR (Example 8) or can be used to build a classification algorithm as described here.

Classification

Classification algorithms are used to identify sets of genes and formulas for the expression levels of those genes that can be applied as diagnostic and disease monitoring tests. The same classification algorithms can be applied to all types of expression and proteomic data, including microarray and PCR based expression data. The discussion below describes the algorithms that were used and how they were used.

Classification and Regression Trees (CART) is a decision tree classification algorithm (Breiman 1984). From gene expression and or other data, CART can develop a decision tree for the classification of samples. Each node on the decision tree involves a query about the expression level of one or more genes or variables. Samples that are above the threshold go down one branch of the decision tree and samples that are not go down the other branch. Genes from expression data sets can be selected for classification building with CART by significant differential expression in SAM analysis (or other significance test), identification by supervised tree-harvesting analysis, high fold change between sample groups, or known relevance to classification of the target diseases. In addition, clinical data can be used as independent variables for CART that are of known importance to the clinical question or are found to be significant predictors by multivariate analysis or some other technique. CART identifies predictive variables and their associated decision rules for classification (diagnosis). CART also identifies surrogates for each splitter (genes that are the next best substitute for a useful gene in classification). Analysis is performed in CART by weighting misclassification costs to optimize desired performance of the assay. For example, it may be most important that the sensitivity of a test for a given diagnosis be >90%. CART models can be built and tested using 10 fold cross-validation or v-fold cross validation (see below). CART works best with a smaller number of variables (5-50).

Multiple Additive Regression Trees (Friedman, J H 1999, MART) is similar to CART in that it is a classification algorithm that builds decision trees to distinguish groups. MART builds numerous trees for any classification problem and the resulting model involves a combination of the multiple trees. MART can select variables as it build models and thus can be used on large data sets, such as those derived from an 8000 gene microarray. Because MART uses a combination of many trees and does not take too much information from any one tree, it resists over training. MART identifies a set of genes and an algorithm for their use as a classifier.

A Nearest Shrunken Centroids Classifier can be applied to microarray or other data sets by the methods described by Tibshirani et al. 2002. This algorithms also identified gene sets for classification and determines their 10 fold cross validation error rates for each class of samples. The algorithm determines the error rates for models of any size, from one gene to all genes in the set. The error rates for either or both sample classes can are minimized when a particular number of genes are used. When this gene number is determined, the algorithm associated with the selected genes can be identified and employed as a classifier on prospective sample.

For each classification algorithm and for significance analysis, gene sets and diagnostic algorithms that are built are tested by cross validation and prospective validation. Validation of the algorithm by these means yields an estimate of the predictive value of the algorithm on the target population. There are many approaches, including a 10 fold cross validation analysis in which 10% of the training samples are left out of the analysis and the classification algorithm is built with the remaining 90%. The 10% are then used as a test set for the algorithm. The process is repeated 10 times with 10% of the samples being left out as a test set each time. Through this analysis, one can derive a cross validation error which helps estimate the robustness of the algorithm for use on prospective (test) samples. Any % of the samples can be left out for cross validation (v-fold cross validation, LOOCV). When a gene set is established for a diagnosis with an acceptable cross validation error, this set of genes is tested using samples that were not included in the initial analysis (test samples). These samples may be taken from archives generated during the clinical study. Alternatively, a new prospective clinical study can be initiated, where samples are obtained and the gene set is used to predict patient diagnoses.

Example 10

Assay Sample Preparation

In order to show that the leukocyte-specific markers of the present invention can be detected in whole blood, we collected whole blood RNA using the PAXgene whole blood collection, stabilization, and RNA isolation kit (PreAnalytix). Varying amounts of the whole blood RNA were used in the initial RT reaction (1, 2, 4, and 8 ug), and varying dilutions of the different RT reactions were tested (1:5, 1:10, 1:20, 1:40, 1:80, 1:160). We did real-time PCR assays with primers specific to XDx's markers and showed that we can reliably detect these markers in whole blood.

Total RNA was prepared from 14 mononuclear samples (CPT, BD) paired with 14 whole blood samples (PAXgene, PreAnalytix) from transplant recipients. cDNA was prepared from each sample using 2 μg total RNA as starting material. Resulting cDNA was diluted 1:10 and Sybr green real-time PCR assays were performed.

For real-time PCR assays, Ct values of 15-30 are desired for each gene. If a gene's Ct value is much above 30, the result may be variable and non-linear. For PAX sample, target RNA will be more dilute than in CPT samples. cDNA dilutions must be appropriate to bring Ct values to less than 30.

Ct values for the first 5 genes tested in this way are shown in the table below for both whole blood RNA (PAX) and mononuclear RNA (CPT).

| Gene | Ct PAX | Ct CPT |
|---|---|---|
| CD20 | 27.41512 | 26.70474 |
| 4761 | 28.45656 | 26.52635 |
| 3096 | 29.09821 | 27.83281 |
| GranzymeB | 31.18779 | 30.56954 |
| IL4 | 33.11774 | 34.8002 |
| Actin | 19.17622 | 18.32966 |
| B-GUS | 26.89142 | 26.92735 |

With one exception, the genes have higher Ct values in whole blood. Using this protocol, all genes can be detected with Cts<35. For genes found to have Ct values above 30 in target samples, less diluted cDNA may be needed.

Example 11

Identification and Validation of Gene Expression Markers for Diagnosis and Monitoring of Lupus and Autoimmune Diseases Patients were enrolled in a clinical study as described in example 4.

58 peripheral blood samples from 22 patients meeting ACR criteria for SLE, 20 patients with rheumatoid arthritis (RA), 6 patients with osteoarthritis (OA), and 10 healthy donors (HD) were collected (see Table 1). Within 1 hour of collection, samples were processed by density gradient centrifugation and mononuclear cells were lysed and frozen using the technique described in example 1. Total RNA was prepared from cell pellets, amplified and labeled with fluorescent Cy3, and hybridized to a custom oligonucleotide microarray of 8143 DNA sequences selected by virtue of differential or specific expression in activated or resting leukocytes (methods used are described in examples 5-7). After normalization, the log ratio of Cy3 (donor sample) to Cy5 (pooled reference leukocyte RNA) was used for analysis of gene sequences differentially expressed by the SLE samples versus all non-SLE samples. SLE samples were divided into classic or highly probable SLE diagnosis according to American College of Rheumatology clinical criteria or patients with the clinical diagnosis of SLE, but less with fewer classic signs or symptoms or recent treatment with increased immunosuppression.

Significance analysis of microarrays (SAM, Tusher et al. 2001) was used to identify genes that are differentially expressed between Lupus patients and controls (Example 9). These data are shown in Table 2A where genes are listed that were over- or under-expressed in SLE and control samples at various levels of false detection rates (FDR). Each of these genes may have a correlation to disease or disease activity. Also using the methods of example 9, Multiple Additive Regression Trees (MART) was also used to identify genes that best distinguished SLE from control samples in using multi-gene classification models (Table 2C). This analysis identifies gene sets and formulae that relate the genes to create a diagnostic or monitoring assay for lupus. Genes that are a part of a multi-gene algorithm with a low classification error rate on patient samples and a high level of importance in the algorithm are high priority gene markers.

Real-time PCR by techniques described in example 8 was used to confirm and quantify differential expression of selected gene sequences (Table 2B). PCR primers for all marker genes can be designed by these same methods. Many of the genes tested were validated and showed highly significant correlation or anti-correlation to lupus samples.

Hierarchical cluster analysis (Eisen et al. 1998, Example 9) identified both known and undescribed genes that are coexpressed with genes that showed promise in either the array or PCR data as being markers of SLE (Table 2D). Genes were thus grouped into pathways.

Among the genes identified by the significance and classification analysis, at many are members of the IFN regulatory factor or interferon-induced gene families. The interferon alpha family of molecules and pathways have been implicated in the pathogenesis of Lupus for some time. Patients treated with interferon alpha for chronic viral infections can have the side effect of autoimmune phenomena and Lupus. IFN-a levels are elevated in sera from patients with SLE, RA, Sjogren's syndrome, and scleroderma. IFN-a may also be involved in the very earliest events that initiate autoimmunity. Identification of the specific IFN-a gene products expressed in SLE may allow selective therapeutic targeting of pathogenic cytokines while sparing those IFN's that are protective in the setting of virus infection.

TABLE 1

Samples used in array and PCR expression profiling experiments

| Patient | PrimaryDx | Dx1 | Dx2 | PCR |
|---|---|---|---|---|
| 1 | C | 0 | 0 | |
| 2 | C | 0 | 0 | x |
| 3 | C | 0 | 2 | x |
| 4 | C | 0 | 0 | |
| 5 | C | 0 | 0 | x |
| 6 | C | 0 | 0 | |
| 7 | C | 0 | 0 | x |
| 8 | C | 0 | 0 | x |
| 9 | C | 0 | 0 | |
| 10 | C | 0 | 0 | |
| 11 | OA | 0 | 0 | x |
| 12 | OA | 0 | 0 | x |
| 13 | OA | 0 | 0 | x |
| 14 | OA | 0 | 0 | x |
| 15 | OA | 0 | 0 | x |
| 16 | OA | 0 | 0 | |
| 17 | RA | 0 | 0 | x |
| 18 | RA | 0 | 0 | |
| 19 | RA | 0 | 0 | |
| 20 | RA | 0 | 0 | |
| 21 | RA | 0 | 0 | |
| 22 | RA | 0 | 0 | x |
| 23 | RA | 0 | 0 | |
| 24 | RA | 0 | 0 | x |
| 25 | RA | 0 | 0 | |
| 26 | RA | 0 | 0 | x |
| 27 | RA | 0 | 0 | x |
| 28 | RA | 0 | 0 | |
| 29 | RA | 0 | 0 | x |
| 30 | RA | 0 | 0 | x |
| 31 | RA | 0 | 2 | x |
| 32 | RA | 0 | 0 | |
| 33 | RA | 0 | 0 | x |
| 34 | RA | 0 | 0 | |
| 35 | RA | 0 | 0 | |
| 36 | RA | 0 | 0 | |
| 37 | SLE | 1 | 2 | x |
| 38 | SLE | 1 | 2 | |
| 39 | SLE | 1 | 1 | |
| 40 | SLE | 1 | 1 | x |
| 41 | SLE | 1 | 2 | x |
| 42 | SLE | 1 | 1 | x |
| 43 | SLE | 1 | 1 | |
| 44 | SLE | 1 | 1 | x |
| 45 | SLE | 1 | 2 | x |
| 46 | SLE | 1 | 2 | x |
| 47 | SLE | 1 | 1 | x |
| 48 | SLE | 1 | 1 | x |
| 49 | SLE | 1 | 1 | x |
| 50 | SLE | 1 | 1 | |
| 51 | SLE | 1 | 1 | x |
| 52 | SLE | 1 | 1 | x |
| 53 | SLE | 1 | 2 | x |
| 54 | SLE | 1 | 1 | |
| 55 | SLE | 1 | 2 | x |
| 56 | SLE | 1 | 2 | x |
| 57 | SLE | 1 | 1 | |
| 58 | SLE | 1 | 1 | |

TABLE 2A

Significance analysis for Microarrays, Lupus/Autoimmune merkers

| SEQ ID 50mer | ACC | SEQ ID Full length | HS | Gene | SAM FDR | SAM Up/Down |
|---|---|---|---|---|---|---|
| 515 | NM_031157 | 13 | Hs.249495 | heterogeneous nuclear ribonucleoprotein A1 (HNRPA1), transcript variant 2, mRNA /cds = (104, 1222) | 0.0909 | down |
| 516 | D23660 | 14 | Hs.334822 | *Homo sapiens*, Similar to ribosomal protein L4, clone MGC: 2966 IMAGE: 3139805, mRNA, complete cds /cds = (1616, 2617) | 0.0909 | down |
| 519 | BE550944 | 17 | Hs.61426 | 602329933F1 cDNA | 0.0909 | down |
| 520 | L13385 | 18 | Hs.77318 | Miller-Dieker lissencephaly protein (LIS1) | 0.0909 | down |

TABLE 2A-continued

Significance analysis for Microarrays, Lupus/Autoimmune merkers

| SEQ ID 50mer | ACC | SEQ ID Full length | HS | Gene | SAM FDR | SAM Up/Down |
|---|---|---|---|---|---|---|
| 521 | AF315591 | 19 | Hs.6151 | pumilio (*Drosophila*) homolog 2 (PUM2) | 0.0909 | down |
| 522 | AK025620 | 20 | Hs.5985 | cDNA: FLJ21967 fis, clone HEP05652, highly similar to AF131831 clone 25186 mRNA sequence /cds = UNKNOWN | 0.0909 | down |
| 523 | AK026747 | 21 | Hs.12969 | cDNA: FLJ23094 fis, clone LNG07379 | 0.0909 | down |
| 524 | NM_001731 | 22 | Hs.77054 | B-cell translocation gene 1, anti-proliferative (BTG1), mRNA /cds = (308, 823) | 0.0909 | down |
| 525 | NM_004281 | 23 | Hs.15259 | BCL2-associated athanogene 3 (BAG3), mRNA /cds = (306, 2033) | 0.0909 | down |
| 526 | XM_008738 | 24 | Hs.79241 | B-cell CLL/lymphoma 2 (BCL2), nuclear gene encoding mitochondrial protein, transcript variant alpha, mRNA /cds = (31, 750) | 0.0909 | down |
| 527 | XM_018498 | 25 | Hs.180946 | ribosomal protein L5 pseudogene mRNA, complete cds /cds = UNKNOWN | 0.0909 | down |
| 528 | U67093 | 26 | Hs.194382 | ataxia telangiectasia (ATM) gene, complete cds /cds = (795, 9965) | 0.0909 | down |
| 529 | AJ400717 | 27 | Hs.279860 | tumor protein, translationally-controlled 1 (TPT1), mRNA /cds = (94, 612) | 0.0909 | down |
| 530 | NM_003133 | 28 | Hs.75975 | signal recognition particle 9 kD (SRP9), mRNA /cds = (106, 366) | 0.1042 | down |
| 531 | NM_004261 | 29 | Hs.90606 | 15 kDa selenoprotein (SEP15), mRNA /cds = (4, 492) | 0.1042 | down |
| 532 | NM_002300 | 30 | Hs.234489 | *Homo sapiens*, lactate dehydrogenase B, clone MGC: 3600 IMAGE: 3028947, mRNA, complete cds /cds = (1745, 2749) | 0.1071 | down |
| 533 | NM_003853 | 31 | Hs.158315 | interleukin 18 receptor accessory protein (IL18RAP), mRNA /cds = (483, 2282) | 0.1071 | down |
| 534 | X53777 | 32 | Hs.82202 | ribosomal protein L17 (RPL17), mRNA /cds = (286, 840) | 0.1071 | down |
| 535 | N27575 | 33 | Hs.75613 | CD36 antigen (collagen type I receptor, thrombospondin receptor) (CD36), mRNA /cds = (132, 1550) | 0.1167 | down |
| 536 | NM_006800 | 34 | Hs.88764 | male-specific lethal-3 (*Drosophila*)-like 1 (MSL3L1), mRNA /cds = (105, 1670) | 0.1167 | down |
| 537 | NM_000734 | 35 | Hs.97087 | CD3Z antigen, zeta polypeptide (TiT3 complex) (CD3Z), mRNA /cds = (178, 669) | 0.141 | down |
| 538 | NM_003756 | 36 | Hs.58189 | eukaryotic translation initiation factor 3, subunit 3 (gamma, 40 kD) (EIF3S3), mRNA /cds = (5, 1063) | 0.141 | down |
| 539 | NM_021950 | 37 | Hs.89751 | CD20 antigen | 0.141 | down |
| 540 | AK021632 | 38 | Hs.11571 | cDNA FLJ11570 fis, clone HEMBA1003309 /cds = UNKNOWN | 0.141 | down |
| 541 | AK025583 | 39 | Hs.82845 | cDNA: FLJ21930 fis, clone HEP04301, highly similar to HSU90916 clone 23815 mRNA sequence /cds = UNKNOWN | 0.141 | down |
| 542 | NM_000661 | 40 | Hs.157850 | *Homo sapiens*, clone MGC: 15545 IMAGE: 3050745, mRNA, complete cds /cds = (1045, 1623) | 0.141 | down |
| 543 | NM_001057 | 41 | Hs.161305 | tachykinin receptor 2 (TACR2), mRNA /cds = (0, 1196) | 0.141 | down |
| 544 | X60656 | 42 | Hs.275959 | eukaryotic translation elongation factor 1 beta 2 (EEF1B2), mRNA /cds = (235, 912) | 0.141 | down |
| 545 | NM_004779 | 43 | Hs.26703 | CNOT8 CCR4-NOT transcription complex, subunit 8 | 0.1628 | down |
| 546 | X58529 | 44 | Hs.302063 | rearranged immunoglobulin mRNA for mu heavy chain enhancer and constant region /cds = UNKNOWN | 0.1628 | down |
| 547 | NM_016091 | 45 | Hs.119503 | HSPC025 (HSPC025), mRNA /cds = (33, 1727) | 0.1705 | down |
| 548 | NM_001006 | 46 | Hs.77039 | ribosomal protein S3A (RPS3A), mRNA /cds = (36, 8 | 0.1739 | down |
| 549 | NM_001568 | 47 | Hs.106673 | eukaryotic translation initiation factor 3, subunit 6 (48 kD) (EIF3S6), mRNA /cds = (22, 1359) | 0.1739 | down |
| 550 | BC001854 | 48 | Hs.77502 | , methionine adenosyltransferase II, alpha, c | 0.193 | down |
| 551 | NM_000983 | 49 | Hs.326249 | ribosomal protein L22 (RPL22), mRNA /cds = (51, 437) | 0.193 | down |
| 552 | NM_001006 | 50 | Hs.155101 | mRNA for KIAA1578 protein, partial cds /cds = UNKNOWN | 0.193 | down |
| 553 | NM_001403 | 51 | Hs.274466 | eukaryotic translation elongation factor 1 alpha 1-like 14 (EEF1A1L14), mRNA /cds = (620, 1816) | 0.193 | down |
| 554 | NM_002796 | 52 | Hs.89545 | proteasome (prosome, macropain) subunit, beta type, 4 (PSMB4), mRNA /cds = (23, 817) | 0.193 | down |
| 555 | NM_016304 | 53 | Hs.284162 | 60S ribosomal protein L30 isolog (LOC51187), mRNA /cds = (143, 634) | 0.193 | down |
| 556 | NM_017918 | 54 | Hs.234149 | hypothetical protein FLJ20647 (FLJ20647), mRNA /cds = (90, 836) | 0.193 | down |
| 557 | AA788623 | 55 | Hs.332583 | yc77a06.s1 cDNA, 3' end /clone = IMAGE: 21844 /clone_end = 3' | 0.193 | down |
| 558 | NM_001961 | 56 | Hs.75309 | eukaryotic translation elongation factor 2 (EEF2), mRNA /cds = (0, 2576) | 0.193 | down |
| 559 | AK026309 | 57 | Hs.12436 | cDNA: FLJ22656 fis, clone HSI07655 /cds = UNKNOWN | 0.193 | down |
| 560 | AK026528 | 58 | Hs.334807 | *Homo sapiens*, ribosomal protein L30, clone MGC: 2797, mRNA, complete cds /cds = (29, 376) | 0.1949 | down |
| 561 | BC002971 | 59 | Hs.1600 | *Homo sapiens*, clone IMAGE: 3543711, mRNA, partial cds /cds = (0, 1620) | 0.1949 | down |

TABLE 2A-continued

Significance analysis for Microarrays, Lupus/Autoimmune merkers

| SEQ ID 50mer | ACC | SEQ ID Full length HS | Hs. | Gene | SAM FDR | SAM Up/Down |
|---|---|---|---|---|---|---|
| 562 | U01923 | 60 | Hs.278857 | heterogeneous nuclear ribonucleoprotein H2 (H') (HNRPH2), mRNA /cds = (78, 1427) | 0.2131 | down |
| 563 | U61267 | 61 | Hs.30035 | putative splice factor transformer2-beta mRN | 0.2133 | down |
| 564 | X14356 | 62 | Hs.77424 | high affinity Fc receptor (FcRI) /cds = (36, 116 | 0.2133 | down |
| 565 | AF267856 | 63 | Hs.8084 | HT033 mRNA, complete cds /cds = (203, 931) | 0.2133 | down |
| 566 | AK025306 | 64 | Hs.2083 | cDNA: FLJ21653 fis, clone COL08586, highly similar to HUMKINCDC protein kinase mRNA /cds = UNKNOWN | 0.2133 | down |
| 567 | AL162068 | 65 | Hs.302649 | HSP22-like protein interacting protein (LOC64165), mRNA /cds = (0, 155) | 0.2133 | down |
| 568 | NM_004768 | 66 | Hs.11482 | splicing factor, arginine/serine-rich 11 (SFRS11), mRNA /cds = (83, 1537) | 0.2133 | |
| 569 | NM_005594 | 67 | Hs.158164 | transporter 1, ATP-binding cassette, sub-family B (MDR/TAP) (TAP1), mRNA /cds = (30, 2456) | 0.2133 | down |
| 570 | AI440234 | 68 | Hs.9614 | Nucleophosmin (probe bad, mutations, wrong clone used) (nucleolar phosphoprotein B23, numatrin) | 0.2133 | down |
| 571 | AW194379 | 69 | Hs.203755 | xm08h07.x1 cDNA, 3' end /clone = IMAGE: 2683645 /clone_end = 3' | 0.2133 | down |
| 572 | NM_005826 | 70 | Hs.15265 | heterogeneous nuclear ribonucleoprotein R (HNRPR), mRNA /cds = (90, 1991) | 0.2133 | down |
| 573 | AI568695 | 71 | Hs.75969 | proline-rich protein with nuclear targeting signal (B4-2), mRNA /cds = (113, 1096) | 0.2133 | down |
| 574 | AL110225 | 72 | Hs.89434 | drebrin 1 (DBN1), mRNA /cds = (97, 2046) | 0.2171 | down |
| 575 | AL110151 | 73 | Hs.128797 | mRNA; cDNA DKFZp586D0824 (from clone DKFZp586D0824); partial cds /cds = (0, 1080) | 0.2403 | down |
| 576 | NM_006495 | 74 | Hs.5509 | ecotropic viral integration site 2B (EVI2B), mRNA /cds = (0, 1346) | 0.2628 | down |
| 577 | M74002 | 75 | Hs.11482 | splicing factor, arginine/serine-rich 11 (SFRS11), mRNA /cds = (83, 1537) | 0.2759 | down |
| 578 | AK002173 | 76 | Hs.5518 | cDNA FLJ11311 fis, clone PLACE1010102 /cds = UNKNOWN | 0.2759 | down |
| 579 | AK024976 | 77 | Hs.323378 | coated vesicle membrane protein (RNP24), mRNA /cds = (27, 632) | 0.2759 | down |
| 580 | BC000967 | 78 | Hs.195870 | chronic myelogenous leukemia tumor antigen 66 mRNA, complete cds, alternatively spliced /cds = (232, 1983) | 0.2759 | down |
| 581 | NM_016312 | 79 | Hs.334811 | Npw38-binding protein NpwBP (LOC51729), mRNA /cds = (143, 2068) | 0.2759 | down |
| 582 | X57347 | 80 | Hs.74405 | tyrosine 3-monooxygenase/tryptophan 5-monooxygenase activation protein, theta polypeptide (YWHAQ), mRNA /cds = (100, 837) | 0.2759 | down |
| 583 | BG424974 | 81 | Hs.292457 | Homo sapiens, clone MGC: 16362 IMAGE: 3927795, mRNA, complete cds /cds = (498, 635) | 0.276 | down |
| 584 | U89387 | 82 | Hs.194638 | polymerase (RNA) II (DNA directed) polypeptide D (POLR2D), mRNA /cds = (30, 458) | 0.2784 | down |
| 585 | AB034205 | 83 | Hs.278670 | Acid-inducible phosphoprotein | 0.3 | down |
| 586 | XM_008062 | 84 | Hs.17279 | tyrosylprotein sulfotransferase 1 (TPST1), mRNA /cds = (81, 1193) | 0.3 | down |
| 587 | NM_016099 | 85 | Hs.7953 | HSPC041 protein (LOC51125), mRNA /cds = (141, 455) | 0.3022 | down |
| 588 | NM_022898 | 86 | Hs.57987 | B-cell lymphoma/leukaemia 11B (BCL11B), mRNA /cds = (267, 2738) | 0.3533 | down |
| 589 | NM_006759 | 87 | Hs.77837 | UDP-glucose pyrophosphorylase 2 (UGP2), mRNA /cds = (84, 1610) | 0.367 | down |
| 590 | AF079566 | 88 | Hs.4311 | SUMO-1 activating enzyme subunit 2 (UBA2), mRNA /cds = (25, 1947) | 0.3798 | down |
| 591 | NM_001024 | 89 | Hs.182979 | cDNA: FLJ22838 fis, clone KAIA4494, highly similar to HUML12A ribosomal protein L12 mRNA /cds = UNKNOWN | 0.3798 | down |
| 592 | NM_017761 | 90 | Hs.7862 | hypothetical protein FLJ20312 (FLJ20312), mRNA /cds = (133, 552) | 0.3798 | down |
| 593 | U15085 | 91 | Hs.1162 | major histocompatibility complex, class II, DM beta (HLA-DMB), mRNA /cds = (233, 1024) | 0.3798 | down |
| 594 | AW572538 | 92 | Hs.42915 | ARP2 (actin-related protein 2, yeast) homolog (ACTR2), mRNA /cds = (74, 1258) | 0.3798 | down |
| 595 | AK025557 | 93 | Hs.110771 | cDNA: FLJ21904 fis, clone HEP03585 /cds = UNKNOWN | 0.3798 | down |
| 596 | NM_003854 | 94 | Hs.102865 | interleukin 1 receptor-like 2 (IL1RL2), mRNA /cds = (134, 1822) | 0.3798 | down |
| 597 | AF116679 | 95 | Hs.288036 | tRNA isopentenylpyrophosphate transferase (IPT), mRNA /cds = (60, 1040) | 0.38 | down |
| 598 | AF148537 | 96 | Hs.65450 | reticuion 4a mRNA, complete cds /cds = (141, 3719) | 0.3857 | down |
| 599 | NM_017892 | 97 | Hs.107213 | hypothetical protein FLJ20585 (FLJ20585), mRNA /cds = (99, 746) | 0.3972 | down |
| 600 | NM_000967 | 98 | Hs.119598 | ribosomal protein L3 (RPL3), mRNA /cds = (6, 1217) | 0.4174 | down |

TABLE 2A-continued

Significance analysis for Microarrays, Lupus/Autoimmune merkers

| SEQ ID 50mer | ACC | SEQ ID Full length | HS | Gene | SAM FDR | SAM Up/Down |
|---|---|---|---|---|---|---|
| 601 | NM_000971 | 99 | Hs.153 | ribosomal protein L7 (RPL7), mRNA /cds = (10, 756) | 0.4174 | down |
| 602 | AF012872 | 100 | Hs.334874 | phosphatidylinositol 4-kinase 230 (pi4K230) mRNA, complete cds /cds = (0, 6134) | 0.4174 | down |
| 603 | BC004900 | 101 | Hs.151242 | serine (or cysteine) proteinase inhibitor, clade G (C1 inhibitor), member 1 (SERPING1), mRNA /cds = (60, 1562) | 0.4174 | down |
| 604 | NM_002298 | 102 | Hs.76506 | lymphocyte cytosolic protein 1 (L-plastin) (LCP1), mRNA /cds = (173, 2056) | 0.4174 | down |
| 605 | X59405 | 103 | Hs.83532 | *H. sapiens*, gene for Membrane cofactor protein /cds = UNKNOWN | 0.4174 | down |
| 606 | AL049935 | 104 | Hs.301763 | mRNA; cDNA DKFZp564O1116 (from clone DKFZp564O1116) /cds = UNKNOWN | 0.4174 | down |
| 607 | NM_017860 | 105 | Hs.79457 | hypothetical protein FLJ20519 (FLJ20519), mRNA /cds = (74, 604) | 0.4181 | down |
| 608 | J04142 | 106 | Hs.1799 | CD1D antigen, d polypeptide (CD1D), mRNA /cds = (164, 1171) | 0.4231 | down |
| 609 | NM_016127 | 107 | Hs.279921 | HSPC035 protein (LOC51669), mRNA /cds = (16, 1035) | 0.4622 | down |
| 610 | AK023379 | 108 | Hs.155160 | *Homo sapiens*, Similar to splicing factor, arginine/serine-rich 2 (SC-35) | 0.4798 | down |
| 611 | L11284 | 109 | Hs.3446 | mitogen-activated protein kinase kinase 1 (MAP2K1), mRNA /cds = (72, 1253) | 0.4798 | down |
| 612 | NM_002710 | 110 | Hs.79081 | protein phosphatase 1, catalytic subunit, gamma isoform (PPP1CC), mRNA /cds = (154, 1125) | 0.4798 | down |
| 613 | NM_004380 | 111 | Hs.23598 | CREB binding protein (Rubinstein-Taybi syndrome) (CREBBP), mRNA /cds = (198, 7526) | 0.4798 | down |
| 614 | AW028193 | 112 | Hs.135872 | wv61h08.x1 cDNA, 3' end /clone = IMAGE: 2534079 /clone_end = 3' | 0.4798 | down |
| 615 | NM_001436 | 113 | Hs.99853 | fibrillarin (FBL), mRNA /cds = (59, 1024) | 0.484 | down |
| 616 | AB007916 | 114 | Hs.214646 | mRNA for KIAA0447 protein, partial cds /cds = (233, 1633) | 0.5 | down |
| 617 | AL137681 | 115 | Hs.173912 | eukaryotic translation initiation factor 4A, isoform 2 (EIF4A2), mRNA /cds = (15, 1238) | 0.5 | down |
| 618 | BC003090 | 116 | Hs.75193 | COP9 homolog (COP9), mRNA /cds = (49, 678) | 0.5 | down |
| 619 | U15173 | 117 | Hs.155596 | BCL2/adenovirus E1B 19 kD-interacting protein 2 (BNIP2), mRNA /cds = (211, 1155) | 0.5 | down |
| 620 | NM_014210 | 118 | Hs.70499 | ecotropic viral integration site 2A (EVI2A), mRNA /cds = (219, 917) | 0.5301 | down |
| 621 | NM_001011 | 119 | Hs.301547 | ribosomal protein S7 (RPS7), mRNA /cds = (81, 665) | 0.5331 | down |
| 622 | U07802 | 120 | Hs.78909 | Tis11d gene, complete cds /cds = (291, 1739) | 0.5331 | down |
| 623 | AI817153 | 121 | Hs.86693 | EST380760 cDNA | 0.5331 | down |
| 624 | NM_006791 | 122 | Hs.6353 | MORF-related gene 15 (MRG15), mRNA /cds = (131, 1102) | 0.56 | down |
| 625 | NM_004500 | 123 | Hs.182447 | heterogeneous nuclear ribonucleoprotein C (C1/C2) (HNRPC), transcript variant 1, mRNA /cds = (191, 1102) | 0.5616 | down |
| 626 | M16660 | 124 | Hs.318720 | *Homo sapiens*, clone MGC: 12387 IMAGE: 3933019, mRNA, complete cds /cds = (63, 863) | 0.588 | down |
| 627 | NM_001000 | 125 | Hs.300141 | cDNA FLJ14163 fis, clone NT2RP1000409 /cds = UNKNOWN | 0.5909 | down |
| 628 | BC008737 | 126 | Hs.164280 | *Homo sapiens*, Similar to solute carrier family 25 (mitochondrial carrier; adenine nucleotide translocator), member 5, clone MGC: 3042 IMAGE: 3342722, mRNA, complete cds /cds = (88, 984) | 0.5938 | down |
| 629 | BE222392 | 127 | Hs.79914 | lumican (LUM), mRNA /cds = (84, 1100) | 0.6062 | down |
| 630 | BC010112 | 128 | Hs.79037 | *Homo sapiens*, heat shock 60 kD protein 1 (chaperonin), clone MGC: 19755 IMAGE: 3630225, mRNA, complete cds /cds = (1705, 3396) | 0.6062 | down |
| 631 | AK025586 | 129 | Hs.27268 | cDNA: FLJ21933 fis, clone HEP04337 /cds = UNKNOWN | 0.6224 | down |
| 632 | NM_015057 | 130 | Hs.151411 | KIAA0916 protein (KIAA0916), mRNA /cds = (146, 14071) | 0.6351 | down |
| 633 | U10550 | 131 | Hs.79022 | GTP-binding protein overexpressed in skeletal muscle (GEM), mRNA /cds = (213, 1103) | 0.6433 | down |
| 634 | NM_000986 | 132 | Hs.184582 | DPP7 alveolar r | 0.6487 | down |
| 635 | NM_000993 | 133 | Hs.184014 | ribosomal protein L31 (RPL31), mRNA /cds = (7, 384) | 0.6487 | down |
| 636 | NM_001688 | 134 | Hs.81634 | ATP synthase, H+ transporting, mitochondrial F0 complex, subunit b, isoform 1 (ATP5F1), mRNA /cds = (32, 802) | 0.6487 | down |
| 637 | AI356505 | 135 | Hs.228874 | qz22b04.x1 cDNA, 3' end /clone = IMAGE: 2027599 /clone_end = 3' | 0.6487 | down |
| 638 | AF119850 | 136 | Hs.2186 | *Homo sapiens*, eukaryotic translation elongation factor 1 gamma, clone MGC: 4501 IMAGE: 2964623, mRNA, complete cds /cds = (2278, 3231) | 0.6487 | down |
| 639 | AF132197 | 137 | Hs.301824 | hypothetical protein PRO1331 (PRO1331), mRNA /cds = (422, 616) | 0.6667 | down |

TABLE 2A-continued

Significance analysis for Microarrays, Lupus/Autoimmune merkers

| SEQ ID 50mer | ACC | SEQ ID Full length | HS | Gene | SAM FDR | SAM Up/Down |
|---|---|---|---|---|---|---|
| 640 | NM_006925 | 138 | Hs.166975 | splicing factor, arginine/serine-rich 5 (SFRS5), mRNA /cds = (218, 541) | 0.6667 | down |
| 641 | NM_002001 | 139 | Hs.897 | Fc fragment of IgE, high affinity I, receptor for; alpha polypeptide (FCER1A), mRNA /cds = (106, 879) | 0.6667 | down |
| 513 | BC036402 | 11 | NA | 116C9 | 0.6691 | up |
| 642 | W00466 | 140 | Hs.44189 | yz99f01.s1 cDNA, 3' end /clone = IMAGE: 291193 /clone_end = 3' | 0.6691 | up |
| 643 | D17042 | 141 | Hs.50651 | Janus kinase 1 (a protein tyrosine kinase) (JAK1), mRNA /cds = (75, 3503) | 0.6867 | down |
| 644 | NM_003380 | 142 | Hs.297753 | vimentin (VIM), mRNA /cds = (122, 1522) | 0.6867 | down |
| 645 | NM_016824 | 143 | Hs.324470 | adducin 3 (gamma) (ADD3), transcript variant 1, mRNA /cds = (31, 2151) | 0.6867 | down |
| 646 | AI581383 | 144 | Hs.327922 | to71c02.x1 cDNA, 3' end /clone = IMAGE: 2183714 /clone_end = 3' | 0.6867 | down |
| 647 | BC005913 | 145 | Hs.1074 | surfactant, pulmonary-associated protein C (SFTPC), mRNA /cds = (27, 620) | 0.6994 | down |
| 648 | NM_004811 | 146 | Hs.49587 | leupaxin (LPXN), mRNA /cds = (93, 1253) | 0.6994 | down |
| 649 | AL357536 | 147 | Hs.3576 | Homo sapiens, Similar to RIKEN cDNA 5730494N06 gene, clone MGC: 13348 IMAGE: 4132400, mRNA, complete cds /cds = (132, 494) | 0.7029 | down |
| 650 | NM_022570 | 148 | Hs.161786 | C-type (calcium dependent, carbohydrate-recognition domain) lectin, superfamily member 12 (CLECSF12), mRNA /cds = (71, 676) | 0.7029 | down |
| 651 | NM_004396 | 149 | Hs.76053 | DEAD/H (Asp-Glu-Ala-Asp/His) box polypeptide 5 (RNA helicase, 68 kD) (DDX5), mRNA /cds = (170, 2014) | 0.7151 | down |
| 652 | AK026372 | 150 | Hs.143631 | cDNA: FLJ22719 fis, clone HSI14307 /cds = UNKNOWN | 0.7225 | down |
| 653 | XM_012059 | 151 | Hs.154938 | hypothetical protein MDS025 (MDS025), mRNA /cds = (5, 769) | 0.7299 | down |
| 654 | XM_011914 | 152 | Hs.180450 | ribosomal protein S24 (RPS24), transcript variant 1, mRNA /cds = (37, 429) | 0.7301 | down |
| 655 | NM_020414 | 153 | Hs.286233 | sperm autoantigenic protein 17 (SPA17), mRNA /cds = (1210, 1665) | 0.7301 | down |
| 656 | S73591 | 154 | Hs.179526 | upregulated by 1,25-dihydroxyvitamin D-3 (VDUP1), mRNA /cds = (221, 1396) | 0.7373 | down |
| 657 | J00194 | 155 | Hs.76807 | major histocompatibility complex, class II, DR alpha (HLA-DRA), mRNA /cds = (26, 790) | 0.7989 | down |
| 658 | AK021715 | 156 | Hs.271541 | cDNA FLJ11653 fis, clone HEMBA1004538 /cds = UNKNOWN | 0.7989 | down |
| 659 | AK027187 | 157 | Hs.289071 | cDNA: FLJ22245 fis, clone HRC02612 /cds = UNKNOWN | 0.7989 | down |
| 660 | AL117595 | 158 | Hs.4055 | mRNA; cDNA DKFZp564C2063 (from clone DKFZp564C2063) /cds = UNKNOWN | 0.7989 | down |
| 661 | NM_002823 | 159 | Hs.250655 | prothymosin, alpha (gene sequence 28) (PTMA), mRNA /cds = (155, 487) | 0.7989 | down |
| 662 | NM_004327 | 160 | Hs.234799 | breakpoint cluster region (BCR), transcript variant 1, mRNA /cds = (488, 4303) | 0.7989 | down |
| 663 | NM_017830 | 161 | Hs.132071 | ovarian carcinoma immunoreactive antigen (OCIA), mRNA /cds = (167, 904) | 0.7989 | down |
| 664 | X06557 | 162 | Hs.2014 | mRNA for T-cell receptor delta /cds = UNKNOWN | 0.7989 | down |
| 665 | AI146787 | 163 | Hs.156601 | qb83f02.x1 cDNA, 3' end /clone = IMAGE: 1706715 /clone_end = 3' | 0.7989 | down |
| 666 | AI568771 | 164 | Hs.327876 | th15h04.x1 cDNA, 3' end /clone = IMAGE: 2118391 /clone_end = 3' | 0.7989 | down |
| 667 | AW195119 | 165 | Hs.253151 | xn66b07.x1 cDNA, 3' end /clone = IMAGE: 2699413 /clone_end = 3' | 0.7989 | down |
| 668 | NM_016316 | 166 | Hs.110347 | REV1 (yeast homolog)-like (REV1L), mRNA /cds = (212, 3967) | 0.8132 | down |
| 669 | AV724531 | 167 | Hs.76728 | 602570065F1 cDNA, 5' end /clone = IMAGE: 4694321 /clone_end = 5' | 0.8594 | down |
| 670 | AK002059 | 168 | Hs.92918 | hypothetical protein (BM-009), mRNA /cds = (385, 1047) | 0.8594 | down |
| 671 | NM_001503 | 169 | Hs.272529 | glycosylphosphatidylinositol specific phospholipase D1 (GPLD1), mRNA /cds = (32, 2557) | 0.8653 | down |
| 672 | AA251806 | 170 | Hs.177712 | zs09c03.s1 cDNA, 3' end /clone = IMAGE: 684676 /clone_end = 3' | 0.8734 | up |
| 517 | NM_006276 | 15 | Hs.184167 | splicing factor, arginine/serine-rich 7 (35 kD) (SFRS7) mRNA /cds = (105, 490) | 0.8883 | down |
| 673 | NM_004315 | 171 | Hs.75811 | N-acylsphingosine amidohydrolase (acid ceramidase) (ASAH), mRNA /cds = (17, 1204) | 0.8883 | down |
| 674 | NM_004371 | 172 | Hs.75887 | coatomer protein complex, subunit alpha (COPA), mRNA /cds = (466, 4140) | 0.8883 | down |
| 675 | AF054284 | 173 | Hs.334826 | splicing factor 3b, subunit 1, 155 kD (SF3B1), mRNA /cds = (0, 3914) | 0.8889 | down |

TABLE 2A-continued

Significance analysis for Microarrays, Lupus/Autoimmune merkers

| SEQ ID 50mer | ACC | SEQ ID Full length | HS | Gene | SAM FDR | SAM Up/Down |
|---|---|---|---|---|---|---|
| 676 | BE613237 | 174 | Hs.146381 | RNA binding motif protein, X chromosome (RBMX), mRNA /cds = (11, 1186) | 0.9257 | down |
| 677 | NM_003367 | 175 | Hs.93649 | upstream transcription factor 2, c-fos intera | 0.9542 | up |
| 678 | AB014522 | 176 | Hs.11238 | mRNA for KIAA0622 protein, partial cds /cds = (0, 3869) | 0.9542 | up |
| 679 | AW137104 | 177 | Hs.8121 | Notch (*Drosophila*) homolog 2 (NOTCH2), mRNA /cds = (12, 7427) | 0.9542 | up |
| 680 | BF897042 | 178 | Hs.120219 | FLJ32028 hypothetical protein FLJ32028 | 0.9542 | up |
| 681 | BC002900 | 179 | Hs.181309 | proteasome (prosome, macropain) subunit, alpha type, 2 (PSMA2), mRNA /cds = (0, 704) | 0.9563 | down |
| 682 | AL578975 | 180 | Hs.5057 | AL578975 cDNA /clone = CS0DK012YN01-(3-prime) | 0.9563 | down |
| 683 | NM_000988 | 181 | Hs.111611 | ribosomal protein L27 (RPL27), mRNA /cds = (17, 427) | 0.9662 | down |
| 684 | NM_003769 | 182 | Hs.77608 | splicing factor, arginine/serine-rich 9 (SFRS9), mRNA /cds = (52, 717) | 1.0167 | down |
| 685 | U94855 | 183 | Hs.7811 | eukaryotic translation initiation factor 3, subunit 5 (epsilon, 47 kD) (EIF3S5), mRNA /cds = (6, 1079) | 1.0167 | down |
| 686 | AV749844 | 184 | Hs.26670 | PAC clone RP3-515N1 from 22q11.2-q22 /cds = (0, 791) | 1.0236 | down |
| 687 | BC003352 | 185 | Hs.326456 | hypothetical protein FLJ20030 (FLJ20030), mRNA /cds = (1, 1239) | 1.0236 | down |
| 688 | AU135154 | 186 | Hs.172028 | a disintegrin and metalloproteinase domain 10 (ADAM10), mRNA /cds = (469, 2715) | 1.0327 | down |
| 689 | AF208850 | 187 | Hs.82911 | BM-008 mRNA, complete cds /cds = (341, 844) | 1.0822 | down |
| 690 | D29805 | 188 | Hs.198248 | UDP-Gal:betaGlcNAc beta 1,4-galactosyltransferase, polypeptide 1 (B4GALT1), mRNA /cds = (72, 1268) | 1.0822 | down |
| 691 | NM_006098 | 189 | Hs.5662 | guanine nucleotide binding protein (G protein), beta polypeptide 2-like 1 (GNB2L1), mRNA /cds = (95, 1048) | 1.0822 | down |
| 692 | NM_001755 | 190 | Hs.179881 | core-binding factor, beta subunit (CBFB), transcript variant 2, mRNA /cds = (11, 559) | 1.0905 | down |
| 693 | NM_007355 | 191 | Hs.74335 | heat shock 90 kD protein 1, beta (HSPCB), mRNA /cds = (0, 2174) | 1.0905 | down |
| 694 | W47229 | 192 | Hs.173334 | ELL-RELATED RNA POLYMERASE II, ELONGATION FACTOR (ELL2), mRNA /cds = (0, 1922) | 1.1 | |
| 695 | X51345 | 193 | Hs.198951 | jun B proto-oncogene (JUNB), mRNA /cds = (253, 1296) | 1.1 | |
| 506 | NM_006417 | 4 | Hs.82316 | interferon-induced, hepatitis C-associated microtubular aggregate protein (44 kD) (MTAP44), mRNA /cds = (0, 1334) | 1.1077 | up |
| 696 | AI364677 | 194 | Hs.368853 | ESTs | 1.1077 | up |
| 697 | AI380594 | 195 | Hs.231261 | tf95h06.x1 cDNA, 3' end /clone = IMAGE: 2107067 /clone_end = 3' | 1.1077 | up |
| 698 | NM_001641 | 196 | Hs.73722 | APEX nuclease (multifunctional DNA repair enzyme) (APEX), mRNA /cds = (205, 1161) | 1.1138 | down |
| 699 | NM_002786 | 197 | Hs.82159 | proteasome (prosome, macropain) subunit, alpha type, 1 (PSMA1), mRNA /cds = (105, 896) | 1.1138 | down |
| 700 | J02621 | 198 | Hs.251064 | high-mobility group (nonhistone chromosomal) protein 14 (HMG14), mRNA /cds = (150, 452) | 1.115 | down |
| 701 | NM_019111 | 199 | Hs.76807 | major histocompatibility complex, class II, DR alpha (HLA-DRA), mRNA /cds = (26, 790) | 1.115 | down |
| 702 | AF248966 | 200 | Hs.183434 | ATPase, H+ transporting, lysosomal (vacuolar proton pump) membrane sector associated protein M8-9 (APT6M8-9) | 1.1336 | down |
| 703 | D31767 | 201 | Hs.75416 | DAZ associated protein 2 (DAZAP2), mRNA /cds = (69, 575) | 1.1336 | down |
| 704 | NM_006839 | 202 | Hs.78504 | inner membrane protein, mitochondrial (mitofilin) (IMMT), mRNA /cds = (92, 2368) | 1.1336 | down |
| 705 | AI581732 | 203 | Hs.229918 | ar74f03.x1 cDNA, 3' end /clone = IMAGE: 2128349 /clone_end = 3' | 1.1336 | down |
| 706 | NM_019059 | 204 | Hs.274248 | hypothetical protein FLJ20758 (FLJ20758), mRNA /cds = (464, 1306) | 1.1438 | down |
| 707 | NM_001033 | 205 | Hs.2934 | ribonucleotide reductase M1 polypeptide (RRM1), mRNA /cds = (187, 2565) | 1.1525 | down |
| 708 | NM_002719 | 206 | Hs.171734 | protein phosphatase 2, regulatory subunit B (B56), gamma isoform (PPP2R5C), mRNA /cds = (88, 1632) | 1.1525 | down |
| 709 | NM_003791 | 207 | Hs.75890 | membrane-bound transcription factor protease, site 1 (MBTPS1), mRNA /cds = (496, 3654) | 1.1772 | down |
| 710 | NM_001105 | 208 | Hs.150402 | activin A receptor, type I (ACVR1), mRNA /cds = (340, 1869) | 1.1833 | down |
| 711 | BG179517 | 209 | Hs.99093 | chromosome 19, cosmid R28379 /cds = (0, 633) | 1.1833 | down |
| 712 | BF940103 | 210 | Hs.26136 | hypothetical protein MGC14156 (MGC14156), mRNA /cds = (82, 426) | 1.1833 | down |
| 713 | AF061736 | 211 | Hs.169895 | ubiquitin-conjugating enzyme E2L 6 (UBE2L6), mRNA /cds = (47, 508) | 1.6 | |
| 714 | AK023680 | 212 | Hs.17448 | cDNA FLJ13618 fis, clone PLACE1010925 /cds = UNKNOWN | 1.6 | |

TABLE 2A-continued

Significance analysis for Microarrays, Lupus/Autoimmune merkers

| SEQ ID 50mer | ACC | SEQ ID Full length | HS | Gene | SAM FDR | SAM Up/Down |
|---|---|---|---|---|---|---|
| 715 | NM_001295 | 213 | Hs.301921 | chemokine (C-C motif) receptor 1 (CCR1), mRNA /cds = (62, 1129) | 1.6 | |
| 716 | NM_003811 | 214 | Hs.1524 | tumor necrosis factor (ligand) superfamily, member 9 (TNFSF9), mRNA /cds = (3, 767) | 1.6 | |
| 717 | X02812 | 215 | Hs.1103 | transforming growth factor, beta 1 (TGFB1), mRNA /cds = (841, 2016) | 1.6 | |
| 718 | NM_002205 | 216 | Hs.149609 | integrin, alpha 5 (fibronectin receptor, alpha polypeptide) (ITGA5), mRNA /cds = (23, 3172) | 1.6 | |
| 719 | AI818777 | 217 | Hs.229990 | wl11f10.x1 cDNA, 3' end /clone = IMAGE: 2424619 /clone_end = 3' | 1.6 | |
| 720 | NM_005892 | 218 | Hs.100217 | formin-like (FMNL), mRNA /cds = (39, 1430) | 1.6 | |
| 721 | M26252 | 219 | Hs.198281 | pyruvate kinase, muscle (PKM2), mRNA /cds = (109, 1704) | 1.6 | |
| 722 | AB002377 | 220 | Hs.32556 | mRNA for KIAA0379 protein, partial cds /cds = (0, 3180) | 1.6324 | up |
| 723 | AI381586 | 221 | Hs.87908 | Snf2-related CBP activator protein (SRCAP), mRNA /cds = (210, 9125) | 1.6662 | up |
| 724 | BG760189 | 222 | Hs.37617 | 602144947F1 cDNA, 5' end /clone = IMAGE: 4308683 /clone_end = 5' | 2.0136 | up |
| 725 | NM_006913 | 223 | Hs.216354 | ring finger protein 5 (RNF5), mRNA /cds = (0, 542) | 2.0853 | up |
| 726 | AF189011 | 224 | Hs.49163 | ribonuclease III (RN3) mRNA, complete cds /cds = (245, 4369) | 2.246 | up |
| 727 | AK022834 | 225 | Hs.58488 | catenin (cadherin-associated protein), alpha-like 1 (CTNNAL1), mRNA /cds = (43, 2247) | 2.3244 | up |
| 728 | NM_002878 | 226 | Hs.125244 | RAD51 (S. cerevisiae)-like 3 (RAD51L3), mRNA /cds = (124, 993) | 2.3244 | up |
| 729 | BF899464 | 227 | NA | IL5-MT0211-011200-317-f03 MT0211 cDNA, mRNA sequence | 2.3244 | up |
| 730 | AW452510 | 228 | Hs.300479 | UI-H-BW1-ame-a-12-0-UI.s1 cDNA, 3' end /clone = IMAGE: 3069598 /clone_end = 3' | 2.3244 | up |
| 731 | NM_005508 | 229 | Hs.184926 | chemokine (C-C motif) receptor 4 (CCR4), mRNA /cds = (182, 1264) | 2.3244 | up |
| 732 | X16354 | 230 | Hs.50964 | mRNA for transmembrane carcinoembryonic antigen BGPa (formerly TM1-CEA) /cds = (72, 1652) | 2.468 | up |
| 733 | AA581115 | 231 | Hs.291129 | oe10d02.s1 cDNA /clone = IMAGE: 1385475 | 2.468 | up |
| 734 | NM_005485 | 232 | Hs.271742 | ADP-ribosyltransferase (NAD+; poly (ADP-ribose) polymerase)-like 3 (ADPRTL3), mRNA /cds = (246, 1847) | 2.468 | up |
| 735 | NM_005816 | 233 | Hs.142023 | T cell activation, increased late expression (TACTILE), mRNA /cds = (928, 2637) | 2.468 | up |
| 736 | BG033294 | 234 | Hs.118787 | transforming growth factor, beta-induced, 68 kD (TGFBI), mRNA /cds = (47, 2098) | 2.468 | up |
| 737 | K01566 | 235 | Hs.69771 | B-factor, properdin | 2.468 | up |
| 738 | T25714 | 236 | Hs.330530 | ESTDIR309 cDNA, 3' end /clone = CDDIRX9 /clone_end = 3' | 2.468 | up |
| 739 | NM_022873 | 237 | Hs.265827 | interferon, alpha-inducible protein (clone IFI-6-16) (G1P3), transcript variant 3, mRNA /cds = (107, 523) | 2.468 | up |
| 740 | X99699 | 238 | Hs.139262 | XIAP associated factor-1 (HSXIAPAF1), mRNA /cds = (0, 953) | 2.67 | |
| 741 | AF067519 | 239 | Hs.307357 | PITSLRE protein kinase beta SV1 isoform (CDC2L2) mRNA, complete cds /cds = (79, 2412) | 2.7771 | up |
| 742 | BG387694 | 240 | Hs.170980 | cell cycle progression 2 protein (CPR2), mRNA /cds = (126, 1691) | 2.7771 | up |
| 743 | AF104032 | 241 | Hs.184601 | L-type amino acid transporter subunit LAT1 mRNA, complete cds /cds = (66, 1589) | 2.7771 | up |
| 744 | NM_012177 | 242 | Hs.272027 | F-box only protein 5 (FBXO5), mRNA /cds = (61, 1404) | 2.7771 | up |
| 745 | AL042370 | 243 | Hs.79709 | phosphotidylinositol transfer protein (PITPN), mRNA /cds = (216, 1028) | 2.9579 | up |
| 746 | BC009469 | 244 | Hs.287797 | mRNA for FLJ00043 protein, partial cds /cds = (0, 4248) | 2.9579 | up |
| 747 | AA319163 | 245 | Hs.424299 | RPLP1; germinal | 2.9579 | up |
| 748 | AI393970 | 246 | Hs.76239 | hypothetical protein FLJ20608 (FLJ20608), mRNA /cds = (81, 680) | 2.9579 | up |
| 749 | NM_014481 | 247 | Hs.154149 | *Homo sapiens*, apurinic/apyrimidinic endonuclease(APEX nuclease)-like 2 protein, clone MGC: 1418 IMAGE: 3139156, mRNA, complete cds /cds = (38, 1594) | 2.9579 | up |
| 750 | NM_017774 | 248 | Hs.306668 | cDNA FLJ14089 fis, clone MAMMA1000257 /cds = UNKNOWN | 2.9579 | up |
| 751 | NM_017859 | 249 | Hs.39850 | hypothetical protein FLJ20517 (FLJ20517), mRNA /cds = (44, 1690) | 2.9579 | up |
| 752 | R44202 | 250 | Hs.240013 | mRNA; cDNA DKFZp547A166 (from clone DKFZp547A166) /cds = UNKNOWN | 2.9579 | up |
| 753 | NM_002904 | 251 | Hs.106061 | RD RNA-binding protein (RDBP), mRNA /cds = (108, 1250) | 2.9579 | up |

TABLE 2A-continued

Significance analysis for Microarrays, Lupus/Autoimmune merkers

| SEQ ID 50mer | ACC | SEQ ID Full length | HS | Gene | SAM FDR | SAM Up/Down |
|---|---|---|---|---|---|---|
| 754 | AL133642 | 252 | Hs.241471 | mRNA; cDNA DKFZp586G1721 (from clone DKFZp586G1721); partial cds /cds = (0, 669) | 3.09 | up |
| 755 | AF160973 | 253 | Hs.258503 | P53 inducible protein | 3.0908 | up |
| 756 | NM_001972 | 254 | Hs.99863 | elastase 2, neutrophil (ELA2), | 3.0908 | up |
| 757 | AA282774 | 255 | NA | cDNA clone IMAGE: 713136 5' | 3.0908 | up |
| 758 | AB000115 | 256 | Hs.75470 | hypothetical protein, expressed in osteoblast (GS3686), mRNA /cds = (241, 1482) | 3.0908 | up |
| 759 | AJ277247 | 257 | Hs.287369 | interleukin 22 (IL22), mRNA /cds = (71, 610) | 3.0908 | up |
| 760 | D38081 | 258 | Hs.89887 | thromboxane A2 receptor (TBXA2R), mRNA /cds = (991, 2022) | 3.0908 | up |
| 761 | NM_001250 | 259 | Hs.25648 | tumor necrosis factor receptor superfamily, member 5 (TNFRSF5), mRNA /cds = (47, 880) | 3.0908 | up |
| 762 | AI524266 | 260 | Hs.230874 | th11g12.x1 cDNA, 3' end /clone = IMAGE: 2118022 /clone_end = 3' | 3.0908 | up |
| 763 | AL573787 | 261 | Hs.21732 | AL573787 cDNA /clone = CS0DI055YM17-(3-prime) | 3.0908 | up |
| 764 | AK001503 | 262 | Hs.265891 | cDNA FLJ10641 fis, clone NT2RP2005748 /cds = UNKNOWN | 3.0908 | up |
| 765 | X04430 | 263 | Hs.93913 | IFN-beta 2a mRNA for interferon-beta-2, T-cells, macrophages | 3.0908 | up |
| 766 | AF480557 | 264 | NA | 142E4 | 3.0908 | up |
| 767 | AL550229 | 265 | Hs.271599 | cDNA FLJ12347 fis, clone MAMMA1002298 /cds = UNKNOWN | 3.0908 | up |
| 768 | AV727063 | 266 | Hs.245798 | hypothetical protein DKFZp564I0422 (DKFZP564I0422), mRNA /cds = (510, 1196) | 3.0908 | up |
| 769 | NM_000389 | 267 | Hs.179665 | cyclin-dependent kinase inhibitor 1A (p21, Cip1) (CDKN1A), mRNA /cds = (75, 569) | 3.0908 | up |
| 770 | NM_001761 | 268 | Hs.1973 | cyclin F (CCNF), mRNA /cds = (43, 2403) | 3.0908 | up |
| 771 | NM_002741 | 269 | Hs.2499 | protein kinase C-like 1 (PRKCL1), mRNA /cds = (84, 2912) | 3.0908 | up |
| 772 | NM_002880 | 270 | Hs.279474 | HSPC070 protein (HSPC070), mRNA /cds = (331, 1581) | 3.0908 | up |
| 773 | NM_014373 | 271 | Hs.97101 | putative G protein-coupled receptor (GPCR150), mRNA /cds = (321, 1337) | 3.0908 | up |
| 774 | U53347 | 272 | Hs.183556 | solute carrier family 1 (neutral amino acid transporter), member 5 (SLC1A5), mRNA /cds = (590, 2215) | 3.0908 | up |
| 775 | W19201 | 273 | Hs.17778 | neuropilin 2 (NRP2), mRNA /cds = (0, 2780) | 3.0908 | up |
| 776 | W79598 | 274 | Hs.163846 | putative N6-DNA-methyltransferase (N6AMT1), mRNA /cds = (29, 673) | 3.0908 | up |
| 777 | XM_001939 | 275 | Hs.55468 | H4 histone, family 2 | 3.0908 | up |
| 778 | AI270476 | 276 | Hs.270341 | 602307338F1 cDNA, 5' end /clone = IMAGE: 4398848 /clone_end = 5' | 3.0908 | up |
| 779 | AA992299 | 277 | Hs.129332 | ot53b06.s1 cDNA, 3' end /clone = IMAGE: 1620467 /clone_end = 3' | 3.0908 | up |
| 780 | AF044595 | 278 | Hs.248078 | lymphocyte-predominant Hodgkin's disease case #7 immunoglobulin heavy chain gene, variable region | 3.0908 | up |
| 781 | BI091076 | 279 | Hs.127128 | ok13e12.s1 cDNA, 3' end /clone = IMAGE: 1507726 /clone_end = 3' | 3.0908 | up |
| 782 | H13491 | 280 | Hs.303450 | yj15f02.r1 cDNA, 5' end /clone = IMAGE: 148827 /clone_end = 5' | 3.0908 | up |
| 783 | M55420 | 281 | Hs.247930 | IgE chain, last 2 exons | 3.0908 | up |
| 784 | NM_014271 | 282 | Hs.241385 | interleukin 1 receptor accessory protein-like 1 (IL1RAPL1), mRNA /cds = (510, 2600) | 3.0908 | up |
| 785 | AI378091 | 283 | Hs.369056 | ESTs | 3.0908 | up |
| 786 | AI381601 | 284 | Hs.159025 | td05g03.x1 cDNA, 3' end /clone = IMAGE: 2074804 /clone_end = 3' | 3.0908 | up |
| 787 | AI634972 | 285 | Hs.319825 | 602021477F1 cDNA, 5' end /clone = IMAGE: 4156915 /clone_end = 5' | 3.0908 | up |
| 788 | AW005376 | 286 | Hs.173280 | ws94a12.x1 cDNA, 3' end /clone = IMAGE: 2505598 /clone_end = 3' | 3.0908 | up |
| 789 | AW088500 | 287 | Hs.389655 | EST, Weakly similar to A35098 MHC class III histocompatibility antigen HLA-B-associated transcript 3 | 3.0908 | up |
| 790 | AW195270 | 288 | Hs.330019 | xn67c04.x1 cDNA, 3' end /clone = IMAGE: 2699526 /clone_end = 3' | 3.0908 | up |
| 791 | AW296797 | 289 | Hs.255579 | UI-H-BW0-ajb-e-07-0-UI.s1 cDNA, 3' end /clone = IMAGE: 2731117 /clone_end = 3' | 3.0908 | up |
| 792 | BF827734 | 290 | Hs.156766 | ESTs | 3.0908 | up |
| 793 | M11233 | 291 | Hs.79572 | cathepsin D (lysosomal aspartyl protease) (CTSD), mRNA /cds = (2, 1240) | 3.0908 | up |
| 794 | AL050218 | 292 | Hs.15020 | DNA sequence from clone 51J12 on chromosome 6q26-27. | 3.1014 | up |
| 795 | NM_016063 | 293 | Hs.32826 | CGI-130 protein (LOC51020), mRNA /cds = (63, 575) | 3.1014 | up |
| 796 | BU678165 | 294 | Hs.377992 | 479H5, not in ref seq, Rab geranylgeranyltransferase, alpha subunit (RABGGTA), | 3.1014 | up |
| 797 | AL050371 | 295 | Hs.8128 | phosphatidylserine decarboxylase (PISD), mRNA /cds = (223, 1350) | 3.33 | up |

TABLE 2A-continued

Significance analysis for Microarrays, Lupus/Autoimmune merkers

| SEQ ID 50mer | ACC | SEQ ID Full length | HS | Gene | SAM FDR | SAM Up/Down |
|---|---|---|---|---|---|---|
| 798 | NM_152545 | 296 | Hs.335815 | 62C9, hypothetical protein FLJ31695 | 3.3318 | up |
| 799 | XM_007156 | 297 | Hs.159492 | sacsin (SACS) gene, complete cds /cds = (76, 11565) | 3.3318 | up |
| 800 | NM_014339 | 298 | Hs.129751 | interleukin 17 receptor (IL17R), mRNA /cds = (32, 2632) | 3.3318 | up |
| 801 | NM_019598 | 299 | Hs.159679 | kallikrein 12 (KLK12), mRNA /cds = UNKNOWN | 3.3318 | up |
| 802 | AI061258 | 300 | Hs.134590 | oy67c11.x1 cDNA, 3' end /clone = IMAGE: 1670900 /clone_end = 3' | 3.3318 | up |
| 803 | AW468621 | 301 | Hs.257743 | he42e03.x1 cDNA, 3' end /clone = IMAGE: 2921692 /clone_end = 3' | 3.3318 | up |
| 804 | NM_001873 | 302 | Hs.75360 | carboxypeptidase E (CPE), mRNA /cds = (290, 1720) | 3.369 | up |
| 805 | NM_032839 | 303 | Hs.11360 | hypothetical protein FLJ14784 (FLJ14784), mRNA /cds = (133, 1569) | 3.369 | up |
| 806 | X16277 | 304 | Hs.339703 | zv26f06.r1 cDNA, 5' end /clone = IMAGE: 754787 /clone_end = 5' | 3.4341 | up |
| 807 | NM_000395 | 305 | Hs.285401 | colony stimulating factor 2 receptor, beta, low-affinity (granulocyte-macrophage) (CSF2RB), mRNA /cds = (28, 2721) | 3.4341 | |
| 808 | NM_013252 | 306 | Hs.126355 | C-type (calcium dependent, carbohydrate-recognition domain) lectin, superfamily member 5 (CLECSF5), mRNA /cds = (197, 763) | 3.5169 | up |
| 809 | 129F10 | 307 | NA | 129F10, chromosome hit | 3.7268 | up |
| 810 | AK024331 | 308 | Hs.287631 | cDNA FLJ14269 fis, clone PLACE1003864 /cds = UNKNOWN | 3.7268 | up |
| 811 | NM_000195 | 309 | Hs.83951 | Hermansky-Pudlak syndrome (HPS), mRNA /cds = (206, 2308) | 3.7268 | up |
| 812 | NM_030756 | 310 | Hs.173638 | transcription factor 7-like 2 (T-cell specific, HMG-box) (TCF7L2), mRNA /cds = (307, 2097) | 3.7268 | up |
| 813 | M26683 | 311 | Hs.303649 | interferon gamma treatment inducible mRNA Monocytes | 3.7833 | |
| 814 | AA214691 | 312 | Hs.111377 | LOC286530 hypothetical protein LOC286530 | 3.7833 | up |
| 815 | AB049113 | 313 | Hs.82113 | dUTP pyrophosphatase (DUT), mRNA /cds = (29, 523) | 3.7833 | up |
| 816 | AK026819 | 314 | Hs.20242 | hypothetical protein FLJ12788 (FLJ12788), mRNA /cds = (9, 866) | 3.7833 | up |
| 817 | L21961 | 315 | Hs.181125 | Homo sapiens, clone MGC: 12849 IMAGE: 4308973, mRNA, complete cds /cds = (24, 725) | 3.7833 | up |
| 818 | NM_001278 | 316 | Hs.306440 | mRNA; cDNA DKFZp566L084 (from clone DKFZp566L084) /cds = UNKNOWN | 3.7833 | up |
| 819 | NM_002385 | 317 | Hs.69547 | myelin basic protein (MBP), mRNA /cds = (10, 570) | 3.7833 | up |
| 820 | NM_005121 | 318 | Hs.11861 | thyroid hormone receptor-associated protein, 240 kDa subunit (TRAP240), mRNA /cds = (77, 6601) | 3.7833 | up |
| 821 | NM_007220 | 319 | Hs.283646 | carbonic anhydrase VB, mitochondrial (CA5B), nuclear gene encoding mitochondrial protein, mRNA /cds = (137, 1090) | 3.7833 | up |
| 822 | NM_012381 | 320 | Hs.74420 | origin recognition complex, subunit 3 (yeast homolog)-like (ORC3L), mRNA /cds = (26, 2161) | 3.7833 | up |
| 823 | NM_014225 | 321 | Hs.173902 | protein phosphatase 2 (formerly 2A), regulatory subunit A (PR 65), alpha isoform (PPP2R1A), mRNA /cds = (138, 1907) | 3.7833 | up |
| 824 | BF966028 | 322 | Hs.5324 | hypothetical protein (CL25022), mRNA /cds = (157, 1047) | 3.7833 | up |
| 825 | AL157438 | 323 | Hs.66151 | mRNA; cDNA DKFZp434A115 (from clone DKFZp434A115) /cds = UNKNOWN | 3.7833 | up |
| 826 | NM_004488 | 324 | Hs.73734 | glycoprotein V (platelet) (GP5), mRNA /cds = (270, 1952) | 3.7833 | up |
| 827 | NM_006929 | 325 | Hs.153299 | DOM-3 (C. elegans) homolog Z (DOM3Z), transcript variant 2, mRNA /cds = (129, 1319) | 3.7833 | up |
| 828 | NM_021976 | 326 | Hs.79372 | retinoid X receptor, beta (RXRB), mRNA /cds = (179, 1780) | 3.7833 | up |
| 829 | T93822 | 327 | Hs.294092 | EST375308 cDNA | 3.7833 | up |
| 830 | AI524202 | 328 | Hs.171122 | th10d11.x1 cDNA, 3' end /clone = IMAGE: 2117877 /clone_end = 3' | 3.7833 | up |
| 831 | AI684022 | 329 | Hs.90744 | proteasome (prosome, macropain) 26S subunit, non-ATPase, 11 (PSMD11), mRNA /cds = (0, 1268) | 3.7833 | up |
| 832 | AW452545 | 330 | Hs.257582 | UI-H-BW1-ame-d-12-0-UI.s1 cDNA, 3' end /clone = IMAGE: 3069742 /clone_end = 3' | 3.7833 | up |
| 833 | NM_153341 | 331 | Hs.64239 | DNA sequence from clone RP5-1174N9 on chromosome 1p34.1-35.3. Contains the gene for a novel protein with IBR domain, a (pseudo?) gene for a novel protein similar to MT1E (metallothionein 1E (functional)), ESTs, STSs, GSSs and two putative CpG islands /cd | 3.7833 | up |
| 834 | BF698885 | 332 | Hs.5890 | hypothetical protein FLJ23306 (FLJ23306), mRNA /cds = (562, 930) | 3.7833 | up |
| 835 | NM_000073 | 333 | Hs.2259 | CD3G antigen, gamma polypeptide (TiT3 complex) (CD3G), mRNA /cds = (37, 585) | 3.8053 | up |
| 836 | NM_004761 | 334 | Hs.170160 | RAB2, member RAS oncogene family-like (RAB2L), mRNA /cds = (0, 2333) | 3.8053 | up |

TABLE 2A-continued

Significance analysis for Microarrays, Lupus/Autoimmune merkers

| SEQ ID 50mer | ACC | SEQ ID Full length | HS | Gene | SAM FDR | SAM Up/Down |
|---|---|---|---|---|---|---|
| 837 | NM_015898 | 335 | Hs.104640 | HIV-1 inducer of short transcripts binding protein (FBI1), mRNA /cds = (0, 1754) | 3.8053 | up |
| 838 | NM_014348 | 336 | Hs.296429 | similar to rat integral membrane glycoprotein POM121 (POM121L1), mRNA /cds = (0, 1286) | 3.8053 | up |
| 839 | AW500534 | 337 | Hs.145668 | fmfc5 cDNA /clone = CR6-21 | 3.8053 | up |
| 840 | AA765569 | 338 | Hs.104157 | EST380899 cDNA | 3.8053 | up |
| 841 | AI084553 | 339 | Hs.105621 | HNC29-1-B1.R cDNA | 3.8053 | up |
| 842 | AI523617 | 340 | Hs.171098 | tg95b03.x1 cDNA, 3' end /clone = IMAGE: 2116493 /clone_end = 3' | 3.8053 | up |
| 843 | AI969716 | 341 | Hs.13034 | hv63f09.x1 cDNA, 3' end /clone = IMAGE: 3178121 /clone_end = 3' | 3.8053 | up |
| 844 | NM_002076 | 342 | Hs.164036 | glucosamine (N-acetyl)-6-sulfatase (Sanfilippo disease IIID) (GNS), mRNA /cds = (87, 1745) | 3.8053 | up |
| 925 | BG505271 | 423 | Hs.86437 | 602411368F1 cDNA, 5' end /clone = IMAGE: 4540096 /clone_end = 5' | 4.1189 | up |
| 926 | BE965319 | 424 | Hs.286754 | 601659229R1 cDNA, 3' end /clone = IMAGE: 3895783 /clone_end = 3' | 4.1189 | up |
| 927 | NM_003264 | 425 | Hs.63668 | toll-like receptor 2 (TLR2), mRNA /cds = (129, 2483) | 4.246 | up |
| 928 | BU540019 | 426 | NA | 485A6, EST | 4.2464 | up |
| 929 | AV719442 | 427 | Hs.256959 | AV719442 cDNA, 5' end /clone = GLCBNA01 /clone_end = 5' | 4.2464 | up |
| 930 | NM_000879 | 428 | Hs.2247 | interleukin 5 (colony-stimulating factor, eosinophil) (IL5), mRNA /cds = (44, 448) | 4.2464 | up |
| 931 | NM_001916 | 429 | Hs.289271 | cytochrome c-1 (CYC1), mRNA /cds = (8, 985) | 4.2464 | up |
| 932 | NM_002460 | 430 | Hs.82132 | interferon regulatory factor 4 (IRF4), mRNA /cds = (105, 1460) | 4.2464 | up |
| 933 | NM_002994 | 431 | Hs.89714 | small inducible cytokine subfamily B (Cys-X-Cys), member 5 | 4.2464 | up |
| 934 | NM_007015 | 432 | Hs.97932 | chondromodulin I precursor (CHM-I), mRNA /cds = (0, 1004) | 4.2464 | up |
| 935 | NM_017644 | 433 | Hs.246875 | hypothetical protein FLJ20059 (FLJ20059), mRNA /cds = (25, 1290) | 4.2464 | up |
| 936 | X57025 | 434 | Hs.85112 | IGF-I mRNA for insulin-like growth factor I /cds = (166, 627) | 4.2464 | up |
| 937 | BF892532 | 435 | Hs.38664 | IL0-MT0152-061100-501-e04 cDNA | 4.2464 | up |
| 938 | BG028577 | 436 | Hs.279009 | matrix Gla protein (MGP), mRNA /cds = (46, 357) | 4.2464 | up |
| 939 | AF116909 | 437 | Hs.167827 | clone HH419 unknown mRNA /cds = (189, 593) | 4.2464 | up |
| 940 | AL136842 | 438 | Hs.260024 | mRNA; cDNA DKFZp434A0530 (from clone DKFZp434A0530); complete cds /cds = (968, 1732) | 4.2464 | up |
| 941 | AW327360 | 439 | Hs.250605 | dq02e11.x1 cDNA, 5' end /clone = IMAGE: 2846685 /clone_end = 5' | 4.2464 | up |
| 942 | AI538420 | 440 | Hs.231292 | td06a03.x1 cDNA, 3' end /clone = IMAGE: 2074828 /clone_end = 3' | 4.2464 | up |
| 943 | AI805144 | 441 | NA | EST | 4.2464 | up |
| 944 | AW064160 | 442 | Hs.279141 | SP0594 cDNA, 3' end /clone_end = 3' | 4.2464 | up |
| 945 | AW078847 | 443 | Hs.244816 | xb18g07.x1 cDNA, 3' end /clone = IMAGE: 2576700 /clone_end = 3' | 4.2464 | up |
| 946 | AW236252 | 444 | Hs.253747 | xn71g08.x1 cDNA, 3' end /clone = IMAGE: 2699966 /clone_end = 3' | 4.2464 | up |
| 947 | AW297026 | 445 | Hs.255600 | UI-H-BW0-ajf-e-06-0-UI.s1 cDNA, 3' end /clone = IMAGE: 2731499 /clone_end = 3' | 4.2464 | up |
| 948 | NM_016095 | 446 | Hs.108196 | HSPC037 protein (LOC51659), mRNA /cds = (78, 635) | 4.2464 | up |
| 949 | AK000575 | 447 | Hs.279581 | hypothetical protein FLJ20568 (FLJ20568), mRNA /cds = (6, 422) | 4.2892 | Up |
| 950 | NM_002462 | 448 | Hs.76391 | myxovirus (influenza) resistance 1, homolog of murine (interferon-inducible protein p78) (MX1), mRNA /cds = (345, 2333) | 4.2892 | up |
| 951 | NM_003841 | 449 | Hs.119684 | tumor necrosis factor receptor superfamily, member 10c, decoy without an intracellular domain (TNFRSF10C), mRNA /cds = (29, 928) | 4.2892 | up |
| 952 | NM_004834 | 450 | Hs.3628 | mitogen-activated protein kinase kinase kinase kinase 4 (MAP4K4), mRNA /cds = (79, 3576) | 4.2892 | up |
| 953 | NM_013368 | 451 | Hs.169138 | RPA-binding trans-activator (RBT1), mRNA /cds = (291, 881) | 4.2892 | up |
| 954 | X12451 | 452 | Hs.78056 | cathepsin L (CTSL), mRNA /cds = (288, 1289) | 4.2892 | up |
| 955 | Y13936 | 453 | Hs.17883 | protein phosphatase 1G (formerly 2C), magnesium-dependent, gamma isoform (PPM1G), mRNA /cds = (24, 1664) | 4.2892 | up |
| 956 | AW190635 | 454 | Hs.15200 | EST379783 cDNA | 4.2892 | up |
| 957 | AI378123 | 455 | Hs.327454 | tc80e02.x1 cDNA, 3' end /clone = IMAGE: 2072474 /clone_end = 3' | 4.2892 | up |
| 958 | AJ275405 | 456 | Hs.272362 | partial IGVL1 gene for immunoglobulin lambda light chain V region | 4.2892 | up |

TABLE 2A-continued

Significance analysis for Microarrays, Lupus/Autoimmune merkers

| SEQ ID 50mer | ACC | SEQ ID Full length | HS | Gene | SAM FDR | SAM Up/Down |
|---|---|---|---|---|---|---|
| 959 | AA729508 | 457 | Hs.307486 | nx54a03.s1 cDNA /clone = IMAGE: 1266028 | 4.2892 | up |
| 960 | AI865603 | 458 | Hs.341208 | wk47g03.x1 cDNA, 3' end /clone = IMAGE: 2418580 /clone__end = 3' | 4.2892 | up |
| 961 | NM_080612 | 459 | Hs.102630 | 128F5, GRB2-associated binding protein 3 (GAB3), | 4.2892 | up |
| 962 | NM_014086 | 460 | Hs.6975 | PRO1073 protein (PRO1073), | 4.3699 | up |
| 963 | L11695 | 461 | Hs.220 | transforming growth factor, beta receptor I (activin A receptor type II-like kinase, 53 kD) (TGFBR1), mRNA /cds = (76, 1587) | 4.3699 | up |
| 964 | NM_002995 | 462 | Hs.3195 | small inducible cytokine subfamily C, member 1 (lymphotactin) (SCYC1), mRNA /cds = (20, 364) | 4.3699 | up |
| 965 | BF968963 | 463 | Hs.5064 | 602490910F1 cDNA, 5' end /clone = IMAGE: 4619835 /clone__end = 5' | 4.3699 | up |
| 966 | BG286649 | 464 | Hs.323950 | zinc finger protein 6 (CMPX1) (ZNF6), mRNA /cds = (1265, 3361) | 4.3699 | up |
| 967 | NM_014148 | 465 | Hs.278944 | HSPC048 protein (HSPC048), mRNA /cds = (87, 419) | 4.3699 | up |
| 968 | BF195579 | 466 | Hs.232257 | RST2302 cDNA | 4.3699 | up |
| 969 | BF509758 | 467 | Hs.144265 | UI-H-BI4-apg-d-04-0-UI.s1 cDNA, 3' end /clone = IMAGE: 3087390 /clone__end = 3' | 4.3699 | up |
| 970 | AF118274 | 468 | Hs.128740 | DNb-5 mRNA, partial cds /cds = (0, 1601) | 4.4485 | up |
| 971 | NM_005082 | 469 | Hs.1579 | zinc finger protein 147 (estrogen-responsive finger protein) (ZNF147), mRNA /cds = (39, 1931) | 4.4485 | up |
| 972 | AA576947 | 470 | Hs.188886 | nm82b04.s1 cDNA, 3' end /clone = IMAGE: 1074703 /clone__end = 3' | 4.4485 | up |
| 973 | AA628833 | 471 | NA | EST | 4.4485 | up |
| 974 | AI631850 | 472 | Hs.340604 | wa36h07.x1 cDNA, 3' end /clone = IMAGE: 2300221 /clone__end = 3' | 4.4485 | up |
| 975 | AW006867 | 473 | Hs.231987 | 602320903F1 cDNA, 5' end /clone = IMAGE: 4424065 /clone__end = 5' | 4.4485 | up |
| 976 | M94046 | 474 | Hs.7647 | MYC-associated zinc finger protein (purine-binding transcription factor) (MAZ), mRNA /cds = (91, 1584) | 4.4977 | up |
| 977 | AB007861 | 475 | Hs.118047 | 602971981F1 cDNA, 5' end /clone = IMAGE: 5111324 /clone__end = 5' | 4.5272 | up |
| 978 | AF061944 | 476 | Hs.432900 | PRKWNK1 protein kinase, lysine deficient 1 | 4.5272 | up |
| 979 | AL136797 | 477 | Hs.273294 | mRNA; cDNA DKFZp434N031 (from clone DKFZp434N031); complete cds /cds = (18, 3608) | 4.5272 | up |
| 980 | D42040 | 478 | Hs.75243 | bromodomain-containing 2 (BRD2), mRNA /cds = (1701, 4106) | 4.5272 | up |
| 981 | AI089359 | 479 | Hs.130232 | qb05h03.x1 cDNA, 3' end /clone = IMAGE: 1695413 /clone__end = 3' | 4.5272 | up |
| 982 | NM_004776 | 480 | Hs.107526 | UDP-Gal:betaGlcNAc beta 1,4-galactosyltransferase, polypeptide 5 (B4GALT5), mRNA /cds = (112, 1278) | 4.5272 | up |
| 983 | NM_020428 | 481 | Hs.105509 | cDNA FLJ14613 fis, clone NT2RP1001113, highly similar to CTL2 gene /cds = UNKNOWN | 4.5272 | up |
| 984 | NM_020530 | 482 | Hs.248156 | oncostatin M (OSM), mRNA /cds = (0, 758) | 4.5272 | up |
| 985 | NM_003321 | 483 | Hs.12084 | Tu translation elongation factor, mitochondrial (TUFM) | 4.5631 | up |
| 986 | BE901218 | 484 | Hs.285122 | Homo sapiens, hypothetical protein FLJ21839, clone MGC: 2851 IMAGE: 2967512, mRNA, complete cds /cds = (444, 2618) | 4.5631 | up |
| 987 | AI361733 | 485 | Hs.157811 | qz24b02.x1 cDNA, 3' end /clone = IMAGE: 2027787 /clone__end = 3' | 4.5631 | up |
| 988 | AK026410 | 486 | Hs.236449 | hypothetical protein FLJ22757 (FLJ22757), mRNA /cds = (92, 2473) | 4.6078 | up |
| 989 | BG254292 | 487 | NA | cDNA clone IMAGE: 4477042 5' | 4.6078 | up |
| 990 | NM_001504 | 488 | Hs.198252 | G protein-coupled receptor 9 (GPR9), mRNA /cds = (68, 1174) | 4.6078 | up |
| 991 | BE964596 | 489 | Hs.184052 | PP1201 protein (PP1201), mRNA /cds = (75, 1010) | 4.6078 | up |
| 992 | AB011098 | 490 | Hs.59403 | serine palmitoyltransferase, long chain base subunit 2 (SPTLC2), mRNA /cds = (188, 1876) | 4.6346 | up |
| 993 | BE745645 | 491 | Hs.127951 | hypothetical protein FLJ14503 (FLJ14503), mRNA /cds = (19, 2217) | 4.6346 | up |
| 994 | AI827950 | 492 | Hs.342617 | ha15h10.x1 cDNA, 3' end /clone = IMAGE: 2873827 /clone__end = 3' | 4.6346 | up |
| 995 | AL521097 | 493 | Hs.13144 | HSPC160 protein (HSPC160), mRNA /cds = (53, 514) | 4.6346 | up |
| 996 | BE222032 | 494 | Hs.128675 | hr61g11.x1 cDNA, 3' end /clone = IMAGE: 3133028 /clone__end = 3' | 4.6346 | up |
| 997 | AA516406 | 495 | Hs.180201 | hypothetical protein FLJ20671 (FLJ20671), mRNA /cds = (72, 494) | 4.7382 | up |
| 998 | AJ277832 | 496 | Hs.56247 | mRNA for inducible T-cell co-stimulator (ICOS gene) /cds = (67, 666) | 4.7426 | up |
| 999 | AV653169 | 497 | Hs.5897 | cDNA FLJ13388 fis, clone PLACE1001168 /cds = UNKNOWN | 4.7426 | up |

TABLE 2A-continued

Significance analysis for Microarrays, Lupus/Autoimmune merkers

| SEQ ID 50mer | ACC | SEQ ID Full length | HS | Gene | SAM FDR | SAM Up/Down |
|---|---|---|---|---|---|---|
| 1000 | M36820 | 498 | Hs.75765 | GRO2 oncogene (GRO2), mRNA /cds = (74, 397) | 4.7432 | up |
| 1001 | NM_015919 | 499 | Hs.145956 | zinc finger protein mRNA, complete cds /cds = (1073, 3133) | 4.7432 | up |
| 1002 | AI378109 | 500 | Hs.283438 | 7f19b03.x1 cDNA, 3' end /clone = IMAGE: 3295085 /clone_end = 3' | 4.7432 | up |
| 1003 | AI436418 | 501 | Hs.369051 | ESTs, Weakly similar to VAM5_HUMAN Vesicle-associated membrane protein 5 (VAMP-5) (Myobrevin) (HSPC191) | 4.7432 | up |
| 1004 | NM_022488 | 502 | Hs.26367 | PC3-96 protein (PC3-96), mRNA /cds = (119, 586) | 4.8445 | up |
| 845 | AI760224 | 343 | Hs.26873 | wh62g06.x1 cDNA, 3' end /clone = IMAGE: 2385370 /clone_end = 3' | 0.3142, 0.56 | up, down |
| 504 | W16552 | 2 | Hs.306117 | PKR | 0, 0 | up |
| 846 | AL565736 | 344 | Hs.181165 | eukaryotic translation elongation factor 1 alpha 1 (EEF1A1), mRNA /cds = (53, 1441) | 0.0909, 1.6, 0.090 | down |
| 847 | NM_004900 | 345 | Hs.226307 | phorbolin (similar to apolipoprotein B mRNA editing protein) (DJ742C19.2), mRNA /cds = (79, 651) | 0.25, 3.09 | up |
| 848 | AI031624 | 346 | Hs.238954 | 602637935F1 cDNA, 5' end /clone = IMAGE: 4765448 /clone_end = 5' | 0.3142, 0.5638 | up, down |
| 849 | BF059133 | 347 | Hs.144583 | Homo sapiens, clone IMAGE: 3462401, mRNA, partial cds /cds = (0, 153) | 0.669, 0.564 | up, down |
| 850 | AB036432 | 348 | Hs.184 | advanced glycosylation end product-specific receptor (AGER), mRNA /cds = (0, 1214) | 0.6691, 0.9257 | up, down |
| 851 | R64054 | 349 | Hs.208603 | 7f01d11.x1 cDNA, 3' end /clone = IMAGE: 3293397 /clone_end = 3' | 0.6845, 0.926 | up, down |
| 852 | M81601 | 350 | Hs.153179 | fatty acid binding protein 5 (psoriasis-associated) (FABP5), mRNA /cds = (48, 455) | 1.03, 3.0908 | up, down |
| 853 | AY004255 | 351 | Hs.238990 | Homo sapiens, Similar to cyclin-dependent kinase inhibitor 1B (p27, Kip1) | 1.1, 0.0909 | down |
| 854 | NM_002258 | 352 | Hs.169824 | killer cell lectin-like receptor subfamily B, member 1 (KLRB1), mRNA /cds = (60, 737) | 1.1, 0.1071 | down |
| 855 | M11124 | 353 | Hs.198253 | major histocompatibility complex, class II, DQ alpha 1 (HLA-DQA1), mRNA /cds = (43, 810) | 1.1, 0.193 | down |
| 514 | NM_002946 | 12 | Hs.79411 | replication protein A2 (32 kD) (RPA2) | 1.1, 0.4174 | down |
| 856 | AF073705 | 354 | Hs.247721 | clone mcg53-54 immunoglobulin lambda light chain variable region 4a mRNA, partial cds /cds = (0, 324) | 1.1, 0.9542 | up |
| 857 | AJ271326 | 355 | Hs.135187 | unc93 (C. elegans) homolog B (UNC93B), mRNA /cds = (41, 1834) | 1.1, 1.437 | up |
| 858 | NM_138391 | 356 | Hs.17481 | mRNA; cDNA DKFZp434G2415 (from clone DKFZp434G2415) /cds = UNKNOWN | 1.1, 2.246 | up |
| 859 | X97324 | 357 | Hs.3416 | adipose differentiation-related protein (ADFP), mRNA /cds = (0, 1313) | 1.1, 2.32 | up |
| 507 | NM_006187 | 5 | Hs.56009 | 2'-5'-oligoadenylate synthetase 3 (100 kD) (OAS3), mRNA /cds = (34, 3297) | 1.1, 2.47 | up |
| 860 | NM_006289 | 358 | Hs.18420 | talin 1 (TLN1), mRNA /cds = (126, 7751) | 1.1, 3.0908 | up |
| 861 | NM_002935 | 359 | Hs.73839 | ribonuclease, RNase A family, 3 (eosinophil cationic protein) (RNASE3), mRNA /cds = (63, 545) | 1.1, 4.56 | up |
| 862 | Y00345 | 360 | Hs.172182 | poly(A)-binding protein, cytoplasmic 1 (PABPC1), mRNA /cds = (502, 2403) | 1.6, 0.0909 | down |
| 863 | AL567986 | 361 | Hs.77393 | farnesyl diphosphate synthase | 1.6, 0.0909 | down |
| 864 | NM_000311 | 362 | Hs.74621 | prion protein (p27-30) (Creutzfeld-Jakob disease, Gerstmann-Strausler-Scheinker syndrome) | 1.6, 0.141 | down |
| 865 | NM_016523 | 363 | Hs.183125 | killer cell lectin-like receptor subfamily F, member 1 (KLRF1), mRNA /cds = (64, 759) | 1.6, 0.213 | down |
| 866 | AA701193 | 364 | Hs.431104 | EST, Weakly similar to HA21_HUMAN HLA class II histocompatibility antigen, DQ(1) alpha chain precursor (DC-4 alpha chain) | 1.6, 0.2759 | down |
| 510 | NM_004510 | 8 | Hs.38125 | interferon-induced protein 75, 52 kD (IFI75), mRNA /cds = (170, 1396) | 1.6, 1.12 | up |
| 867 | AK026594 | 365 | Hs.251653 | tubulin, beta, 2 (TUBB2), mRNA /cds = (0, 1337) | 1.6, 2.32 | up |
| 503 | NM_000389 | 1 | Hs.179665 | CDKN1A cyclin-dependent kinase inhibitor 1A (p21, Cip1) | 1.6, 3.09 | up |
| 868 | AW063509 | 366 | Hs.279105 | TN1012 cDNA, 3' end /clone_end = 3' | 1.6, 3.09 | up |
| 869 | R14692 | 367 | Hs.170222 | Na+/H+ exchanger NHE-1 isoform [human, heart, mRNA, 4516 nt] /cds = (577, 3024) | 1.6, 3.33 | up |
| 870 | NM_002831 | 368 | Hs.63489 | protein tyrosine phosphatase, non-receptor type 6 (PTPN6), mRNA /cds = (144, 1931) | 1.6, 4.3699 | up |

TABLE 2A-continued

Significance analysis for Microarrays, Lupus/Autoimmune merkers

| SEQ ID 50mer | ACC | SEQ ID Full length | HS | Gene | SAM FDR | SAM Up/Down |
|---|---|---|---|---|---|---|
| 871 | BE868389 | 369 | Hs.179703 | tripartite motif protein 14 (TRIM14), mRNA /cds = (10, 1230) | 1.6, 4.6 | up |
| 509 | BC002409 | 7 | Hs.288061 | actin, beta (ACTB), mRNA | NA | |
| 518 | NM_003033 | 16 | Hs.301698 | BAC 180i23 chromosome 8 map 8q24.3 beta-galactoside alpha-2,3-sialyltransferase (SIAT4A) gene | NA | |
| 872 | AK090404 | 370 | Hs.98531 | 53G7, FLJ00290 protein | NA | |
| 873 | AK024202 | 371 | Hs.289088 | heat shock 90 kD protein 1, alpha (HSPCA), mRNA /cds = (60, 2258) | NA | |
| 874 | AK024240 | 372 | Hs.24115 | cDNA FLJ14178 fis, clone NT2RP2003339 /cds = UNKNOWN | NA | |
| 875 | AK024756 | 373 | Hs.12293 | hypothetical protein FLJ21103 (FLJ21103), mRNA /cds = (88, 1143) | NA | |
| 876 | AK024969 | 374 | Hs.166254 | hypothetical protein DKFZp566I133 (DKFZP566I133), mRNA /cds = (133, 1353) | NA | |
| 877 | AL136542 | 375 | Hs.322456 | hypothetical protein DKFZp761D0211 (DKFZP761D0211), mRNA /cds = (164, 1822) | NA | |
| 878 | NM_015995 | 376 | Hs.7104 | mRNA; cDNA DKFZp761P06121 (from clone DKFZp761P06121) /cds = UNKNOWN | NA, 3.09 | up |

TABLE 2B

Real-time PCR gene expression analysis

| SEQ ID 50 mer | ACC | SEQ ID FL | HS | Gene | PCR Fold | PCR p-value | SEQ ID forward | Forward primer | SEQ ID reverse | Reverse primer |
|---|---|---|---|---|---|---|---|---|---|---|
| 503 | NM_000389 | 1 | Hs.179665 | CDKN1A cyclin-dependent kinase Inhibitor 1A (p21, Cip1) | 2.25 | 0.0000 | 1005 | CTAACGTTG AGCCCCTGG AG | 1006 | ATGGGGAG CCGAGAGA AAAC |
| 504 | W16552 | 2 | Hs.306117 | PKR | 2.60 | 0.0000 | 1007 | TCGACATGG TGAGGTAGA GCA | 1008 | TGTTCTGG CAGCAC-CTC AAG |
| 505 | NM_004031 | 3 | Hs.166120 | interferon regulatory factor 7 (IRF7), transc | 2.76 | 0.0001 | 1009 | AGCGTGAGG GTGTGTCTT CC | 1010 | GGCTGCTC CAGCTCCA TAAG |
| 506 | NM_006417 | 4 | Hs.82316 | interferon-induced, hepatitis C-associated | 4.34 | 0.0001 | 1011 | TGGGAGCTG GACCCTGTA AA | 1012 | GCAGCCCA TAGCATTC GTCT |
| 507 | NM_006187 | 5 | Hs.56009 | 2'-5'-oligoadenylate synthetase 3 (100 kD) (OAS3) | 5.40 | 0.0001 | 1013 | CGCAGTTG GTACCTTCC AT | 1014 | TGCTCTGGT GTCCCACC ATCT |
| 508 | NM_001548 | 6 | Hs.20315 | interferon-induced protein with tetratricopeptide repeats 1 | 10.30 | 0.0019 | 1015 | CTGGAAAGC TTGAGCCTC CTT | 1016 | CTCAGGGC CCGCTCAT AGTA |
| 509 | BC002409 | 7 | Hs.288061 | actin, beta (ACTB), mRNA | 1.29 | 0.0028 | 1017 | CACAATGTG GCCGAGGA CTT | 1018 | TGGCTTTT AGGATGGC AAGG |
| 510 | NM_004510 | 8 | Hs.38125 | interferon-induced protein 75, 52kD (IFI75) | 1.36 | 0.0034 | 1019 | CAAAGACGT GCTCGGTTT TCA | 1020 | TGAATCCT GAGGTGGG GATG |
| 511 | NM_000269 | 9 | Hs.183698 | ribosomal protein L29 (RPL29) | 1.38 | 0.0057 | 1021 | CATCCATTT CCCCTCCTT CC | 1022 | CAGATGGT CGGGGATG GTAA |
| 512 | NM_138391 | 10 | Hs.17481 | *Homo sapiens* chromosome 1 open reading frame 37 (C1orf37) | 1.15 | 0.0160 | 1023 | TCTTGGAGA TTCGAGCAG CA | 1024 | CTGCGACC AGAGTCAG TGGA |

TABLE 2B-continued

Real-time PCR gene expression analysis

| SEQ ID 50 mer | SEQ ACC | SEQ ID FL | HS | Gene | PCR Fold | PCR p-value | SEQ ID forward | Forward primer | SEQ ID reverse | Reverse primer |
|---|---|---|---|---|---|---|---|---|---|---|
| 513 | 8C036402 | 11 | NA | 116C9 | 2.26 | 0.0258 | 1025 | CCTGATTCG CCAATTTGT CC | 1026 | CCCAACCC CAAAATCC CTAA |
| 514 | NM_002946 | 12 | Hs.79411 | replication protein A2 (32kD) (RPA2) | 0.88 | 0.0458 | 1027 | CGTCATGGC AAGTGTGTC AA | 1028 | TGGCCTCT GCCTGTTT TCAT |
| 515 | NM_031157 | 13 | Hs.249495 | heterogeneous nuclear ribonucleoprotein A1 (HNRPA1) | 0.79 | 0.0538 | 1029 | TGGTAAAT TCCCCAACA GTGTG | 1030 | CACCAAGG TTTTCCGA AGACAA |
| 516 | D23660 | 14 | Hs.334822 | *Homo sapiens*, Similar to ribosomal protein L4 | 0.73 | 0.0650 | 1031 | AGCACCACG CAAGAAGAT CC | 1032 | CTGGCGAA GAATGGTG TTCC |
| 517 | NM_006276 | 15 | Hs.184167 | splicing factor, arginine/serine-rich 7 (35kD) (SFRS7) | 0.85 | 0.3054 | 1033 | TTGCGCAGA TACCTAGGC TTG | 1034 | TCAGCCAG TCAAAATTC CAAAA |
| 518 | NM_003033 | 16 | Hs.301698 | beta-galactoside alpha-2,3-siafyitransferase (SIAT4A) gene | 0.88 | 0.3680 | 1035 | ACCCATCTA CCGGCATCC TC | 1036 | GTGCCAGT TCCCTTTGC TGT |
| 519 | 8E550944 | 17 | Hs.61426 | 602329933F1 cDNA | 0.95 | 0.5085 | 1037 | CAAAACCTC GCTTACTGT CATGTG | 1038 | TGGGAAAG GACATCAG TCTTCA |

TABLE 2C

Multiple Additive Regression Trees analysis of Microarray Data

| SEQ ID 50mer | ACC | SEQ ID Full length | HS | Gene | MART Importance | MART error | Imp/error |
|---|---|---|---|---|---|---|---|
| 515 | NM_031157 | 13 | Hs.249495 | heterogeneous nuclear ribonucleoprotein A1 (HNRPA1), transcript variant 2, mRNA /cds = (104, 1222) | 68.5 | 0.202 | 339.108911 |
| 516 | D23660 | 14 | Hs.334822 | *Homo sapiens*, Similar to ribosomal protein L4, clone MGC: 2966 IMAGE: 3139805, mRNA, complete cds /cds = (1616, 2617) | 68.71 | 0.202 | 340.148515 |
| 519 | BE550944 | 17 | Hs.61426 | 602329933F1 cDNA | 100, 66.33 | 0.202 | 347.0, 328.22 |
| 537 | NM_000734 | 35 | Hs.97087 | CD3Z antigen, zeta polypeptide (TiT3 complex) (CD3Z), mRNA /cds = (178, 669) | 67.49 | 0.202 | 334.108911 |
| 538 | NM_003756 | 36 | Hs.58189 | eukaryotic translation initiation factor 3, subunit 3 (gamma, 40 kD) (EIF3S3), mRNA /cds = (5, 1063) | | 0.092 | 996.521739 |
| 624 | NM_006791 | 122 | Hs.6353 | MORF-related gene 15 (MRG15), mRNA /cds = (131, 1102) | 65.53 | 0.202 | 324.405941 |
| 517 | NM_006276 | 15 | Hs.184167 | splicing factor, arginine/serine-rich 7 (35 kD) (SFRS7) mRNA /cds = (105, 490) | 100 | 0.092 | 1086.95652 |
| 754 | AL133642 | 252 | Hs.241471 | mRNA; cDNA DKFZp586G1721 (from clone DKFZp586G1721); partial cds /cds = (0, 669) | 42.88 | 0.288 | 148.888889 |
| 797 | AL050371 | 295 | Hs.8128 | phosphatidylserine decarboxylase (PISD), mRNA /cds = (223, 1350) | 70.07 | 0.288 | 243.298611 |
| 927 | NM_003264 | 425 | Hs.63668 | toll-like receptor 2 (TLR2), mRNA /cds = (129, 2483) | 49.97 | 0.288 | 173.506944 |
| 845 | AI760224 | 343 | Hs.26873 | wh62g06.x1 cDNA, 3' end /clone = IMAGE: 2385370 | 49.83 | 0.288 | 173.020833 |
| 862 | Y00345 | 360 | Hs.172182 | poly(A)-binding protein, cytoplasmic 1 (PABPC1), mRNA /cds = (502, 2403) | 31.53 | 0.202 | 156.089109 |

TABLE 2C-continued

Multiple Additive Regression Trees analysis of Microarray Data

| SEQ ID 50mer | ACC | SEQ ID Full length | HS | Gene | MART Importance | MART error | Imp/error |
|---|---|---|---|---|---|---|---|
| 511 | NM_000269 | 9 | Hs.183698 | ribosomal protein L29 (RPL29), mRNA /cds = (29, 508) | 99.34 | 0.092 | 1079.78261 |
| 882 | NM_003128 | 380 | Hs.324648 | cDNA FLJ13700 fis, clone PLACE2000216, highly similar to SPECTRIN BETA CHAIN, BRAIN /cds = UNKNOWN | 100 | 0.202 | 495.049505 |
| 883 | AL109669 | 381 | Hs.172803 | mRNA full length insert cDNA clone EUROIMAGE 31839 /cds = UNKNOWN | 55.24 | 0.202 | 273.465347 |
| 884 | AI307808 | 382 | Hs.238797 | 602081661F1 cDNA, 5' end /clone = IMAGE: 4245999 | 33.2 | 0.202 | 164.356436 |
| 885 | AF261087 | 383 | Hs.174131 | ribosomal protein L6 (RPL6), mRNA /cds = (26, 892) | 0.68 | 0.202 | 3.36633663 |
| 886 | NM_002546 | 384 | Hs.81791 | tumor necrosis factor receptor superfamily, member 11b (osteoprotegerin) (TNFRSF11B), mRNA /cds = (94, 1299) | 48.54 | 0.202 | 240.29703 |
| 887 | NM_012237 | 385 | Hs.44017 | sirtuin (silent mating type information regulation 2, S. cerevisiae, homolog) 2 (SIRT2), transcript variant 1, mRNA /cds = (200, 1369) | 68.21 | 0.202 | 337.673267 |
| 888 | X68060 | 386 | Hs.75248 | topoisomerase (DNA) II beta (180 kD) (TOP2B), mRNA /cds = (0, 4865) | 48.14 | 0.288 | 167.152778 |
| 889 | AI660405 | 387 | Hs.111941 | qd92a04.x1 cDNA, 3' end /clone = IMAGE: 1736910 | 51.11 | 0.288 | 177.465278 |
| 890 | AI798114 | 388 | Hs.210307 | wh81c01.x1 cDNA, 3' end /clone = IMAGE: 2387136 | 0.96 | 0.202 | 4.75247525 |
| 891 | AW075948 | 389 | Hs.265634 | xa82b03.x1 cDNA, 3' end /clone = IMAGE: 2573261 | 50.06 | 0.202 | 247.821782 |
| 892 | AW294681 | 390 | Hs.255336 | UI-H-BW0-ail-g-10-0-UI.s1 cDNA, 3' end /clone = IMAGE: 2729683 /clone_end = 3' | 50.28 | 0.384 | 130.9375 |
| 893 | R40823 | 391 | Hs.108082 | 602068988F1 cDNA, 5' end /clone = IMAGE: 4067972 | 32.33 | 0.202 | 160.049505 |
| 894 | AA806222 | 392 | Hs.111554 | ADP-ribosylation factor-like 7 (ARL7), mRNA /cds = (14, 592) | 44.47 | 0.288 | 154.409722 |
| 895 | AI380390 | 393 | Hs.158976 | UI-H-BI2-ahi-a-03-0-UI.s1 cDNA, 3' end /clone = IMAGE: 2726692 /clone_end = 3' | 54.86 | 0.202 | 271.584158 |
| 896 | BF435621 | 394 | Hs.293476 | hypothetical protein FKSG44 (FKSG44), mRNA /cds = (126, 1520) | 100 | 0.285 | 350.877193 |
| 897 | AK025781 | 395 | Hs.5076 | cDNA: FLJ22128 fis, clone HEP19543 /cds = UNKNOWN | 51.37 | 0.288 | 178.368056 |
| 898 | X06323 | 396 | Hs.79086 | mitochondrial ribosomal protein L3 (MRPL3), mRNA /cds = (76, 1122) | 47.57 | 0.288 | 165.173611 |
| 899 | X72841 | 397 | Hs.31314 | retinoblastoma-binding protein 7 (RBBP7), mRNA /cds = (287, 1564) | 50.46 | 0.288 | 175.208333 |

TABLE 2D

Hierarchical Clustering of Lupus/Autoimmunity Markers

| SEQ ID 50mer | ACC | SEQ ID Full length | HS | Gene | Hierarchical Cluster OID |
|---|---|---|---|---|---|
| 900 | NM_001015 | 398 | Hs.182740 | ribosomal protein S11 (RPS11), mRNA /cds = (15, 4 | 180 |
| 901 | J02931 | 399 | Hs.62192 | placental tissue factor (two forms) mRNA, complete cd | 180 |
| 914 | NM_001778 | 412 | Hs.901 | CD48 antigen (B-cell membrane protein) (CD48), mRNA /cds = (36, 767) | 180 |
| 862 | Y00345 | 360 | Hs.172182 | poly(A)-binding protein, cytoplasmic 1 (PABPC1), mRNA /cds = (502, 2403) | 2177 |
| 524 | NM_001731 | 22 | Hs.77054 | B-cell translocation gene 1, anti-proliferative (BTG1), mRNA /cds = (308, 823) | 2177 |
| 528 | U67093 | 26 | Hs.194382 | ataxia telangiectasia (ATM) gene, complete cds /cds = (795, 9965) | 2177 |
| 529 | AJ400717 | 27 | Hs.279860 | tumor protein, translationally-controlled 1 (TPT1), mRNA /cds = (94, 612) | 2177 |

TABLE 2D-continued

Hierarchical Clustering of Lupus/Autoimmunity Markers

| SEQ ID 50mer | ACC | SEQ ID Full length | HS | Gene | Hierarchical Cluster OID |
|---|---|---|---|---|---|
| 920 | NM_014065 | 418 | Hs.279040 | HT001 protein (HT001), mRNA /cds = (241, 1203) | 3780 |
| 563 | U61267 | 61 | Hs.30035 | putative splice factor transformer2-beta mRN | 5067 |
| 680 | BF897042 | 178 | Hs.120219 | FLJ32028 hypothetical protein FLJ32028 | 5067 |
| 506 | NM_006417 | 4 | Hs.82316 | interferon-induced, hepatitis C-associated microtubular aggregate protein (44 kD) (MTAP44), mRNA /cds = (0, 1334) | 5067 |
| 504 | W16552 | 2 | Hs.306117 | PKR | 5067 |
| 507 | NM_006187 | 5 | Hs.56009 | 2'-5'-oligoadenylate synthetase 3 (100 kD) (OAS3), mRNA /cds = (34, 3297) | 5067 |
| 715 | NM_001295 | 213 | Hs.301921 | chemokine (C-C motif) receptor 1 (CCR1), mRNA /cds = (62, 1129) | 5067 |
| 739 | NM_022873 | 237 | Hs.265827 | interferon, alpha-inducible protein (clone IFI-6-16) (G1P3), transcript variant 3, mRNA /cds = (107, 523) | 5067 |
| 505 | NM_004031 | 3 | Hs.166120 | interferon regulator factor 7 (IRF7), transc | 5067 |
| 508 | NM_001548 | 6 | Hs.20315 | interferon-induced protein with tetratricopeptide repeats 1 (IFIT1) | 5067 |
| 904 | AF307339 | 402 | Hs.47783 | B aggressive lymphoma gene (BAL), mRNA /cds = (228, 2792) | 5067 |
| 906 | AK027260 | 404 | Hs.152925 | mRNA for KIAA1268 protein, partial cds /cds = (0, 3071) | 5067 |
| 907 | AL360190 | 405 | Hs.318501 | stimulated trans-acting factor (50 kDa) (STAF50), mRNA /cds = (122, 1450) | 5067 |
| 917 | NM_004031 | 415 | Hs.166120 | interferon regulatory factor 7 (IRF7), transcript variant d, mRNA /cds = (335, 1885) | 5067 |
| 921 | NM_017523 | 419 | Hs.139262 | XIAP associated factor-1 (HSXIAPAF1), mRNA /cds = (0, 953) | 5067 |
| 922 | NM_021105 | 420 | Hs.198282 | phospholipid scramblase 1 (PLSCR1), mRNA /cds = (256, 1212) | 5067 |
| 923 | XM_005543 | 421 | Hs.234642 | aquaporin 3 (AQP3), mRNA /cds = (64, 942) | 5067 |
| 642 | W00466 | 140 | Hs.44189 | yz99f01.s1 cDNA, 3' end /clone = IMAGE:291193 /clone_end = 3' | 5083 |
| 679 | AW137104 | 177 | Hs.8121 | Notch (*Drosophila*) homolog 2 (NOTCH2), mRNA /cds = (12, 7427) | 5083 |
| 848 | AI031624 | 346 | Hs.238954 | 602637935F1 cDNA, 5' end /clone = IMAGE:4765448 /clone_end = 5' | 5083 |
| 677 | NM_003367 | 175 | Hs.93649 | upstream transcription factor 2, c-fos intera | 6382 |
| 503 | NM_000389 | 1 | Hs.179665 | CDKN1A cyclin-dependent kinase inhibitor 1A (p21, Cip1) | 6382 |
| 515 | NM_031157 | 13 | Hs.249495 | heterogeneous nuclear ribonucleoprotein A1 (HNRPA1), transcript variant 2, mRNA /cds = (104, 1222) | 6444 |
| 516 | D23660 | 14 | Hs.334822 | *Homo sapiens*, Similar to ribosomal protein L4, clone MGC: 2966 IMAGE:3139805, mRNA, complete cds /cds = (1616, 2617) | 6444 |
| 520 | L13385 | 18 | Hs.77318 | Miller-Dieker lissencephaly protein (LIS1) | 6444 |
| 527 | XM_018498 | 25 | Hs.180946 | ribosomal protein L5 pseudogene mRNA, complete cds /cds = UNKNOWN | 6444 |
| 512 | NM_138391 | 10 | Hs.17481 | *Homo sapiens* chromosome 1 open reading frame 37 (C1orf37), mRNA | 6956 |
| 902 | D49950 | 400 | Hs.83077 | for interferon-gamma inducing activated macrophages | 6956 |
| 908 | AV689330 | 406 | Hs.189402 | Similar to RIKEN cDNA 2210009G21 gene, clone IMAGE:4807023 | 6956 |
| 909 | BC002796 | 407 | Hs.46446 | lymphoblastic leukemia derived sequence 1 (LYL1), mRNA /cds = (0, 803) | 6956 |
| 910 | BE899595 | 408 | NA | cDNA clone IMAGE:3952215 5' | 6956 |
| 912 | NM_001111 | 410 | Hs.7957 | adenosine deaminase, RNA-specific (ADAR), transcript variant ADAR-a, mRNA /cds = (187, 3867) | 6956 |
| 915 | NM_002463 | 413 | Hs.926 | myxovirus (influenza) resistance 2, homolog of murine (MX2), mRNA /cds = (104, 2251) | 6956 |

TABLE 2D-continued

Hierarchical Clustering of Lupus/Autoimmunity Markers

| SEQ ID 50mer | ACC | SEQ ID Full length | HS | Gene | Hierarchical Cluster OID |
|---|---|---|---|---|---|
| 918 | NM_006865 | 416 | Hs.113277 | leukocyte immunoglobulin-like receptor, subfamily A (without TM domain), member 3 (LILRA3), mRNA /cds = (62, 1381) | 6956 |
| 919 | NM_013352 | 417 | Hs.58636 | squamous cell carcinoma antigen recognized by T cell (SART-2), mRNA /cds = (149, 3025) | 6956 |
| 924 | NM_009587 | 422 | Hs.81337 | lectin, galactoside-binding, soluble, 9 (galectin 9) (LGALS9), transcript variant long, mRNA /cds = (56, 1123) | 6956 |
| 807 | NM_000395 | 305 | Hs.285401 | colony stimulating factor 2 receptor, beta, low-affinity (granulocyte-macrophage) (CSF2RB), mRNA /cds = (28, 2721) | 7330 |
| 950 | NM_002462 | 448 | Hs.76391 | myxovirus (influenza) resistance 1, homolog of murine (interferon-inducible protein p78) (MX1), mRNA /cds = (345, 2333) | 7330 |
| 905 | AK024597 | 403 | Hs.10362 | cDNA: FLJ20944 fis, clone ADSE01780 /cds = UNKNOWN | 7330 |
| 913 | NM_001549 | 411 | Hs.181874 | interferon-induced protein with tetratricopeptide repeats 4 (IFIT4), mRNA /cds = (61, 1533) | 7330 |
| 916 | NM_002759 | 414 | Hs.274382 | protein kinase, interferon-inducible double stranded RNA dependent (PRKR), mRNA /cds = (435, 2090) | 7330 |
| 911 | K02766 | 409 | Hs.1290 | complement component 9 (C9), mRNA /cds = (4, 1683) | 7379 |
| 813 | M26683 | 311 | Hs.303649 | interferon gamma treatment inducible mRNA Monocytes | 7238, 6956 |
| 903 | NM_001772 | 401 | Hs.83731 | CD33 antigen (gp67) (CD33), mRNA. | 7238, 6956 |

TABLE 2E

| OID | SEQ ID 50mer | ACC | SEQ ID Full length | HS | Gene |
|---|---|---|---|---|---|
| 6382 | 503 | NM_000389 | 1 | Hs.179665 | CDKN1A cyclin-dependent kinase inhibitor 1A (p21, Cip1) |
| 5067 | 504 | W16552 | 2 | Hs.306117 | PKR |
| 41 | 505 | NM_004031 | 3 | Hs.166120 | interferon regulatory factor 7 (IRF7), transc |
| 2922 | 506 | NM_006417 | 4 | Hs.82316 | interferon-induced, hepatitis C-associated microtubular aggregate protein |
| 7238 | 507 | NM_006187 | 5 | Hs.56009 | 2'-5'-oligoadenylate synthetase 3 (100 kD) (OAS3), mRNA /cds = (34, 3297) |
| 2139 | 508 | NM_001548 | 6 | Hs.20315 | interferon-induced protein with tetratricopeptide repeats 1 (IFIT1) |
| 1436 | 509 | BC002409 | 7 | Hs.288061 | actin, beta (ACTB), mRNA |
| 2648 | 510 | NM_004510 | 8 | Hs.38125 | interferon-induced protein 75, 52 kD (IFI75), mRNA /cds = (170, 1396) |
| 7576 | 511 | NM_000269 | 9 | Hs.183698 | ribosomal protein L29 (RPL29), mRNA /cds = (29, 508) |
| 6956 | 512 | NM_138391 | 10 | Hs.17481 | *Homo sapiens* chromosome 1 open reading frame 37 (C1orf37), mRNA |
| 6957 | 513 | BC036402 | 11 | NA | 116C9 |
| 2412 | 514 | NM_002946 | 12 | Hs.79411 | replication protein A2 (32 kD) (RPA2) |
| 6444 | 515 | NM_031157 | 13 | Hs.249495 | heterogeneous nuclear ribonucleoprotein A1 (HNRPA1), transcript variant 2, mRNA /cds = (104, 1222) |
| 7991 | 516 | D23660 | 14 | Hs.334822 | *Homo sapiens*, Similar to ribosomal protein L4 |
| 4143 | 517 | NM_006276 | 15 | Hs.184167 | splicing factor, arginine/serine-rich 7 (35 kD) (SFRS7) mRNA /cds = (105, 490) |
| 4637 | 518 | NM_003033 | 16 | Hs.301698 | BAC 180i23 chromosome 8 map 8q24.3 beta-galactoside alpha-2,3-sialyltransferase (SIAT4A) gene |
| 6335 | 519 | BE550944 | 17 | Hs.61426 | 602329933F1 cDNA |
| 219 | 520 | L13385 | 18 | Hs.77318 | Miller-Dieker lissencephaly protein (LIS1) |
| 827 | 521 | AF315591 | 19 | Hs.6151 | pumilio (*Drosophila*) homolog 2 (PUM2) |
| 1064 | 522 | AK025620 | 20 | Hs.5985 | cDNA: FLJ21967 fis, clone HEP05652, highly similar to AF131831 clone 25186 mRNA sequence |
| 1125 | 523 | AK026747 | 21 | Hs.12969 | cDNA: FLJ23094 fis, clone LNG07379 |
| 2177 | 524 | NM_001731 | 22 | Hs.77054 | B-cell translocation gene 1, anti-proliferative (BTG1), mRNA /cds = (308, 823) |

TABLE 2E-continued

| OID | SEQ ID 50mer | ACC | SEQ ID Full length | HS | Gene |
|---|---|---|---|---|---|
| 2621 | 525 | NM_004281 | 23 | Hs.15259 | BCL2-associated athanogene 3 (BAG3), mRNA /cds = (306, 2033) |
| 4114 | 526 | XM_008738 | 24 | Hs.79241 | B-cell CLL/lymphoma 2 (BCL2), nuclear gene encoding mitochondrial protein, transcript variant alpha, mRNA /cds = (31, 750) |
| 4141 | 527 | XM_018498 | 25 | Hs.180946 | ribosomal protein L5 pseudogene mRNA, complete cds /cds = UNKNOWN |
| 4142 | 528 | U67093 | 26 | Hs.194382 | ataxia telangiectasia (ATM) gene, complete cds /cds = (795, 9965) |
| 7959 | 529 | AJ400717 | 27 | Hs.279860 | tumor protein, translationally-controlled 1 (TPT1), mRNA /cds = (94, 612) |
| 2459 | 530 | NM_003133 | 28 | Hs.75975 | signal recognition particle 9 kD (SRP9), mRNA /cds = (106, 366) |
| 2620 | 531 | NM_004261 | 29 | Hs.90606 | 15 kDa selenoprotein (SEP15), mRNA /cds = (4, 492) |
| 2278 | 532 | NM_002300 | 30 | Hs.234489 | Homo sapiens, lactate dehydrogenase B, clone MGC: 3600 IMAGE: 3028947, mRNA, complete cds |
| 4653 | 533 | NM_003853 | 31 | Hs.158315 | interleukin 18 receptor accessory protein (IL18RAP), mRNA /cds = (483, 2282) |
| 8056 | 534 | X53777 | 32 | Hs.82202 | ribosomal protein L17 (RPL17), mRNA /cds = (286, 840) |
| 1864 | 535 | N27575 | 33 | Hs.75613 | CD36 antigen (collagen type I receptor, thrombospondin receptor) (CD36), mRNA /cds = (132, 1550) |
| 2963 | 536 | NM_006800 | 34 | Hs.88764 | male-specific lethal-3 (Drosophila)-like 1 (MSL3L1), mRNA /cds = (105, 1670) |
| 1991 | 537 | NM_000734 | 35 | Hs.97087 | CD3Z antigen, zeta polypeptide (TiT3 complex) (CD3Z), mRNA /cds = (178, 669) |
| 2547 | 538 | NM_003756 | 36 | Hs.58189 | eukaryotic translation initiation factor 3, subunit 3 (gamma, 40 kD) (EIF3S3), mRNA /cds = (5, 1063) |
| 275 | 539 | NM_021950 | 37 | Hs.89751 | CD20 antigen |
| 921 | 540 | AK021632 | 38 | Hs.11571 | cDNA FLJ11570 fis, clone HEMBA1003309 /cds = UNKNOWN |
| 1061 | 541 | AK025583 | 39 | Hs.82845 | cDNA: FLJ21930 fis, clone HEP04301, highly similar to HSU90916 clone 23815 mRNA sequence |
| 1987 | 542 | NM_000661 | 40 | Hs.157850 | Homo sapiens, clone MGC: 15545 IMAGE: 3050745, mRNA, complete cds /cds = (1045, 1623) |
| 4552 | 543 | NM_001057 | 41 | Hs.161305 | tachykinin receptor 2 (TACR2), mRNA /cds = (0, 1196) |
| 4903 | 544 | X60656 | 42 | Hs.275959 | eukaryotic translation elongation factor 1 beta 2 (EEF1B2), mRNA /cds = (235, 912) |
| 2687 | 545 | NM_004779 | 43 | Hs.26703 | CNOT8 CCR4-NOT transcription complex, subunit 8 |
| 3763 | 546 | X58529 | 44 | Hs.302063 | rearranged immunoglobulin mRNA for mu heavy chain enhancer and constant region /cds = UNKNOWN |
| 3262 | 547 | NM_016091 | 45 | Hs.119503 | HSPC025 (HSPC025), mRNA /cds = (33, 1727) |
| 218 | 548 | NM_001006 | 46 | Hs.77039 | ribosomal protein S3A (RPS3A), mRNA /cds = (36, 8 |
| 2150 | 549 | NM_001568 | 47 | Hs.106673 | eukaryotic translation initiation factor 3, subunit 6 (48 kD) (EIF3S6), mRNA /cds = (22, 1359) |
| 221 | 550 | BC001854 | 48 | Hs.77502 | , methionine adenosyltransferase II, alpha, c |
| 2032 | 551 | NM_000983 | 49 | Hs.326249 | ribosomal protein L22 (RPL22), mRNA /cds = (51, 437) |
| 2046 | 552 | NM_001006 | 50 | Hs.155101 | mRNA for KIAA1578 protein, partial cds /cds = (0, 3608) |
| 2113 | 553 | NM_001403 | 51 | Hs.274466 | eukaryotic translation elongation factor 1 alpha 1-like 14 (EEF1A1L14), mRNA /cds = (620, 1816) |
| 2374 | 554 | NM_002796 | 52 | Hs.89545 | proteasome (prosome, macropain) subunit, beta type, 4 (PSMB4), mRNA /cds = (23, 817) |
| 3290 | 555 | NM_016304 | 53 | Hs.284162 | 60S ribosomal protein L30 isolog (LOC51187), mRNA /cds = (143, 634) |
| 3353 | 556 | NM_017918 | 54 | Hs.234149 | hypothetical protein FLJ20647 (FLJ20647), mRNA /cds = (90, 836) |
| 4192 | 557 | AA788623 | 55 | Hs.332583 | yc77a06.s1 cDNA, 3' end /clone = IMAGE: 21844 /clone_end = 3' |
| 7248 | 558 | NM_001961 | 56 | Hs.75309 | eukaryotic translation elongation factor 2 (EEF2), mRNA /cds = (0, 2576) |
| 7631 | 559 | AK026309 | 57 | Hs.12436 | cDNA: FLJ22656 fis, clone HSI07655 /cds = UNKNOWN |
| 1112 | 560 | AK026528 | 58 | Hs.334807 | Homo sapiens, ribosomal protein L30, clone MGC: 2797, mRNA, complete cds /cds = (29, 376) |
| 1450 | 561 | BC002971 | 59 | Hs.1600 | Homo sapiens, clone IMAGE: 3543711, mRNA, partial cds /cds = (0, 1620) |
| 3572 | 562 | U01923 | 60 | Hs.278857 | heterogeneous nuclear ribonucleoprotein H2 (H') (HNRPH2), mRNA /cds = (78, 1427) |
| 140 | 563 | U61267 | 61 | Hs.30035 | putative splice factor transformer2-beta mRN |
| 220 | 564 | X14356 | 62 | Hs.77424 | high affinity Fc receptor (FcRI) /cds = (36, 116 |
| 809 | 565 | AF267856 | 63 | Hs.8084 | HT033 mRNA, complete cds /cds = (203, 931) |
| 1048 | 566 | AK025306 | 64 | Hs.2083 | cDNA: FLJ21653 fis, clone COL08586, highly similar to HUMKINCDC protein kinase mRNA /cds = UNKNOWN |
| 1262 | 567 | AL162068 | 65 | Hs.302649 | HSP22-like protein interacting protein (LOC64165), mRNA /cds = (0, 155) |
| 2685 | 568 | NM_004768 | 66 | Hs.11482 | splicing factor, arginine/serine-rich 11 (SFRS11), mRNA /cds = (83, 1537) |

TABLE 2E-continued

| OID | SEQ ID 50mer | ACC | SEQ ID Full length | HS | Gene |
|---|---|---|---|---|---|
| 2793 | 569 | NM_005594 | 67 | Hs.158164 | transporter 1, ATP-binding cassette, sub-family B (MDR/TAP) (TAP1), mRNA /cds = (30, 2456) |
| 5210 | 570 | AI440234 | 68 | Hs.9614 | Nucleophosmin (probe bad, mutations, wrong clone used) (nucleolar phosphoprotein B23, numatrin) |
| 5732 | 571 | AW194379 | 69 | Hs.203755 | xm08h07.x1 cDNA, 3' end /clone = IMAGE: 2683645 /clone_end = 3' |
| 2829 | 572 | NM_005826 | 70 | Hs.15265 | heterogeneous nuclear ribonucleoprotein R (HNRPR), mRNA /cds = (90, 1991) |
| 5318 | 573 | AI568695 | 71 | Hs.75969 | proline-rich protein with nuclear targeting signal (B4-2), mRNA /cds = (113, 1096) |
| 7965 | 574 | AL110225 | 72 | Hs.89434 | drebrin 1 (DBN1), mRNA /cds = (97, 2046) |
| 1198 | 575 | AL110151 | 73 | Hs.128797 | mRNA; cDNA DKFZp586D0824 (from clone DKFZp586D0824); partial cds /cds = (0, 1080) |
| 2933 | 576 | NM_006495 | 74 | Hs.5509 | ecotropic viral integration site 2B (EVI2B), mRNA /cds = (0, 1346) |
| 1846 | 577 | M74002 | 75 | Hs.11482 | splicing factor, arginine/serine-rich 11 (SFRS11), mRNA /cds = (83, 1537) |
| 917 | 578 | AK002173 | 76 | Hs.5518 | cDNA FLJ11311 fis, clone PLACE1010102 /cds = UNKNOWN |
| 1037 | 579 | AK024976 | 77 | Hs.323378 | coated vesicle membrane protein (RNP24), mRNA /cds = (27, 632) |
| 1415 | 580 | BC000967 | 78 | Hs.195870 | chronic myelogenous leukemia tumor antigen 66 mRNA, complete cds, alternatively spliced /cds = (232, 1983) |
| 3291 | 581 | NM_016312 | 79 | Hs.334811 | Npw38-binding protein NpwBP (LOC51729), mRNA /cds = (143, 2068) |
| 3759 | 582 | X57347 | 80 | Hs.74405 | tyrosine 3-monooxygenase/tryptophan 5-monooxygenase activation protein, theta polypeptide (YWHAQ), mRNA /cds = (100, 837) |
| 4045 | 583 | BG424974 | 81 | Hs.292457 | Homo sapiens, clone MGC: 16362 IMAGE: 3927795, mRNA, complete cds /cds = (498, 635) |
| 4155 | 584 | U89387 | 82 | Hs.194638 | polymerase (RNA) II (DNA directed) polypeptide D (POLR2D), mRNA /cds = (30, 458) |
| 153 | 585 | AB034205 | 83 | Hs.278670 | Acid-inducible phosphoprotein |
| 4111 | 586 | XM_008062 | 84 | Hs.17279 | tyrosylprotein sulfotransferase 1 (TPST1), mRNA /cds = (81, 1193) |
| 3263 | 587 | NM_016099 | 85 | Hs.7953 | HSPC041 protein (LOC51125), mRNA /cds = (141, 455) |
| 3510 | 588 | NM_022898 | 86 | Hs.57987 | B-cell lymphoma/leukaemia 11B (BCL11B), mRNA /cds = (267, 2738) |
| 2956 | 589 | NM_006759 | 87 | Hs.77837 | UDP-glucose pyrophosphorylase 2 (UGP2), mRNA /cds = (84, 1610) |
| 694 | 590 | AF079566 | 88 | Hs.4311 | SUMO-1 activating enzyme subunit 2 (UBA2), mRNA /cds = (25, 1947) |
| 2055 | 591 | NM_001024 | 89 | Hs.182979 | cDNA: FLJ22838 fis, clone KAIA4494, highly similar to HUML12A ribosomal protein L12 mRNA |
| 3336 | 592 | NM_017761 | 90 | Hs.7862 | hypothetical protein FLJ20312 (FLJ20312), mRNA /cds = (133, 552) |
| 3595 | 593 | U15085 | 91 | Hs.1162 | major histocompatibility complex, class II, DM beta (HLA-DMB), mRNA /cds = (233, 1024) |
| 6004 | 594 | AW572538 | 92 | Hs.42915 | ARP2 (actin-related protein 2, yeast) homolog (ACTR2), mRNA /cds = (74, 1258) |
| 1060 | 595 | AK025557 | 93 | Hs.110771 | cDNA: FLJ21904 fis, clone HEP03585 /cds = UNKNOWN |
| 4654 | 596 | NM_003854 | 94 | Hs.102865 | interleukin 1 receptor-like 2 (IL1RL2), mRNA /cds = (134, 1822) |
| 721 | 597 | AF116679 | 95 | Hs.288036 | tRNA isopentenylpyrophosphate transferase (IPT), mRNA /cds = (60, 1040) |
| 743 | 598 | AF148537 | 96 | Hs.65450 | reticulon 4a mRNA, complete cds /cds = (141, 3719) |
| 3348 | 599 | NM_017892 | 97 | Hs.107213 | hypothetical protein FLJ20585 (FLJ20585), mRNA /cds = (99, 746) |
| 2020 | 600 | NM_000967 | 98 | Hs.119598 | ribosomal protein L3 (RPL3), mRNA /cds = (6, 1217) |
| 6847 | 601 | NM_000971 | 99 | Hs.153 | ribosomal protein L7 (RPL7), mRNA /cds = (10, 756) |
| 626 | 602 | AF012872 | 100 | Hs.334874 | phosphatidylinositol 4-kinase 230 (pi4K230) mRNA, complete cds /cds = (0, 6134) |
| 1469 | 603 | BC004900 | 101 | Hs.151242 | serine (or cysteine) proteinase inhibitor, clade G (C1 inhibitor), member 1 (SERPING1), mRNA /cds = (60, 1562) |
| 2277 | 604 | NM_002298 | 102 | Hs.76506 | lymphocyte cytosolic protein 1 (L-plastin) (LCP1), mRNA /cds = (173, 2056) |
| 3765 | 605 | X59405 | 103 | Hs.83532 | H. sapiens, gene for Membrane cofactor protein /cds = UNKNOWN |
| 4444 | 606 | AL049935 | 104 | Hs.301763 | mRNA; cDNA DKFZp564O1116 (from clone DKFZp564O1116) /cds = UNKNOWN |
| 3431 | 607 | NM_017860 | 105 | Hs.79457 | hypothetical protein FLJ20519 (FLJ20519), mRNA /cds = (74, 604) |
| 1686 | 608 | J04142 | 106 | Hs.1799 | CD1D antigen, d polypeptide (CD1D), mRNA /cds = (164, 1171) |
| 3267 | 609 | NM_016127 | 107 | Hs.279921 | HSPC035 protein (LOC51669), mRNA /cds = (16, 1035) |

TABLE 2E-continued

| OID | SEQ ID 50mer | ACC | SEQ ID Full length | HS | Gene |
|---|---|---|---|---|---|
| 970 | 610 | AK023379 | 108 | Hs.155160 | *Homo sapiens*, Similar to splicing factor, arginine/serine-rich 2 (SC-35) |
| 1710 | 611 | L11284 | 109 | Hs.3446 | mitogen-activated protein kinase kinase 1 (MAP2K1), mRNA /cds = (72, 1253) |
| 2358 | 612 | NM_002710 | 110 | Hs.79081 | protein phosphatase 1, catalytic subunit, gamma isoform (PPP1CC), mRNA /cds = (154, 1125) |
| 2635 | 613 | NM_004380 | 111 | Hs.23598 | CREB binding protein (Rubinstein-Taybi syndrome) (CREBBP), mRNA /cds = (198, 7526) |
| 8112 | 614 | AW028193 | 112 | Hs.135872 | wv61h08.x1 cDNA, 3' end /clone = IMAGE: 2534079 /clone_end = 3' |
| 2124 | 615 | NM_001436 | 113 | Hs.99853 | fibrillarin (FBL), mRNA /cds = (59, 1024) |
| 453 | 616 | AB007916 | 114 | Hs.214646 | mRNA for KIAA0447 protein, partial cds /cds = (233, 1633) |
| 1250 | 617 | AL137681 | 115 | Hs.173912 | eukaryotic translation initiation factor 4A, isoform 2 (EIF4A2), mRNA /cds = (15, 1238) |
| 1451 | 618 | BC003090 | 116 | Hs.75193 | COP9 homolog (COP9), mRNA /cds = (49, 678) |
| 3596 | 619 | U15173 | 117 | Hs.155596 | BCL2/adenovirus E1B 19 kD-interacting protein 2 (BNIP2), mRNA /cds = (211, 1155) |
| 3127 | 620 | NM_014210 | 118 | Hs.70499 | ecotropic viral integration site 2A (EVI2A), mRNA /cds = (219, 917) |
| 2049 | 621 | NM_001011 | 119 | Hs.301547 | ribosomal protein S7 (RPS7), mRNA /cds = (81, 665) |
| 3585 | 622 | U07802 | 120 | Hs.78909 | Tis11d gene, complete cds /cds = (291, 1739) |
| 5466 | 623 | AI817153 | 121 | Hs.86693 | EST380760 cDNA |
| 2962 | 624 | NM_006791 | 122 | Hs.6353 | MORF-related gene 15 (MRG15), mRNA /cds = (131, 1102) |
| 4678 | 625 | NM_004500 | 123 | Hs.182447 | heterogeneous nuclear ribonucleoprotein C (C1/C2) (HNRPC), transcript variant 1, mRNA /cds = (191, 1102) |
| 1768 | 626 | M16660 | 124 | Hs.318720 | *Homo sapiens*, clone MGC: 12387 IMAGE: 3933019, mRNA, complete cds /cds = (63, 863) |
| 2044 | 627 | NM_001000 | 125 | Hs.300141 | cDNA FLJ14163 fis, clone NT2RP1000409 /cds = UNKNOWN |
| 4486 | 628 | BC008737 | 126 | Hs.164280 | *Homo sapiens*, Similar to solute carrier family 25 (mitochondrial carrier; adenine nucleotide translocator), member 5, clone MGC: 3042 IMAGE: 3342722, mRNA, complete cds /cds = (88, 984) |
| 6028 | 629 | BE222392 | 127 | Hs.79914 | lumican (LUM), mRNA /cds = (84, 1100) |
| 7958 | 630 | BC010112 | 128 | Hs.79037 | *Homo sapiens*, heat shock 60 kD protein 1 (chaperonin), clone MGC: 19755 IMAGE: 3630225, mRNA, complete cds /cds = (1705, 3396) |
| 1062 | 631 | AK025586 | 129 | Hs.27268 | cDNA: FLJ21933 fis, clone HEP04337 /cds = UNKNOWN |
| 3220 | 632 | NM_015057 | 130 | Hs.151411 | KIAA0916 protein (KIAA0916), mRNA /cds = (146, 14071) |
| 3590 | 633 | U10550 | 131 | Hs.79022 | GTP-binding protein overexpressed in skeletal muscle (GEM), mRNA /cds = (213, 1103) |
| 2035 | 634 | NM_000986 | 132 | Hs.184582 | DPP7 alveolar r |
| 2039 | 635 | NM_000993 | 133 | Hs.184014 | ribosomal protein L31 (RPL31), mRNA /cds = (7, 384) |
| 2170 | 636 | NM_001688 | 134 | Hs.81634 | ATP synthase, H+ transporting, mitochondrial F0 complex, subunit b, isoform 1 (ATP5F1), mRNA |
| 4311 | 637 | AI356505 | 135 | Hs.228874 | qz22b04.x1 cDNA, 3' end /clone = IMAGE: 2027599 /clone_end = 3' |
| 7945 | 638 | AF119850 | 136 | Hs.2186 | *Homo sapiens*, eukaryotic translation elongation factor 1 gamma, clone MGC: 4501 IMAGE: 2964623, mRNA, complete cds /cds = (2278, 3231) |
| 739 | 639 | AF132197 | 137 | Hs.301824 | hypothetical protein PRO1331 (PRO1331), mRNA /cds = (422, 616) |
| 2986 | 640 | NM_006925 | 138 | Hs.166975 | splicing factor, arginine/serine-rich 5 (SFRS5), mRNA /cds = (218, 541) |
| 4589 | 641 | NM_002001 | 139 | Hs.897 | Fc fragment of IgE, high affinity I, receptor for; alpha polypeptide (FCER1A), mRNA /cds = (106, 879) |
| 5066 | 642 | W00466 | 140 | Hs.44189 | yz99f01.s1 cDNA, 3' end /clone = IMAGE: 291193 /clone_end = 3' |
| 1588 | 643 | D17042 | 141 | Hs.50651 | Janus kinase 1 (a protein tyrosine kinase) (JAK1), mRNA /cds = (75, 3503) |
| 2505 | 644 | NM_003380 | 142 | Hs.297753 | vimentin (VIM), mRNA /cds = (122, 1522) |
| 3322 | 645 | NM_016824 | 143 | Hs.324470 | adducin 3 (gamma) (ADD3), transcript variant 1, mRNA /cds = (31, 2151) |
| 5332 | 646 | AI581383 | 144 | Hs.327922 | to71c02.x1 cDNA, 3' end /clone = IMAGE: 2183714 /clone_end = 3' |
| 4165 | 647 | BC005913 | 145 | Hs.1074 | surfactant, pulmonary-associated protein C (SFTPC), mRNA /cds = (27, 620) |
| 4691 | 648 | NM_004811 | 146 | Hs.49587 | leupaxin (LPXN), mRNA /cds = (93, 1253) |
| 1265 | 649 | AL357536 | 147 | Hs.3576 | *Homo sapiens*, Similar to RIKEN cDNA 5730494N06 gene, clone MGC: 13348 IMAGE: 4132400, mRNA, complete cds /cds = (132, 494) |
| 3501 | 650 | NM_022570 | 148 | Hs.161786 | C-type (calcium dependent, carbohydrate-recognition domain) lectin, superfamily member 12 (CLECSF12), mRNA /cds = (71, 676) |

TABLE 2E-continued

| OID | SEQ ID 50mer | ACC | SEQ ID Full length | HS | Gene |
|---|---|---|---|---|---|
| 2636 | 651 | NM_004396 | 149 | Hs.76053 | DEAD/H (Asp-Glu-Ala-Asp/His) box polypeptide 5 (RNA helicase, 68 kD) (DDX5), mRNA /cds = (170, 2014) |
| 1101 | 652 | AK026372 | 150 | Hs.143631 | cDNA: FLJ22719 fis, clone HSI14307 /cds = UNKNOWN |
| 4131 | 653 | XM_012059 | 151 | Hs.154938 | hypothetical protein MDS025 (MDS025), mRNA /cds = (5, 769) |
| 4130 | 654 | XM_011914 | 152 | Hs.180450 | ribosomal protein S24 (RPS24), transcript variant 1, mRNA /cds = (37, 429) |
| 8031 | 655 | NM_020414 | 153 | Hs.286233 | sperm autoantigenic protein 17 (SPA17), mRNA /cds = (1210, 1665) |
| 3560 | 656 | S73591 | 154 | Hs.179526 | upregulated by 1,25-dihydroxyvitamin D-3 (VDUP1), mRNA /cds = (221, 1396) |
| 1675 | 657 | J00194 | 155 | Hs.76807 | major histocompatibility complex, class II, DR alpha (HLA DRA), mRNA /cds = (26, 790) |
| 924 | 658 | AK021715 | 156 | Hs.271541 | cDNA FLJ11653 fis, clone HEMBA1004538 /cds = UNKNOWN |
| 1144 | 659 | AK027187 | 157 | Hs.289071 | cDNA: FLJ22245 fis, clone HRC02612 /cds = UNKNOWN |
| 1212 | 660 | AL117595 | 158 | Hs.4055 | mRNA; cDNA DKFZp564C2063 (from clone DKFZp564C2063) /cds = UNKNOWN |
| 2383 | 661 | NM_002823 | 159 | Hs.250655 | prothymosin, alpha (gene sequence 28) (PTMA), mRNA /cds = (155, 487) |
| 2627 | 662 | NM_004327 | 160 | Hs.234799 | breakpoint cluster region (BCR), transcript variant 1, mRNA /cds = (488, 4303) |
| 3343 | 663 | NM_017830 | 161 | Hs.132071 | ovarian carcinoma immunoreactive antigen (OCIA), mRNA /cds = (167, 904) |
| 3717 | 664 | X06557 | 162 | Hs.2014 | mRNA for T-cell receptor delta /cds = UNKNOWN |
| 4244 | 665 | AI146787 | 163 | Hs.156601 | qb83f02.x1 cDNA, 3' end /clone = IMAGE: 1706715 /clone_end = 3' |
| 5323 | 666 | AI568771 | 164 | Hs.327876 | th15h04.x1 cDNA, 3' end /clone = IMAGE: 2118391 /clone_end = 3' |
| 5733 | 667 | AW195119 | 165 | Hs.253151 | xn66b07.x1 cDNA, 3' end /clone = IMAGE: 2699413 /clone_end = 3' |
| 3292 | 668 | NM_016316 | 166 | Hs.110347 | REV1 (yeast homolog)-like (REV1L), mRNA /cds = (212, 3967) |
| 1324 | 669 | AV724531 | 167 | Hs.76728 | 602570065F1 cDNA, 5' end /clone = IMAGE: 4694321 /clone_end = 5' |
| 915 | 670 | AK002059 | 168 | Hs.92918 | hypothetical protein (BM-009), mRNA /cds = (385, 1047) |
| 2132 | 671 | NM_001503 | 169 | Hs.272529 | glycosylphosphatidylinositol specific phospholipase D1 (GPLD1), mRNA /cds = (32, 2557) |
| 4221 | 672 | AA251806 | 170 | Hs.177712 | zs09c03.s1 cDNA, 3' end /clone = IMAGE: 684676 /clone_end = 3' |
| 2626 | 673 | NM_004315 | 171 | Hs.75811 | N-acylsphingosine amidohydrolase (acid ceramidase) (ASAH), mRNA /cds = (17, 1204) |
| 2633 | 674 | NM_004371 | 172 | Hs.75887 | coatomer protein complex, subunit alpha (COPA), mRNA /cds = (466, 4140) |
| 664 | 675 | AF054284 | 173 | Hs.334826 | splicing factor 3b, subunit 1, 155 kD (SF3B1), mRNA /cds = (0, 3914) |
| 6046 | 676 | BE613237 | 174 | Hs.146381 | RNA binding motif protein, X chromosome (RBMX), mRNA /cds = (11, 1186) |
| 278 | 677 | NM_003367 | 175 | Hs.93649 | upstream transcription factor 2, c-fos intera |
| 469 | 678 | AB014522 | 176 | Hs.11238 | mRNA for KIAA0622 protein, partial cds /cds = (0, 3869) |
| 5713 | 679 | AW137104 | 177 | Hs.8121 | Notch (*Drosophila*) homolog 2 (NOTCH2), mRNA /cds = (12, 7427) |
| 7443 | 680 | BF897042 | 178 | Hs.120219 | FLJ32028 hypothetical protein FLJ32028 |
| 1447 | 681 | BC002900 | 179 | Hs.181309 | proteasome (prosome, macropain) subunit, alpha type, 2 (PSMA2), mRNA /cds = (0, 704) |
| 6304 | 682 | AL578975 | 180 | Hs.5057 | AL578975 cDNA /clone = CS0DK012YN01-(3-prime) |
| 2037 | 683 | NM_000988 | 181 | Hs.111611 | ribosomal protein L27 (RPL27), mRNA /cds = (17, 427) |
| 2550 | 684 | NM_003769 | 182 | Hs.77608 | splicing factor, arginine/serine-rich 9 (SFRS9), mRNA /cds = (52, 717) |
| 3679 | 685 | U94855 | 183 | Hs.7811 | eukaryotic translation initiation factor 3, subunit 5 (epsilon, 47 kD) (EIF3S5), mRNA /cds = (6, 1079) |
| 1337 | 686 | AV749844 | 184 | Hs.26670 | PAC clone RP3-515N1 from 22q11.2-q22 /cds = (0, 791) |
| 1453 | 687 | BC003352 | 185 | Hs.326456 | hypothetical protein FLJ20030 (FLJ20030), mRNA /cds = (1, 1239) |
| 1298 | 688 | AU135154 | 186 | Hs.172028 | a disintegrin and metalloproteinase domain 10 (ADAM10), mRNA /cds = (469, 2715) |
| 779 | 689 | AF208850 | 187 | Hs.82911 | BM-008 mRNA, complete cds /cds = (341, 844) |
| 1602 | 690 | D29805 | 188 | Hs.198248 | UDP-Gal:betaGlcNAc beta 1,4-galactosyltransferase, polypeptide 1 (B4GALT1), mRNA /cds = (72, 1268) |
| 2867 | 691 | NM_006098 | 189 | Hs.5662 | guanine nucleotide binding protein (G protein), beta polypeptide 2-like 1 (GNB2L1), mRNA /cds = (95, 1048) |
| 2183 | 692 | NM_001755 | 190 | Hs.179881 | core-binding factor, beta subunit (CBFB), transcript variant 2, mRNA /cds = (11, 559) |
| 3033 | 693 | NM_007355 | 191 | Hs.74335 | heat shock 90 kD protein 1, beta (HSPCB), mRNA /cds = (0, 2174) |

TABLE 2E-continued

| OID | SEQ ID 50mer | ACC | SEQ ID Full length | HS | Gene |
|---|---|---|---|---|---|
| 3692 | 694 | W47229 | 192 | Hs.173334 | ELL-RELATED RNA POLYMERASE II, ELONGATION FACTOR (ELL2), mRNA /cds = (0, 1922) |
| 3741 | 695 | X51345 | 193 | Hs.198951 | jun B proto-oncogene (JUNB), mRNA /cds = (253, 1296) |
| 5114 | 696 | AI364677 | 194 | Hs.368853 | ESTs |
| 5135 | 697 | AI380594 | 195 | Hs.231261 | tf95h06.x1 cDNA, 3' end /clone = IMAGE: 2107067 /clone_end = 3' |
| 2158 | 698 | NM_001641 | 196 | Hs.73722 | APEX nuclease (multifunctional DNA repair enzyme) (APEX), mRNA /cds = (205, 1161) |
| 2369 | 699 | NM_002786 | 197 | Hs.82159 | proteasome (prosome, macropain) subunit, alpha type, 1 (PSMA1), mRNA /cds = (105, 896) |
| 1676 | 700 | J02621 | 198 | Hs.251064 | high-mobility group (nonhistone chromosomal) protein 14 (HMG14), mRNA /cds = (150, 452) |
| 3414 | 701 | NM_019111 | 199 | Hs.76807 | major histocompatibility complex, class II, DR alpha (HLA DRA), mRNA /cds = (26, 790) |
| 801 | 702 | AF248966 | 200 | Hs.183434 | ATPase, H+ transporting, lysosomal (vacuolar proton pump) membrane sector associated protein M8-9 (APT6M8-9) |
| 1605 | 703 | D31767 | 201 | Hs.75416 | DAZ associated protein 2 (DAZAP2), mRNA |
| 2974 | 704 | NM_006839 | 202 | Hs.78504 | inner membrane protein, mitochondrial (mitofilin) (IMMT), mRNA /cds = (92, 2368) |
| 5333 | 705 | AI581732 | 203 | Hs.229918 | ar74f03.x1 cDNA, 3' end /clone = IMAGE: 2128349 /clone_end = 3' |
| 3411 | 706 | NM_019059 | 204 | Hs.274248 | hypothetical protein FLJ20758 (FLJ20758), mRNA /cds = (464, 1306) |
| 2061 | 707 | NM_001033 | 205 | Hs.2934 | ribonucleotide reductase M1 polypeptide (RRM1), mRNA /cds = (187, 2565) |
| 2361 | 708 | NM_002719 | 206 | Hs.171734 | protein phosphatase 2, regulatory subunit B (B56), gamma isoform (PPP2R5C), mRNA /cds = (88, 1632) |
| 2553 | 709 | NM_003791 | 207 | Hs.75890 | membrane-bound transcription factor protease, site 1 (MBTPS1), mRNA /cds = (496, 3654) |
| 2068 | 710 | NM_001105 | 208 | Hs.150402 | activin A receptor, type I (ACVR1), mRNA /cds = (340, 1869) |
| 4153 | 711 | BG179517 | 209 | Hs.99093 | chromosome 19, cosmid R28379 /cds = (0, 633) |
| 6179 | 712 | BF940103 | 210 | Hs.26136 | hypothetical protein MGC14156 (MGC14156), mRNA /cds = (82, 426) |
| 668 | 713 | AF061736 | 211 | Hs.169895 | ubiquitin-conjugating enzyme E2L 6 (UBE2L6), mRNA /cds = (47, 508) |
| 981 | 714 | AK023680 | 212 | Hs.17448 | cDNA FLJ13618 fis, clone PLACE1010925 /cds = UNKNOWN |
| 2102 | 715 | NM_001295 | 213 | Hs.301921 | chemokine (C-C motif) receptor 1 (CCR1), mRNA /cds = (62, 1129) |
| 2560 | 716 | NM_003811 | 214 | Hs.1524 | tumor necrosis factor (ligand) superfamily, member 9 (TNFSF9), mRNA /cds = (3, 767) |
| 3701 | 717 | X02812 | 215 | Hs.1103 | transforming growth factor, beta 1 (TGFB1), mRNA /cds = (841, 2016) |
| 4601 | 718 | NM_002205 | 216 | Hs.149609 | integrin, alpha 5 (fibronectin receptor, alpha polypeptide) (ITGA5), mRNA /cds = (23, 3172) |
| 5468 | 719 | AI818777 | 217 | Hs.229990 | wl11f10.x1 cDNA, 3' end /clone = IMAGE: 2424619 /clone_end = 3' |
| 7641 | 720 | NM_005892 | 218 | Hs.100217 | formin-like (FMNL), mRNA /cds = (39, 1430) |
| 8015 | 721 | M26252 | 219 | Hs.198281 | pyruvate kinase, muscle (PKM2), mRNA |
| 446 | 722 | AB002377 | 220 | Hs.32556 | mRNA for KIAA0379 protein, partial cds /cds = (0, 3180) |
| 4359 | 723 | AI381586 | 221 | Hs.87908 | Snf2-related CBP activator protein (SRCAP), mRNA /cds = (210, 9125) |
| 5034 | 724 | BG760189 | 222 | Hs.37617 | 602144947F1 cDNA, 5' end /clone = IMAGE: 4308683 /clone_end = 5' |
| 4752 | 725 | NM_006913 | 223 | Hs.216354 | ring finger protein 5 (RNF5), mRNA /cds = (0, 542) |
| 765 | 726 | AF189011 | 224 | Hs.49163 | ribonuclease III (RN3) mRNA, complete cds /cds = (245, 4369) |
| 949 | 727 | AK022834 | 225 | Hs.58488 | catenin (cadherin-associated protein), alpha-like 1 (CTNNAL1), mRNA /cds = (43, 2247) |
| 2398 | 728 | NM_002878 | 226 | Hs.125244 | RAD51 (S. cerevisiae)-like 3 (RAD51L3), mRNA /cds = (124, 993) |
| 7445 | 729 | BF899464 | 227 | NA | IL5-MT0211-011200-317-f03 MT0211 cDNA, mRNA sequence |
| 7748 | 730 | AW452510 | 228 | Hs.300479 | UI-H-BW1-ame-a-12-0-UI.s1 cDNA, 3' end /clone = IMAGE: 3069598 /clone_end = 3' |
| 2778 | 731 | NM_005508 | 229 | Hs.184926 | chemokine (C-C motif) receptor 4 (CCR4), mRNA /cds = (182, 1264) |
| 3734 | 732 | X16354 | 230 | Hs.50964 | mRNA for transmembrane carcinoembryonic antigen BGPa (formerly TM1-CEA) /cds = (72, 1652) |
| 4364 | 733 | AA581115 | 231 | Hs.291129 | oe10d02.s1 cDNA /clone = IMAGE: 1385475 |
| 2776 | 734 | NM_005485 | 232 | Hs.271742 | ADP-ribosyltransferase (NAD+; poly (ADP-ribose) polymerase)-like 3 (ADPRTL3), mRNA /cds = (246, 1847) |

TABLE 2E-continued

| OID | SEQ ID 50mer | ACC | SEQ ID Full length | HS | Gene |
|---|---|---|---|---|---|
| 2826 | 735 | NM_005816 | 233 | Hs.142023 | T cell activation, increased late expression (TACTILE), mRNA /cds = (928, 2637) |
| 3987 | 736 | BG033294 | 234 | Hs.118787 | transforming growth factor, beta-induced, 68 kD (TGFBI), mRNA /cds = (47, 2098) |
| 4501 | 737 | K01566 | 235 | Hs.69771 | B-factor, properdin |
| 6244 | 738 | T25714 | 236 | Hs.330530 | ESTDIR309 cDNA, 3' end /clone = CDDIRX9 |
| 7346 | 739 | NM_022873 | 237 | Hs.265827 | interferon, alpha-inducible protein (clone IFI-6-16) (G1P3), transcript variant 3, mRNA /cds = (107, 523) |
| 3827 | 740 | X99699 | 238 | Hs.139262 | XIAP associated factor-1 (HSXIAPAF1), mRNA /cds = (0, 953) |
| 676 | 741 | AF067519 | 239 | Hs.307357 | PITSLRE protein kinase beta SV1 isoform (CDC2L2) mRNA, complete cds /cds = (79, 2412) |
| 4988 | 742 | BG387694 | 240 | Hs.170980 | cell cycle progression 2 protein (CPR2), mRNA /cds = (126, 1691) |
| 707 | 743 | AF104032 | 241 | Hs.184601 | L-type amino acid transporter subunit LAT1 mRNA, complete cds /cds = (66, 1589) |
| 7351 | 744 | NM_012177 | 242 | Hs.272027 | F-box only protein 5 (FBXO5), mRNA /cds = (61, 1404) |
| 1158 | 745 | AL042370 | 243 | Hs.79709 | phosphotidylinositol transfer protein (PITPN), mRNA /cds = (216, 1028) |
| 4489 | 746 | BC009469 | 244 | Hs.287797 | mRNA for FLJ00043 protein, partial cds /cds = (0, 4248) |
| 4924 | 747 | AA319163 | 245 | Hs.424299 | RPLP1; germinal |
| 6275 | 748 | AI393970 | 246 | Hs.76239 | hypothetical protein FLJ20608 (FLJ20608), mRNA /cds = (81, 680) |
| 3157 | 749 | NM_014481 | 247 | Hs.154149 | *Homo sapiens*, apurinic/apyrimidinic endonuclease(APEX nuclease)-like 2 protein, clone MGC: 1418 IMAGE: 3139156, mRNA, complete cds |
| 3338 | 750 | NM_017774 | 248 | Hs.306668 | cDNA FLJ14089 fis, clone MAMMA1000257 /cds = UNKNOWN |
| 3346 | 751 | NM_017859 | 249 | Hs.39850 | hypothetical protein FLJ20517 (FLJ20517), mRNA /cds = (44, 1690) |
| 3544 | 752 | R44202 | 250 | Hs.240013 | mRNA; cDNA DKFZp547A166 (from clone DKFZp547A166) /cds = UNKNOWN |
| 4626 | 753 | NM_002904 | 251 | Hs.106061 | RD RNA-binding protein (RDBP), mRNA /cds = (108, 1250) |
| 7339 | 754 | AL133642 | 252 | Hs.241471 | mRNA; cDNA DKFZp586G1721 (from clone DKFZp586G1721); partial cds /cds = (0, 669) |
| 109 | 755 | AF160973 | 253 | Hs.258503 | P53 inducible protein |
| 285 | 756 | NM_001972 | 254 | Hs.99863 | elastase 2, neutrophil (ELA2), |
| 406 | 757 | AA282774 | 255 | NA | cDNA clone IMAGE: 713136 5' |
| 436 | 758 | AB000115 | 256 | Hs.75470 | hypothetical protein, expressed in osteoblast (GS3686), mRNA /cds = (241, 1482) |
| 860 | 759 | AJ277247 | 257 | Hs.287369 | interleukin 22 (IL22), mRNA /cds = (71, 610) |
| 1610 | 760 | D38081 | 258 | Hs.89887 | thromboxane A2 receptor (TBXA2R), mRNA /cds = (991, 2022) |
| 2096 | 761 | NM_001250 | 259 | Hs.25648 | tumor necrosis factor receptor superfamily, member 5 (TNFRSF5), mRNA /cds = (47, 880) |
| 5288 | 762 | AI524266 | 260 | Hs.230874 | th11g12.x1 cDNA, 3' end /clone = IMAGE: 2118022 /clone_end = 3' |
| 5534 | 763 | AL573787 | 261 | Hs.21732 | AL573787 cDNA /clone = CS0DI055YM17-(3-prime) |
| 7347 | 764 | AK001503 | 262 | Hs.265891 | cDNA FLJ10641 fis, clone NT2RP2005748 /cds = UNKNOWN |
| 279 | 765 | X04430 | 263 | Hs.93913 | IFN-beta 2a mRNA for interferon-beta-2, T-cells, macrophages |
| 349 | 766 | AF480557 | 264 | NA | 142E4 |
| 1284 | 767 | AL550229 | 265 | Hs.271599 | cDNA FLJ12347 fis, clone MAMMA1002298 /cds = UNKNOWN |
| 1328 | 768 | AV727063 | 266 | Hs.245798 | hypothetical protein DKFZp564I0422 (DKFZP564I0422), mRNA /cds = (510, 1196) |
| 1939 | 769 | NM_000389 | 267 | Hs.179665 | cyclin-dependent kinase inhibitor 1A (p21, Cip1) (CDKN1A), mRNA /cds = (75, 569) |
| 2186 | 770 | NM_001761 | 268 | Hs.1973 | cyclin F (CCNF), mRNA /cds = (43, 2403) |
| 2364 | 771 | NM_002741 | 269 | Hs.2499 | protein kinase C-like 1 (PRKCL1), mRNA /cds = (84, 2912) |
| 2400 | 772 | NM_002880 | 270 | Hs.279474 | HSPC070 protein (HSPC070), mRNA /cds = (331, 1581) |
| 3146 | 773 | NM_014373 | 271 | Hs.97101 | putative G protein-coupled receptor (GPCR150), mRNA /cds = (321, 1337) |
| 3633 | 774 | U53347 | 272 | Hs.183556 | solute carrier family 1 (neutral amino acid transporter), member 5 (SLC1A5), mRNA /cds = (590, 2215) |
| 3689 | 775 | W19201 | 273 | Hs.17778 | neuropilin 2 (NRP2), mRNA /cds = (0, 2780) |
| 3695 | 776 | W79598 | 274 | Hs.163846 | putative N6-DNA-methyltransferase (N6AMT1), mRNA /cds = (29, 673) |
| 4079 | 777 | XM_001939 | 275 | Hs.55468 | H4 histone, family 2 |
| 4254 | 778 | AI270476 | 276 | Hs.270341 | 602307338F1 cDNA, 5' end /clone = IMAGE: 4398848 /clone_end = 5' |
| 4316 | 779 | AA992299 | 277 | Hs.129332 | ot53b06.s1 cDNA, 3' end /clone = IMAGE: 1620467 /clone_end = 3' |

TABLE 2E-continued

| OID | SEQ ID 50mer | ACC | SEQ ID Full length | HS | Gene |
|---|---|---|---|---|---|
| 4394 | 780 | AF044595 | 278 | Hs.248078 | lymphocyte-predominant Hodgkin's disease case #7 immunoglobulin heavy chain gene, variable region |
| 4492 | 781 | BI091076 | 279 | Hs.127128 | ok13e12.s1 cDNA, 3' end /clone = IMAGE: 1507726 /clone_end = 3' |
| 4498 | 782 | H13491 | 280 | Hs.303450 | yj15f02.r1 cDNA, 5' end /clone = IMAGE: 148827 /clone_end = 5' |
| 4507 | 783 | M55420 | 281 | Hs.247930 | IgE chain, last 2 exons |
| 4778 | 784 | NM_014271 | 282 | Hs.241385 | interleukin 1 receptor accessory protein-like 1 (IL1RAPL1), mRNA /cds = (510, 2600) |
| 5126 | 785 | AI378091 | 283 | Hs.369056 | ESTs |
| 5138 | 786 | AI381601 | 284 | Hs.159025 | td05g03.x1 cDNA, 3' end /clone = IMAGE: 2074804 /clone_end = 3' |
| 5347 | 787 | AI634972 | 285 | Hs.319825 | 602021477F1 cDNA, 5' end /clone = IMAGE: 4156915 /clone_end = 5' |
| 5561 | 788 | AW005376 | 286 | Hs.173280 | ws94a12.x1 cDNA, 3' end /clone = IMAGE: 2505598 /clone_end = 3' |
| 5706 | 789 | AW088500 | 287 | Hs.389655 | EST, Weakly similar to A35098 MHC class III histocompatibility antigen HLA-B-associated transcript 3 |
| 5735 | 790 | AW195270 | 288 | Hs.330019 | xn67c04.x1 cDNA, 3' end /clone = IMAGE: 2699526 /clone_end = 3' |
| 5836 | 791 | AW296797 | 289 | Hs.255579 | UI-H-BW0-ajb-e-07-0-UI.s1 cDNA, 3' end /clone = IMAGE: 2731117 /clone_end = 3' |
| 7438 | 792 | BF827734 | 290 | Hs.156766 | ESTs |
| 8009 | 793 | M11233 | 291 | Hs.79572 | cathepsin D (lysosomal aspartyl protease) (CTSD), mRNA /cds = (2, 1240) |
| 1182 | 794 | AL050218 | 292 | Hs.15020 | DNA sequence from clone 51J12 on chromosome 6q26- |
| 3260 | 795 | NM_016063 | 293 | Hs.32826 | CGI-130 protein (LOC51020), mRNA /cds = (63, 575) |
| 6702 | 796 | BU678165 | 294 | Hs.377992 | 479H5, not in ref seq, Rab geranylgeranyltransferase, alpha subunit (RABGGTA), |
| 1186 | 797 | AL050371 | 295 | Hs.8128 | phosphatidylserine decarboxylase (PISD), mRNA /cds = (223, 1350) |
| 330 | 798 | NM_152545 | 296 | Hs.335815 | 62C9, hypothetical protein FLJ31695 |
| 4107 | 799 | XM_007156 | 297 | Hs.159492 | sacsin (SACS) gene, complete cds /cds = (76, 11565) |
| 4780 | 800 | NM_014339 | 298 | Hs.129751 | interleukin 17 receptor (IL17R), mRNA /cds = (32, 2632) |
| 4821 | 801 | NM_019598 | 299 | Hs.159679 | kallikrein 12 (KLK12), mRNA /cds = UNKNOWN |
| 5091 | 802 | AI081258 | 300 | Hs.134590 | oy67c11.x1 cDNA, 3' end /clone = IMAGE: 1670900 /clone_end = 3' |
| 6000 | 803 | AW468621 | 301 | Hs.257743 | he42e03.x1 cDNA, 3' end /clone = IMAGE: 2921692 /clone_end = 3' |
| 2202 | 804 | NM_001873 | 302 | Hs.75360 | carboxypeptidase E (CPE), mRNA /cds = (290, 1720) |
| 4886 | 805 | NM_032839 | 303 | Hs.11360 | hypothetical protein FLJ14784 (FLJ14784), mRNA /cds = (133, 1569) |
| 3733 | 806 | X16277 | 304 | Hs.339703 | zv26f06.r1 cDNA, 5' end /clone = IMAGE: 754787 /clone_end = 5' |
| 4526 | 807 | NM_000395 | 305 | Hs.285401 | colony stimulating factor 2 receptor, beta, low-affinity (granulocyte-macrophage) (CSF2RB), mRNA /cds = (28, 2721) |
| 3085 | 808 | NM_013252 | 306 | Hs.126355 | C-type (calcium dependent, carbohydrate-recognition domain) lectin, superfamily member 5 (CLECSF5), mRNA /cds = (197, 763) |
| 343 | 809 | 129F10 | 307 | NA | 129F10, chromosome hit |
| 1008 | 810 | AK024331 | 308 | Hs.287631 | cDNA FLJ14269 fis, clone PLACE1003864 /cds = UNKNOWN |
| 1911 | 811 | NM_000195 | 309 | Hs.83951 | Hermansky-Pudiak syndrome (HPS), mRNA /cds = (206, 2308) |
| 7307 | 812 | NM_030756 | 310 | Hs.173638 | transcription factor 7-like 2 (T-cell specific, HMG-box) (TCF7L2), mRNA /cds = (307, 2097) |
| 150 | 813 | M26683 | 311 | Hs.303649 | interferon gamma treatment inducible mRNA Monocytes |
| 399 | 814 | AA214691 | 312 | Hs.111377 | LOC286530 hypothetical protein LOC286530 |
| 599 | 815 | AB049113 | 313 | Hs.82113 | dUTP pyrophosphatase (DUT), mRNA /cds = (29, 523) |
| 1129 | 816 | AK026819 | 314 | Hs.20242 | hypothetical protein FLJ12788 (FLJ12788), mRNA /cds = (9, 866) |
| 1717 | 817 | L21961 | 315 | Hs.181125 | Homo sapiens, clone MGC: 12849 IMAGE: 4308973, mRNA, complete cds /cds = (24, 725) |
| 2101 | 818 | NM_001278 | 316 | Hs.306440 | mRNA; cDNA DKFZp566L084 (from clone DKFZp566L084) /cds = UNKNOWN |
| 2290 | 819 | NM_002385 | 317 | Hs.69547 | myelin basic protein (MBP), mRNA /cds = (10, 570) |
| 2736 | 820 | NM_005121 | 318 | Hs.11861 | thyroid hormone receptor-associated protein, 240 kDa subunit (TRAP240), mRNA /cds = (77, 6601) |
| 3018 | 821 | NM_007220 | 319 | Hs.283646 | carbonic anhydrase VB, mitochondrial (CA5B), nuclear gene encoding mitochondrial protein, mRNA /cds = (137, 1090) |
| 3068 | 822 | NM_012381 | 320 | Hs.74420 | origin recognition complex, subunit 3 (yeast homolog)-like (ORC3L), mRNA /cds = (26, 2161) |

TABLE 2E-continued

| OID | SEQ ID 50mer | ACC | SEQ ID Full length | HS | Gene |
|---|---|---|---|---|---|
| 3128 | 823 | NM_014225 | 321 | Hs.173902 | protein phosphatase 2 (formerly 2A), regulatory subunit A (PR 65 |
| 3965 | 824 | BF966028 | 322 | Hs.5324 | hypothetical protein (CL25022), mRNA /cds = (157, 1047) |
| 4450 | 825 | AL157438 | 323 | Hs.66151 | mRNA; cDNA DKFZp434A115 (from clone DKFZp434A115) /cds = UNKNOWN |
| 4677 | 826 | NM_004488 | 324 | Hs.73734 | glycoprotein V (platelet) (GP5), mRNA /cds = (270, 1952) |
| 4753 | 827 | NM_006929 | 325 | Hs.153299 | DOM-3 (*C. elegans*) homolog Z (DOM3Z), transcript variant 2, mRNA /cds = (129, 1319) |
| 4841 | 828 | NM_021976 | 326 | Hs.79372 | retinoid X receptor, beta (RXRB), mRNA /cds = (179, 1780) |
| 4891 | 829 | T93822 | 327 | Hs.294092 | EST375308 cDNA |
| 5284 | 830 | AI524202 | 328 | Hs.171122 | th10d11.x1 cDNA, 3' end /clone = IMAGE: 2117877 /clone_end = 3' |
| 5359 | 831 | AI684022 | 329 | Hs.90744 | proteasome (prosome, macropain) 26S subunit, non-ATPase, 11 (PSMD11), mRNA /cds = (0, 1268) |
| 5965 | 832 | AW452545 | 330 | Hs.257582 | UI-H-BW1-ame-d-12-0-UI.s1 cDNA, 3' end /clone = IMAGE: 3069742 /clone_end = 3' |
| 6434 | 833 | NM_153341 | 331 | Hs.64239 | DNA sequence from clone RP5-1174N9 on chromosome 1p34.1-35.3. |
| 7175 | 834 | BF698885 | 332 | Hs.5890 | hypothetical protein FLJ23306 (FLJ23306), mRNA /cds = (562, 930) |
| 1884 | 835 | NM_000073 | 333 | Hs.2259 | CD3G antigen, gamma polypeptide (TiT3 complex) (CD3G), mRNA /cds = (37, 585) |
| 2683 | 836 | NM_004761 | 334 | Hs.170160 | RAB2, member RAS oncogene family-like (RAB2L), mRNA /cds = (0, 2333) |
| 3240 | 837 | NM_015898 | 335 | Hs.104640 | HIV-1 inducer of short transcripts binding protein (FBI1), mRNA /cds = (0, 1754) |
| 4781 | 838 | NM_014348 | 336 | Hs.296429 | similar to rat integral membrane glycoprotein POM121 (POM121L1), mRNA /cds = (0, 1286) |
| 4950 | 839 | AW500534 | 337 | Hs.145668 | fmfc5 cDNA /clone = CR6-21 |
| 5076 | 840 | AA765569 | 338 | Hs.104157 | EST380899 cDNA |
| 5092 | 841 | AI084553 | 339 | Hs.105621 | HNC29-1-B1.R cDNA |
| 5264 | 842 | AI523617 | 340 | Hs.171098 | tg95b03.x1 cDNA, 3' end /clone = IMAGE: 2116493 /clone_end = 3' |
| 5514 | 843 | AI969716 | 341 | Hs.13034 | hv63f09.x1 cDNA, 3' end /clone = IMAGE: 3178121 /clone_end = 3' |
| 7301 | 844 | NM_002076 | 342 | Hs.164036 | glucosamine (N-acetyl)-6-sulfatase (Sanfilippo disease IIID) (GNS), mRNA /cds = (87, 1745) |
| 5387 | 845 | AI760224 | 343 | Hs.26873 | wh62g06.x1 cDNA, 3' end /clone = IMAGE: 2385370 /clone_end = 3' |
| 5530 | 846 | AL565736 | 344 | Hs.181165 | eukaryotic translation elongation factor 1 alpha 1 (EEF1A1), mRNA /cds = (53, 1441) |
| 7330 | 847 | NM_004900 | 345 | Hs.226307 | phorbolin (similar to apolipoprotein B mRNA editing protein) (DJ742C19.2), mRNA /cds = (79, 651) |
| 5083 | 848 | AI031624 | 346 | Hs.238954 | 602637935F1 cDNA, 5' end /clone = IMAGE: 4765448 /clone_end = 5' |
| 6130 | 849 | BF059133 | 347 | Hs.144583 | *Homo sapiens*, clone IMAGE: 3462401, mRNA, partial cds /cds = (0, 153) |
| 555 | 850 | AB036432 | 348 | Hs.184 | advanced glycosylation end product-specific receptor (AGER), mRNA /cds = (0, 1214) |
| 3547 | 851 | R64054 | 349 | Hs.208603 | 7f01d11.x1 cDNA, 3' end /clone = IMAGE: 3293397 /clone_end = 3' |
| 1849 | 852 | M81601 | 350 | Hs.153179 | fatty acid binding protein 5 (psoriasis-associated) (FABP5), mRNA /cds = (48, 455) |
| 1390 | 853 | AY004255 | 351 | Hs.238990 | *Homo sapiens*, Similar to cyclin-dependent kinase inhibitor 1B (p27, Kip1) |
| 4604 | 854 | NM_002258 | 352 | Hs.169824 | killer cell lectin-like receptor subfamily B, member 1 (KLRB1), mRNA /cds = (60, 737) |
| 1750 | 855 | M11124 | 353 | Hs.198253 | major histocompatibility complex, class II, DQ alpha 1 (HLA-DQA1), mRNA /cds = (43, 810) |
| 4400 | 856 | AF073705 | 354 | Hs.247721 | clone mcg53-54 immunoglobulin lambda light chain variable region 4a mRNA, partial cds /cds = (0, 324) |
| 855 | 857 | AJ271326 | 355 | Hs.135187 | unc93 (*C. elegans*) homolog B (UNC93B), mRNA /cds = (41, 1834) |
| 6566 | 858 | NM_138391 | 356 | Hs.17481 | mRNA; cDNA DKFZp434G2415 (from clone DKFZp434G2415) /cds = UNKNOWN |
| 3825 | 859 | X97324 | 357 | Hs.3416 | adipose differentiation-related protein (ADFP), mRNA /cds = (0, 1313) |
| 2895 | 860 | NM_006289 | 358 | Hs.18420 | talin 1 (TLN1), mRNA /cds = (126, 7751) |
| 4631 | 861 | NM_002935 | 359 | Hs.73839 | ribonuclease, RNase A family, 3 (eosinophil cationic protein) (RNASE3), mRNA /cds = (63, 545) |
| 3832, 8069 | 862 | Y00345 | 360 | Hs.172182 | poly(A)-binding protein, cytoplasmic 1 (PABPC1), mRNA /cds = (502, 2403) |
| 5531 | 863 | AL567986 | 361 | Hs.77393 | farnesyl diphosphate synthase |

TABLE 2E-continued

| OID | SEQ ID 50mer | ACC | SEQ ID Full length | HS | Gene |
|---|---|---|---|---|---|
| 4149 | 864 | NM_000311 | 362 | Hs.74621 | prion protein (p27-30) (Creutzfeld-Jakob disease, Gerstmann-Strausler-Scheinker syndrome) |
| 3305 | 865 | NM_016523 | 363 | Hs.183125 | killer cell lectin-like receptor subfamily F, member 1 (KLRF1), mRNA /cds = (64, 759) |
| 5074 | 866 | AA701193 | 364 | Hs.431104 | EST, Weakly similar to HA21_HUMAN HLA class II histocompatibility antigen, DQ(1) alpha chain precursor (DC-4 alpha chain) |
| 8095 | 867 | AK026594 | 365 | Hs.251653 | tubulin, beta, 2 (TUBB2), mRNA /cds = (0, 1337) |
| 5607 | 868 | AW063509 | 366 | Hs.279105 | TN1012 cDNA, 3' end /clone_end = 3' |
| 3541 | 869 | R14692 | 367 | Hs.170222 | Na+/H+ exchanger NHE-1 isoform [human, heart, mRNA, 4516 nt] /cds = (577, 3024) |
| 2386 | 870 | NM_002831 | 368 | Hs.63489 | protein tyrosine phosphatase, non-receptor type 6 (PTPN6), mRNA /cds = (144, 1931) |
| 1535 | 871 | BE868389 | 369 | Hs.179703 | tripartite motif protein 14 (TRIM14), mRNA |
| 328 | 872 | AK090404 | 370 | Hs.98531 | 53G7, FLJ00290 protein |
| 1001 | 873 | AK024202 | 371 | Hs.289088 | heat shock 90 kD protein 1, alpha (HSPCA), mRNA /cds = (60, 2258) |
| 1003 | 874 | AK024240 | 372 | Hs.24115 | cDNA FLJ14178 fis, clone NT2RP2003339 /cds = UNKNOWN |
| 1025 | 875 | AK024756 | 373 | Hs.12293 | hypothetical protein FLJ21103 (FLJ21103), mRNA /cds = (88, 1143) |
| 1035 | 876 | AK024969 | 374 | Hs.166254 | hypothetical protein DKFZp566I133 (DKFZP566I133), mRNA /cds = (133, 1353) |
| 1227 | 877 | AL136542 | 375 | Hs.322456 | hypothetical protein DKFZp761D0211 (DKFZP761D0211), mRNA /cds = (164, 1822) |
| 3249 | 878 | NM_015995 | 376 | Hs.7104 | mRNA; cDNA DKFZp761P06121 (from clone DKFZp761P06121) /cds = UNKNOWN |
| 2060 | 879 | NM_001032 | 377 | Hs.539 | ribosomal protein S29 (RPS29), mRNA /cds = (30, 200) |
| 4902 | 880 | X58397 | 378 | Hs.81220 | CLL-12 transcript of unrearranged immunoglobulin V(H)5 gene /cds = (39, 425) |
| 5782 | 881 | AW293895 | 379 | Hs.255249 | UI-H-BW0-ain-f-10-0-UI.s1 cDNA, 3' end /clone = IMAGE: 2729995 /clone_end = 3' |
| 7626 | 882 | NM_003128 | 380 | Hs.324648 | cDNA FLJ13700 fis, clone PLACE2000216, highly similar to SPECTRIN BETA CHAIN, BRAIN /cds = UNKNOWN |
| 1195 | 883 | AL109669 | 381 | Hs.172803 | mRNA full length insert cDNA clone EUROIMAGE 31839 /cds = UNKNOWN |
| 8111 | 884 | AI307808 | 382 | Hs.238797 | 602081661F1 cDNA, 5' end /clone = IMAGE: 4245999 /clone_end = 5' |
| 805 | 885 | AF261087 | 383 | Hs.174131 | ribosomal protein L6 (RPL6), mRNA /cds = (26, 892) |
| 2330 | 886 | NM_002546 | 384 | Hs.81791 | tumor necrosis factor receptor superfamily, member 11b (osteoprotegerin) (TNFRSF11B), mRNA /cds = (94, 1299) |
| 3053 | 887 | NM_012237 | 385 | Hs.44017 | sirtuin (silent mating type information regulation 2, S. cerevisiae, homolog) 2 (SIRT2), transcript variant 1, mRNA /cds = (200, 1369) |
| 3779 | 888 | X68060 | 386 | Hs.75248 | topoisomerase (DNA) II beta (180 kD) (TOP2B), mRNA /cds = (0, 4865) |
| 5353 | 889 | AI660405 | 387 | Hs.111941 | qd92a04.x1 cDNA, 3' end /clone = IMAGE: 1736910 /clone_end = 3' |
| 5442 | 890 | AI798114 | 388 | Hs.210307 | wh81c01.x1 cDNA, 3' end /clone = IMAGE: 2387136 /clone_end = 3' |
| 5690 | 891 | AW075948 | 389 | Hs.265634 | xa82b03.x1 cDNA, 3' end /clone = IMAGE: 2573261 /clone_end = 3' |
| 5791 | 892 | AW294681 | 390 | Hs.255336 | UI-H-BW0-ail-g-10-0-UI.s1 cDNA, 3' end /clone = IMAGE: 2729683 /clone_end = 3' |
| 6239 | 893 | R40823 | 391 | Hs.108082 | 602068988F1 cDNA, 5' end /clone = IMAGE: 4067972 /clone_end = 5' |
| 6260 | 894 | AA806222 | 392 | Hs.111554 | ADP-ribosylation factor-like 7 (ARL7), mRNA /cds = (14, 592) |
| 6273 | 895 | AI380390 | 393 | Hs.158976 | UI-H-BI2-ahi-a-03-0-UI.s1 cDNA, 3' end /clone = IMAGE: 2726692 /clone_end = 3' |
| 6351 | 896 | BF435621 | 394 | Hs.293476 | hypothetical protein FKSG44 (FKSG44), mRNA /cds = (126, 1520) |
| 7171 | 897 | AK025781 | 395 | Hs.5076 | cDNA: FLJ22128 fis, clone HEP19543 /cds = UNKNOWN |
| 8053 | 898 | X06323 | 396 | Hs.79086 | mitochondrial ribosomal protein L3 (MRPL3), mRNA /cds = (76, 1122) |
| 8065 | 899 | X72841 | 397 | Hs.31314 | retinoblastoma-binding protein 7 (RBBP7), mRNA /cds = (287, 1564) |
| 78 | 900 | NM_001015 | 398 | Hs.182740 | ribosomal protein S11 (RPS11), mRNA /cds = (15, 4 |
| 174 | 901 | J02931 | 399 | Hs.62192 | placental tissue factor (two forms) mRNA, complete cd |
| 252 | 902 | D49950 | 400 | Hs.83077 | for interferon-gamma inducing activated macrophages |
| 255 | 903 | NM_001772 | 401 | Hs.83731 | CD33 antigen (gp67) (CD33), mRNA. |
| 824 | 904 | AF307339 | 402 | Hs.47783 | B aggressive lymphoma gene (BAL), mRNA /cds = (228, 2792) |
| 1022 | 905 | AK024597 | 403 | Hs.10362 | cDNA: FLJ20944 fis, clone ADSE01780 |
| 1155 | 906 | AK027260 | 404 | Hs.152925 | mRNA for KIAA1268 protein, partial cds /cds = (0, 3071) |

TABLE 2E-continued

| OID | SEQ ID 50mer | ACC | SEQ ID Full length | HS | Gene |
|---|---|---|---|---|---|
| 1270 | 907 | AL360190 | 405 | Hs.318501 | stimulated trans-acting factor (50 kDa) (STAF50), mRNA /cds = (122, 1450) |
| 1301 | 908 | AV689330 | 406 | Hs.189402 | Similar to RIKEN cDNA 2210009G21 gene, clone IMAGE: 4807023 |
| 1443 | 909 | BC002796 | 407 | Hs.46446 | lymphoblastic leukemia derived sequence 1 (LYL1), mRNA /cds = (0, 803) |
| 1561 | 910 | BE899595 | 408 | NA | cDNA clone IMAGE: 3952215 5' |
| 1695 | 911 | K02766 | 409 | Hs.1290 | complement component 9 (C9), mRNA /cds = (4, 1683) |
| 2070 | 912 | NM_001111 | 410 | Hs.7957 | adenosine deaminase, RNA-specific (ADAR), transcript variant ADAR-a, mRNA /cds = (187, 3867) |
| 2140 | 913 | NM_001549 | 411 | Hs.181874 | interferon-induced protein with tetratricopeptide repeats 4 (IFIT4), mRNA /cds = (61, 1533) |
| 2190 | 914 | NM_001778 | 412 | Hs.901 | CD48 antigen (B-cell membrane protein) (CD48), mRNA /cds = (36, 767) |
| 2312 | 915 | NM_002463 | 413 | Hs.926 | myxovirus (influenza) resistance 2, homolog of murine (MX2), mRNA /cds = (104, 2251) |
| 2367 | 916 | NM_002759 | 414 | Hs.274382 | protein kinase, interferon-inducible double stranded RNA dependent (PRKR), mRNA /cds = (435, 2090) |
| 2593 | 917 | NM_004031 | 415 | Hs.166120 | interferon regulatory factor 7 (IRF7), transcript variant d, mRNA /cds = (335, 1885) |
| 2979 | 918 | NM_006865 | 416 | Hs.113277 | leukocyte immunoglobulin-like receptor, subfamily A (without TM domain), member 3 (LILRA3), mRNA /cds = (62, 1381) |
| 3097 | 919 | NM_013352 | 417 | Hs.58636 | squamous cell carcinoma antigen recognized by T cell (SART-2), mRNA /cds = (149, 3025) |
| 3114 | 920 | NM_014065 | 418 | Hs.279040 | HT001 protein (HT001), mRNA /cds = (241, 1203) |
| 3328 | 921 | NM_017523 | 419 | Hs.139262 | XIAP associated factor-1 (HSXIAPAF1), mRNA /cds = (0, 953) |
| 3454 | 922 | NM_021105 | 420 | Hs.198282 | phospholipid scramblase 1 (PLSCR1), mRNA /cds = (256, 1212) |
| 4096 | 923 | XM_005543 | 421 | Hs.234642 | aquaporin 3 (AQP3), mRNA /cds = (64, 942) |
| 7264 | 924 | NM_009587 | 422 | Hs.81337 | lectin, galactoside-binding, soluble, 9 (galectin 9) (LGALS9), transcript variant long, mRNA /cds = (56, 1123) |
| 4060 | 925 | BG505271 | 423 | Hs.86437 | 602411368F1 cDNA, 5' end /clone = IMAGE: 4540096 /clone_end = 5' |
| 6122 | 926 | BE965319 | 424 | Hs.286754 | 601659229R1 cDNA, 3' end /clone = IMAGE: 3895783 /clone_end = 3' |
| 2481 | 927 | NM_003264 | 425 | Hs.63668 | toll-like receptor 2 (TLR2), mRNA /cds = (129, 2483) |
| 379 | 928 | BU540019 | 426 | NA | 485A6, EST |
| 1318 | 929 | AV719442 | 427 | Hs.256959 | AV719442 cDNA, 5' end /clone = GLCBNA01 |
| 2005 | 930 | NM_000879 | 428 | Hs.2247 | interleukin 5 (colony-stimulating factor, eosinophil) (IL5), mRNA /cds = (44, 448) |
| 2208 | 931 | NM_001916 | 429 | Hs.289271 | cytochrome c-1 (CYC1), mRNA /cds = (8, 985) |
| 2309 | 932 | NM_002460 | 430 | Hs.82132 | interferon regulatory factor 4 (IRF4), mRNA /cds = (105, 1460) |
| 2434 | 933 | NM_002994 | 431 | Hs.89714 | small inducible cytokine subfamily B (Cys-X-Cys), member 5 |
| 2994 | 934 | NM_007015 | 432 | Hs.97932 | chondromodulin I precursor (CHM-I), mRNA /cds = (0, 1004) |
| 3332 | 935 | NM_017644 | 433 | Hs.246875 | hypothetical protein FLJ20059 (FLJ20059), mRNA /cds = (25, 1290) |
| 3757 | 936 | X57025 | 434 | Hs.85112 | IGF-I mRNA for insulin-like growth factor I |
| 3960 | 937 | BF892532 | 435 | Hs.38664 | IL0-MT0152-061100-501-e04 cDNA |
| 3984 | 938 | BG028577 | 436 | Hs.279009 | matrix Gla protein (MGP), mRNA /cds = (46, 357) |
| 4403 | 939 | AF116909 | 437 | Hs.167827 | clone HH419 unknown mRNA /cds = (189, 593) |
| 4447 | 940 | AL136842 | 438 | Hs.260024 | mRNA; cDNA DKFZp434A0530 (from clone DKFZp434A0530); complete cds /cds = (968, 1732) |
| 4463 | 941 | AW327360 | 439 | Hs.250605 | dq02e11.x1 cDNA, 5' end /clone = IMAGE: 2846685 /clone_end = 5' |
| 5295 | 942 | AI538420 | 440 | Hs.231292 | td06a03.x1 cDNA, 3' end /clone = IMAGE: 2074828 /clone_end = 3' |
| 5452 | 943 | AI805144 | 441 | NA | EST |
| 5642 | 944 | AW064160 | 442 | Hs.279141 | SP0594 cDNA, 3' end /clone_end = 3' |
| 5699 | 945 | AW078847 | 443 | Hs.244816 | xb18g07.x1 cDNA, 3' end /clone = IMAGE: 2576700 /clone_end = 3' |
| 5746 | 946 | AW236252 | 444 | Hs.253747 | xn71g08.x1 cDNA, 3' end /clone = IMAGE: 2699966 /clone_end = 3' |
| 5841 | 947 | AW297026 | 445 | Hs.255600 | UI-H-BW0-ajf-e-06-0-UI.s1 cDNA, 3' end /clone = IMAGE: 2731499 /clone_end = 3' |
| 7608 | 948 | NM_016095 | 446 | Hs.108196 | HSPC037 protein (LOC51659), mRNA /cds = (78, 635) |
| 877 | 949 | AK000575 | 447 | Hs.279581 | hypothetical protein FLJ20568 (FLJ20568), mRNA /cds = (6, 422) |
| 2311 | 950 | NM_002462 | 448 | Hs.76391 | myxovirus (influenza) resistance 1, homolog of murine (interferon-inducible protein p78) (MX1), mRNA /cds = (345, 2333) |

TABLE 2E-continued

| OID | SEQ ID 50mer | ACC | SEQ ID Full length | HS | Gene |
|---|---|---|---|---|---|
| 2566 | 951 | NM_003841 | 449 | Hs.119684 | tumor necrosis factor receptor superfamily, member 10c, decoy without an intracellular domain (TNFRSF10C), mRNA /cds = (29, 928) |
| 2693 | 952 | NM_004834 | 450 | Hs.3628 | mitogen-activated protein kinase kinase kinase kinase 4 (MAP4K4), mRNA /cds = (79, 3576) |
| 3098 | 953 | NM_013368 | 451 | Hs.169138 | RPA-binding trans-activator (RBT1), mRNA /cds = (291, 881) |
| 3723 | 954 | X12451 | 452 | Hs.78056 | cathepsin L (CTSL), mRNA /cds = (288, 1289) |
| 3847 | 955 | Y13936 | 453 | Hs.17883 | protein phosphatase 1G (formerly 2C), magnesium-dependent, gamma isoform (PPM1G), mRNA /cds = (24, 1664) |
| 4324 | 956 | AW190635 | 454 | Hs.15200 | EST379783 cDNA |
| 4373 | 957 | AI378123 | 455 | Hs.327454 | tc80e02.x1 cDNA, 3' end /clone = IMAGE: 2072474 /clone_end = 3' |
| 4429 | 958 | AJ275405 | 456 | Hs.272362 | partial IGVL1 gene for immunoglobulin lambda light chain V_region |
| 5075 | 959 | AA729508 | 457 | Hs.307486 | nx54a03.s1 cDNA /clone = IMAGE: 1266028 |
| 5490 | 960 | AI865603 | 458 | Hs.341208 | wk47g03.x1 cDNA, 3' end /clone = IMAGE: 2418580 /clone_end = 3' |
| 6958 | 961 | NM_080612 | 459 | Hs.102630 | 128F5, GRB2-associated binding protein 3 (GAB3), |
| 183 | 962 | NM_014086 | 460 | Hs.6975 | PRO1073 protein (PRO1073), |
| 1712 | 963 | L11695 | 461 | Hs.220 | transforming growth factor, beta receptor I (activin A receptor type II-like kinase, 53 kD) (TGFBR1), mRNA /cds = (76, 1587) |
| 2435 | 964 | NM_002995 | 462 | Hs.3195 | small inducible cytokine subfamily C, member 1 (lymphotactin) (SCYC1), mRNA /cds = (20, 364) |
| 3971 | 965 | BF968963 | 463 | Hs.5064 | 602490910F1 cDNA, 5' end /clone = IMAGE: 4619835 /clone_end = 5' |
| 4024 | 966 | BG286649 | 464 | Hs.323950 | zinc finger protein 6 (CMPX1) (ZNF6), mRNA /cds = (1265, 3361) |
| 4773 | 967 | NM_014148 | 465 | Hs.278944 | HSPC048 protein (HSPC048), mRNA /cds = (87, 419) |
| 6140 | 968 | BF195579 | 466 | Hs.232257 | RST2302 cDNA |
| 6164 | 969 | BF509758 | 467 | Hs.144265 | UI-H-BI4-apg-d-04-0-UI.s1 cDNA, 3' end /clone = IMAGE: 3087390 /clone_end = 3' |
| 724 | 970 | AF118274 | 468 | Hs.128740 | DNb-5 mRNA, partial cds /cds = (0, 1601) |
| 2729 | 971 | NM_005082 | 469 | Hs.1579 | zinc finger protein 147 (estrogen-responsive finger protein) (ZNF147), mRNA /cds = (39, 1931) |
| 4267 | 972 | AA576947 | 470 | Hs.188886 | nm82b04.s1 cDNA, 3' end /clone = IMAGE: 1074703 /clone_end = 3' |
| 5073 | 973 | AA628833 | 471 | NA | EST |
| 5345 | 974 | AI631850 | 472 | Hs.340604 | wa36h07.x1 cDNA, 3' end /clone = IMAGE: 2300221 /clone_end = 3' |
| 5564 | 975 | AW006867 | 473 | Hs.231987 | 602320903F1 cDNA, 5' end /clone = IMAGE: 4424065 /clone_end = 5' |
| 1856 | 976 | M94046 | 474 | Hs.7647 | MYC-associated zinc finger protein (purine-binding transcription factor) (MAZ), mRNA /cds = (91, 1584) |
| 449 | 977 | AB007861 | 475 | Hs.118047 | 602971981F1 cDNA, 5' end /clone = IMAGE: 5111324 /clone_end = 5' |
| 670 | 978 | AF061944 | 476 | Hs.432900 | PRKWNK1 protein kinase, lysine deficient 1 |
| 1237 | 979 | AL136797 | 477 | Hs.273294 | mRNA; cDNA DKFZp434N031 (from clone DKFZp434N031); complete cds /cds = (18, 3608) |
| 1616 | 980 | D42040 | 478 | Hs.75243 | bromodomain-containing 2 (BRD2), mRNA /cds = (1701, 4106) |
| 4268 | 981 | AI089359 | 479 | Hs.130232 | qb05h03.x1 cDNA, 3' end /clone = IMAGE: 1695413 /clone_end = 3' |
| 4690 | 982 | NM_004776 | 480 | Hs.107526 | UDP-Gal: betaGlcNAc beta 1,4-galactosyltransferase, polypeptide 5 (B4GALT5), mRNA /cds = (112, 1278) |
| 4828 | 983 | NM_020428 | 481 | Hs.105509 | cDNA FLJ14613 fis, clone NT2RP1001113, highly similar to CTL2 gene /cds = UNKNOWN |
| 4829 | 984 | NM_020530 | 482 | Hs.248156 | oncostatin M (OSM), mRNA /cds = (0, 758) |
| 300 | 985 | NM_003321 | 483 | Hs.12084 | Tu translation elongation factor, mitochondrial (TUFM) |
| 1562 | 986 | BE901218 | 484 | Hs.285122 | *Homo sapiens*, hypothetical protein FLJ21839, clone MGC: 2851 IMAGE: 2967512, mRNA, complete cds /cds = (444, 2618) |
| 5112 | 987 | AI361733 | 485 | Hs.157811 | qz24b02.x1 cDNA, 3' end /clone = IMAGE: 2027787 /clone_end = 3' |
| 1104 | 988 | AK026410 | 486 | Hs.236449 | hypothetical protein FLJ22757 (FLJ22757), mRNA /cds = (92, 2473) |
| 4017 | 989 | BG254292 | 487 | NA | cDNA clone IMAGE: 4477042 5' |
| 4565 | 990 | NM_001504 | 488 | Hs.198252 | G protein-coupled receptor 9 (GPR9), mRNA /cds = (68, 1174) |
| 6121 | 991 | BE964596 | 489 | Hs.184052 | PP1201 protein (PP1201), mRNA/cds = (75, 1010) |
| 458 | 992 | AB011098 | 490 | Hs.59403 | serine palmitoyltransferase, long chain base subunit 2 (SPTLC2), mRNA /cds = (188, 1876) |

TABLE 2E-continued

| OID | SEQ ID 50mer | ACC | SEQ ID Full length | HS | Gene |
|---|---|---|---|---|---|
| 1519 | 993 | BE745645 | 491 | Hs.127951 | hypothetical protein FLJ14503 (FLJ14503), mRNA /cds = (19, 2217) |
| 5477 | 994 | AI827950 | 492 | Hs.342617 | ha15h10.x1 cDNA, 3' end /clone = IMAGE: 2873827 /clone_end = 3' |
| 5522 | 995 | AL521097 | 493 | Hs.13144 | HSPC160 protein (HSPC160), mRNA /cds = (53, 514) |
| 6026 | 996 | BE222032 | 494 | Hs.128675 | hr61g11.x1 cDNA, 3' end /clone = IMAGE: 3133028 /clone_end = 3' |
| 4283 | 997 | AA516406 | 495 | Hs.180201 | hypothetical protein FLJ20671 (FLJ20671), mRNA /cds = (72, 494) |
| 861 | 998 | AJ277832 | 496 | Hs.56247 | mRNA for inducible T-cell co-stimulator (ICOS gene) /cds = (67, 666) |
| 5550 | 999 | AV653169 | 497 | Hs.5897 | cDNA FLJ13388 fis, clone PLACE1001168 /cds = UNKNOWN |
| 1813 | 1000 | M36820 | 498 | Hs.75765 | GRO2 oncogene (GRO2), mRNA /cds = (74, 397) |
| 3242 | 1001 | NM_015919 | 499 | Hs.145956 | zinc finger protein mRNA, complete cds /cds = (1073, 3133) |
| 5128 | 1002 | AI378109 | 500 | Hs.283438 | 7f19b03.x1 cDNA, 3' end /clone = IMAGE: 3295085 /clone_end = 3' |
| 5195 | 1003 | AI436418 | 501 | Hs.369051 | ESTs, Weakly similar to VAM5_HUMAN Vesicule-associated membrane protein 5 (VAMP-5) (Myobrevin) (HSPC101) |
| 3497 | 1004 | NM_022488 | 502 | Hs.26367 | PC3-96 protein (PC3-96), mRNA /cds = (119, 586) |

TABLE 3

| Disease Classification | Disease/Patient Group |
|---|---|
| Endocrine Disease | Diabetes Mellitus I and II |
|  | Thyroiditis |
|  | Autoimmune polyglandular syndrome |
|  | Autoimmune oophoritis |
|  | Autoimmune hypophysitis |
|  | Addisson's Disease |
| Inflammatory/Rheumatic | Rheumatoid Arthritis |
|  | Systemic Lupus Erythematosis |
|  | Sjogrens Disease |
|  | CREST syndrome |
|  | Scleroderma |
|  | Ankylosing Spondylitis |
|  | Crohn's |
|  | Ulcerative Colitis |
|  | Primary Sclerosing Cholangitis |
| Inflammatory/Rheumatic | Appendicitis |
|  | Diverticulitis |
|  | Primary Biliary Sclerosis |
|  | Wegener's Granulomatosis |
|  | Polyarteritis nodosa |
|  | Whipple's Disease |
|  | Psoriasis |
|  | Microscopic Polyanngiitis |
|  | Takayasu's Disease |
|  | Kawasaki's Disease |
|  | Autoimmune hepatitis |
|  | Asthma |
|  | Churg-Strauss Disease |
|  | Beurger's Disease |
|  | Raynaud's Disease |
|  | Cholecystitis |
|  | Sarcoidosis |
|  | Asbestosis |
|  | Pneumoconioses |
|  | Otic inflammatory disease |
|  | Ophthalmic inflammatory disease |
|  | Antinflammatory drug use |
| Neurological Disease | Alzheimer's Dementia |
|  | Pick's Disease |
|  | Multiple Sclerosis |
|  | Guillain Barre Syndrome |
|  | Post-viral neuropathies |
|  | Peripheral Neuropathy |

TABLE 4

Real-time PCR assay chemistries. Various combinations of reporter and quencher dyes are useful for real-time PCR assays.

| Reporter | Quencher |
|---|---|
| FAM | TAMRA |
|  | BHQ1 |
| TET | TAMRA |
|  | BHQ1 |
| JOE | TAMRA |
|  | BHQ1 |
| HEX | TAMRA |
|  | BHQ1 |
| VIC | TAMRA |
|  | BHQ1 |
| ROX | BHQ2 |
| TAMRA | BHQ2 |

Two copies of compact discs labeled Copy 1 and Copy 2 of the Sequence Listing are attached to this application. Each compact disc contains a single file, SEQLIST506612000103.text (created on Dec. 8, 2006, 1.31 MB), the contents of which are hereby incorporated by reference.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07604936B2). An electronic copy of the "Sequence Listing" will also be available from the USPTO upon request and payment of the fee set forth in 37 CFR 1.19(b)(3).

We claim:

1. A method of diagnosing or monitoring an autoimmune or chronic inflammatory disease in a patient, comprising detecting the expression level of a gene in said patient to diagnose or monitor said auto immune or chronic inflammatory disease in said patient wherein said gene comprises the nucleotide sequence of SEQ ID NO:739.

2. The method of claim 1, wherein said auto immune or chronic inflammatory disease is selected from the group consisting of: Rheumatoid Arthritis, Cholecystitis, Systemic Lupus Erythematosis, Sjogrens Disease, CREST syndrome, Scleroderma, Ankylosing Spondylitis, Crohn's, Ulcerative Colitis, Primary Sclerosing Cholangitis, Appendicitis, Diverticulitis, Primary Biliary Sclerosis, Wegener's Granulomatosis, Polyarteritis nodosa, Whipple's Disease, Psoriasis, Microscopic Polyanngiitis, Takayasu's Disease, Kawasaki's Disease, Autoimmune hepatitis, Asthma, Churg-Strauss Disease, Beurger's Disease, Raynaud's Disease, and Cholecystitis.

3. The method of claim 1 wherein said disease is Systemic Lupus Erythematosis.

4. The method of claim 1 wherein said disease is Rheumatoid Arthritis.

5. The method of claim 1 wherein said expression level is detected by measuring the RNA level expressed by said gene.

6. The method of claim 5, further including isolating RNA from said patient prior to detecting said RNA level expressed by said gene.

7. The method of claim 6 wherein said RNA level is detected by PCR.

8. The method of claim 6 wherein said RNA level is detected by hybridization.

9. The method of claim 6 wherein said RNA level is detected by hybridization to an oligonucleotide.

10. The method of claim 9 wherein said oligonucleotide comprises DNA, RNA, cDNA, PNA, genomic DNA, or synthetic oligonucleotides.

11. The method of claim 1, wherein said expression level detected is expression level in the patient's bodily fluid.

12. The method of claim 11, wherein said bodily fluid is peripheral blood.

* * * * *

UNITED STATES PATENT AND TRADEMARK OFFICE
CERTIFICATE OF CORRECTION

| | | |
|---|---|---|
| PATENT NO. | : 7,604,936 B2 | Page 1 of 1 |
| APPLICATION NO. | : 10/512028 | |
| DATED | : October 20, 2009 | |
| INVENTOR(S) | : Wohlgemuth et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 830 days.

Signed and Sealed this

Fifth Day of October, 2010

David J. Kappos
*Director of the United States Patent and Trademark Office*